(12) United States Patent
Butterworth et al.

(10) Patent No.: US 10,017,493 B2
(45) Date of Patent: Jul. 10, 2018

(54) 2-(2,4,5-SUBSTITUTED-ANILINO)PYRIMIDINE COMPOUNDS

(71) Applicant: AstraZeneca AB, Sodertalje (SE)

(72) Inventors: Sam Butterworth, Macclesfield (GB); Maurice Raymond Verschoyle Finlay, Macclesfield (GB); Richard Andrew Ward, Macclesfield (GB); Heather Marie Redfearn, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/649,068

(22) Filed: Jul. 13, 2017

(65) Prior Publication Data

US 2018/0162832 A1    Jun. 14, 2018

Related U.S. Application Data

(60) Continuation of application No. 14/576,721, filed on Dec. 19, 2014, now Pat. No. 9,732,058, which is a division of application No. 13/557,871, filed on Jul. 25, 2012, now Pat. No. 8,946,235.

(60) Provisional application No. 61/591,363, filed on Jan. 27, 2012, provisional application No. 61/512,061, filed on Jul. 27, 2011.

(51) Int. Cl.
| | |
|---|---|
| *C07D 401/04* | (2006.01) |
| *C07D 487/10* | (2006.01) |
| *C07D 401/14* | (2006.01) |
| *C07D 471/04* | (2006.01) |
| *C07D 401/02* | (2006.01) |
| *C07D 403/04* | (2006.01) |

(52) U.S. Cl.
CPC ......... *C07D 401/04* (2013.01); *C07D 401/02* (2013.01); *C07D 401/14* (2013.01); *C07D 403/04* (2013.01); *C07D 471/04* (2013.01); *C07D 487/10* (2013.01)

(58) Field of Classification Search
CPC .................................................. C07D 401/04
See application file for complete search history.

(56) References Cited

U.S. PATENT DOCUMENTS

| | | |
|---|---|---|
| 2010/0016296 A1 | 1/2010 | Singh et al. |
| 2011/0046370 A1 | 2/2011 | Sim et al. |
| 2011/0207736 A1 | 8/2011 | Gray et al. |
| 2011/0263541 A1 | 10/2011 | Luo et al. |

FOREIGN PATENT DOCUMENTS

| | | |
|---|---|---|
| WO | WO 9719065 A1 | 5/1997 |
| WO | WO 2002/083653 A1 | 10/2002 |
| WO | WO 2006075152 A1 | 7/2006 |
| WO | WO 2006/084058 A2 | 8/2006 |
| WO | WO 2007/056221 A2 | 5/2007 |
| WO | WO 2007/062805 A1 | 6/2007 |
| WO | WO 2007149427 A2 | 12/2007 |
| WO | WO 2009/051822 A1 | 4/2009 |
| WO | WO 2009/158571 A1 | 12/2009 |
| WO | WO 2010/028236 A1 | 3/2010 |
| WO | WO 2010/051781 A1 | 5/2010 |
| WO | WO 2010/129053 A2 | 11/2010 |
| WO | WO 2010/129053 A3 | 11/2010 |
| WO | WO 2011/034907 A2 | 3/2011 |
| WO | WO 2011/053476 A1 | 5/2011 |
| WO | WO 2011/079231 A1 | 6/2011 |
| WO | WO 2011/090760 A4 | 7/2011 |
| WO | WO 2011/140338 A1 | 11/2011 |
| WO | WO 2011/162515 A2 | 12/2011 |
| WO | WO 2012/017239 A2 | 2/2012 |

OTHER PUBLICATIONS

Anderton et al., AACF [Apr. 5-9, 2014; San Diego, USA] Influence of early toxicology assessment on the selection of the EGFR-TKI inhibitor AZD9291. Proceedings of the 105th Annual Meeting of the American Association for Cancer Research; Apr. 5-9, 2014; San Diego, CA. Philadelphia (PA): AACR; 2014.

Anderton et al., AACR [Apr. 5-9, 2014; San Diego, USA] Influence of early toxicology assessment on the selection of AZD9291. Abstract No. 3676 published online on Mar. 5, 2014 in advance of the proceedings of the 105th Annual Meeting of the American Association for Cancer Research; Apr. 5-9, 2014; San Diego, CA. Philadelphia (PA): AACR: 2014.

Ashton et al., 'Pre-clinical In vivo Xenograft models to develop third generation EGFR mutant Tyrosine Kinase Inhibitors for NSCLC'. Poster presented at 5th Freiburg Symposium on Anticancer Drug Discovery; [Apr. 24-27, 2013; Freiburg, Germany.

Ballard et al., 'Integrating the pre-clinical pharmacokinetic, pharmacodynamic and efficacy data for AZD9291, an oral, irreversible inhibitor of EGFR activating (EGFRm+) and resistant (EGFRm+/T790M) mutations and an active metabolite to predict the human pharmacokinetics and potential efficacious dose in patients'. Poster presented at AACR-NCI-EORTC 2013; Oct. 19-23, 2013: Boston. USA.

(Continued)

*Primary Examiner* — Shawquia Jackson
(74) *Attorney, Agent, or Firm* — Meaghan Richmond

(57) ABSTRACT

The present invention relates to certain 2-(2,4,5-substituted-anilino)pyrimidine compounds and pharmaceutically acceptable salts thereof which may be useful in the treatment or prevention of a disease or medical condition mediated through certain mutated forms of epidermal growth factor receptor (for example the L858R activating mutant, the Exon19 deletion activating mutant and the T790M resistance mutant). Such compounds and salts thereof may be useful in the treatment or prevention of a number of different cancers. The invention also relates to pharmaceutical compositions comprising said compounds and salts thereof, especially useful polymorphic forms of these compounds and salts, intermediates useful in the manufacture of said compounds and to methods of treatment of diseases mediated by various different forms of EGFR using said compounds and salts thereof.

14 Claims, 21 Drawing Sheets

(56) References Cited

OTHER PUBLICATIONS

Figure 1:
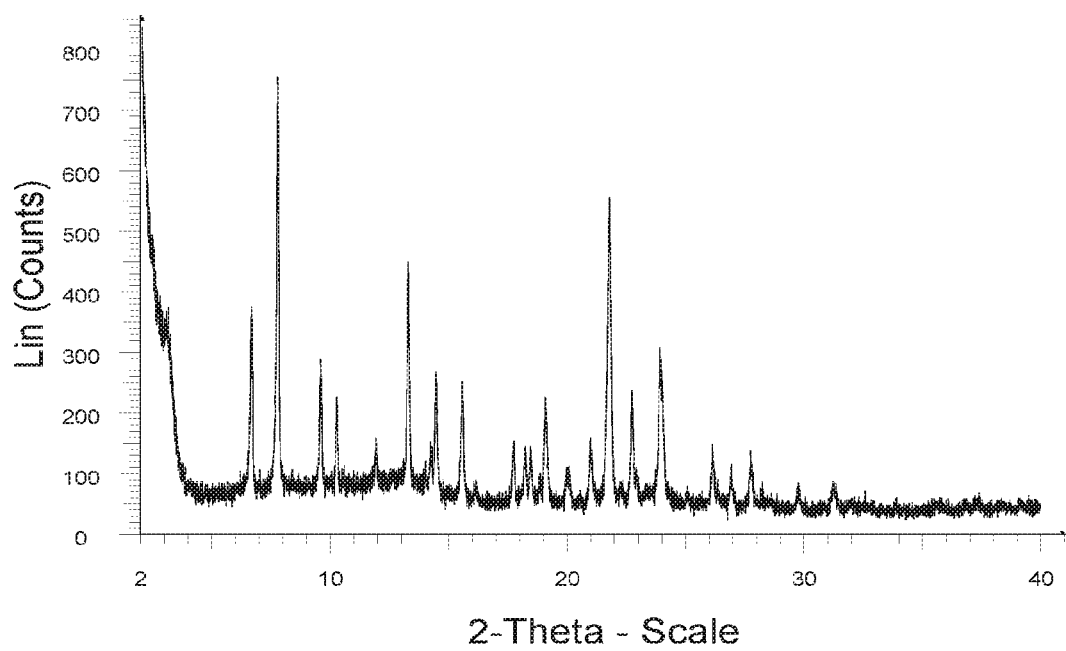

Cancer [online]. [retrieved Jul. 6, 2007]. Retrieved from the Internet. URL: <http://www.nlm.nih.gov/medlineplus/cancer.html>.
Cancer [online]. [Retrieved on Jul. 6, 2007]. Retrieved from the Internet. URL: <http://en.wikipedia.orglwikilCancer>.
Cross et al., 'AZD9291: an irreversible, potent and selective third generation tyrosine kinase inhibitor (TKI) targeting EGFR activating (EGFRm+) and resistance (T790M) mutations in advanced lung adenocarcinoma'. Poster presented at AACR-NCI-EORTC 2013; Oct. 19-23, 2013; Boston, USA.
Finlay et al., 'Discovery of and first disclosure of the clinical candidate AZD9291: a potent and selective, third generation EGFR inhibitor of both activating and T790M resistant mutations that spares the wild type form of the receptor'. Poster presented at AACR-NCI-EORTC 2013; Oct. 19-23, 2013; Boston, USA.
Finlay et al., 'Discovery of a Potent and Selective EGFR Inhibitor (AZD9291) of Both Sensitizing and T790M Resistance Mutations That Spares the Wild Type Form of the Receptor', J. Med. Chem.; 2014; 57; 20; 8249-8267. Web Publication Date: Oct. 1, 2014.
Golub et al., 'Molecular Classification of Cancer: Class Discovery and Class Prediction by Gene Expression Monitoring', Science; 1999; 286; 531-537.
Lala et al., 'Role of Nitric Oxide in Tumor Progression: Lessons from Experimental Tumors', Cancer and Metastasis Reviews; 1998; 17; 1; 91-106.
Meador et al., 'Acquired resistance to afatinib plus cetuximab in EGFR-mutant lung adenocarcinoma may be mediated by EGFR amplification and overcome by the mutant-specific EGFR inhibitor, AZD9291'. Poster presented at AACR-IASLC Joint Conference on Molecular Origins of Lung Cancer; Jan. 6-9, 2014; San Diego, USA.
Ranson et al., 'Preliminary results from a Phase I study with AZD9291: An irreversible inhibitor of epidermal growth factor receptor (EGFR) activating and resistance mutations in non-small cell lung cancer (NSCLC)', Eur J Cancer (Sep. 2013); 49(Suppl 3); S15; abs LBA33.
Ranson et al., 'Preliminary results from a Phase I study with AZD9291: an irreversible inhibitor of epidermal growth factor receptor (EGFR) activating and resistance mutations in non-small-cell lung cancer (NSCLC)'. Presentation at ESMO 2013; Sep. 27-Oct. 1, 2013; Amsterdam, The Netherlands.
Ranson et al., 'AZD9291; an irreversible potent and selective tyrosine kinase inhibitor of activating (EGFRm+) and resistance (EGFRm+/T790M+) mutations in NSCLC', J Thorac Oncol (Nov. 2013); 8 (Suppl 8); S389; abs MO21.12.
Ranson et al., 'AZD9291; an irreversible potent and selective tyrosine kinase inhibitor of activating (EGFRm+) and resistance (EGFRm+/T790M+) mutations in NSCLC'. Presentation at WCLC 2013; Oct. 27-30, 2013; Sydney, Australia.
Ward et al., 'Structure- and Reactivity-Based Development of Covalent Inhibitors of the Activating and Gatekeeper Mutant Forms of the Epidermal Growth Factor Receptor (EGFR)', Journal of Medicinal Chemistry (2013); 56; 17; 7025-7048.
Ward et al., British Association for Cancer Research, Third Special Conference of "Advances in Cancer Drug Discovery" [Mar. 30-Apr. 1, 2014; Cambridge, UK] Structure-based development of covalent inhibitors of the activating and T790M gatekeeper mutant forms of the epidermal growth factor receptor (EGFR) leading to the discovery of AZD9291.
Written Opinion of the International Searching Authority for Corresponding PCTApplication PCT/GB2012/051783; dated Oct. 17, 2012.
Yun et al., 'The T790M mutation in EGFR kinase causes drug resistance by increasing the affinity for ATP,' Proceedings of the National Academy of Sciences of the USA, vol. 105(6), Feb. 12, 2008, pp. 2070-2075.
Zhou et al., 'Discovery of Selective Irreversible Inhibitors for EGFR-T790M', Bioorganic & Medicinal Chemistry Letters; 2011; 21; 638-643.

2-(2,4,5-SUBSTITUTED-ANILINO)PYRIMIDINE COMPOUNDS

This application is a continuation of U.S. application Ser. No. 14/576,721 filed Dec. 19, 2014 which is a divisional U.S. application Ser. No. 13/557,871, filed Jul. 25, 2012, granted as U.S. Pat. No. 8,946,235 on Feb. 3, 2015, which claims the benefit under 35 U.S.C. § 119(e) of U.S. Application No. 61/512,061, filed 27 Jul. 2011 and U.S. Application No. 61/591,363, filed 27 Jan. 2012.

The present invention relates to certain 2-(2,4,5-substituted-anilino)pyrimidine compounds and pharmaceutically salts thereof which may be useful in the treatment or prevention of a disease or medical condition mediated through certain mutated forms of epidermal growth factor receptor (for example the L858R activating mutant, the Exon19 deletion activating mutant and the T790M resistance mutant). Such compounds and salts thereof may be useful in the treatment or prevention of a number of different cancers. The invention also relates to pharmaceutical compositions comprising said compounds and salts thereof, especially useful polymorphic forms of these compounds and salts, intermediates useful in the manufacture of said compounds and to methods of treatment of diseases mediated by various different forms of EGFR using said compounds and salts thereof.

EGFR is a transmembrane protein tyrosine kinase member of the erbB receptor family. Upon binding of a growth factor ligand such as epidermal growth factor (EGF), the receptor can homo-dimerise with another EGFR molecule or hetero-dimerise with another family member such as erbB2 (HER2), erbB3 (HER3), or erbB4 (HER4).

Homo- and/or hetero-dimerisation of erbB receptors results in the phosphorylation of key tyrosine residues in the intracellular domain and leads to the stimulation of numerous intracellular signal transduction pathways involved in cell proliferation and survival. Deregulation of erbB family signalling promotes proliferation, invasion, metastasis, angiogenesis, and tumour cell survival and has been described in many human cancers, including those of the lung, head and neck and breast.

The erbB family therefore represents a rational target for anticancer drug development and a number of agents targeting EGFR or erbB2 are now clinically available, including gefitinib (IRESSA™), erlotinib (TARCEVA™) and lapatinib (TYKERB™, TYVERB™). Detailed reviews of erbB receptor signalling and its involvement in tumourigenesis are provided in *New England Journal of Medicine* (2008) Vol. 358, 1160-74 and *Biochemical and Biophysical Research Communications* (2004) Vol. 319, 1-11.

In 2004 it was reported (*Science* [2004] Vol. 304, 1497-500 and *New England Journal of Medicine* [2004] Vol. 350, 2129-39) that activating mutations in EGFR correlated with response to gefitinib therapy in non-small-cell lung cancer (NSCLC). The most common EGFR activating mutations, L858R and delE746_A750, result in an increase in affinity for small molecule tyrosine kinase inhibitors such as gefitinib and erlotinib and a decrease in affinity for adenosine triphosphate (ATP) relative to wild type (WT) EGFR. Ultimately, acquired resistance to therapy with gefitinib or erlotinib arises, for example by mutation of the gatekeeper residue T790M, which is reportedly detected in 50% of clinically resistant patients. This mutation is not believed to hinder the binding of gefitinib or erlotinib to EGFR sterically, merely to alter the affinity to ATP to levels comparable to WT EGFR.

In view of the importance of this mutation in resistance to existing therapies targeting EGFR, we believe that agents which can inhibit EGFR harbouring the gatekeeper mutation may be especially useful in the treatment of cancer.

There remains a need for compounds that may exhibit favourable potency profiles against WT EGFR versus activating mutant forms of EGFR (for example the L858R EGFR mutant, or the delE746_A750 mutant or the Exon19 deletion EGFR mutant) and/or resistant mutant forms of EGFR (for example T790M EGFR mutant), and/or selectivity over other enzyme receptors which may make the compounds especially promosing for development as therapeutic agents. In this regard, there remains a need for compounds that show a higher inhibition of certain activating or resistance mutant forms of EGFR while at the same time showing relatively low inhibition of WT EGFR. Such compounds may be expected to be more suitable as therapeutic agents, particularly for the treatment of cancer, due to reduction of toxicology associated with WT EGFR inhibition. Such toxicologies are known to manifest themselves in man as skin rashes and/or diarrhoea. The applicants have surprisingly found that one or more 2-(2,4,5-substituted-anilino)pyrimidine compounds have high potency against several mutant forms of EGFR, while at the same showing relatively low inhibition of WT EGFR.

The compound(s) of the invention may also exhibit advantageous physical properties (for example, higher aqueous solubility, higher permeability, and/or lower plasma protein binding) and/or favourable toxicity profiles (for example a decreased hERG blocking liability) and/or favourable metabolic profiles in comparison with other known EGFR/EGFR-mutant inhibitors. Therefore, such compound(s) may be especially useful in the treatment of disease states in which EGFR and/or activating mutations of EGFR and/or resistance mutations of EGFR are implicated, for example in the treatment of cancer.

In the first aspect of the invention there is provided a compound of Formula (I):

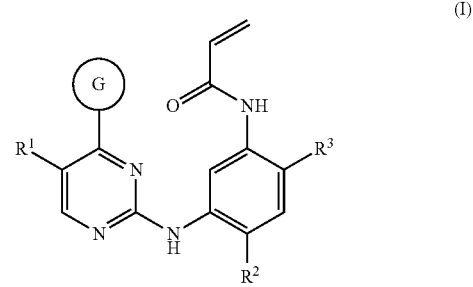

wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, fluoro, chloro, methyl and cyano;
$R^2$ is selected from methoxy and methyl; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxo-ethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof.

In one embodiment there is provided a compound of Formula (I), as shown above, wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, fluoro, chloro, methyl and cyano;
$R^2$ is selected from methoxy and methyl; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3,4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxo-ethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof.

In one embodiment there is provided a compound of Formula (I), as shown above, wherein:
G is selected from 1H-indol-3-yl, 1-methyl-1H-indol-3-yl and pyrazolo[1,5-a]-pyridin-3-yl;
$R^1$ is selected from hydrogen, fluoro, chloro, methyl and cyano;
$R^2$ is selected from methoxy and methyl; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxo-ethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof.

A suitable pharmaceutically acceptable salt of a compound of Formula (I) is, for example, an acid-addition salt. For example, an acid addition salt may be formed using an inorganic or organic acid. An acid addition salt may be formed using an inorganic acid selected from hydrochloric acid, hydrobromic acid, sulphuric acid and phosphoric acid. An acid addition salt may be formed using an organic acid selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and p-toluenesulfonic acid.

In one embodiment there is provided the mesylate salt of N-(2-{2-dimethylamino-ethyl-methylamino}-4-methoxy-5-{[4-(1-methylindol-3-yl)pyrimidin-2-yl]amino}phenyl)-prop-2-enamide.

It will be understood that the compound of Formula (I), and pharmaceutically acceptable salts thereof, may exist in solvated forms and unsolvated forms. For example a solvated form may be a hydrated form. It is to be understood that the present invention encompasses all such solvated and unsolvated forms.

The compound of Formula (I) may be administered in the form of a prodrug which is broken down in the human or animal body to give a compound of the Formula (I). Examples of prodrugs include in-vivo hydrolysable esters of a compound of the Formula (I). In-vivo hydrolysable esters may be formed by esterification of the hydroxyl group in the compound of Formula (I). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and N. Kakeya, et al., Chem Pharm Bull, 32, 692 (1984).

One aspect of the invention provides compounds of Formula (I) that inhibit one or more activating or resistance mutations of EGFR, for example the L858R activating mutant, the Exon19 deletion EGFR activating mutant and the T790M resistance mutant. Advantageously such compounds may be useful for the treatment of cancer in a patient who has developed, or may be at risk of developing a level of resistance to an existing therapy based on an EGFR inhibitor.

In one aspect of the invention there are provided compounds of Formula (I) that show a higher inhibition of activating or resistance mutant forms of EGFR than of WT EGFR. Such compounds may be expected to be more suitable as therapeutic agents, particularly for the treatment of cancer, due to reduction of toxicology associated with WT EGFR inhibition. Such toxicologies are known to manifest themselves in man as skin rashes and/or diarrhoea.

In one embodiment there is provided a compound of Formula (I), as shown hereinbefore, wherein:
G is selected from 1H-indol-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)-ethyl](methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydro-pyridin-4-yl; 4-methylpiperizin-1-yl, 4-[2-(dimethylamino)-2-oxo-ethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-amino-propanoyl]piperazin-1-yl;

or a pharmaceutically acceptable salt thereof.

In a further embodiment there is provided a compound of Formula (I), as shown hereinabove, wherein:
G is selected from 1H-indol-3-yl;
$R^1$ is selected from hydrogen, chloro, methyl and cyano;
$R^2$ is methoxy; and
$R^3$ is selected from (3R)-3-(dimethylamino)pyrrolidin-1-yl, 3-(dimethylamino)-azetidin-1-yl, [2-(dimethyl-amino)ethyl](methyl)amino, 1-methyl-1,2,3,6-tetrahydropyridin-4-yl and 4-methylpiperizin-1-yl;

or a pharmaceutically acceptable salt thereof.

In a further embodiment there is provided a compound of Formula (I), as shown hereinabove, wherein:

G is 1-methyl-1H-indol-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl](methyl)amino, 5-methyl-2,5-diazaspiro[3.4]oct-2-yl, (3aR,6aR)-5-methyl-hexahydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydro-pyridin-4-yl and 4-[(2S)-2-aminopropanoyl]piperazin-1-yl;
or a pharmaceutically acceptable salt thereof.

In a further embodiment there is provided a compound of Formula (I), as shown hereinabove, wherein:
G is 1-methyl-1H-indol-3-yl;
$R^1$ is selected from hydrogen, chloro, methyl and cyano;
$R^2$ is methoxy; and
$R^3$ is selected from (3R)-3-(dimethylamino)pyrrolidin-1-yl, 3-(dimethylamino)-azetidin-1-yl, [2-(dimethylamino)ethyl](methyl)amino and 4-methylpiperizin-1-yl;
or a pharmaceutically acceptable salt thereof.

In a further embodiment there is provided a compound of Formula (I), as shown hereinabove, wherein:
G is pyrazolo[1,5-a]pyridin-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)]-(methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;
or a pharmaceutically acceptable salt thereof.

In a further embodiment there is provided a compound of Formula (I), as shown hereinabove, wherein:
G is pyrazolo[1,5-a]pyridin-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)-ethyl](methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;
or a pharmaceutically acceptable salt thereof.

In a further embodiment there is provided a compound of Formula (I), as shown hereinabove, wherein:
G is 4,5,6,7-tetrahydropyrazolo[1,5-a]pyridin-3-yl;
$R^1$ is selected from hydrogen, chloro, methyl and cyano;
$R^2$ is methoxy; and
$R^3$ is selected from [2-(dimethylamino)-ethyl](methyl)amino, (3aR,6aR)-5-methylhexahydropyrrolo[3,4-b]pyrrol-1(2H)-yl, (3R)-3-(dimethylamino)pyrrolidin-1-yl, 1-methyl-1,2,3,6-tetrahydropyridin-4-yl, 3-(dimethylamino)azetidin-1-yl, 5-methyl-2,5-diazaspiro[3.4]oct-2-yl;
or a pharmaceutically acceptable salt thereof.

In a further embodiment there is provided a compound of Formula (I), as shown hereinabove, wherein:
G is 4,5,6,7-tetrahydropyrazolo[1,5-a]pyridin-3-yl;
$R^1$ is hydrogen;
$R^2$ is methoxy; and
$R^3$ is selected from [2-(dimethylamino)-ethyl](methyl)amino, (3aR,6aR)-5-methylhexahydropyrrolo[3,4-b]pyrrol-1(2H)-yl, (3R)-3-(dimethylamino)pyrrolidin-1-yl, 1-methyl-1,2,3,6-tetrahydropyridin-4-yl, 3-(dimethylamino)azetidin-1-yl, 5-methyl-2,5-diazaspiro[3.4]oct-2-yl;
or a pharmaceutically acceptable salt thereof.

In one embodiment there is provided a compound of Formula (I), as shown above, wherein:
G is 1H-indol-3-yl or 1-methyl-1H-indol-3-yl;
$R^1$ is hydrogen;
$R^2$ is methoxy; and
$R^3$ is [2-(dimethylamino)ethyl]-(methyl)amino or [2-(methylamino)ethyl](methyl)amino;
or a pharmaceutically acceptable salt thereof.

Some values of variable groups are as follows. Such values may be used in combination with any of the definitions, claims, aspects or embodiments defined herein to provide further embodiments of the invention:
G is 1H-indol-3-yl.
G is 1-methyl-1H-indol-3-yl.
G is pyrazolo[1,5-a]pyridin-3-yl.
G is 4,5,6,7-tetrahydropyrazolo[1,5-a]pyridin-3-yl.
$R^1$ is hydrogen.
$R^1$ is chloro.
$R^1$ is methyl.
$R^1$ is cyano.
$R^2$ is methoxy.
$R^3$ is (3R)-3-(dimethylamino)pyrrolidin-1-yl.
$R^3$ is (3S)-3-(dimethylamino)pyrrolidin-1-yl.
$R^3$ is 3-(dimethylamino)azetidin-1-yl.
$R^3$ is [2-(dimethylamino)ethyl](methyl)amino.
$R^3$ is [2-(methylamino)ethyl](methyl)amino.
$R^3$ is 5-methyl-2,5-diazaspiro[3.4]oct-2-yl.
$R^3$ is (3aR,6aR)-5-methylhexahydropyrrolo[3,4-b]pyrrol-1(2H)-yl.
$R^3$ is 1-methyl-1,2,3,6-tetrahydropyridin-4-yl.
$R^3$ is 4-methylpiperizin-1-yl.
$R^3$ is 4-[2-(dimethylamino)-2-oxoethyl]piperazin-1-yl.
$R^3$ is methyl[2-(4-methylpiperazin-1-yl)ethyl]amino.
$R^3$ is methyl[2-(morpholin-4-yl)ethyl]amino.
$R^3$ is 1-amino-1,2,3,6-tetrahydropyridin-4-yl.
$R^3$ is 4-[(2S)-2-aminopropanoyl]piperazin-1-yl.

In a further embodiment of the invention, relating to any claim or embodiment of Formula (I) described or derivable herein, or a pharmaceutically acceptable salt thereof, there is provided such a claim or embodiment where one of the Example compounds of this application is disclaimed. For the avoidance of doubt, the Example compounds are those listed as Example 1, Example 2, etc, in the experimental section hereinafter.

Therefore, for example, in one embodiment there is provided a compound of Formula (I), as shown above, wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;

R¹ is selected from hydrogen, fluoro, chloro, methyl and cyano;

R² is selected from methoxy and methyl; and

R³ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof, wherein the compound of Formula (I) is other than N-(2-{2-dimethylaminoethyl-methylamino}-4-methoxy-5-{[4-(1-methyl-indol-3-yl)pyrimidin-2-yl]amino}phenyl)prop-2-enamide.

Therefore, in one embodiment there is provided a compound of Formula (I), as shown above, wherein:

G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;

R¹ is selected from hydrogen, fluoro, chloro, methyl and cyano;

R² is selected from methoxy and methyl; and

R³ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof, wherein the compound of Formula (I) is other than N-(2-{2-dimethylaminoethyl-methylamino}-4-methoxy-5-{[4-(1-methyl-indol-3-yl)pyrimidin-2-yl]amino}phenyl)prop-2-enamide.

Therefore, in a further embodiment there is provided a compound of Formula (I), as shown above, wherein:

G is selected from 1H-indol-3-yl, 1-methyl-1H-indol-3-yl and pyrazolo[1,5-a]-pyridin-3-yl;

R¹ is selected from hydrogen, fluoro, chloro, methyl and cyano;

R² is selected from methoxy and methyl; and

R³ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof, wherein the compound of Formula (I) is other than N-(2-{2-dimethylaminoethyl-methylamino}-4-methoxy-5-{[4-(1-methyl-indol-3-yl)pyrimidin-2-yl]amino}phenyl)prop-2-enamide.

In further embodiments of the invention there is provided any one of the Example compounds, (as named hereinafter in the Experimental section, in its free base form).

In further embodiments of the invention there is provided any one of the Example compounds (as named hereinafter in the Experimental section in its free base form), or a pharmaceutically acceptable salt thereof.

Therefore, examples of just some of the above-mentioned embodiments are given below:

In one embodiment there is provided N-(5-{[5-chloro-4-(1H-indol-3-yl)pyrimidin-2-yl]amino}-2-{(3R)-3-dimethylaminopyrrolidin-1-yl}-4-methoxyphenyl)prop-2-enamide.

In one embodiment there is provided N-(5-{[5-chloro-4-(1H-indol-3-yl)pyrimidin-2-yl]amino}-2-{2-dimethylaminoethyl-methylamino}-4-methoxyphenyl)prop-2-enamide, or a pharmaceutically acceptable salt thereof.

yl)pyrimidin-2-yl]amino}-2-{2-dimethylaminoethyl-methylamino}-4-methoxyphenyl)-prop-2-enamide, or a pharmaceutically acceptable salt thereof.

In one embodiment there is provided N-(5-{[5-chloro-4-(1-methylindol-3-yl)pyrimidin-2-yl]amino}-2-{2-dimethylaminoethyl-methylamino}-4-methoxyphenyl)-prop-2-enamide.

In one embodiment there is provided N-(5-{[5-cyano-4-(1H-indol-3-yl)pyrimidin-2-yl]amino}-4-methoxy-2-{4-methylpiperazin-1-yl}phenyl)prop-2-enamide, or a pharmaceutically acceptable salt thereof.

In one embodiment there is provided N-(5-{[5-cyano-4-(1H-indol-3-yl)pyrimidin-2-yl]amino}-4-methoxy-2-{4-methylpiperazin-1-yl}phenyl)prop-2-enamide.

In one embodiment there is provided N-(2-{2-dimethylaminoethyl-methylamino}-4-methoxy-5-{[4-(1-methylindol-3-yl)pyrimidin-2-yl]amino}phenyl)prop-2-enamide, or a pharmaceutically acceptable salt thereof.

In one embodiment there is provided N-(2-{2-dimethylaminoethyl-methylamino}-4-methoxy-5-{[4-(1-methylindol-3-yl)pyrimidin-2-yl]amino}phenyl)prop-2-enamide.

In one embodiment there is provided N-(5-{[5-cyano-4-(1-methylindol-3-yl)pyrimidin-2-yl]amino}-2-{2-dimethylaminoethyl-methylamino}-4-methoxyphenyl)prop-2-enamide, or a pharmaceutically acceptable salt thereof.

In one embodiment there is provided N-(5-{[5-cyano-4-(1-methylindol-3-yl)pyrimidin-2-yl]amino}-2-{2-dimethylaminoethyl-methylamino}-4-methoxyphenyl)prop-2-enamide.

In one embodiment there is provided N-{5-[(5-cyano-4-pyrazolo[1,5-a]pyridin-3-ylpyrimidin-2-yl)amino]-2-[2-dimethylaminoethyl-methylamino]-4-methoxyphenyl}prop-2-enamide, or a pharmaceutically acceptable salt thereof.

In one embodiment there is provided N-{5-[(5-cyano-4-pyrazolo[1,5-a]pyridin-3-ylpyrimidin-2-yl)amino]-2-[2-dimethylaminoethyl-methylamino]-4-methoxyphenyl}prop-2-enamide.

In one embodiment there is provided N-{5-[(5-cyano-4-pyrazolo[1,5-a]pyridin-3-ylpyrimidin-2-yl)amino]-2-[3-dimethylaminoazetidin-1-yl]-4-methoxyphenyl}prop-2-enamide, or a pharmaceutically acceptable salt thereof.

In one embodiment there is provided N-{5-[(5-cyano-4-pyrazolo[1,5-a]pyridin-3-ylpyrimidin-2-yl)amino]-2-[3-dimethylaminoazetidin-1-yl]-4-methoxyphenyl}prop-2-enamide.

In one embodiment there is provided N-(2-{2-dimethylaminoethyl-methylamino}-4-methoxy-5-{[4-(4,5,6,7-tetrahydropyrazolo[1,5-a]pyridin-3-yl)pyrimidin-2-yl]amino}phenyl)prop-2-enamide.

In one embodiment there is provided N-(2-{2-dimethyl-aminoethyl-methylamino}-4-methoxy-5-{[4-(4,5,6,7-tetrahydropyrazolo[1,5-a]pyridin-3-yl)pyrimidin-2-yl]amino}phenyl)prop-2-enamide, or a pharmaceutically acceptable salt thereof.

In one embodiment there is provided N-{2-[2-dimethyl-aminoethyl-methylamino]-4-methoxy-5-[(4-pyrazolo[1,5-a]pyridin-3-ylpyrimidin-2-yl)amino]phenyl}prop-2-enamide.

In one embodiment there is provided N-{2-[2-dimethyl-aminoethyl-methylamino]-4-methoxy-5-[(4-pyrazolo[1,5-a]pyridin-3-ylpyrimidin-2-yl)amino]phenyl}prop-2-enamide, or a pharmaceutically acceptable salt thereof.

In one embodiment there is provided N-(2-[2-dimethyl-aminoethyl-methylamino]-5-{[4-(1H-indol-3-yl)pyrimidin-2-yl]amino}-4-methoxyphenyl)prop-2-enamide.

In one embodiment there is provided N-(2-[2-dimethyl-aminoethyl-methylamino]-5-{[4-(1H-indol-3-yl)pyrimidin-2-yl]amino}-4-methoxyphenyl)prop-2-enamide, or a pharmaceutically acceptable salt thereof.

In one embodiment there is provided N-(4-methoxy-5-{[4-(1-methylindol-3-yl)pyrimidin-2-yl]amino}-2-[methyl-(2-methylaminoethyl)amino]phenyl)prop-2-enamide, or a pharmaceutically acceptable salt thereof.

In one embodiment there is provided N-(4-methoxy-5-{[4-(1-methylindol-3-yl)pyrimidin-2-yl]amino}-2-[methyl-(2-methylaminoethyl)amino]phenyl)prop-2-enamide.

The compounds of Formula (I) may be prepared by reaction of a compound of Formula (II):

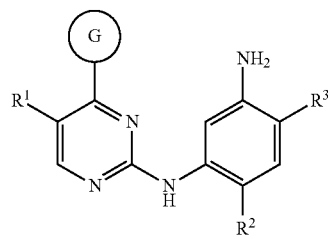

(II)

or a salt thereof, (wherein G, $R^1$, $R^2$ and $R^3$ are as defined herein) with an activated acrylic acid derivative (e.g. acroyl chloride or a corresponding activated ester), in a solvent such as $CH_2Cl_2$, tetrahydrofuran, N,N-dimethylformamide or N,N-dimethylacetamide. The intermediate compounds of Formula (II) therefore provide a further aspect of the present invention.

Therefore, in a further aspect of the invention there is provided a compound of Formula (II), (as shown above) wherein:

G is selected from 1H-indol-3-yl, 1-methyl-1H-indol-3-yl and pyrazolo[1,5-a]-pyridin-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-(tert-butoxycarbonyl)amino-propanoyl]piperazin-1-yl;
or a salt thereof.

In one embodiment there is provided a compound of Formula (II), (as shown above) wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-(tert-butoxycarbonyl)amino-propanoyl]piperazin-1-yl;
or a salt thereof.

In a further embodiment there is provided a compound of Formula (II), (as shown above) wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;
or a salt thereof.

In further embodiments of the invention there is provided any one of the Intermediate compounds, (as named hereinafter in the Experimental section, in its free base form).

In further embodiments of the invention there is provided any one of the Intermediate compounds (as named hereinafter in the Experimental section in its free base form), or a pharmaceutically acceptable salt thereof.

Therefore, examples of just some of the above-mentioned embodiments are given below:

In one embodiment there is provided Intermediate 100, or a salt thereof.

Therefore, in this case, there is provided $N^1$-(2-dimethylaminoethyl)-5-methoxy-$N^1$-methyl-$N^4$-[4-(1-methylindol-3-yl)pyrimidin-2-yl]benzene-1,2,4-triamine, or a salt thereof.

In one embodiment there is provided $N^1$-(2-dimethylaminoethyl)-5-methoxy-$N^1$-methyl-$N^4$-[4-(1-methylindol-3-yl)pyrimidin-2-yl]benzene-1,2,4-triamine.

In one embodiment there is provided Intermediate 168, or a salt thereof.

Therefore, in this case there is provided $N^1$-(2-dimethylaminoethyl)-$N^4$-[4-(1H-indol-3-yl)pyrimidin-2-yl]-5-methoxy-$N^1$-methylbenzene-1,2,4-triamine or a salt thereof.

In one embodiment there is provided $N^1$-(2-dimethylaminoethyl)-$N^4$-[4-(1H-indol-3-yl)pyrimidin-2-yl]-5-methoxy-$N^1$-methylbenzene-1,2,4-triamine.

The amine compounds of Formula (II) may be prepared by reduction of the corresponding nitro compounds. Where G is indol-3-yl then the nitrogen atom of the indole group may be protected by a suitable nitrogen protecting group, for example a phenylsulfonyl protecting group. For examples of protecting groups, including protecting groups suitable for protecting nitrogen atoms (as well as means of formation and eventual deprotection), see T. W. Greene and P. G. M. Wuts, "Protective Groups in Organic Synthesis", Second Edition, John Wiley & Sons, New York, 1991.

These further intermediates provide a further aspect of the invention.

Therefore, an a further aspect of the invention there is provided a compound of Formula (III):

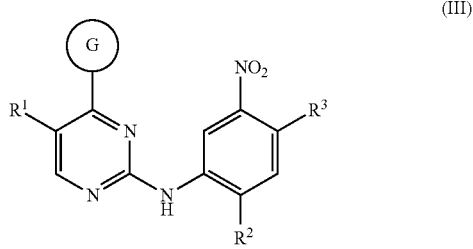

(III)

wherein:
G is selected from 1H-indol-3-yl, 1-methyl-1H-indol-3-yl an 1-(N-protecting group)-indol-3-yl and pyrazolo[1,5-a]pyridin-3-yl;
$R^1$ is selected from hydrogen, chloro, methyl and cyano;
$R^2$ is methoxy; and
$R^3$ is selected (3R)-3-(dimethylamino)pyrrolidin-1-yl, (3S)-3-(dimethylamino)-pyrrolidin-1-yl; 3-(dimethylamino)azetidin-1-yl, [2-(dimethylamino)ethyl](methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-(tert-butoxycarbonyl)amino-propanoyl]piperazin-1-yl;
or a salt thereof.

In one embodiment of this aspect of the invention there is provided a compound of Formula (III), as shown above, wherein:
G is selected from 4,5,6,7-tetrahydropyrazolo[1,5-a]pyridin-3-yl, 1H-indol-3-yl, 1-methyl-1H-indol-3-yl an 1-(N-protecting group)-indol-3-yl and pyrazolo[1,5-a]pyridin-3-yl;
$R^1$ is selected from hydrogen, chloro, methyl and cyano;
$R^2$ is methoxy; and
$R^3$ is selected (3R)-3-(dimethylamino)pyrrolidin-1-yl, (3S)-3-(dimethylamino)-pyrrolidin-1-yl; 3-(dimethylamino)azetidin-1-yl, [2-(dimethylamino)ethyl](methyl)amino, 5-methyl-2,5-diazaspiro[3.4]oct-2-yl, (3aR,6aR)-5-methylhexahydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-(tert-butoxycarbonyl)amino-propanoyl]piperazin-1-yl;
or a salt thereof.

In a further embodiment of this aspect of the invention there is provided a compound of Formula (III), as shown above, wherein:
G is selected from 4,5,6,7-tetrahydropyrazolo[1,5-a]pyridin-3-yl, 1H-indol-3-yl, 1-methyl-1H-indol-3-yl an 1-(N-protecting group)-indol-3-yl and pyrazolo[1,5-a]pyridin-3-yl;
$R^1$ is selected from hydrogen, chloro, methyl and cyano;
$R^2$ is methoxy; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;
or a salt thereof.

One example of the 'N-protecting group' within a '1-(N-protecting group)-indol-3-yl' is a phenylsulfonyl group.

In one embodiment there is provided Intermediate 101, or a salt thereof.

Therefore, in this case, there is provided N'-(2-dimethylaminoethyl)-2-methoxy-N'-methyl-N-[4-(1-methylindol-3-yl)pyrimidin-2-yl]-5-nitrobenzene-1,4-diamine, or a salt thereof.

In one embodiment there is provided N'-(2-dimethylaminoethyl)-2-methoxy-N'-methyl-N-[4-(1-methylindol-3-yl)pyrimidin-2-yl]-5-nitrobenzene-1,4-diamine.

In one embodiment there is provided Intermediate 169, or a salt thereof.

Therefore, in this case there is provided N'-(2-dimethylaminoethyl)-N-[4-(1H-indol-3-yl)pyrimidin-2-yl]-2-methoxy-N'-methyl-5-nitrobenzene-1,4-diamine, or a salt thereof.

In one embodiment there is provided N'-(2-dimethylaminoethyl)-N-[4-(1H-indol-3-yl)pyrimidin-2-yl]-2-methoxy-N'-methyl-5-nitrobenzene-1,4-diamine.

In one embodiment there is provided Intermediate 175, or a salt thereof.

Therefore, in this case there is provided $N^4$-(2-dimethylaminoethyl)-2-methoxy-$N^4$-methyl-$N^1$-[4-(1-methylindol-3-yl)pyrimidin-2-yl]-5-nitro-benzene-1,4-diamine, or a salt thereof.

In one embodiment there is provided $N^4$-(2-dimethylaminoethyl)-2-methoxy-$N^4$-methyl-$N^1$-[4-(1-methylindol-3-yl)pyrimidin-2-yl]-5-nitro-benzene-1,4-diamine.

Some compounds of Formula (III) have the $R^3$ group attached to the phenyl ring of Formula (III) via a nitrogen atom of the $R^3$ group: These compounds may be prepared by reacting the appropriate amine with the appropriate fluoro compound. Such intermediates provide a further aspect of the invention.

Therefore in a further aspect of the invention there is provided a compound of Formula (IV):

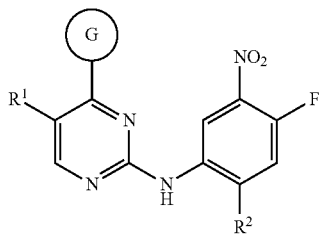

(IV)

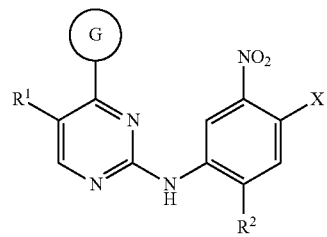

(V)

wherein:
G is selected from 1H-indol-3-yl, 1-methyl-1H-indol-3-yl and pyrazolo[1,5-a]pyridin-3-yl;
$R^1$ is selected from hydrogen, chloro, methyl and cyano; and
$R^2$ is methoxy;
or a salt thereof.

In one embodiment of this aspect of the invention there is provided a compound of Formula (IV), as shown above, wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, chloro, methyl and cyano; and
$R^2$ is methoxy;
or a salt thereof.

In one embodiment there is provided Intermediate 68, or a salt thereof.

Therefore, in this case there is provided N-(4-fluoro-2-methoxy-5-nitrophenyl)-4-(1H-indol-3-yl)pyrimidin-2-amine, or a salt thereof.

In one embodiment there is provided N-(4-fluoro-2-methoxy-5-nitrophenyl)-4-(1H-indol-3-yl)pyrimidin-2-amine.

In one embodiment there is provided Intermediate 129, or a salt thereof.

Therefore in this case there is provided N-(4-fluoro-2-methoxy-5-nitrophenyl)-4-(1-methylindol-3-yl)pyrimidin-2-amine, or a salt thereof.

In one embodiment there is provided N-(4-fluoro-2-methoxy-5-nitrophenyl)-4-(1-methylindol-3-yl)pyrimidin-2-amine.

In one embodiment there is provided Intermediate 176, or a salt thereof.

Therefore, in this case there is provided N-(4-fluoro-2-methoxy-5-nitro-phenyl)-4-(1-methylindol-3-yl)-pyrimidin-2-amine, or a salt thereof.

In one embodiment there is provided N-(4-fluoro-2-methoxy-5-nitro-phenyl)-4-(1-methylindol-3-yl)-pyrimidin-2-amine.

Some compounds of Formula (III) have the $R^3$ group attached to the phenyl ring of Formula (III) via a carbon atom of the $R^3$ group. These compounds may be prepared by reacting the appropriate organoboron compound (for example a boronate ester compound) with the appropriate aryl bromide or aryl chloride compound. For example, the organoboron compound may be (4,4,5,5-tetramethyl-1,3,2-dioxaborolan-2-yl)-$R^3$. These intermediates provide a further aspect of the present invention.

Therefore, in a further aspect of the invention there is provided a compound of Formula (V):

wherein:
X is bromo or chloro;
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, chloro, methyl and cyano; and
$R^2$ is methoxy;
or a salt thereof.

In one embodiment for the compound of Formula (V), X is bromo.

In one embodiment for the compound of Formula (V), X is chloro.

In one embodiment there is provided Intermediate 145.

Therefore, in this case there is provided N-(4-bromo-2-methoxy-5-nitrophenyl)-4-(1-methylindol-3-yl)pyrimidin-2-amine, or a salt thereof.

In one embodiment there is provided N-(4-bromo-2-methoxy-5-nitrophenyl)-4-(1-methylindol-3-yl)pyrimidin-2-amine.

Advantageously, compounds of the present invention may be prepared by reaction of a compound of Formula (II) with 3-chloropropanoyl chloride in the presence of a base (for example an alkali metal carbonate base, for example potassium carbonate, in a suitable solvent, for example acetone. An intermediate compound of Formula (VI) is thus formed, which may be isolated as a solid (in free base form or as a salt), or it may be kept in solution and treated with a base (for example an alkali metal hydroxide, for example NaOH), to convert the compound of Formula (VI) to the corresponding compound of Formula (I). Therefore, compounds of Formula (VI), and salts thereof are useful chemical intermediates in the formation of the compounds of Formula (I). Therefore, in a further aspect of the invention there is provided a compound of Formula (VI):

(VI)

or a salt thereof, wherein G, $R^1$, $R^2$ and $R^3$ are as defined herein.

In one embodiment there is provided the compound of Formula (VI), as shown above, or a salt thereof, wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^1$ is selected from hydrogen, fluoro, chloro, methyl and cyano;
$R^2$ is selected from methoxy and methyl; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl.

In a further embodiment, there is provided the compound of Formula (VI), as shown above, or a salt thereof, wherein:
G is selected from 1H-indol-3-yl, 1-methyl-1H-indol-3-yl and pyrazolo[1,5-a]-pyridin-3-yl;
$R^1$ is selected from hydrogen, fluoro, chloro, methyl and cyano;
$R^2$ is selected from methoxy and methyl; and
$R^3$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl.

In a further embodiment there is provided Intermediate 174, or a salt thereof.

Therefore, in this case, there is provided 3-chloro-N-[2-[2-dimethylaminoethyl-(methyl)amino]-4-methoxy-5-[[4-(1-methylindol-3-yl)pyrimidin-2-yl]amino]phenyl]-propanamide, or a salt thereof.

In one embodiment there is provided 3-chloro-N-[2-[2-dimethylaminoethyl-(methyl)amino]-4-methoxy-5-[[4-(1-methylindol-3-yl)pyrimidin-2-yl]amino]phenyl]-propanamide.

Other intermediates are be useful in the preparation of some compounds of Formula (I). Therefore, for example, in one embodiment there is provided Intermediate 170, or a salt thereof. In a further embodiment there is provided Intermediate 171 or a salt thereof. In a further embodiment there is provided Intermediate 172, or a salt thereof. In one embodiment there is provided Intermediate 144, or a salt thereof.

According to a further aspect of the invention there is provided a pharmaceutical composition, which comprises the compound of the Formula (I), or a pharmaceutically acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The compound of Formula (I) will normally be administered to a warm-blooded animal at a unit dose within the range 5-5000 mg/m$^2$ body area of the animal, i.e. approximately 0.1-100 mg/kg, and this normally provides a therapeutically-effective dose. A unit dose form such as a tablet or capsule will usually contain, for example 1-250 mg of active ingredient. The daily dose will necessarily be varied depending upon the host treated, the particular route of administration, and the severity of the illness being treated. Accordingly the practitioner who is treating any particular patient may determine the optimum dosage.

In the context of the present specification, the term "therapy" also includes "prophylaxis" unless there are specific indications to the contrary. The terms "therapeutic" and "therapeutically" should be construed accordingly.

As used herein, the term "treatment" is intended to have its normal everyday meaning of dealing with a disease in order to entirely or partially relieve one, some or all of its symptoms, or to correct or compensate for the underlying pathology.

As used herein, the term "prophylaxis" is intended to have its normal everyday meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

As a result of its inhibitory activity against the L858R EGFR mutant, the T790M EGFR mutant and the Exon19 deletion activating mutant, the compound of Formula (I), and pharmaceutically acceptable salts thereof, are expected to be useful in the treatment of diseases or medical conditions mediated alone or in part by EGFR mutant activity, for example cancer. The types of cancers which may be susceptible to treatment using the compound of Formula (I), or pharmaceutically acceptable salts thereof, include, but are not limited to, ovarian cancer, cervical cancer, colorectal cancer, breast cancer, pancreatic cancer, glioma, glioblastoma, melanoma, prostate cancer, leukaemia, lymphoma, non-Hodgkins lymphoma, gastric cancer, lung cancer, hepatocellular cancer, gastric cancer, gastrointestinal stromal tumour (GIST), thyroid cancer, bile duct cancer, endometrial cancer, renal cancer, anaplastic large cell lymphoma, acute myeloid leukaemia (AML), multiple myeloma, melanoma and mesothelioma.

It is envisaged that for the methods of treatment of cancer mentioned herein, the compound of Formula (I) will be administered to a mammal, more particularly a human being. Similarly, for the uses of the compound of Formula (I) for the treatment of cancer mentioned herein, it is envisaged that the compound of Formula (I) will be administered to a mammal, more particularly a human being.

According to a another aspect of the invention, there is therefore provided the compound of Formula (I) as defined hereinbefore, or a pharmaceutically acceptable salt thereof, for use as a medicament.

According to a further aspect of the invention, there is provided the compound of Formula (I) as defined hereinbefore, or a pharmaceutically acceptable salt thereof, for use in the treatment of a disease mediated through L858R EGFR mutant and/or T790M EGFR and/or the Exon19 deletion activating mutant. In one embodiment of the invention, said disease mediated through L858R EGFR mutant and/or T790M EGFR mutant and/or the Exon19 deletion activating mutant is cancer.

According to a further aspect of the invention, there is provided the use of the compound of Formula (I) as defined hereinbefore, or a pharmaceutically acceptable salt thereof, for the manufacture of a medicament for the treatment of a disease mediated through L858R EGFR mutant and/or T790M EGFR mutant and/or the Exon19 deletion activating mutant. In one embodiment of the invention, said disease mediated through L858R EGFR mutant and/or T790M EGFR mutant and/or the Exon19 deletion activating mutant is cancer.

According to a further aspect of the invention, there is provided the use of the compound of Formula (I) as defined hereinbefore, or a pharmaceutically acceptable salt thereof, for the manufacture of a medicament for the treatment of cancer.

According to a further aspect of the invention, there is provided a method of using a compound of Formula (I) as defined hereinbefore, or a pharmaceutically acceptable salt thereof, for the treatment of cancer.

According to this aspect of the invention there is provided a method for producing an anti-cancer effect in a warm-blooded animal, such as man, in need of such treatment, which comprises administering to said animal an effective amount of the compound of Formula (I), or a pharmaceutically acceptable salt thereof, as defined herein.

According to a further aspect of the invention, there is provided a method of treating a human suffering from a disease in which inhibition of L858R EGFR mutant and/or T790M EGFR mutant and/or the Exon19 deletion activating mutant is beneficial, comprising the steps of administering to a person in need thereof of a therapeutically effective amount of the compound of Formula (I) as defined hereinbefore, or a pharmaceutically acceptable salt thereof. In one embodiment of the invention, the disease in which inhibition of L858R EGFR mutant and/or T790M EGFR mutant and/or the Exon19 deletion activating mutant is beneficial is cancer.

In any of the aspects or embodiments mentioned herein where cancer is mentioned in a general sense, said cancer may be selected from ovarian cancer, cervical cancer, colorectal cancer, breast cancer, pancreatic cancer, glioma, glioblastoma, melanoma, prostate cancer, leukaemia, lymphoma, non-Hodgkins lymphoma, gastric cancer, lung cancer, hepatocellular cancer, gastric cancer, gastrointestinal stromal tumour (GIST), thyroid cancer, bile duct cancer, endometrial cancer, renal cancer, anaplastic large cell lymphoma, acute myeloid leukaemia (AML), multiple myeloma, melanoma and mesothelioma.

In any aspect or embodiment of the invention where cancer is mentioned in a general sense the following embodiments may apply:

In one embodiment the cancer is ovarian cancer.
In one embodiment the cancer is cervical cancer.
In one embodiment the cancer is colorectal cancer.
In one embodiment the cancer is breast cancer.
In one embodiment the cancer is pancreatic cancer.
In one embodiment the cancer is glioma.
In one embodiment the cancer is glioblastoma.
In one embodiment the cancer is melanoma.
In one embodiment the cancer is prostate cancer.
In one embodiment the cancer is leukaemia.
In one embodiment the cancer is lymphoma.
In one embodiment the cancer is non-Hodgkins lymphoma.
In one embodiment the cancer is gastric cancer.
In one embodiment the cancer is lung cancer.
In one embodiment the cancer is non-small cell lung cancer.
In one embodiment the cancer is hepatocellular cancer.
In one embodiment the cancer is gastric cancer.
In one embodiment the cancer is gastrointestinal stromal tumour (GIST).
In one embodiment the cancer is thyroid cancer.
In one embodiment the cancer is bile duct cancer.
In one embodiment the cancer is endometrial cancer.
In one embodiment the cancer is renal cancer.
In one embodiment the cancer is anaplastic large cell lymphoma.
In one embodiment the cancer is acute myeloid leukaemia (AML).
In one embodiment the cancer is multiple myeloma.
In one embodiment the cancer is melanoma.
In one embodiment the cancer is mesothelioma.

The anti-cancer treatment described hereinbefore may be applied as a sole therapy or may involve, in addition to the compound of the invention, conventional surgery or radiotherapy or chemotherapy or immunotherapy. Such chemotherapy could be administered concurrently, simultaneously, sequentially or separately to treatment with the compound of the invention and may include one or more of the following categories of anti-tumour agents:—

(i) antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline [AZD0530 (saracatinib); WO01/94341], N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stem et al. Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)-quinazolin-4-amine (gefitinib, ZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as famesyl transferase inhibitors, for example sorafenib (BAY 43-9006), tipifamib (R115777) and lonafamib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD 1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in WO97/22596, WO97/30035, WO97/32856 and WO98/13354 and compounds that work by other mechanisms (for example linomide, inhibitors of integrin αvβ3 function and angiostatin)];

(vi) vascular damaging agents such as Combretastatin A4 and compounds disclosed in WO99/02166, WO00/40529, WO00/41669, WO01/92224, WO02/04434 and WO02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines, approaches using anti-idiotypic antibodies, approaches to decrease the function of immune suppressive cells such as regulatory T cells, myeloid-derived suppressor cells or IDO (indoleamine 2,3,-deoxygenase)-expressing dendritic cells, and approaches using cancer vaccines consisting of proteins or peptides derived from tumour-associated antigens such as NY-ESO-1, MAGE-3, WT1 or Her2/neu.

Therefore, in a further aspect of the invention there is provided a pharmaceutical product comprising the compound of Formula (I) as defined hereinbefore, and an additional anti-tumour substance, as defined hereinbefore, for the conjoint treatment of cancer.

In such an aspect of the invention there is provided a pharmaceutical product comprising the compound of Formula (I), or a pharmaceutically acceptable salt thereof, as defined herein, and an additional anti-tumour substance, as defined hereinbefore, for the conjoint treatment of cancer.

Herein, where the term "conjoint treatment" is used in reference to a combination treatment, it is to be understood that this may refer to simultaneous, separate or sequential administration. Refrerenes to "conjoint administration" should be construed similarly. In one aspect of the invention "conjoint treatment" refers to simultaneous administration. In another aspect of the invention "conjoint treatment" refers to separate administration. In a further aspect of the invention "conjoint treatment" refers to sequential administration. Where the administration is sequential or separate, the delay in administering the second component should not be such as to lose the benefit of the effect arising from use of the combination. Therefore, in one embodiment sequential treatment involves administration of each component of the combination within a period of 11 days. In another embodiment this period is 10 days. In another embodiment this period is 9 days. In another embodiment this period is 8 days. In another embodiment this period is 7 days. In another embodiment this period is within 6 days. In another embodiment this period is within 5 days. In another embodiment this period is within 4 days. In another embodiment this period is within 3 days. In another embodiment this period is within 2 days. In another embodiment this period is within 24 hours. In another embodiment this period is within 12 hours.

Therefore, in one embodiment of the invention there is provided the use of a compound of Formula (I), or a pharmaceutically acceptable salt thereof, as defined herein, and an additional anti-tumour substance for the conjoint treatment of cancer.

In one embodiment of the invention there is provided the use of a compound of Formula (I), or a pharmaceutically acceptable salt thereof, as defined herein, and an additional anti-tumour substance for the simultaneous, separate or sequential treatment of cancer.

In one embodiment there is provided a method of producing an anti-cancer effect in a warm-blooded animal, such as man, who is in need of such treatment, which comprises administering to said mammal a compound of Formula (I), or a pharmaceutically acceptable salt thereof, and conjointly administering an additional anti-tumour substance to said mammal, wherein the amounts of the compound of Formula (I), or pharmaceutically acceptable salt thereof, and the additional anti-tumour substance are jointly effective in producing an anti-cancer effect.

In one embodiment there is provided a method of producing an anti-cancer effect in a warm-blooded animal, such as man, who is in need of such treatment, which comprises administering to said mammal a compound of Formula (I), or a pharmaceutically acceptable salt thereof, and simultaneously, separately or sequentially administering an additional anti-tumour substance to said mammal, wherein the amounts of the compound of Formula (I), or pharmaceutically acceptable salt thereof, and the additional anti-tumour substance are jointly effective in producing an anti-cancer effect.

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active compound.

The different physical properties of the crystalline forms with respect to each other and with respect to the non-crystalline state may influence markedly the chemical and pharmaceutical processing of a compound, particularly when the compound is prepared or used on an industrial scale.

Further, in the manufacture of oral drug compositions, it is important that a reliable and reproducible plasma concentration profile of drug is provided following administration to a patient. Inter-patient variability in the absorption profile of a drug within the stomach, intestine or bloodstream can have an effect on drug safety and efficacy.

Chemical stability, solid state stability and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous materials may present problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, it is important, wherever possible, to provide drug in a crystalline, and stable, form.

It is to be noted, however, that this goal is not always achievable. Indeed, typically, it is not possible to predict, from molecular structure alone, what the crystallisation behaviour of a compound, either as such or in the form of a salt, will be. This can only be determined empirically.

In a further aspect of the invention, certain compounds and salts thereof may be prepared in crystalline forms. These crystalline forms may be characterised as being a particular polymorphic form. When it is stated that the present invention relates to a crystalline form, the degree of crystallinity is conveniently greater than about 60%, more conveniently greater than about 80%, preferably greater than about 90% and more preferably greater than about 95%. Most preferably the degree of crystallinity is greater than about 98%.

The specific solid forms described herein provide X-ray powder diffraction patterns substantially the same as the X-ray powder diffraction patterns shown in the Figures and have the various 2-theta values as shown in the Tables included herein. It will be understood that the 2-theta values of a X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the solid forms of the present invention are not limited to the crystals that provide X-ray powder diffraction patterns that are identical to the X-ray powder diffraction pattern shown in the Figures, and any crystals providing X-ray powder diffraction patterns substantially the same as those shown in the Figures fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 μm in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in the Figures and when reading data contained in the Tables included herein. Furthermore, it should be understood that intensities might fluctuate depending on experimental conditions and sample preparation (preferred orientation).

In this specification N-(2-{2-dimethylaminoethyl-methylamino}-4-methoxy-5-{[4-(1-methylindol-3-yl)pyrimidin-2-yl]amino}phenyl)prop-2-enamide is referred to as "Compound X". The initially produced Compound X was found to be an amorphous solid. Several useful crystalline polymorphic forms have subsequently been produced using the conditions described hereinafter in the experimental section. In all of the embodiments relating to solid forms recited herein, the peaks of the X-ray diffraction patterns are measured using CuKa radiation.

Polymorphic Form A of Compound X

Therefore in a further aspect of the invention there is provided polymorphic Form A of Compound X. This polymorphic form may be characterised in that it provides at least one of the following 2θ values measured using CuKa radiation: 7.8 and 21.8.

Polymorphic Form A of Compound X is characterised in providing an X-ray powder diffraction pattern, substantially as shown in FIG. 1.

Ten X-Ray powder diffraction peaks for this polymorphic form [Angle 2-theta (2θ), Intensity (%)] are 7.8 (100%), 21.8 (73.4%), 13.3 (59.4%), 6.6 (49.5%), 23.9 (40.5%), 9.6 (38.1%), 14.5 (35.3%), 15.6 (33.2%), 22.7 (31.2%) and 19.1 (29.8%).

According to the present invention there is provided the polymorphic Form A of Compound X, which has an X-ray powder diffraction pattern with at least one specific peak at about 2-theta=7.8°.

According to the present invention there is provided the polymorphic Form A of Compound X, which has an X-ray powder diffraction pattern with at least one specific peak at about 2-theta=21.8°.

According to the present invention there is provided the polymorphic Form A of Compound X, which has an X-ray powder diffraction pattern with at least two specific peaks at about 2-theta=7.80 and 21.8°.

According to the present invention there is provided the polymorphic Form A of Compound X, which has an X-ray powder diffraction pattern with specific peaks at about 2-theta=7.8, 21.8, 13.3, 6.6, 23.9, 9.6, 14.5, 15.6, 22.7 and 19.1°.

According to the present invention there is provided polymorphic Form A of Compound X which has an X-ray powder diffraction pattern substantially the same as the X-ray powder diffraction pattern shown in FIG. 1.

According to the present invention there is provided polymorphic Form A of Compound X, which has an X-ray powder diffraction pattern with at least one specific peak at 2-theta=7.8° plus or minus 0.2° 2-theta.

According to the present invention there is provided a polymorphic Form A of Compound X, which has an X-ray powder diffraction pattern with at least one specific peak at 2-theta=21.8° plus or minus 0.2° 2-theta.

According to the present invention there is provided the polymorphic Form A of Compound X, which has an X-ray powder diffraction pattern with at least two specific peaks at 2-theta=7.8° and 21.8° wherein said values may be plus or minus 0.2° 2-theta.

According to the present invention there is provided a polymorphic Form A of Compound X, which has an X-ray powder diffraction pattern with specific peaks at 2-theta=7.8, 21.8, 13.3, 6.6, 23.9, 9.6, 14.5, 15.6, 22.7 and 19.10 wherein said values may be plus or minus 0.2° 2-theta.

Polymorphic Form B of Compound X

In a further aspect of the invention there is provided polymorphic Form B of Compound X. This polymorphic form may be characterised in that it provides at least one of the following 2θ values measured using CuKa radiation: 9.3 and 23.4.

Figure 3:
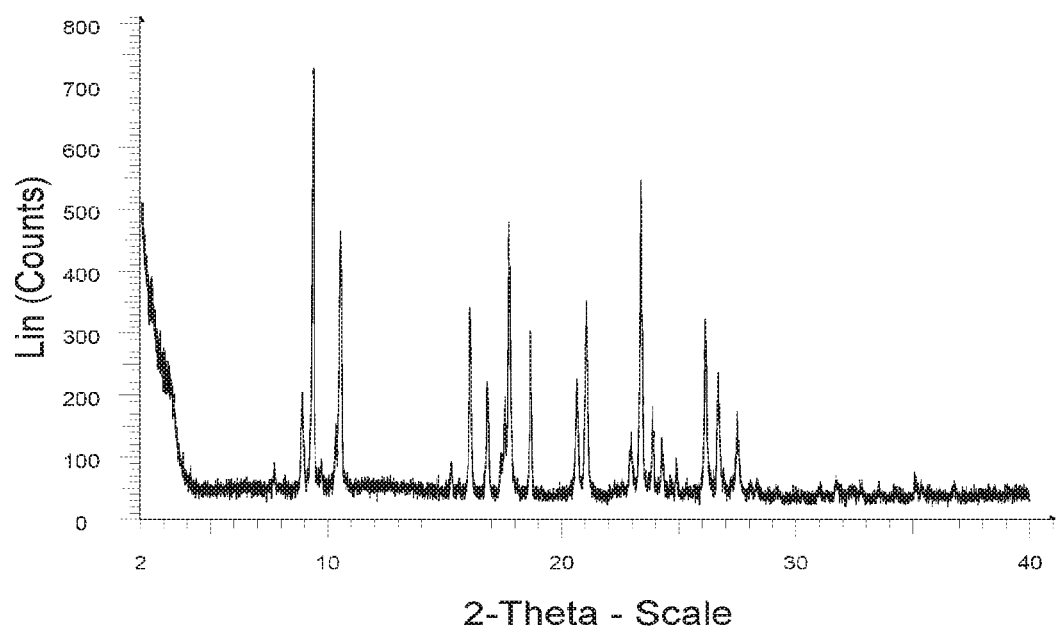

Polymorphic Form B of Compound X is characterised in providing an X-ray powder diffraction pattern, substantially as shown in FIG. 3.

Ten X-Ray powder diffraction peaks for this polymorphic form [Angle 2-theta (2θ), Intensity (%)] are 9.3 (100%), 23.4 (75.0%), 10.5 (63.6%), 17.7 (54.3%), 21.0 (48.1%), 16.1 (46.4%), 26.1 (44.2%), 18.6 (41.8%), 26.7 (32.2%) and 20.6 (30.9%).

According to the present invention there is provided the polymorphic Form B of Compound X, which has an X-ray powder diffraction pattern with at least one specific peak at about 2-theta=9.30°.

According to the present invention there is provided the polymorphic Form B of Compound X, which has an X-ray powder diffraction pattern with at least one specific peak at about 2-theta=23.4°.

According to the present invention there is provided the polymorphic Form B of Compound X, which has an X-ray powder diffraction pattern with at least two specific peaks at about 2-theta=9.30 and 23.4°.

According to the present invention there is provided the polymorphic Form B of Compound X, which has an X-ray powder diffraction pattern with specific peaks at about 2-theta=9.3, 23.4, 10.5, 17.7, 21.0, 16.1, 26.1, 18.6, 26.7 and 20.6°.

According to the present invention there is provided polymorphic Form B of Compound X which has an X-ray powder diffraction pattern substantially the same as the X-ray powder diffraction pattern shown in FIG. 3.

According to the present invention there is provided polymorphic Form B of Compound X, which has an X-ray powder diffraction pattern with at least one specific peak at 2-theta=9.3° plus or minus 0.2° 2-theta.

According to the present invention there is provided the polymorphic Form B of Compound X, which has an X-ray powder diffraction pattern with at least one specific peak at 2-theta=23.4° plus or minus 0.2° 2-theta.

According to the present invention there is provided the polymorphic Form B of Compound X, which has an X-ray powder diffraction pattern with at least two specific peaks at 2-theta=9.3° and 23.4° wherein said values may be plus or minus 0.2° 2-theta.

According to the present invention there is provided the polymorphic Form B of Compound X, which has an X-ray powder diffraction pattern with specific peaks at 2-theta=9.3, 23.4, 10.5, 17.7, 21.0, 16.1, 26.1, 18.6, 26.7 and 20.6° wherein said values may be plus or minus 0.2° 2-theta.

Polymorphic Form C of Compound X

In a further aspect of the invention there is provided polymorphic Form C of Compound X. This polymorphic form may be characterised in that it provides at least one of the following 2θ values measured using CuKa radiation: 6.0 and 11.3.

Figure 5:
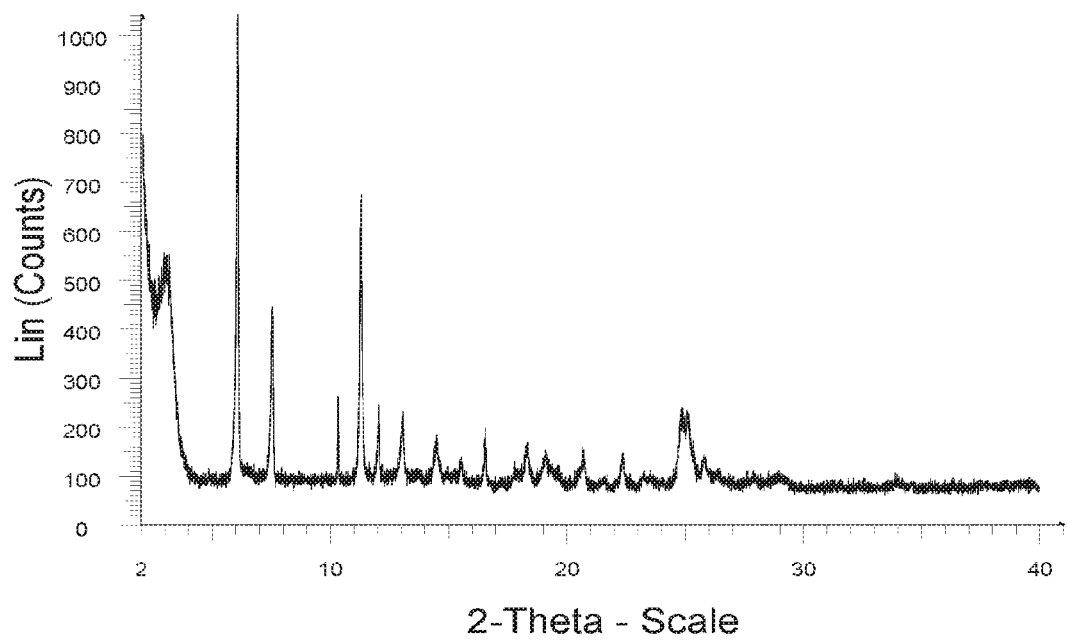

Polymorphic Form C of Compound X is characterised in providing an X-ray powder diffraction pattern, substantially as shown in FIG. 5.

Ten X-Ray powder diffraction peaks for this polymorphic form [Angle 2-theta (2θ), Intensity (%)] are 6.0 (100%), 11.3 (58.2%), 7.5 (40.5%), 10.3 (21.9%), 12.0 (20.1%), 24.9 (19.4%), 13.0 (16.9%), 14.5 (13.5%), 16.5 (13.5%) and 18.3 (11.8%).

According to the present invention there is provided the polymorphic Form C of Compound X, which has an X-ray powder diffraction pattern with at least one specific peak at about 2-theta=6.0°.

According to the present invention there is provided the polymorphic Form C of Compound X, which has an X-ray powder diffraction pattern with at least one specific peak at about 2-theta=11.3°.

According to the present invention there is provided the polymorphic Form C of Compound X, which has an X-ray powder diffraction pattern with at least two specific peaks at about 2-theta=6.0° and 11.3°.

According to the present invention there is provided the polymorphic Form C of Compound X, which has an X-ray powder diffraction pattern with specific peaks at about 2-theta=6.0, 11.3, 7.5, 10.3, 12.0, 24.9, 13.0, 14.5, 16.5, and 18.30°.

According to the present invention there is provided polymorphic Form C of Compound X which has an X-ray powder diffraction pattern substantially the same as the X-ray powder diffraction pattern shown in FIG. 5.

According to the present invention there is provided polymorphic Form C of Compound X, which has an X-ray powder diffraction pattern with at least one specific peak at 2-theta=6.0° plus or minus 0.2° 2-theta.

According to the present invention there is provided the polymorphic Form C of Compound X, which has an X-ray powder diffraction pattern with at least one specific peak at 2-theta=11.3° plus or minus 0.2° 2-theta.

According to the present invention there is provided the polymorphic Form C of Compound X, which has an X-ray powder diffraction pattern with at least two specific peaks at 2-theta=6.00 and 11.30 wherein said values may be plus or minus 0.2° 2-theta.

According to the present invention there is provided the polymorphic Form C of Compound X, which has an X-ray powder diffraction pattern with specific peaks at 2-theta=6.0, 11.3, 7.5, 10.3, 12.0, 24.9, 13.0, 14.5, 16.5, and 18.3° wherein said values may be plus or minus 0.2° 2-theta.

Polymorphic Form D of Compound X

In a further aspect of the invention there is provided polymorphic Form D of Compound X which is believed to be a monohydrate crystalline form. This polymorphic form may be characterised in that it provides at least one of the following 2θ values measured using CuKa radiation: 9.3 and 10.5.

Figure 7:
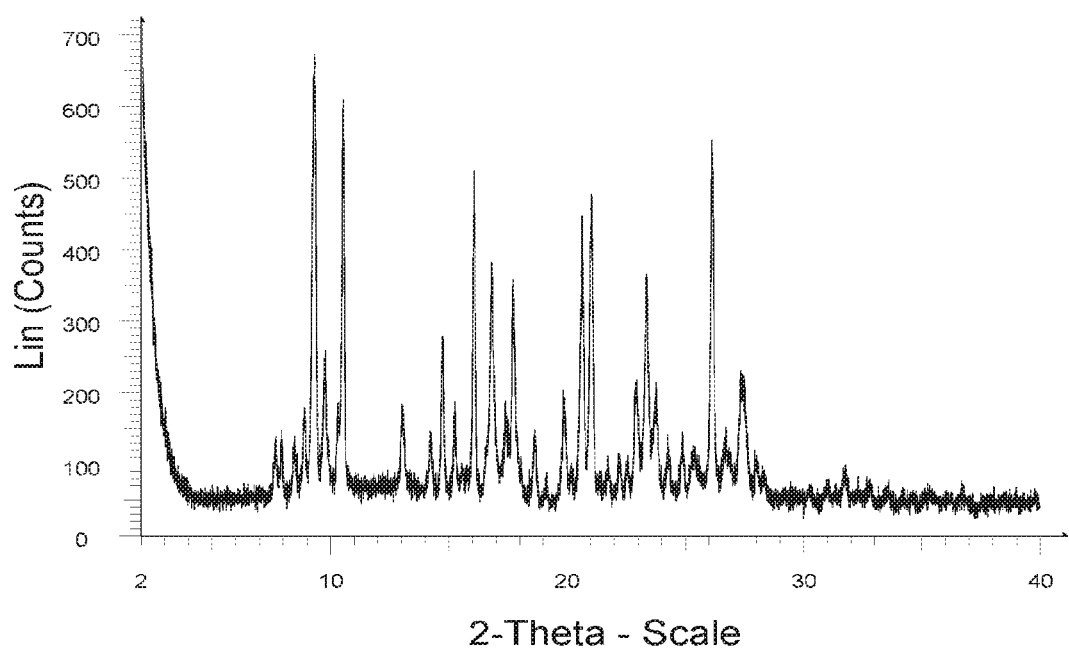

Polymorphic Form D of Compound X is characterised in providing an X-ray powder diffraction pattern, substantially as shown in FIG. 7.

Ten X-Ray powder diffraction peaks for this polymorphic form [Angle 2-theta (2θ), Intensity (%)] are 9.3 (100%), 10.5 (90.6%), 16.1 (75.8%), 26.1 (75.2%), 21.0 (70.9%), 20.6 (56.9%), 16.8 (56.5%), 17.7 (53.3%), 14.7 (41.3%) and 9.7 (38.3%).

According to the present invention there is provided the polymorphic Form D of Compound X, which has an X-ray powder diffraction pattern with at least one specific peak at about 2-theta=9.30°.

According to the present invention there is provided the polymorphic Form D of Compound X, which has an X-ray powder diffraction pattern with at least one specific peak at about 2-theta=10.50°.

According to the present invention there is provided the polymorphic Form D of Compound X, which has an X-ray powder diffraction pattern with at least two specific peaks at about 2-theta=9.3° and 10.5°.

According to the present invention there is provided the polymorphic Form D of Compound X, which has an X-ray powder diffraction pattern with specific peaks at about 2-theta=9.3, 10.5, 16.1, 26.1, 21.0, 20.6, 16.8, 17.7, 14.7, and 9.7°.

According to the present invention there is provided polymorphic Form D of Compound X which has an X-ray powder diffraction pattern substantially the same as the X-ray powder diffraction pattern shown in FIG. 7.

According to the present invention there is provided polymorphic Form D of Compound X which has an X-ray powder diffraction pattern with at least one specific peak at 2-theta=9.3° plus or minus 0.2° 2-theta.

According to the present invention there is provided polymorphic Form D of Compound X which has an X-ray powder diffraction pattern with at least one specific peak at 2-theta=10.5° plus or minus 0.2° 2-theta.

According to the present invention there is provided the polymorphic Form D of Compound X, which has an X-ray powder diffraction pattern with at least two specific peaks at 2-theta=9.30 and 10.5° wherein said values may be plus or minus 0.2° 2-theta.

According to the present invention there is provided the polymorphic Form D of Compound X, which has an X-ray powder diffraction pattern with specific peaks at 2-theta=9.3, 10.5, 16.1, 26.1, 21.0, 20.6, 16.8, 17.7, 14.7, and 9.7° wherein said values may be plus or minus 0.2° 2-theta.

Polymorphic Form E of Compound X

In a further aspect of the invention there is provided polymorphic Form E of Compound X which is believed to be a 1.25 stoichiometry hydrated form of Compound X. This polymorphic form may be characterised in that it provides at least one of the following 2θ values measured using CuKa radiation: 9.2 and 22.9.

Figure 10:
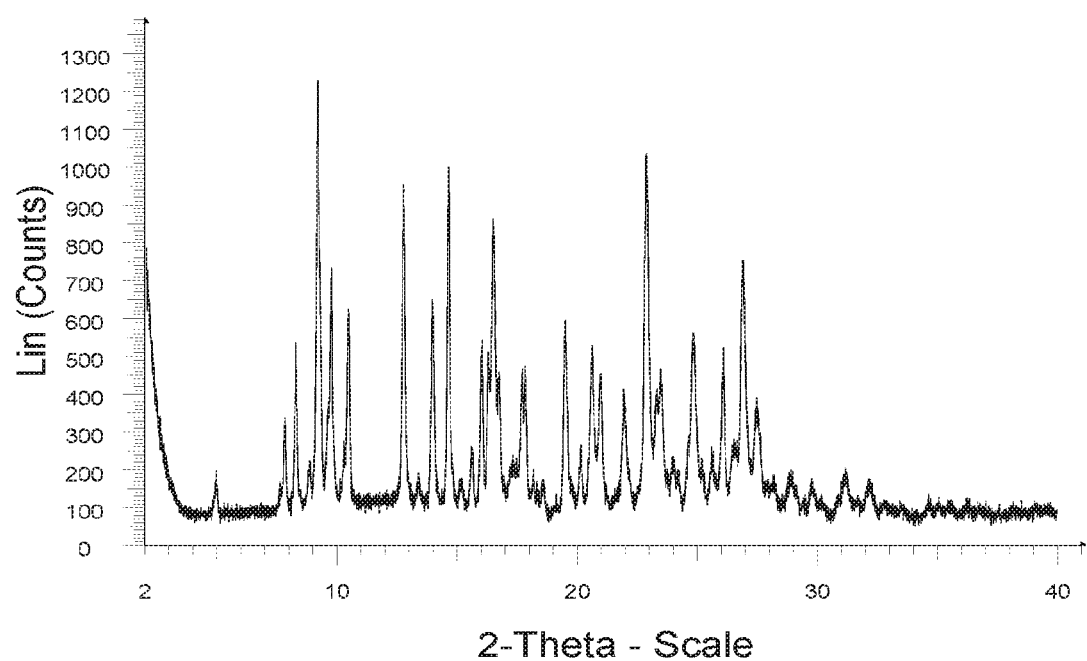

Polymorphic Form E of Compound X is characterised in providing an X-ray powder diffraction pattern, substantially as shown in FIG. 10.

Ten X-Ray powder diffraction peaks for this polymorphic form [Angle 2-theta (2θ), Intensity (%)] are: 9.2 (100%), 22.9 (84.0%), 14.6 (80.3%), 12.7 (77.8%), 16.5 (66.4%), 26.9 (60.3%), 9.7 (95.6%), 14.0 (52.3%), 10.4 (49.9%) and 19.5 (48.3%).

According to the present invention there is provided the polymorphic Form E of Compound X which has an X-ray powder diffraction pattern with at least one specific peak at about 2-theta=9.2°.

According to the present invention there is provided the polymorphic Form E of Compound X which has an X-ray powder diffraction pattern with at least one specific peak at about 2-theta=22.9°.

According to the present invention there is provided the polymorphic Form E of Compound X which has an X-ray powder diffraction pattern with at least two specific peaks at about 2-theta=9.20 and 22.9°.

According to the present invention there is provided the polymorphic Form E of Compound X which has an X-ray powder diffraction pattern with specific peaks at about 2-theta=9.2, 22.9, 14.6, 12.7, 16.5, 26.9, 9.7, 14.0, 10.4 and 19.5°.

According to the present invention there is provided the polymorphic Form E of Compound X which has an X-ray powder diffraction pattern substantially the same as the X-ray powder diffraction pattern shown in FIG. 10.

According to the present invention there is provided polymorphic Form E of Compound X which has an X-ray powder diffraction pattern with at least one specific peak at 2-theta=9.2° plus or minus 0.2° 2-theta.

According to the present invention there is provided the polymorphic Form E of Compound X which has an X-ray powder diffraction pattern with at least one specific peak at 2-theta=22.9° plus or minus 0.2° 2-theta.

According to the present invention there is provided the polymorphic Form E of Compound X which has an X-ray powder diffraction pattern with at least two specific peaks at 2-theta=9.2° and 22.9° wherein said values may be plus or minus 0.2° 2-theta.

According to the present invention there is provided the polymorphic Form E of Compound X which has an X-ray powder diffraction pattern with specific peaks at 2-theta=9.2, 22.9, 14.6, 12.7, 16.5, 26.9, 9.7, 14.0, 10.4, and 19.5° wherein said values may be plus or minus 0.2° 2-theta.

Polymorphic Form F of Compound X

In a further aspect of the invention there is provided polymorphic Form F of Compound X which is believed to be a 0.25 stoichiometry hydrated form of Compound X. This polymorphic form may be characterised in that it provides at least one of the following 2θ values measured using CuKa radiation: 18.7 and 8.9.

Figure 13:
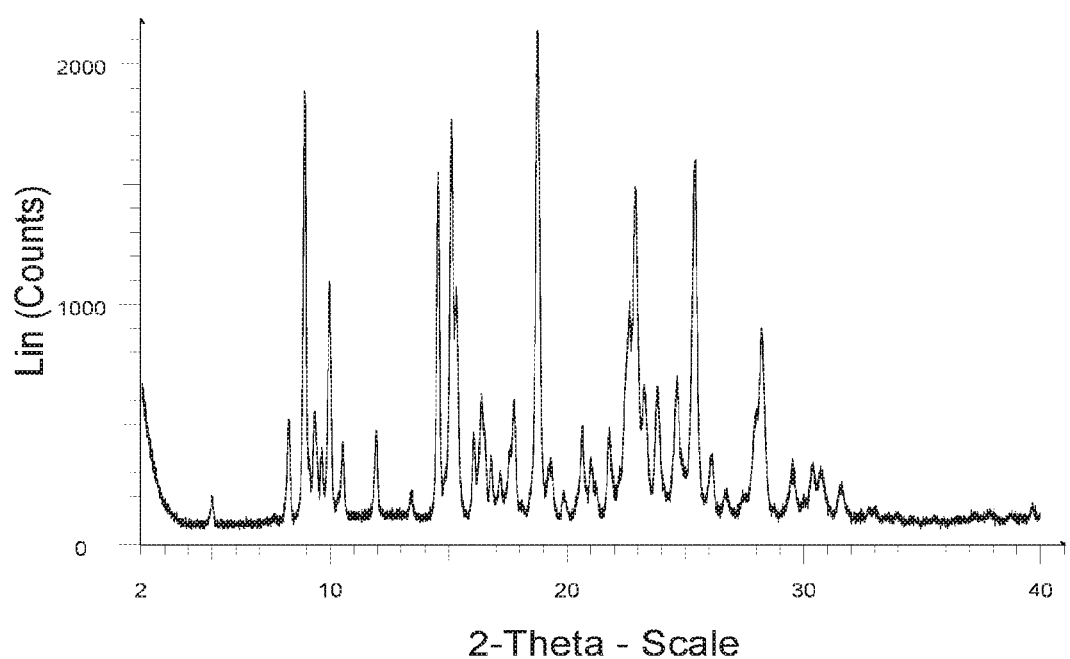

Polymorphic Form F of Compound X is characterised in providing an X-ray powder diffraction pattern, substantially as shown in FIG. 13.

Ten X-Ray powder diffraction peaks for this polymorphic form [Angle 2-theta (2θ), Intensity (%)] are: 18.7 (100%), 8.9 (87.7%), 15.1 (80.3%), 25.4 (74.6%), 14.5 (72.3%), 22.9 (69.6%), 9.9 (51.1%), 28.2 (42.0%), 8.2 (24.2%) and 11.9 (22.3%).

According to the present invention there is provided the polymorphic Form F of Compound X, which has an X-ray powder diffraction pattern with at least one specific peak at about 2-theta=18.7°.

According to the present invention there is provided the polymorphic Form F of Compound X, which has an X-ray powder diffraction pattern with at least one specific peak at about 2-theta=8.9°.

According to the present invention there is provided the polymorphic Form F of Compound X, which has an X-ray powder diffraction pattern with at least two specific peaks at about 2-theta=18.70 and 8.9°.

According to the present invention there is provided the polymorphic Form F of Compound X, which has an X-ray powder diffraction pattern with specific peaks at about 2-theta=18.7, 8.9, 15.1, 25.4, 14.5, 22.9, 9.9, 28.2, 8.2 and 11.9°.

According to the present invention there is provided polymorphic Form F of Compound X which has an X-ray powder diffraction pattern substantially the same as the X-ray powder diffraction pattern shown in FIG. 13.

According to the present invention there is provided polymorphic Form F of Compound X, which has an X-ray powder diffraction pattern with at least one specific peak at 2-theta=18.7° plus or minus 0.2° 2-theta.

According to the present invention there is provided the polymorphic Form F of Compound X, which has an X-ray powder diffraction pattern with at least one specific peak at 2-theta=8.9° plus or minus 0.2° 2-theta.

According to the present invention there is provided the polymorphic Form F of Compound X, which has an X-ray powder diffraction pattern with at least two specific peaks at 2-theta=18.70 and 8.90 wherein said values may be plus or minus 0.2° 2-theta.

According to the present invention there is provided the polymorphic Form F of Compound X, which has an X-ray powder diffraction pattern with specific peaks at 2-theta=18.7, 8.9, 15.1, 25.4, 14.5, 22.9, 9.9, 28.2, 8.2 and 11.90 wherein said values may be plus or minus 0.2° 2-theta.

Polymorphic Form K of Compound X

In a further aspect of the invention there is provided polymorphic Form K of Compound X. This polymorphic form may be characterised in that it provides at least one of the following 2θ values measured using CuKa radiation: 8.4 and 9.7.

Figure 16:
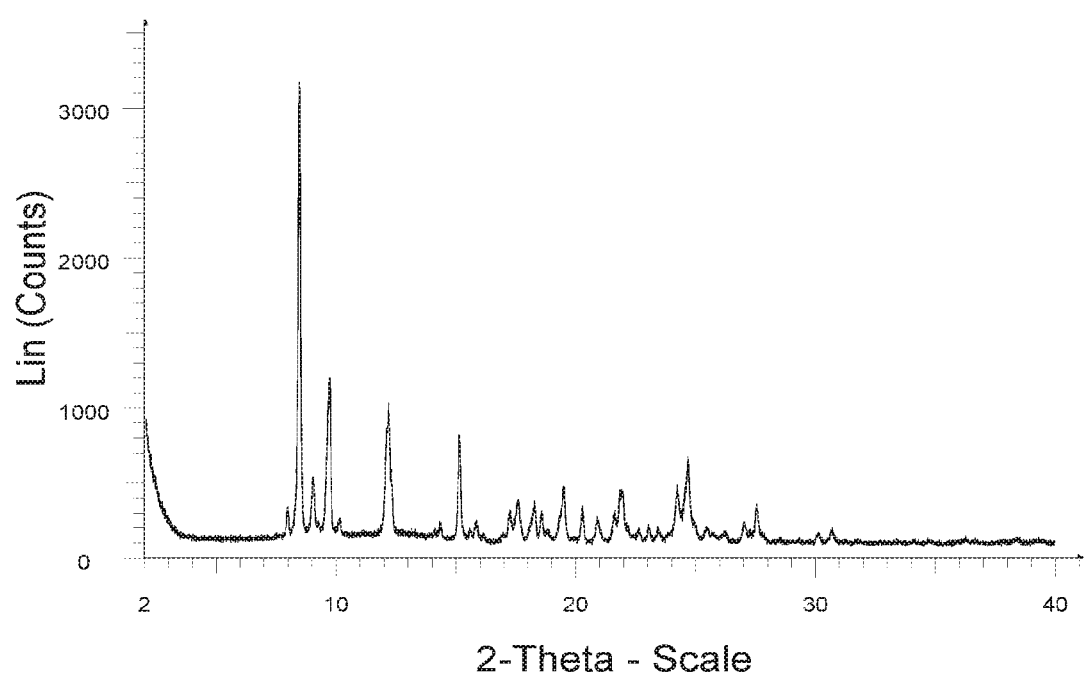

Polymorphic Form F of Compound X is characterised in providing an X-ray powder diffraction pattern, substantially as shown in FIG. 16.

Ten X-Ray powder diffraction peaks for this polymorphic form [Angle 2-theta (2θ), Intensity (%)] are: 8.4 (100%), 9.7 (37.7%), 12.2 (32.4%), 15.1 (25.2%), 24.7 (20.7%), 9.0 (16.8%), 21.9 (13.9%), 19.5 (13.9%), 24.2 (13.8%) and 18.3 (11.8%).

According to the present invention there is provided the polymorphic Form K of Compound X, which has an X-ray powder diffraction pattern with at least one specific peak at about 2-theta=8.4°.

According to the present invention there is provided the polymorphic Form K of Compound X, which has an X-ray powder diffraction pattern with at least one specific peak at about 2-theta=9.70°.

According to the present invention there is provided the polymorphic Form K of Compound X, which has an X-ray powder diffraction pattern with at least two specific peaks at about 2-theta=8.40 and 9.7°.

According to the present invention there is provided the polymorphic Form K of Compound X, which has an X-ray powder diffraction pattern with specific peaks at about 2-theta=8.4, 9.7, 12.2, 15.1, 24.7, 9.0, 21.9, 19.5, 24.2 and 18.30.

According to the present invention there is provided the polymorphic Form K of Compound X which has an X-ray powder diffraction pattern substantially the same as the X-ray powder diffraction pattern shown in FIG. 16.

According to the present invention there is provided the polymorphic Form K of Compound X, which has an X-ray powder diffraction pattern with at least one specific peak at 2-theta=8.4° plus or minus 0.2° 2-theta.

According to the present invention there is provided the polymorphic Form K of Compound X, which has an X-ray powder diffraction pattern with at least one specific peak at 2-theta=9.7° plus or minus 0.2° 2-theta.

According to the present invention there is provided the polymorphic Form K of Compound X, which has an X-ray powder diffraction pattern with at least two specific peaks at 2-theta=8.4° and 9.7° wherein said values may be plus or minus 0.2° 2-theta.

According to the present invention there is provided the polymorphic Form K of Compound X, which has an X-ray powder diffraction pattern with specific peaks at 2-theta=8.4, 9.7, 12.2, 15.1, 24.7, 9.0, 21.9, 19.5, 24.2 and 18.3° wherein said values may be plus or minus 0.2° 2-theta.

In this specification the mesylate salt of N-(2-{2-dimethylaminoethyl-methylamino}-4-methoxy-5-{[4-(1-methylindol-3-yl)pyrimidin-2-yl]amino}phenyl)prop-2-enamide is referred to as "Mesylate Salt Y".

Polymorphic Form A of Mesylate Salt Y

In a further aspect of the invention there is provided polymorphic Form A of Mesylate Salt Y. This polymorphic form may be characterised in that it provides at least one of the following 2θ values measured using CuKa radiation: 5.6 and 6.5.

Figure 18:
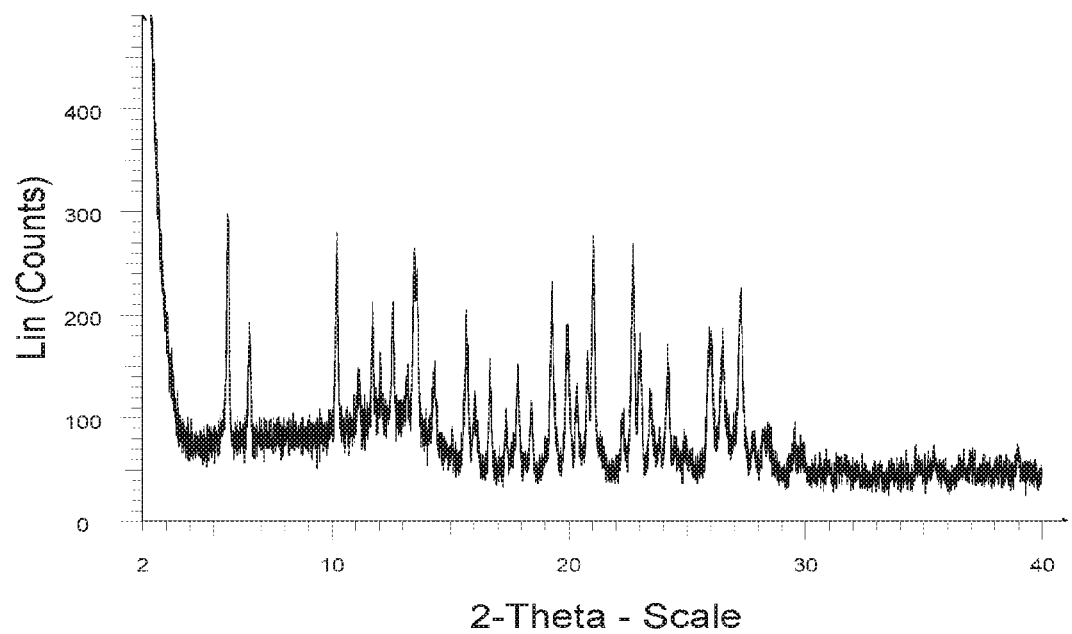

Polymorphic Form A of Mesylate Salt Y is characterised in providing an X-ray powder diffraction pattern, substantially as shown in FIG. 18.

Ten X-Ray powder diffraction peaks for this polymorphic form [Angle 2-theta (2θ), Intensity (%)] are: 5.6 (100%), 6.5 (66.7%), 10.2 (97.2%), 21.0 (96.2%), 13.5 (91.7%), 22.7 (89.6%), 19.3 (80.6%), 27.3 (75.7%), 15.7 (71.2%) and 19.9 (66.7%).

According to the present invention there is provided the polymorphic Form A of Mesylate Salt Y, which has an X-ray powder diffraction pattern with at least one specific peak at about 2-theta=5.60°.

According to the present invention there is provided the polymorphic Form A of Mesylate Salt Y, which has an X-ray powder diffraction pattern with at least one specific peak at about 2-theta=6.50°.

According to the present invention there is provided the polymorphic Form A of Mesylate Salt Y, which has an X-ray powder diffraction pattern with at least two specific peaks at about 2-theta=5.60 and 6.50°.

According to the present invention there is provided the polymorphic Form A of Mesylate Salt Y, which has an X-ray powder diffraction pattern with specific peaks at about 2-theta=5.6, 6.5, 10.2, 21.0, 13.5, 22.7, 19.3, 27.3, 15.7 and 19.9°.

According to the present invention there is provided polymorphic Form A of Mesylate Salt Y which has an X-ray powder diffraction pattern substantially the same as the X-ray powder diffraction pattern shown in FIG. 18.

According to the present invention there is provided polymorphic Form A of Mesylate Salt Y, which has an X-ray powder diffraction pattern with at least one specific peak at 2-theta=5.6° plus or minus 0.2° 2-theta.

According to the present invention there is provided the polymorphic Form A of Mesylate Salt Y, which has an X-ray powder diffraction pattern with at least one specific peak at 2-theta=6.5° plus or minus 0.2° 2-theta.

According to the present invention there is provided the polymorphic Form A of Mesylate Salt Y, which has an X-ray powder diffraction pattern with at least two specific peaks at 2-theta=5.6° and 6.5° wherein said values may be plus or minus 0.2° 2-theta.

According to the present invention there is provided the polymorphic Form A of Mesylate Salt Y, which has an X-ray powder diffraction pattern with specific peaks at 2-theta=5.6, 6.5, 10.2, 21.0, 13.5, 22.7, 19.3, 27.3, 15.7 and 19.9° wherein said values may be plus or minus 0.2° 2-theta.

Polymorphic Form B of Mesylate Salt Y

In a further aspect of the invention there is provided polymorphic Form B of Mesylate Salt Y. This polymorphic form may be characterised in that it provides at least one of the following 2θ values measured using CuKa radiation: 7.2 and 8.6.

Figure 20:
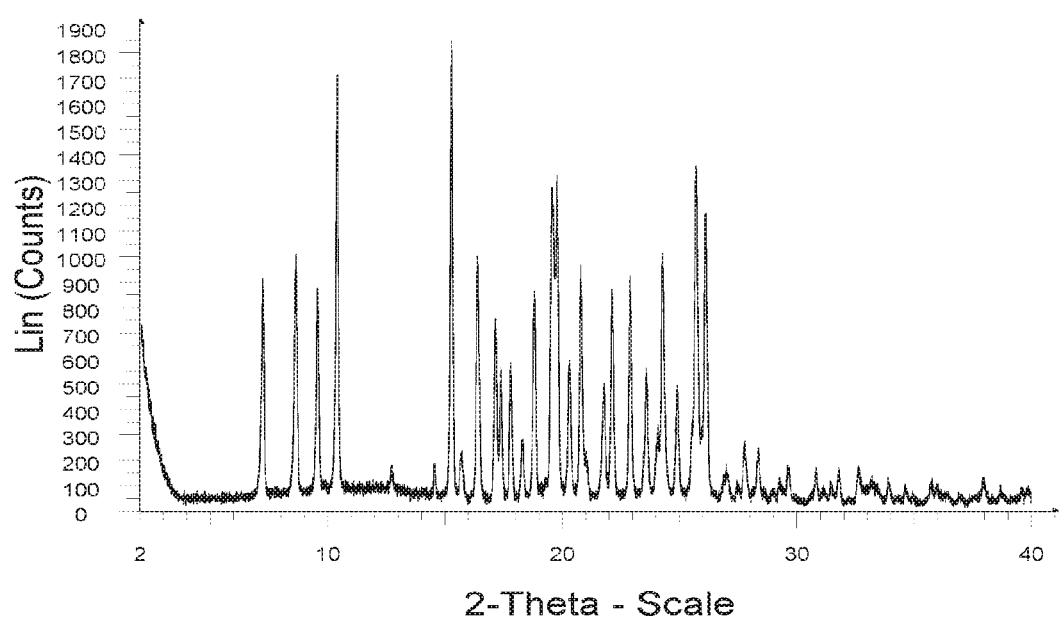

Polymorphic Form A of Mesylate Salt Y is characterised in providing an X-ray powder diffraction pattern, substantially as shown in FIG. 20.

Ten X-Ray powder diffraction peaks for this polymorphic form [Angle 2-theta (2θ), Intensity (%)] are: 7.2 (50.2%), 8.6 (55.2%), 15.3 (100%), 10.4 (92.6%), 25.7 (74.0%), 26.1 (63.9%), 16.4 (55.2%), 9.5 (47.5%), 22.1 (46.9%) and 18.8 (47.7%).

According to the present invention there is provided the polymorphic Form B of Mesylate Salt Y, which has an X-ray powder diffraction pattern with at least one specific peak at about 2-theta=7.2°.

According to the present invention there is provided the polymorphic Form B of Mesylate Salt Y, which has an X-ray powder diffraction pattern with at least one specific peak at about 2-theta=8.6°.

According to the present invention there is provided the polymorphic Form B of Mesylate Salt Y, which has an X-ray powder diffraction pattern with at least two specific peaks at about 2-theta=7.2° and 8.6°.

According to the present invention there is provided the polymorphic Form B of Mesylate Salt Y, which has an X-ray powder diffraction pattern with specific peaks at about 2-theta=7.2, 8.6, 15.3, 10.4, 25.7, 26.1, 16.4, 9.5, 22.1 and 18.80.

According to the present invention there is provided polymorphic Form B of Mesylate Salt Y which has an X-ray powder diffraction pattern substantially the same as the X-ray powder diffraction pattern shown in FIG. 20.

According to the present invention there is provided the polymorphic Form B of Mesylate Salt Y, which has an X-ray powder diffraction pattern with at least one specific peak at 2-theta=7.2° plus or minus 0.2° 2-theta.

According to the present invention there is provided the polymorphic Form B of Mesylate Salt Y, which has an X-ray powder diffraction pattern with at least one specific peak at 2-theta=8.6° plus or minus 0.2° 2-theta.

According to the present invention there is provided the polymorphic Form B of Mesylate Salt Y, which has an X-ray powder diffraction pattern with at least two specific peaks at 2-theta=7.2° and 8.6° wherein said values may be plus or minus 0.2° 2-theta.

According to the present invention there is provided the polymorphic Form B of Mesylate Salt Y, which has an X-ray powder diffraction pattern with specific peaks at 2-theta=7.2, 8.6, 15.3, 10.4, 25.7, 26.1, 16.4, 9.5, 22.1 and 18.8° wherein said values may be plus or minus 0.2° 2-theta.

LIST OF FIGURES

All figures relate to solid forms of the compound: N-(2-{2-dimethylaminoethyl-methylamino}-4-methoxy-5-{[4-(1-methylindol-3-yl)pyrimidin-2-yl]amino}phenyl)prop-2-enamide ("Compound X") or its mesylate salt where indicated ("Mesylate Salt Y").

FIG. 1: X-Ray Powder Diffraction Pattern—Form A
FIG. 2: DSC Thermogram—Form A
FIG. 3: X-Ray Powder Diffraction Pattern—Form B
FIG. 4: DSC Thermogram—Form B
FIG. 5: X-Ray Powder Diffraction Pattern—Form C
FIG. 6: DSC Thermogram—Form C
FIG. 7: X-Ray Powder Diffraction Pattern—Form D (Monohydrate)
FIG. 8: DSC Thermogram—Form D Monohydrate
FIG. 9: TGA Thermogram—Form D Monohydrate
FIG. 10: X-Ray Powder Diffraction Pattern—Form E (Hydrated Form)
FIG. 11: DSC Thermogram—Form E (Hydrated Form)
FIG. 12: TGA Thermogram—Form E (Hydrated form)
FIG. 13: X-Ray Powder Diffraction—Form F (Hydrated Form)
FIG. 14: DSC Thermogram—Form F (Hydrated Form)
FIG. 15: TGA Thermogram—Form F (Hydrated form)
FIG. 16: X-Ray Powder Diffraction Pattern—Form K
FIG. 17: DSC Thermogram—Form K
FIG. 18: X-Ray Powder Diffraction Pattern—Mesylate salt Form A
FIG. 19: DSC Thermogram—Mesylate salt Form A
FIG. 20: X-Ray Powder Diffraction Pattern—Mesylate salt Form B
FIG. 21: DSC Thermogram—Mesylate salt Form B

CHEMICAL SYNTHESIS AND BIOLOGICAL ASSAY PROCEDURES

The following abbreviations may be used: Abbreviations: THF=tetrahydrofuran; DIPEA=diisopropylethylamine; sat.=saturated aqueous solution; FCC=flash column chroatography using silica; TFA=trifluoroacetic acid; r.t.=room temperature; DMF=N,N-dimethylformamide; DMSO=dimethylsulfoxide; DMA=N,N-dimethylacetamide; EtOAc=ethyl acetate; h.=hour(s); Proton NMR: ($^1$H NMR) was determined using deuterated dimethylsulfoxide at 400 or 500 MHz at around 20-30° C., unless otherwise stated. Standard NMR abbreviations are used, (s=singlet; d=doublet; dd=double of doublets; t=triplet; q=quartet; p=pentet; m=multiplet; br=broad; etc.). Where iron was mentioned as a reagent, it was iron powder, 325 mesh and hydrogen reduced. Quoted assay values (μM) for a given Example are IC$_{50}$ values. X-Ray Powder Diffraction (XRPD) was carried out using a Bruker D4 instrument. The X-ray powder diffractogram was determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms (CuKa radiation). The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+ software. Differential Scanning Calorimetry (DSC) was carried out using a "TA Instruments Q1000 differential scanning calorimeter. Typically less than 5 mg of material contained in a standard aluminium pan fitted with a lid was heated over the temperature range 25° C. to 300° C. at a constant heating rate of 10° C. per minute. A purge gas using nitrogen was used—flow rate 50 mL per minute. Any crystal form that provides a XRPD diffractogram or DSC thermogram substantially identical to those disclosed herein fall within the scope of the present inventions. One skilled in the art will have the ability to determine substantial identities of diffractograms and thermograms.

Assay 1: Exon19 Deletion EGFR (Activating Single Mutant) Cellular Phosphorylation Assay The human lung cell line PC9 (Exon 19 deletion EGFR) were obtained from the American type Culture Collection. PC9 were maintained in RPMI 1640, containing 10% fetal calf serum and 2 mM glutamine. Cells were grown in a humidified incubator at 37° C. with 5% $CO_2$. Assays to measure cellular phosphorylation of endogenous p-EGFR in cell lysates were carried out according to the protocol described in the R&D Systems DuoSet IC Human Phospho-EGF R ELISA (R&D Systems catalogue number #DYC1095). 40 μL of cells were seeded (10000 cells/well) in growth medium in Corning black, clear-bottomed 384-well plates and incubated at 37° C. with 5% $CO_2$ overnight. Cells were acoustically dosed using an Echo 555, with compounds serially diluted in 100% DMSO. Plates were incubated for a further 2 h, then following aspiration of medium, 40 μL 1× lysis buffer was added to each well. Greiner black high bind 384-well plates were coated with capture antibody and then blocked with 3% BSA. Following removal of block, 15 μL of lysate were transferred to the Greiner black high bind 384-well plates and incubated for 2 hours. Following aspiration and washing of the plates with PBS, 20 μL of detection antibody were added and incubated for 2 hours. Following aspiration and washing of the plates with PBS, 20 μL of QuantaBlu fluorogenic peroxidase substrate (Thermo Fisher Scientific catalogue number 15169) were added and incubated for 1 hour. 20 μL QuantaBlu stop solution were added to plates and fluorescence read on an Envision plate reader using Excitation 352 nm wavelength and emission 460 nm wavelength. The data obtained with each compound was exported into a suitable software package (such as Origin) to perform curve fitting analysis. From this data an IC$_{50}$ value was determined by calculation of the concentration of compound that is required to give a 50% effect.

Assay 2: L858R/T790M EGFR (Double Mutant) Cellular Phosphorylation Assay

The human lung cell lines NCI-H1975 were obtained from the American type Culture Collection. NCI-H1975 were maintained in RPMI 1640, containing 10% fetal calf serum and 2 mM glutamine. Cells were grown in a humidified incubator at 37° C. with 5% $CO_2$. Assays to measure cellular phosphorylation of endogenous p-EGFR in cell lysates were carried out according to the protocol described in the R&D Systems DuoSet IC Human Phospho-EGF R ELISA (R&D Systems catalogue number #DYC1095).

40 μL of cells were seeded (10000 cells/well) in growth medium in Corning black, clear-bottomed 384-well plates and incubated at 37° C. with 5% $CO_2$ overnight. Cells were acoustically dosed using an Echo 555, with compounds serially diluted in 100% DMSO. Plates were incubated for a further 2 h and following aspiration of medium, 40 μL 1× lysis buffer was added to each well. Greiner black high bind 384-well plates were coated with capture antibody and then blocked with 3% BSA. Following removal of block, 15 μL of lysate were transferred to the Greiner black high bind 384-well plates and incubated for 2 hours. Following aspiration and washing of the plates with PBS, 20 μL of detection antibody were added and incubated for 2 hours. Following aspiration and washing of the plates with PBS, 20 μL of QuantaBlu fluorogenic peroxidase substrate (Thermo Fisher Scientific catalogue number 15169) were added and incubated for 1 hour. 20 μL QuantaBlu stop solution were added to plates and fluorescence read on an Envision plate reader using Excitation 352 nm wavelength and emission 460 nm wavelength. The data obtained with each compound was exported into a suitable software package (such as Origin) to perform curve fitting analysis. From this data an IC$_{50}$ value was determined by calculation of the concentration of compound that is required to give a 50% effect.

Assay 3: Wild-Type EGFR Cellular Phosphorylation Assay

The human colon cell line LoVo were obtained from the American type Culture Collection. LoVo were maintained in RPMI 1640, containing 3% stripped fetal calf serum and 2 mM glutamine. Cells were grown in a humidified incubator at 37° C. with 5% $CO_2$.

Assays to measure cellular phosphorylation of endogenous p-EGFR in cell lysates were carried out according to the protocol described in the R&D Systems DuoSet IC Human Phospho-EGF R ELISA (R&D Systems catalogue number #DYC1095).

40 μL of cells were seeded (15000 cells/well) in growth medium in Corning black, clear-bottomed 384-well plates and incubated at 37° C. with 5% $CO_2$ overnight. Cells were acoustically dosed using an Echo 555, with compounds serially diluted in 100% DMSO. Plates were incubated for a further 2 h then stimulated with 100 ng/ml for 10 minutes and following aspiration of medium, 40 μL 1× lysis buffer was added to each well. Greiner black high bind 384-well plates were coated with capture antibody and then blocked with 3% BSA. Following removal of block, 15 μL of lysate were transferred to the Greiner black high bind 384-well plates and incubated for 2 hours. Following aspiration and washing of the plates with PBS, 20 μL of detection antibody were added and incubated for 2 hours. Following aspiration and washing of the plates with PBS, 20 μL of QuantaBlu fluorogenic peroxidase substrate (Thermo Fisher Scientific catalogue number 15169) were added and incubated for 1 hour. 20 μL QuantaBlu stop solution were added to plates and fluorescence read on an Envision plate reader using Excitation 352 nm wavelength and emission 460 nm wavelength. The data obtained with each compound was exported into a suitable software package (such as Origin) to perform curve fitting analysis. From this data an $IC_{50}$ value was determined by calculation of the concentration of compound that is required to give a 50% effect.

The assay data (μM) for the Examples of this application are shown in the table below. While assay data is stated with a certain number of significant figures, this should not be taken as a representation that the data has been determined to be accurate to that number of significant figures.

| Ex. No. | Assay 1 | Assay 2 | Assay 3 |
|---|---|---|---|
| 1 | 0.007614 | 0.004956 | 0.4744 |
| 2 | 0.001291 | 0.001504 | 0.04122 |
| 3 | 0.01054 | 0.01549 | 0.5222 |
| 4 | 0.01273 | 0.0016 | 0.5099 |
| 5 | 0.02059 | 0.003402 | 0.8225 |
| 6 | 0.002183 | 0.0006695 | 0.1959 |
| 7 | 0.003262 | 0.0006825 | 0.1606 |
| 8 | 0.02239 | 0.005481 | 1.17 |
| 9 | 0.009959 | 0.002818 | 0.8744 |
| 10 | 0.07377 | 0.03998 | 8.427 |
| 11 | 0.02854 | 0.01871 | 1.599 |
| 12 | 0.03613 | 0.005821 | 1.393 |
| 13 | 0.1388 | 0.01926 | 11.91 |
| 14 | 0.05328 | 0.01912 | 12.48 |
| 15 | 0.01399 | 0.05524 | 1.067 |
| 16 | 0.1437 | 0.07052 | >18.92 |
| 17 | 0.02344 | 0.005644 | 0.772 |
| 18 | 0.06644 | 0.03138 | 2.696 |
| 19 | 0.002149 | 0.001463 | 0.07081 |
| 20 | 0.007487 | 0.005276 | 0.1929 |
| 21 | 0.002948 | 0.002339 | 0.1283 |
| 22 | 0.002137 | 0.001524 | 0.07336 |
| 23 | 0.01694 | 0.01759 | 3.018 |
| 24 | 0.001327 | 0.0008856 | 0.03567 |
| 25 | 0.0005811 | 0.000238 | 0.01092 |
| 26 | 0.002289 | 0.001925 | 0.05831 |
| 27 | 0.00561 | 0.01142 | 0.3177 |
| 28 | 0.01292 | 0.01144 | 0.4938 |
| 28A | 0.01975 | 0.01271 | 1.443 |
| 29 | 0.001228 | 0.0008846 | 0.04652 |
| 30 | 0.07375 | 0.05211 | 1.613 |
| 31 | 0.03746 | 0.00734 | 2.506 |
| 32 | 0.138 | 0.02378 | 10.53 |
| 33 | 0.8916 | 1.158 | 11.86 |
| 34 | 0.009044 | 0.003767 | 0.1526 |
| 35 | 0.008571 | 0.006772 | 0.2623 |
| 36 | 0.04329 | 0.03272 | 1.051 |
| 37 | 0.002112 | 0.001814 | 0.04859 |
| 38 | 0.005092 | 0.004405 | 0.5384 |
| 39 | 0.002336 | 0.001005 | 0.2484 |
| 40 | 0.0124 | 0.01477 | >30 |
| 41 | 0.02863 | 0.0295 | 1.841 |
| 42 | 0.005192 | 0.005161 | 0.4542 |
| 43 | 0.01817 | 0.01055 | 1.34 |
| 44 | 0.03329 | 0.0256 | 3.64 |
| 45 | 0.1102 | 0.041 | 7.396 |
| 46 | 0.1289 | 0.09293 | 7.091 |
| 47 | 0.1939 | 0.1192 | 15.45 |
| 48 | 0.03988 | 0.03098 | 1.579 |
| 49 | 0.0742 | 0.05097 | 3.093 |
| 50 | 0.1145 | 0.1297 | 7.626 |
| 51 | 0.01296 | 0.007713 | 0.4622 |
| 52 | 0.02603 | 0.01501 | 1.4 |
| 53 | 0.03537 | 0.02824 | 2.638 |
| 54 | 0.003217 | 0.002803 | 0.1832 |
| 55 | 0.006433 | 0.002863 | 0.5066 |
| 56 | 0.04433 | 0.02922 | 3.504 |
| 57 | 0.006455 | 0.01452 | 0.08931 |
| 58 | 0.007085 | 0.01683 | 0.1786 |
| 59 | 0.002266 | 0.003021 | 0.02816 |
| 60 | 0.0146 | 0.04886 | 0.6241 |

Example 1: N-{4-Methoxy-2-[1-methyl-3,6-dihydro-2H-pyridin-4-yl]-5-[(5-methyl-4-pyrazolo[1,5-a]pyridin-3-ylpyrimidin-2-yl)amino]phenyl}prop-2-enamide Acryloyl chloride (0.331 mL, 1M in THF, 0.33 mmol) was added dropwise to a solution of 6-methoxy-4-(1-methyl-1,2,3,6-tetrahydropyridin-4-yl)-N1-[5-methyl-4-(pyrazolo[1,5-a]-pyridin-3-yl)pyrimidin-2-yl]benzene-1,3-diamine (Intermediate 1, 146 mg, 0.33 mmol) and DIPEA (0.086 mL, 0.50 mmol) in THF (4 mL) at −10° C. over a period of 1 minute under $N_2$. The resulting mixture was stirred at 0° C. for 15 minutes and then concentrated in vacuo. The residue was dissolved in $CH_2Cl_2$ (5 mL) plus a little $CH_3OH$. This solution was then washed with sat. $NaHCO_3$ (2 mL), dried ($MgSO_4$) and then concentrated in vacuo. Purification by FCC, eluting with 5-25% $CH_3OH$ in $CH_2Cl_2$ and concentration of appropriate fractions in vacuo provided material that was dissolved in $CH_2Cl_2$:7N methanolic ammonia 100:8 (1 mL) and filtered through a 1g silica plug. Concentration of the resulting solution provided the title compound (70 mg, 38%) as a pale orange foam; $^1$H NMR: 2.27 (3H, s), 2.37 (2H, m), 2.42 (3H, s), 2.53-2.57 (2H, m), 2.97 (2H, m), 3.87 (3H, d), 5.66 (2H, d), 6.14 (1H, d), 6.39 (1H, d), 6.86 (1H, s), 7.07 (1H, t), 7.42 (1H, m), 7.98 (1H, s), 8.17 (1H, s), 8.32 (1H, s), 8.48 (1H, d), 8.58 (1H, s), 8.81 (1H, d), 9.29 (1H, s); m/z: $ES^+$ $MH^+$ 496.

Example 2: N-(5-{[5-Chloro-4-(1H-indol-3-yl)pyrimidin-2-yl]amino}-4-methoxy-2-[1-methyl-3,6-dihydro-2H-pyridin-4-yl]phenyl)prop-2-enamide Acryloyl chloride (0.217 mL, 1M in THF, 0.22 mmol) was added dropwise to a slurry of N'-[5-chloro-4-(1H-indol-3-yl)pyrimidin-2-yl]-4-methoxy-6-(1-methyl-3,6-dihydro-2H-pyridin-4-yl)benzene-1,3-diamine (Intermediate 7, 100 mg, 0.22 mmol) and DIPEA (0.057 mL, 0.33 mmol) in THF (3 mL) at −5° C. over a period of 1 minute under $N_2$. The resulting mixture was stirred at 0° C. for 15 minutes and then concentrated in vacuo. The residue was dissolved in $CH_2Cl_2$ (5 mL) plus a few drops of $CH_3OH$, and washed with sat. $NaHCO_3$ (2 mL). The organic solution was then dried ($MgSO_4$) and loaded onto silica in vacuo. Purification by FCC, eluting with 5-25% $CH_3OH$ in $CH_2Cl_2$ and concentration of appropriate fractions in vacuo provided a residue that was washed with $CH_3OH$ (0.3 mL) and dried in air to give the title compound (37 mg, 31%) as a beige crystalline solid. $^1$H NMR: 2.28 (3H, s), 2.38 (2H, m), 2.55 (2H, m), 2.98 (2H, d), 3.85 (3H, s), 5.6-5.72 (2H, m), 6.15 (1H, m), 6.41 (1H, m), 6.88 (1H, s), 7.10 (1H, t), 7.18 (1H, t), 7.47 (1H, d), 7.98 (1H, s), 8.33 (1H, s), 8.36 (1H, d), 8.42 (1H, s), 8.49 (1H, s), 9.29 (1H, s), 11.86 (1H, s); m/z: $ES^+$ $MH^+$ 515.

Example 3: N-(5-{[4-(1H-Indol-3-yl)-5-methylpyrimidin-2-yl]amino}-4-methoxy-2-[4-methylpiperazin-1-yl]phenyl)prop-2-enamide Acryloyl chloride (0.025 mL, 0.30 mmol) was added dropwise to N'-[4-(1H-indol-3-yl)-5-methylpyrimidin-2-yl]-4-methoxy-6-(4-methylpiperazin-1-yl)benzene-1,3-diamine (Intermediate 12, 135 mg, 0.30 mmol) and DIPEA (0.090 mL, 0.33 mmol) in $CH_2Cl_2$ (10 mL) and DMF (2 mL) at 0° C. under $N_2$. The resulting suspension was stirred at 0° C. for 2 h. then allowed to warm to r.t. The mixture was then diluted with water (15 mL) and extracted with $CH_2Cl_2$ (40 mL). The resulting organic solution was washed with sat.

Na$_2$CO$_3$ (20 mL) and then sat. brine (20 mL). The solution was then dried (MgSO$_4$) and concentrated in vacuo. Purification by FCC, eluting with 1-5% 7M methanolic ammonia in CH$_2$Cl$_2$ gave crude product. Further purification by preparative HPLC (Waters SunFire column, 5µ silica, 19 mm diameter, 100 mm length), eluting with decreasingly polar mixtures of water (containing 0.1% formic acid) and CH$_3$CN, followed by HPLC (Waters XBridge Prep C18 OBD column, 5µ silica, 19 mm diameter, 100 mm length), eluting with decreasingly polar mixtures of water (containing 1% NH$_3$) and CH$_3$CN, gave the title compound (23 mg, 15%) as a white solid; $^1$H NMR: 2.26 (3H, s), 2.37 (3H, s), 2.48-2.57 (4H, m), 2.87 (4H, t), 3.84 (3H, s), 5.70 (1H, d), 6.18 (1H, dd), 6.59 (1H, dd), 6.87 (1H, s), 7.05 (1H, dd), 7.15 (1H, t), 7.44 (1H, d), 7.83 (1H, s), 7.98 (1H, d), 8.22 (1H, s), 8.34 (1H, d), 8.49 (1H, s), 8.97 (1H, s), 11.68 (1H, s); m/z: ES$^+$ MH$^+$ 498.60.

Example 4: N-{5-1(5-Chloro-4-pyrazolo[1,5-a]pyridin-3-ylpyrimidin-2-yl)amino}-2-[(3R)-3-dimethylaminopyrrolidin-1-yl]-4-methoxyphenyl prop-2-enamide A solution of acryloyl chloride (0.042 mL, 0.51 mmol) in CH$_2$Cl$_2$ (1 mL) was added dropwise to a mixture of N-(5-chloro-4-pyrazolo[1,5-a]pyridin-3-ylpyrimidin-2-yl)-4-[(3R)-3-dimethylamino-pyrrolidin-1-yl]-6-methoxybenzene-1,3-diamine (Intermediate 18, 245 mg, 0.51 mmol) and DIPEA (0.097 mL, 0.56 mmol) in CH$_2$Cl$_2$ (10 mL), which was cooled in an ice/water bath. The mixture was stirred for 2 h and then washed with brine, dried (Na$_2$SO$_4$) and concentrated in vacuo. Purification by FCC, eluting with 2% 7N methanolic ammonia in CH$_2$Cl$_2$ gave a foam after concentration in vacuo. This foam was triturated using CH$_2$Cl$_2$ and diethyl ether, and the resulting solid was collected by filtration and dried to give the title compound (157 mg, 58%) as a yellow solid; $^1$H NMR: 1.68-1.83 (1H, m), 2.05-2.16 (1H, m), 2.18 (6H, s), 2.64-2.76 (1H, m), 3.18-3.29 (3H, m), 3.36-3.47 (1H, m), 3.77 (3H, s), 5.67 (1H, dd), 6.16 (1H, dd), 6.48 (1H, dd), 6.54 (1H, s), 7.12 (1H, t), 7.37 (1H, t), 7.43 (1H, s), 8.28-8.46 (2H, m), 8.55 (1H, s), 8.83 (1H, d), 8.94 (1H, s), 9.37 (1H, s); m/z: ES$^+$ MH$^+$ 533.5.

Example 5: N-{5-[(5-Chloro-4-pyrazolo[1,5-a]pyridin-3-ylpyrimidin-2-yl)amino]-2-[3-dimethylaminoazetidin-1-yl]-4-methoxyphenyl}prop-2-enamide A solution of acryloyl chloride (0.038 mL, 0.47 mmol) in CH$_2$Cl$_2$ (1 mL) was added dropwise to a stirred solution of N-(5-chloro-4-pyrazolo[1,5-a]pyridin-3-ylpyrimidin-2-yl)-4-(3-dimethylamino-azetidin-1-yl)-6-methoxybenzene-1,3-diamine (Intermediate 24, 220 mg, 0.47 mmol) and DIPEA (0.090 mL, 0.52 mmol) in CH$_2$Cl$_2$ (5 mL), which was cooled in an ice/water bath. The mixture was stirred for 3 h and then washed with brine, dried (Na$_2$SO$_4$) and concentrated in vacuo. Purification by FCC, eluting with 0-5% 7N methanolic ammonia in CH$_2$Cl$_2$ gave the title compound (221 mg, 90%) as a yellow solid; $^1$H NMR: 2.09 (6H, s), 3.08 (1H, p), 3.55-3.62 (2H, m), 3.76 (3H, s), 3.97 (2H, t), 5.66 (1H, dd), 6.16 (1H, dd), 6.25 (1H, s), 6.45 (1H, dd), 7.10 (1H, dd), 7.35 (1H, s), 7.39 (1H, dd), 8.25-8.40 (1H, m), 8.35 (1H, s), 8.45 (1H, s), 8.81 (1H, d), 8.92 (1H, s), 9.24 (1H, s); m/z: ES$^+$ MH$^+$ 519.56.

Example 6: N-{5-[(5-Chloro-4-pyrazolo[1,5-a]pyridin-3-ylpyrimidin-2-yl)amino]-2-[2-dimethylaminoethyl-methylamino]-4-methoxyphenyl}prop-2-enamide Acryloyl chloride (1.248 mL, 1M in THF, 1.25 mmol) was added dropwise to N$^4$-[5-chloro-4-(pyrazolo[1,5-a]pyridin-3-yl)pyrimidin-2-yl]-N$^1$-[2-(dimethylamino)ethyl]-5-methoxy-N$^1$-methylbenzene-1,2,4-triamine (Intermediate 33, 530 mg, 1.13 mmol) and DIPEA (0.244 mL, 1.36 mmol) in THF (20 mL), which was cooled to 0° C. The mixture was stirred at 0° C. for 2 h. The mixture was then concentrated in vacuo. The resulting residue was dissolved in CH$_2$Cl$_2$ (100 mL), then washed sequentially with sat. NaHCO$_3$ (25 mL), water (25 mL), and sat. brine (25 mL). The organic solution was concentrated in vacuo. Purification by FCC, eluting with 0-20% 2M methanolic ammonia in CH$_2$Cl$_2$ and further purification by FCC, eluting with 0-20% CH$_3$OH in CH$_2$Cl$_2$ gave a brown gum. LCMS analysis indicated that impurities were still present. A further attempt at purification was made by FCC, eluting with 0-20% CH$_3$OH in CH$_2$Cl$_2$. Appropriate fractions were concentrated to provide a brown gum containing the title compound. Attempts to make this gum into a solid by trituration were unsuccessful. Lyophilisation from CH$_3$CN/water also failed but lyophilisation from CH$_3$OH/water gave a brown semi-solid. Trituration of the semi-solid with diethyl ether followed by evaporation of the ether gave the title compound (191 mg, 32%) as a pale yellow, free-flowing solid; $^1$H NMR: (CDCl$_3$) 2.28 (6H, s), 2.32 (2H, t), 2.71 (3H, s), 2.84-2.92 (2H, m), 3.87 (3H, s), 5.67 (1H, dd), 6.29 (1H, dd), 6.37 (1H, dd), 6.80 (1H, s), 6.89 (1H, td), 7.23-7.33 (1H, m), 7.46 (1H, s), 8.45 (1H, s), 8.52 (1H, d), 8.56 (1H, d), 8.94 (1H, s), 9.39 (1H, s), 10.09 (1H, s); m/z: ES$^+$ MH$^+$ 521.29.

Example 7: N-{2-[(3aR,6aR)-5-Methyl-2,3,3a,4,6,6a-hexahydropyrrolo[3,2-c]pyrrol-1-yl]-5-[(5-chloro-4-pyrazolo[1,5-a]pyridin-3-ylpyrimidin-2-yl)amino]-4-methoxyphenyl}prop-2-enamide Acryloyl chloride (1M in THF, 0.225 mL, 0.22 mmol) in CH$_2$Cl$_2$ (1 mL) was added dropwise to a mixture of 4-[(3aR,6aR)-5-methyl-2,3,3a,4,6,6a-hexahydropyrrolo[3,2-c]pyrrol-1-yl]-N-(5-chloro-4-pyrazolo[1,5-a]pyridin-3-ylpyrimidin-2-yl)-6-methoxybenzene-1,3-diamine (Intermediate 35, 105 mg, 0.21 mmol) and DIPEA (0.041 mL, 0.24 mmol) in CH$_2$Cl$_2$ (3 mL), which was cooled in an ice/water bath. The mixture was stirred for 0.5 h, washed with brine and then concentrated in vacuo. Purification by FCC, eluting with 0-2.5% 7N methanolic ammonia in CH$_2$Cl$_2$ gave the title compound (60 mg, 52%) as a pale yellow solid; $^1$H NMR: 1.77-1.81 (1H, m), 1.95-2.16 (5H, m), 2.24-2.35 (1H, m), 2.38-2.48 (1H, m), 2.86-2.90 (1H, m), 3.18-3.22 (1H, m), 3.37-3.45 (1H, m), 3.76 (3H, s), 4.33-4.37 (1H, m), 5.68 (1H, dd), 6.18 (1H, dd), 6.51 (1H, dd), 6.66 (1H, s), 7.10 (1H, dt), 7.33-7.41 (1H, m), 7.65 (1H, s), 8.3-8.4 (2H, m), 8.56 (1H, s), 8.81 (1H, d), 8.94 (1H, s), 9.38 (1H, s); m/z: ES$^+$, MH$^+$ 545.57.

Example 8: N-{5-[(5-Chloro-4-pyrazolo[1,5-a]pyridin-3-ylpyrimidin-2-yl)amino]-4-methoxy-2-[5-methyl-2,5-diazaspiro[3.4]octan-2-yl]phenyl}prop-2-enamide A solution of acryloyl chloride (5.71 mg, 0.06 mmol) in CH$_2$Cl$_2$ (1 mL) was added dropwise to a mixture of N'-(5-chloro-4-pyrazolo[1,5-a]pyridin-3-ylpyrimidin-2-yl)-4-methoxy-6-(5-methyl-2,5-diazaspiro[3.4]octan-2-yl)benzene-1,3-diamine (Intermediate 45, 31 mg, 0.06 mmol) in CH$_2$Cl$_2$ (5 mL), which was cooled in an ice/water bath. The mixture was stirred for 3 h and then washed with brine, dried (Na$_2$SO$_4$) and concentrated in vacuo. Purification by FCC, eluting with 0-2% 7N methanolic ammonia in CH$_2$Cl$_2$ gave the title compound (21 mg, 61%) as a yellow foam; $^1$H NMR: 1.70 (2H, dd), 1.98-2.11 (2H, m), 2.37 (3H, s), 2.62 (2H, t), 3.65 (2H, d), 3.76 (3H, s), 3.95 (2H, d), 5.67 (1H, d), 6.09-6.27 (2H, m), 6.43 (1H, dd), 7.10 (1H, t), 7.30 (1H, s), 7.34-7.45 (1H, m), 8.35 (2H, s), 8.44 (1H, s), 8.81 (1H, d), 8.92 (1H, s), 9.20 (1H, s); m/z: ES$^+$ MH$^+$ 545.5.

Example 9: N-{5-[(5-Chloro-4-pyrazolo[1,5-a]pyridin-3-ylpyrimidin-2-yl)amino]-4-methoxy-2-[1-methyl-3,6-dihydro-2H-pyridin-4-yl]phenyl}prop-2-enamide A solution of acryloyl chloride (0.026 mL, 0.32 mmol) in CH$_2$Cl$_2$ (1 mL) was added dropwise to a mixture of N'-(5-chloro-4-pyrazolo[1,5-a]pyrimidin-3-ylpyrimidin-2-yl)-4-methoxy-6-(1-methyl-3,6-dihydro-2H-pyridin-4-yl)benzene-1,3-diamine (Intermediate 55, 150 mg, 0.32 mmol) and DIPEA (0.062 mL, 0.36 mmol) in CH$_2$Cl$_2$ (5 mL), which was cooled in an ice/water bath. The mixture was stirred for 3 h and then washed with brine, dried (Na$_2$SO$_4$) and concentrated in vacuo. Purification by FCC, eluting with 2.5% 7N methanolic ammonia in CH$_2$Cl$_2$ gave the title compound (120 mg, 72%) as a yellow foam; $^1$H NMR: 2.28 (3H, s), 2.38 (2H, s), 2.54 (2H, t), 2.98 (2H, d), 3.81 (3H, s), 5.62-5.73 (2H, m), 6.14 (1H, dd), 6.43 (1H, dd), 6.88 (1H, s), 7.12 (1H, dt), 7.39-7.47 (1H, m), 7.83 (1H, s), 8.41-8.50 (2H, m), 8.63 (1H, s), 8.85 (1H, d), 8.95 (1H, s), 9.36 (1H, s); m/z: ES$^+$ MH$^+$ 516.25.

Example 10: N-{5-[(5-Chloro-4-pyrazolo[1,5-a]pyridin-3-ylpyrimidin-2-yl)amino]-2-[4-(2-dimethylamino-2-oxoethyl)piperazin-1-yl]-4-methoxyphenyl}prop-2-enamide A solution of acryloyl chloride (0.030 mL, 0.37 mmol) in CH$_2$Cl$_2$ (1 mL) was added dropwise to a stirred solution of 2-(4-{2-amino-4-[(5-chloro-4-pyrazolo[1,5-a]pyridin-3-ylpyrimidin-2-yl)amino]-5-methoxyphenyl}piperazin-1-yl)-N,N-dimethylacetamide (Intermediate 57, 0.19 g, 0.35 mmol) and DIPEA (0.067 mL, 0.39 mmol) in CH$_2$Cl$_2$ (5 mL). The mixture was stirred for 0.5 h, then diluted with CH$_2$Cl$_2$ (20 mL) and washed with sat. brine (2×25 mL). The organic solution was dried (MgSO$_4$), and concentrated in vacuo. Purification by FCC, eluting with 5% CH$_3$OH in CH$_2$Cl$_2$ gave the title compound (0.157 g, 75%) as a yellow solid; $^1$H NMR: (CDCl$_3$) 2.76 (4H, s), 2.90-2.96 (4H, m), 2.98 (3H, s), 3.12 (3H, s), 3.30 (2H, s), 3.87 (3H, s), 5.65-5.77 (1H, m), 6.18-6.37 (2H, m), 6.80 (1H, s), 6.90 (1H, t), 7.28 (1H, d), 7.42 (1H, s), 8.44 (1H, s), 8.46-8.59 (3H, m), 8.93 (1H, s), 9.33 (1H, s); m/z: ES$^+$ MH$^+$ 590.52.

Example 11: (S)—N-{2-[4-(2-Aminopropanoyl)piperazin-1-yl]-5-(5-chloro-4-pyrazolo[1,5-a]pyridin-3-ylpyrimidin-2-yl)amino]-4-methoxyphenyl}prop-2-enamide A solution of acryloyl chloride (10.2 µL, 0.13 mmol) in CH$_2$Cl$_2$ (3 mL) was added dropwise to a stirred solution of (S)-tert-butyl N-[1-(4-{2-amino-4-[(5-chloro-4-pyrazolo[1,5-a]pyridin-3-ylpyrimidin-2-yl)amino]-5-methoxyphenyl}piperazin-1-yl)-1-oxopropan-2-yl]carbamate (Intermediate 59, 65 mg) and DIPEA (0.75 mL) in CH$_2$Cl$_2$ (10 mL), which was cooled in an ice/water bath. The mixture was stirred for 0.75 h. then quenched with water (10 mL) and 2M Na$_2$CO$_3$ (5 mL). The phases were separated and the organic solution was dried (MgSO$_4$) and concentrated in vacuo. The resulting residue was dissolved in CH$_2$Cl$_2$ (3 mL) and was then treated with TFA (0.1 mL). After standing for 0.25 h a second portion of TFA (0.2 mL) was added. After a further 0.25 h the solution was concentrated in vacuo and purified by preparative HPLC (Waters SunFire column, 5µ silica, 19 mm diameter, 100 mm length), eluting with decreasingly polar mixtures of water (containing 0.1% formic acid) and CH$_3$CN. Fractions containing the desired compound were concentrated in vacuo to give the title compound (17 mg, 6% from 5-chloro-N-(4-fluoro-2-methoxy-5-nitrophenyl)-4-pyrazolo[1,5-a]pyridin-3-ylpyrimidin-2-amine) as a white solid; $^1$H NMR: 1.25 (3H, s), 2.83-2.96 (4H, m), 3.65-3.82 (7H, m), 4.14-4.23 (1H, m), 5.73 (1H, d), 61.9 (1H, d), 6.64-6.70 (1H, m), 6.69 (1H, s), 7.08-7.12 (1H, m) 7.30-7.37 (1H, m), 8.20-8.28 (2H, m), 8.35-8.41 (2H, m), 8.68 (1H, s), 8.80-8.84 (1H, m), 8.95 (1H, s), 9.11-9.15 (1H, m); m/z: ES$^+$ MH$^+$ 576.60.

Example 12: N-{5-[(5-Chloro-4-pyrazolo[1,5-a]pyridin-3-ylpyrimidin-2-yl)amino]-2-[(3S)-3-dimethylaminopyrrolidin-1-yl]-4-methoxyphenyl}prop-2-enamide A solution of acryloyl chloride (0.042 mL, 0.52 mmol) in CH$_2$Cl$_2$ (1 mL) was added dropwise to a mixture of (S)—N$^1$-[5-chloro-4-(pyrazolo[1,5-a]pyridin-3-yl)pyrimidin-2-yl]-4-[3-(dimethylamino)pyrrolidin-1-yl]-6-methoxybenzene-1,3-diamine (Intermediate 61, 250 mg, 0.52 mmol) and DIPEA (0.099 mL, 0.57 mmol) in CH$_2$Cl$_2$ (5 mL), which was cooled in an ice/water bath. The mixture was stirred for 3 h and then washed with brine, dried (Na$_2$SO$_4$) and concentrated in vacuo. Purification by FCC, eluting with 2% 7N methanolic ammonia in CH$_2$Cl$_2$ gave the title compound (194 mg, 70%) as a yellow solid; $^1$H NMR: 1.69-1.83 (1H, m), 2.05-2.16 (1H, m), 2.19 (6H, s), 2.65-2.78 (1H, m), 3.18-3.29 (3H, m), 3.35-3.46 (1H, m), 3.77 (3H, s), 5.67 (1H, dd), 6.16 (1H, dd), 6.48 (1H, dd), 6.54 (1H, s), 7.12 (1H, t), 7.37 (1H, t), 7.43 (1H, s), 8.3-8.46 (2H, m), 8.55 (1H, s), 8.83 (1H, d), 8.94 (1H, s), 9.37 (1H, s); m/z: ES$^+$ MH$^+$ 533.5.

Example 13: N-{5-[(5-Chloro-4-pyrazolo[1,5-a]pyridin-3-ylpyrimidin-2-yl)amino]-4-methoxy-2-[4-methylpiperazin-1-yl]phenyl}prop-2-enamide A solution of acryloyl chloride (0.092 mL, 1.14 mmol) in CH$_2$Cl$_2$ (1 mL) was added dropwise to a mixture of N'-(5-chloro-4-pyrazolo[1,5-a]pyridin-3-ylpyrimidin-2-yl)-4-methoxy-6-(4-methylpiperazin-1-yl)benzene-1,3-diamine (Intermediate 63, 480 mg, 1.03 mmol) and DIPEA (0.214 mL, 1.24 mmol) in CH$_2$Cl$_2$ (18 mL) at r.t. After 0.25 h, additional acrolyl chloride (15 mg in 0.15 mL CH$_2$Cl$_2$) was added. The mixture was stirred for 0.5 h and then washed with brine, dried (Na$_2$SO$_4$) and concentrated in vacuo. Purification by FCC, eluting with 2.5% 7N methanolic ammonia in CH$_2$Cl$_2$ gave the title compound (390 mg, 73%) as a yellow solid, after trituration with CH$_3$OH; $^1$H NMR: 2.27 (3H, s), 2.53-2.61 (4H, m), 2.84-2.97 (4H, m), 3.77 (3H, s), 5.70 (1H, d), 6.17 (1H, d), 6.61 (1H, dd), 6.89 (1H, s), 7.11 (1H, t), 7.3-7.42 (1H, m), 8.10 (1H, s), 8.26-8.47 (2H, m), 8.70 (1H, s), 8.83 (1H, d), 8.96 (1H, s), 9.02 (1H, s); m/z: ES$^+$ MH$^+$ 519.

Example 14: N-{5-[(5-Cyano-4-pyrazolo[1,5-a]pyridin-3-ylpyrimidin-2-yl)amino]-4-methoxy-2-[4-methylpiperazin-1-yl]phenyl}prop-2-enamide A solution of acryloyl chloride (0.017 mL, 0.21 mmol) in CH$_2$Cl$_2$ (0.6 mL) was added to a mixture of 2-{[5-amino- 2-methoxy-4-(4-methylpiperazin-1-yl)phenyl]amino}-4-pyrazolo[1,5-a]pyridin-3-ylpyrimidine-5-carbonitrile (Intermediate 65, 87 mg, 0.19 mmol) and DIPEA (0.063 mL, 0.38 mmol) in $CH_2Cl_2$ (1.5 mL) at 0° C. The mixture was then stirred at 0° C. for 4 h. (during this time a further 0.5 eq acryloyl chloride was added). The mixture was then diluted with $CH_2Cl_2$, washed twice with sat. $NaHCO_3$, then with water, and then dried ($MgSO_4$). Purification by FCC, eluting with 0-6% methanolic ammonia in $CH_2Cl_2$ gave the title compound (67 mg, 69%) as a yellow solid; $^1H$ NMR: (102° C.) 2.30 (3H, s), 2.56-2.59 (4H, m), 2.93-2.96 (4H, m), 3.78 (3H, s), 5.67-5.7 (1H, m), 6.16 (1H, d), 6.44-6.51 (1H, m), 6.95 (1H, s), 7.11 (1H, t), 7.35 (1H, t), 8.20 (1H, s), 8.32 (1H, d), 8.66 (1H, s), 8.72 (1H, br s), 8.76 (1H, d), 8.91 (1H, s), 8.96 (1H, br s); m/z: $ES^+$ $MH^+$ 510.5.

Example 15: N-(5-{[4-(1H-Indol-3-yl)pyrimidin-2-yl]amino}-4-methoxy-2-{4-methylpiperazin-1-yl}phenyl)prop-2-enamide To a stirred solution of N'-[4-(1H-indol-3-yl)pyrimidin-2-yl]-4-methoxy-6-(4-methylpiperazin-1-yl)benzene-1,3-diamine (Intermediate 66, 96 mg, 0.22 mmol) in $CH_2Cl_2$ (15 mL) at 2° C. was added DIPEA (0.039 mL, 0.22 mmol) and acryloyl chloride (0.018 mL, 0.22 mmol). The resulting solution was stirred at 2° C. for 0.25 h, then allowed to warm to r.t. and stirred for a further 3.5 h. The mixture was then diluted with $CH_3OH$ (10 mL), loaded directly onto silica. Purification by FCC, eluting with 0-10% $CH_3OH$ in $CH_2Cl_2$ (containing 1% concentrated ammonia (aq) gave the an off-white solid which appeared to contain DIPEA.HCl according to MNR analysis. The solid was then dissolved in a 1:1 mixture of $CH_2Cl_2$/2-methyltetrahydrofuran (30 mL) and the resulting solution was washed with NaOH solution (2M, 2×30 mL), water (2×30 mL) and then sat. brine (30 mL). The organic solution was dried ($MgSO_4$) and concentrated in vacuo to give the title compound (2 mg, 2%) as a white solid after trituration with diethyl ether. The liquors from the trituration were concentrated in vacuo to give a second sample of the title compound (10 mg, 9%) as a white solid; $^1H$ NMR: 2.27 (3H, s), 2.55 (4H, s), 2.82-2.95 (4H, m), 3.84 (3H, d), 5.73 (1H, d), 6.24 (1H, dd), 6.62 (1H, dd), 6.89 (1H, s), 7.07-7.21 (2H, m), 7.25 (1H, d), 7.46 (1H, d), 7.89 (1H, d), 8.29 (1H, d), 8.32 (1H, d), 8.42 (1H, s), 8.69 (1H, s), 9.01 (1H, s); m/z: $ES^+$ $MH^+$ 484.62.

Example 16: N-[4-Methoxy-2-(4-methylpiperazin-1-yl)-5-[(4-pyrazolo[1,5-a]pyridin-3-ylpyrimidin-2-yl)amino]phenyl]prop-2-enamide (2,3,4,5,6-Pentafluorophenyl) prop-2-enoate (0.030 mL, 0.19 mmol) was added dropwise to a solution of 4-methoxy-6-(4-methylpiperazin-1-yl)-N'-(4-pyrazolo[1,5-a]-pyridin-3-ylpyrimidin-2-yl)benzene-1,3-diamine (Intermediate 69, 67 mg, 0.16 mmol) in DMF (0.6 mL) at r.t. under $N_2$. The resulting solution was stirred at r.t. for 1.5 h and then diluted with $CH_2Cl_2$ (9 mL). This solution was added to 1.5 g flash silica which was wet with $CH_2Cl_2$ in a dry-loaded cartridge, and the crude product was eluted from the silica using $CH_2Cl_2$. Further purification by FCC, eluting with 2-7% of 2N methanolic ammonia in $CH_2Cl_2$ provided material which was further purified by FCC, eluting with 5-20% $CH_3OH$ in $CH_2Cl_2$. Appropriate fractions were concentrated in vacuo and trituration provided a crystalline solid that was washed with THF (0.1 mL) to give the title compound (23 mg, 28%) as a beige crystalline solid; $^1H$ NMR: 2.33-2.43 (3H, m), 2.62-2.81 (4H, m), 2.94 (4H, s), 3.85 (3H, s), 5.72 (1H, d), 6.18 (1H, m), 6.55-6.69 (1H, m), 6.89 (1H, s), 7.05 (1H, m), 7.26 (1H, d), 7.35-7.43 (1H, m), 8.15 (1H, s), 8.34 (1H, d), 8.44 (1H, d), 8.49 (1H, s), 8.79 (1H, d), 8.80 (1H, s), 9.03 (1H, s); m/z: $ES^+$ $MH^+$ 485.

Example 17: N-(5-{[5-Chloro-4-(1H-indol-3-yl)pyrimidin-2-yl]amino}-4-methoxy-2-{4-methylpiperazin-1-yl}phenyl)prop-2-enamide Acryloyl chloride (0.621 mL, 1M in THF, 0.62 mmol) was added dropwise to N'-[5-chloro-4-(1H-indol-3-yl)pyrimidin-2-yl]-4-methoxy-6-(4-methylpiperazin-1-yl)benzene-1,3-diamine (Intermediate 74, 288 mg, 0.62 mmol) and DIPEA (0.119 mL, 0.68 mmol) in THF (15 mL) at 0° C. under $N_2$. The resulting suspension was stirred at 0° C. for 1 h, and then allowed to warm to r.t. The mixture was then diluted with water (15 mL) and concentrated in vacuo. The resulting residue was dissolved in a mixture of $CH_2Cl_2$ (20 mL) and $CH_3OH$ (5 mL) and the resulting solution was washed with water and sat. brine. The organic solution was dried ($MgSO_4$) and concentrated in vacuo. Purification by FCC, eluting with 1-8% 7M methanolic ammonia in $CH_2Cl_2$ gave crude product as a pale brown dry film. This material was dissolved in $CH_2Cl_2$ and a beige solid precipitated from the solution. The solution was diluted with diethyl ether and then mixture filtered. The collected solid was washed with further diethyl ether and dried to give the title compound (134 mg, 42%) as a beige solid; $^1H$ NMR: 2.27 (3H, s), 2.53-2.59 (4H, m), 2.87-2.94 (4H, m), 3.79 (3H, s), 5.70 (1H, d), 6.17 (1H, dd), 6.60 (1H, dd), 6.89 (1H, s), 7.01 (1H, t), 7.16 (1H, t), 7.45 (1H, d), 8.20 (1H, s), 8.27 (1H, d), 8.35 (1H, s), 8.43 (1H, s), 8.49 (1H, d), 8.96 (1H, s), 11.81 (1H, s); m/z: $ES^+$ $MH^+$ 518.51.

Example 18: N-(4-Methoxy-5-{[5-methyl-4-(1-methylindol-3-yl)pyrimidin-2-yl]amino}-2-{4-methylpiperazin-1-yl}phenyl)prop-2-enamide Acryloyl chloride (0.358 mL, 1M in THF, 0.36 mmol) was added dropwise to a mixture of 4-methoxy-N'-[5-methyl-4-(1-methylindol-3-yl)pyrimidin-2-yl]-6-(4-methylpiperazin-1-yl)benzene-1,3-diamine (Intermediate 77, 164 mg, 0.36 mmol) and DIPEA (0.069 mL, 0.39 mmol) in THF (15 mL) at 0° C. under $N_2$. The resulting suspension was stirred at 0° C. for 1 h, then allowed to warm to r.t. The mixture was then diluted with water (15 mL) and concentrated in vacuo. The resulting material was dissolved in a mixture of $CH_2Cl_2$ (20 mL) and $CH_3OH$ (5 mL). The resulting solution was washed with water, and sat. brine. The organic solution was then dried ($MgSO_4$) and concentrated in vacuo. Purification by FCC, eluting with 1-8% 7M methanolic ammonia in $CH_2Cl_2$ gave a pale yellow dry film after concentration of the appropriate fractions in vacuo. This material was dissolved in $CH_2Cl_2$ and the resulting solution was diluted with diethyl ether, which resulted in a beige solid precipitating from the solution. This solid was collected by filtration, washed with diethyl ether and then dried to give the title compound (96 mg, 52%); $^1H$ NMR: 2.26 (3H, s), 2.37 (3H, s), 2.51 (4H, s), 2.87 (4H, s), 3.83 (3H, s), 3.89 (3H, s), 5.70 (1H, d), 6.17 (1H, d), 6.60 (1H, dd), 6.86 (1H, s), 7.09 (1H, t), 7.22 (1H, t), 7.48 (1H, d), 7.87 (1H, s), 8.05 (1H, s), 8.21 (1H, s), 8.37 (1H, d), 8.46 (1H, s), 9.00 (1H, s); m/z: $ES^+$ $MH^+$ 512.46.

Example 19: N-(2-{2-Dimethylaminoethyl-methyl-amino}-4-methoxy-5-{[5-methyl-4-(1-methylindol-3-yl)pyrimidin-2-yl]amino}phenyl)prop-2-enamide Acryloyl chloride (0.026 mL, 1M in THF, 0.32 mmol) was added dropwise to a mixture of $N^1$-(2-dimethylaminoethyl)-5-methoxy-N$^1$-methyl-N$^4$-[5-methyl-4-(1-methylindol-3-yl)pyrimidin-2-yl]benzene-1,2,4-triamine (Intermediate 81, 147 mg, 0.32 mmol) and DIPEA (0.061 mL, 0.35 mmol) in THF (15 mL) at 0° C. under N$_2$. The resulting suspension was stirred at 0° C. for 1 h then allowed to warm to r.t. The mixture was then diluted with water (15 mL) and concentrated in vacuo. The resulting material was dissolved in a mixture of CH$_2$Cl$_2$ (20 mL) and CH$_3$OH (5 mL). The resulting solution was washed with water and sat. brine, and was then dried (MgSO$_4$) and concentrated in vacuo. Purification by FCC, eluting with 1-8% 7M methanolic ammonia in CH$_2$Cl$_2$ gave a yellow dry film after concentrating the appropriate fractions in vacuo. This material was dissolved in CH$_2$Cl$_2$ and the resulting solution was diluted with diethyl ether. This was concentrated in vacuo and dried to give the title compound (93 mg, 57%) as a beige solid; $^1$H NMR: 2.21 (6H, s), 2.28-2.34 (2H, m), 2.37 (3H, s), 2.73 (3H, s), 2.89 (2H, t), 3.81 (3H, s), 3.89 (3H, s), 5.72 (1H, dd), 6.19 (1H, dd), 6.38 (1H, dd), 7.02 (1H, d), 7.06 (1H, d), 7.18-7.23 (1H, min), 7.48 (1H, d), 7.91 (1H, s), 8.06 (1H, s), 8.22 (1H, s), 8.36 (1H, d), 8.75 (1H, s), 10.11 (1H, s); m/z: ES$^+$ MH$^+$ 514.36.

Example 20: N-(2-{(3R)-3-Dimethylaminopyrrolidin-1-yl}-4-methoxy-5-{[5-methyl-4-(1-methylindol-3-yl)pyrimidin-2-yl]amino}phenyl)prop-2-enamide Acryloyl chloride (0.043 mL, 1M in THF, 0.53 mmol) was added dropwise to a mixture of 4-[(3R)-3-dimethylaminopyrrolidin-1-yl]-6-methoxy-N-[5-methyl-4-(1-methylindol-3-yl)-pyrimidin-2-yl]benzene-1,3-diamine (Intermediate 83, 252 mg, 0.53 mmol) and DIPEA (0.103 mL, 0.59 mmol) in THF (15 mL) at 0° C. under N$_2$. The resulting suspension was stirred at 0° C. for 1 h, and then allowed to warm to r.t. The mixture was then diluted with water (15 mL) and concentrated in vacuo. The resulting material was dissolved in a mixture of CH$_2$Cl$_2$ (20 mL) and CH$_3$OH (5 mL). The resulting solution was washed with water and sat. brine. The aqueous washes were re-extracted three times using CH$_2$Cl$_2$. The combined organic solutions were dried (MgSO$_4$) and concentrated in vacuo. Purification by FCC, eluting with 1-8% CH$_3$OH in CH$_2$Cl$_2$ gave a yellow dry film after concentration of the appropriate fractions in vacuo. This material was dissolved in CH$_2$Cl$_2$ and the resulting solution was diluted with diethyl ether. The resulting mixture was stirred for 30 minutes and then concentrated in vacuo to give the title compound (133 mg, 47%) as a yellow solid; $^1$H NMR: 1.67-1.81 (1H, m), 2.09 (1H, s), 2.19 (6H, s), 2.35 (3H, s), 2.72 (1H, s), 3.20 (3H, t), 3.30-3.43 (1H, m), 3.84 (3H, s), 3.89 (3H, s), 5.66 (1H, d), 6.16 (1H, d), 6.49 (1H, dd), 6.55 (1H, s), 7.12 (1H, t), 7.22 (1H, t), 7.48 (1H, d), 7.75 (1H, s), 7.92 (1H, s), 8.02 (1H, s), 8.18 (1H, s), 8.40 (1H, d), 9.32 (1H, s); m/z: ES$^+$ MH$^+$ 526.66.

Example 21: N-(5-{[5-Chloro-4-(1-methylindol-3-yl)pyrimidin-2-yl]amino}-2-{(3R)-3-dimethylaminopyrrolidin-1-yl}-4-methoxyphenyl)prop-2-enamide Acryloyl chloride (0.459 mL, 1M in THF, 0.46 mmol) was added dropwise to a mixture of N-[5-chloro-4-(1-methylindol-3-yl)pyrimidin-2-yl]-4-[(3R)-3-dimethylaminopyrrolidin-1-yl]-6-methoxybenzene-1,3-diamine (Intermediate 85, 226 mg, 0.46 mmol) and DIPEA (0.088 mL, 0.51 mmol) in THF (15 mL) at 0° C. under N$_2$. The resulting suspension was stirred at 0° C. for 1 h, then allowed to warm to r.t. The mixture was then diluted with water (15 mL) and concentrated in vacuo. The resulting material was dissolved in a mixture of CH$_2$Cl$_2$ (20 mL) and CH$_3$OH (5 mL). The resulting solution was washed with water and sat. brine. The organic solution was dried (MgSO$_4$) and concentrated in vacuo. Purification by FCC, eluting with 1-8% 7M methanolic ammonia in CH$_2$Cl$_2$ gave a yellow dry film after concentration of appropriate fractions in vacuo. This material was dissolved in CH$_2$Cl$_2$ and the resulting solution was diluted with diethyl ether. This resulted in a yellow gelatinous solid precipitating from the solution. The mixture was concentrated in vacuo and dried to give the title compound (142 mg, 57%) as a yellow solid; $^1$H NMR: 1.68-1.81 (1H, m), 2.04-2.14 (1H, m), 2.18 (6H, s), 2.64-2.75 (1H, m), 3.22 (3H, dd), 3.32-3.44 (1H, m), 3.78 (3H, s), 3.90 (3H, s), 5.66 (1H, dd), 6.16 (1H, dd), 6.49 (1H, dd), 6.54 (1H, s), 7.08 (1H, t), 7.23 (1H, t), 7.49 (1H, d), 7.54 (1H, s), 8.29-8.39 (3H, m), 8.53 (1H, s), 9.35 (1H, s); m/z: ES$^+$ MH$^+$ 546.57.

Example 22: N-(5-{[5-Cyano-4-(1-methylindol-3-yl)pyrimidin-2-yl]amino}-2-{(3R)-3-dimethylaminopyrrolidin-1-yl}-4-methoxyphenyl)prop-2-enamide Acryloyl chloride (0.373 mL, 1M in THF, 0.37 mmol) was added dropwise to a mixture of 2-({5-amino-4-[(3R)-3-dimethylaminopyrrolidin-1-yl]-2-methoxyphenyl}amino)-4-(1-methylindol-3-yl)pyrimidine-5-carbonitrile (Intermediate 89, 180 mg, 0.37 mmol) and DIPEA (0.072 mL, 0.41 mmol) in THF (15 mL) at 0° C. under N$_2$. The resulting suspension was stirred at 0° C. for 1 h, then allowed to warm to r.t. The mixture was diluted with water (15 mL) and then concentrated in vacuo. The resulting material was dissolved in a mixture of CH$_2$Cl$_2$ (20 mL) and CH$_3$OH (5 mL). The resulting solution was washed with water and sat. brine. The organic solution was dried (MgSO$_4$) and concentrated in vacuo. Purification by FCC, eluting with 1-8% 7M methanolic ammonia in CH$_2$Cl$_2$ gave a yellow dry film after concentration of the appropriate fractions in vacuo. This material was dissolved in CH$_2$Cl$_2$ and the resulting solution was diluted with diethyl ether. A yellow gelatinous solid then precipitated from the solution. Concentration of the mixture in vacuo gave the title compound (91 mg, 46%) as a yellow solid; $^1$H NMR: (100° C.) 1.82 (1H, dq), 2.04-2.11 (1H, m), 2.22 (6H, d), 2.85 (1H, dd), 3.20-3.39 (4H, m), 3.79 (3H, s), 3.90 (3H, s), 5.62 (1H, d), 6.16 (1H, dd), 6.45 (1H, dd), 6.62 (1H, s), 7.10 (1H, t), 7.25 (1H, t), 7.49 (1H, d), 7.65 (1H, s), 8.26 (1H, d), 8.42 (1H, s), 8.59 (1H, s), 8.72 (1H, s), 8.93 (1H, s); m/z: ES$^+$ MH$^+$ 537.61.

Example 23: N-(5-{[5-Cyano-4-(1-methylindol-3-yl)pyrimidin-2-yl]amino}-4-methoxy-2-{4-methylpiperazin-1-yl}phenyl) prop-2-enamide A solution of acryloyl chloride (39 mg, 0.43 mmol) in CH$_2$Cl$_2$ (1 mL) was added dropwise to a stirred solution of 2-{[5-amino-2-methoxy-4-(4-methylpiperazin-1-yl)phenyl]amino}-4-(1-methylindol-3-yl)pyrimidine-5-carbonitrile (Intermediate 90, 200 mg, 0.43 mmol) and DIPEA (0.081 mL, 0.47 mmol) in CH$_2$Cl$_2$ (5 mL), which was cooled in an ice/water bath. The mixture was stirred for 1.5 h and then diluted with CH$_2$Cl$_2$ (25 mL). This mixture was then washed with sat. NaHCO$_3$ (50 mL). The aqueous washes were further extracted with CH$_2$Cl$_2$ (2×25 mL). The combined organic solutions were dried (MgSO$_4$) and concentrated in vacuo. Purification by FCC, eluting with 5% 7N methanolic ammonia in CH$_2$Cl$_2$ gave the title compound together with some residual starting material. Further purification by FCC, eluting with 0-5% CH$_3$OH in CH$_2$Cl$_2$ gave a residue after concentration of the appropriate fractions in vacuo. This residue was dissolved in a small amount of CH$_2$Cl$_2$ and trituration with diethyl ether gave a solid that was collected by filtration and dried in vacuo to give the title compound (106 mg, 48%) as a cream solid; $^1$H NMR: 2.27 (3H, s), 2.57 (4H, br s), 2.92 (4H, br s), 3.74 (3H, s), 3.91 (3H, s), 5.70 (1H, d), 6.17 (1H, d), 6.63 (1H, dd), 6.90 (1H, s), 7.01 (1H, br s), 7.25 (1H, s), 7.52 (1H, d), 7.88 (1H, br s), 8.02 (1H, s), 8.48 (1H, s), 8.67 (1H, s), 9.03 (1H, s), 9.40 (1H, s); m/z: ES$^+$ MH$^+$ 523.27.

Example 24: N-(5-{[5-Chloro-4-(1H-indol-3-yl)pyrimidin-2-yl]amino}-2-{(3R)-3-dimethylaminopyrrolidin-1-yl}-4-methoxyphenyl)prop-2-enamide A solution of acryloyl chloride (0.044 mL, 0.54 mmol) in CH$_2$Cl$_2$ (1 mL) was added dropwise to a mixture of N-[5-chloro-4-(1H-indol-3-yl)pyrimidin-2-yl]-4-[(3R)-3-dimethylaminopyrrolidin-1-yl]-6-methoxybenzene-1,3-diamine (Intermediate 93, 258 mg, 0.54 mmol) and DIPEA (0.103 mL, 0.59 mmol) in CH$_2$Cl$_2$ (5 mL), which was cooled in an ice/water bath. The mixture was stirred for 3 h and then washed with brine, dried (Na$_2$SO$_4$) and concentrated in vacuo. The resulting residue was was suspended in CH$_3$OH and filtered to give some of the title compound (67 mg). The filtrate was then concentrated in vacuo and purified by FCC, eluting with 2% 7N methanolic ammonia in CH$_2$Cl$_2$. Appropriate fractions were combined and concentrated in vacuo to give a solid which was suspended in CH$_3$OH and collected by filtration to give more of the title compound (64 mg). The two batches of product were combined to give the title compound (131 mg, 46%) as a yellow solid; $^1$H NMR: 1.68-1.83 (1H, m), 2.04-2.16 (1H, m), 2.18 (6H, s), 2.63-2.77 (1H, m), 3.15-3.29 (3H, m), 3.35-3.46 (1H, m), 3.78 (3H, s), 5.66 (1H, dd), 6.16 (1H, dd), 6.49 (1H, dd), 6.54 (1H, s), 7.04 (1H, t), 7.16 (1H, t), 7.45 (1H, d), 7.53 (1H, s), 8.23-8.4 (3H, m), 8.48 (1H, d), 9.34 (1H, s), 11.84 (1H, s); m/z: ES$^+$ MH$^+$ 532.5.

Example 25: N-(5-{[5-Chloro-4-(1H-indol-3-yl)pyrimidin-2-yl]amino}-2-{2-dimethyl-aminoethylmethylamino}-4-methoxyphenyl)prop-2-enamide A solution of acryloyl chloride (0.027 mL, 0.33 mmol) in CH$_2$Cl$_2$ (1 mL) was added dropwise to a mixture of N$^4$-[5-chloro-4-(1H-indol-3-yl)pyrimidin-2-yl]-N$^1$-(2-dimethylaminoethyl)-5-methoxy-N$^1$-methylbenzene-1,2,4-triamine (Intermediate 95, 155 mg, 0.33 mmol) and DIPEA (0.063 mL, 0.37 mmol) in CH$_2$Cl$_2$ (5 mL), which was cooled in an ice/water bath. The mixture was stirred for 1 h and then washed with brine, dried (Na$_2$SO$_4$) and concentrated in vacuo. Purification by FCC, eluting with 2% 7N methanolic ammonia in CH$_2$Cl$_2$ gave the title compound (120 mg, 69%) as a white solid after trituration with diethyl ether; $^1$H NMR: 2.22 (6H, s), 2.34 (2H, br t), 2.75 (3H, s), 2.91 (2H, br t), 3.76 (3H, s), 5.73 (1H, dd), 6.19 (1H, dd), 6.39 (1H, dd), 6.96 (1H, t), 7.05 (1H, s), 7.14 (1H, t), 7.44 (1H, d), 8.26 (1H, d), 8.35 (1H, s), 8.48 (1H, s), 8.50 (1H, d), 8.54 (1H, s), 10.10 (1H, s), 11.85 (1H, s); m/z: ES$^+$ MH$^+$ 520.6.

Example 26: N-(5-{[5-Chloro-4-(1-methylindol-3-yl)pyrimidin-2-yl]amino}-2-{2-dimethylaminoethylmethylamino}-4-methoxyphenyl)prop-2-enamide A solution of acryloyl chloride (0.026 mL, 0.32 mmol) in CH$_2$Cl$_2$ (1 mL) was added to a mixture of N$^4$-[5-chloro-4-(1-methylindol-3-yl)pyrimidin-2-yl]-N$^1$-(2-dimethylaminoethyl)-5-methoxy-N$^1$-methylbenzene-1,2,4-triamine (Intermediate 97, 130 mg, 0.27 mmol) and DIPEA (0.090 mL, 0.54 mmol) in CH$_2$Cl$_2$ (2 mL) at 0° C. The mixture was stirred at 0° C. for 2.5 h (during this time a further 0.2 eq acryloyl chloride was added). The mixture was then diluted with CH$_2$Cl$_2$, washed twice with sat. NaHCO$_3$ and then with water, dried (MgSO$_4$), and concentrated in vacuo. Purification by FCC, eluting with 0-5% methanolic ammonia in CH$_2$Cl$_2$ gave the title compound (111 mg, 77%) as a yellow solid; $^1$H NMR: (CDCl$_3$) 2.26 (6H, s), 2.23-2.33 (2H, m), 2.70 (3H, s), 2.86-2.89 (2H, m), 3.88 (3H, s), 3.91 (3H, s), 5.67 (1H, d), 6.25-6.44 (2H, m), 6.79 (1H, s), 7.20-7.37 (3H, m), 7.57 (1H, s), 8.36-8.45 (3H, m), 9.54 (1H, s), 10.11 (1H, s); m/z: ES$^+$ MH$^+$ 534, 536.

Example 27: N-(5-{[5-Cyano-4-(1H-indol-3-yl)pyrimidin-2-yl]amino}-4-methoxy-2-{4-methylpiperazin-1-yl}phenyl)prop-2-enamide Acryloyl chloride (0.100 mL, 1M in THF, 0.1 mmol) was added dropwise to a fine slurry of 2-{[5-amino-2-methoxy-4-(4-methylpiperazin-1-yl)phenyl]amino}-4-(1H-indol-3-yl)pyrimidine-5-carbonitrile (Intermediate 99, 47 mg, 0.10 mmol) and DIPEA (0.027 mL, 0.16 mmol) in THF (2 mL) at −10° C. over a period of 2 minutes under N$_2$. The mixture was then stirred at 0° C. for 10 minutes then allowed to warm to r.t. over 20 minutes. The mixture was then cooled again to −10° C. and further acryloyl chloride (0.06 mL, 1M in THF, 0.06 mmol) was added dropwise. The mixture was stirred at 0° C. for a further 10 minutes, then allowed to warm to r.t. over 20 minutes. The mixture was then concentrated in vacuo and the resulting reside was dissolved in CH$_2$Cl$_2$ (2 mL). This solution was washed with sat. NaHCO$_3$ (1 mL), dried (MgSO$_4$) and concentrated in vacuo. Purification by FCC, eluting with 1.5-7% 7N methanolic ammonia in CH$_2$Cl$_2$ gave a residue that was washed with CH$_3$OH (0.1 mL) and dried in air to give the title compound (11 mg, 20%) as a cream crystalline solid; $^1$H NMR: 2.28 (3H, s), 2.54-2.65 (4H, m), 2.93 (4H, s), 3.75 (3H, s), 5.71 (1H, d), 6.18 (1H, d), 6.64 (1H, dd), 6.91 (2H, m), 7.18 (1H, s), 7.47 (1H, d), 8.02 (1H, s), 8.52 (1H, s), 8.67 (1H, s), 9.04 (1H, s), 9.40 (1H, s), 11.99 (1H, s); m/z: ES$^+$ MH$^+$ 509.

Example 28: N-(2-{2-Dimethylaminoethyl-methylamino}-4-methoxy-5-{[4-(1-methylindol-3-yl)pyrimidin-2-yl]amino}phenyl)prop-2-enamide

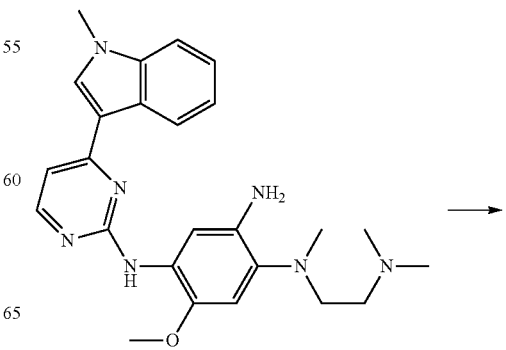

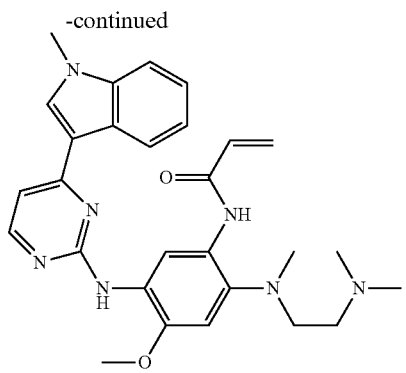

A solution of acryloyl chloride (34.5 mg, 0.38 mmol) in CH$_2$Cl$_2$ (1 mL) was added dropwise to a stirred mixture of N-(2-dimethylaminoethyl)-5-methoxy-N$^1$-methyl-N$^4$-[4-(1-methylindol-3-yl)pyrimidin-2-yl]benzene-1,2,4-triamine (Intermediate 100, 170 mg, 0.38 mmol) and DIPEA (0.073 mL, 0.42 mmol) in CH$_2$Cl$_2$ (5 mL), which was cooled in an ice/water bath. The mixture was stirred for 1.5 h and then diluted with CH$_2$Cl$_2$ (25 mL) and washed with sat.NaHCO$_3$ (50 mL). The aqueous washes were extracted with CH$_2$Cl$_2$ (2×25 mL). The combined organic solutions were dried (MgSO$_4$) and concentrated in vacuo. Purification by FCC, eluting with 0-4% 7N methanolic ammonia in CH$_2$Cl$_2$ gave the title compound (75 mg, 39%) as a cream solid after trituration with diethyl ether; $^1$H NMR: 2.21 (6H, s), 2.29 (2H, t), 2.72 (3H, s), 2.89 (2H, t), 3.86 (3H, s), 3.92 (3H, s), 5.77 (1H, dd), 6.27 (1H, dd), 6.43 (1H, dd), 7.04 (1H, s), 7.15 (1H, t), 7.20-7.27 (2H, m), 7.53 (1H, d), 7.91 (1H, s), 8.24 (1H, d), 8.33 (1H, d), 8.68 (1H, s), 9.14 (1H, s), 10.22 (1H, s); m/z: ES$^+$ MH$^+$ 500.42.

Example 28 (Alternative Synthesis 1): N-(2-{2-Dimethylaminoethyl-methylamino}-4-methoxy-5-{[4-(1-methylindol-3-yl)pyrimidin-2-yl]amino}phenyl)prop-2-enamide

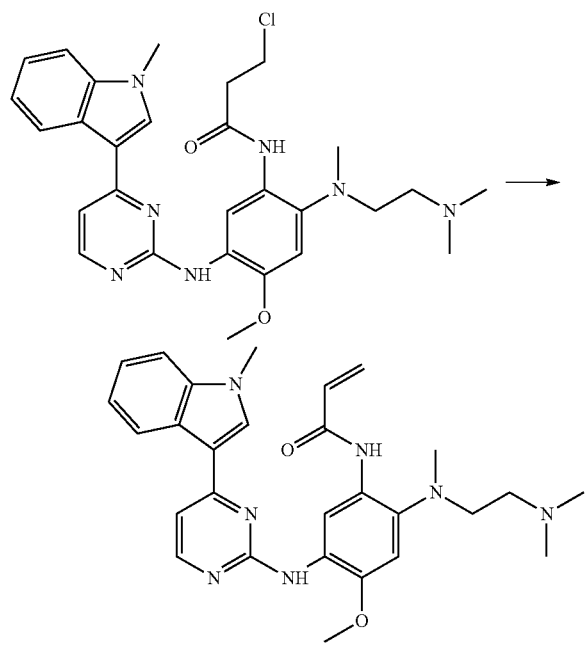

To a stirred solution of 3-chloro-N-[2-[2-dimethylaminoethyl(methyl)amino]-4-methoxy-5-[[4-(1-methylindol-3-yl)pyrimidin-2-yl]amino]phenyl]propanamide (Intermediate 174, 31.5 g, 58.76 mmol) in acetonitrile (310 mL) was added triethylamine (17.84 g, 176.28 mmol) at r.t. The resulting mixture was heated to 80° C. for 6 h then cooled to r.t. Water (130 mL) was then added and the mixture stirred for 12 h. The mixture was then filtered, washed with a mixture of water and acetonitrile (160 mL, 1:1) and dried at 50° C. for overnight to give the title compound (19.2 g, 94%) as a solid form identified herein as polymorphic form D. $^1$H NMR: 2.69 (3H, s), 2.83 (6H, d), 3.35 (4H, s), 3.84 (3H, s), 3.91 (3H, s), 5.75 (1H, d), 6.28 (1H, d), 6.67 (1H, dd), 7.05-7.23 (2H, m), 7.29 (1H, t), 7.43 (1H, d), 7.56 (1H, d), 8.21 (2H, s), 8.81 (1H, s), 9.47 (1H, s), 9.52 (1H, s), m/z: ES$^+$ MH$^+$ 500.26.

Example 28 (Alternative synthesis 2): N-(2-{2-Dimethylaminoethyl-methylamino}-4-methoxy-5-{[4-(1-methylindol-3-yl)pyrimidin-2-yl]amino}phenyl)prop-2-enamide

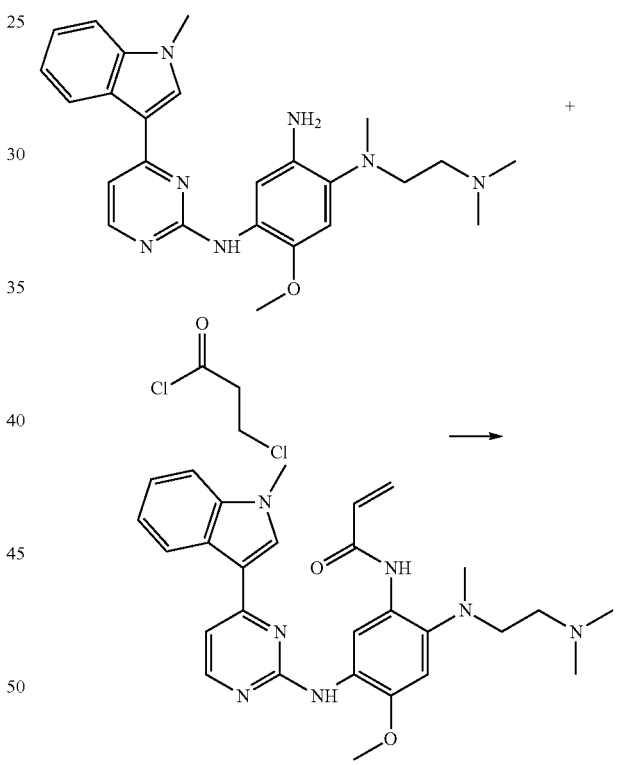

To a stirred solution of N$^1$-(2-dimethylaminoethyl)-5-methoxy-N$^1$-methyl-N$^4$-[4-(1-methylindol-3-yl)pyrimidin-2-yl]benzene-1,2,4-triamine (Intermediate 100, 10 g, 21.32 mmol) in THF (95 mL) and water (9.5 mL) at 0° C. was added the 3-chloropropanoyl chloride (3.28 g, 25.59 mmol). The mixture was stirred at r.t. for 15 minutes then NaOH (3.48 g, 85.28 mmol) was added. The resulting mixture was heated to 65° C. for 10 h. The mixture was then cooled to r.t. and CH$_3$OH (40 mL) and water (70 mL) were added. The resulting mixture was stirred overnight. The resulting solid was collected by filtration, washed with water (25 mL) and dried at 50° C. for 12 h to give the title compound (7.0 g, 94%) as a solid form identified herein as polymorphic Form D. ¹H NMR: 2.69 (3H, s) 2.83 (6H, d) 3.35 (4H, s) 3.84 (3H, s) 3.91 (3H, s) 5.75 (1H, d) 6.28 (1H, d) 6.67 (1H, dd) 7.05-7.23 (2H, m) 7.29 (1H, t) 7.43 (1H, d) 7.56 (1H, d) 8.21 (2H, s) 8.81 (1H, s) 9.47 (1H, s) 9.52 (1H, s) ES⁺ MH⁺ 500.26.

Example 28A: N-(2-{2-Dimethylaminoethyl-methylamino}-4-methoxy-5-{[4-(1-methylindol-3-yl)pyrimidin-2-yl]amino}phenyl)prop-2-enamide mesylate salt

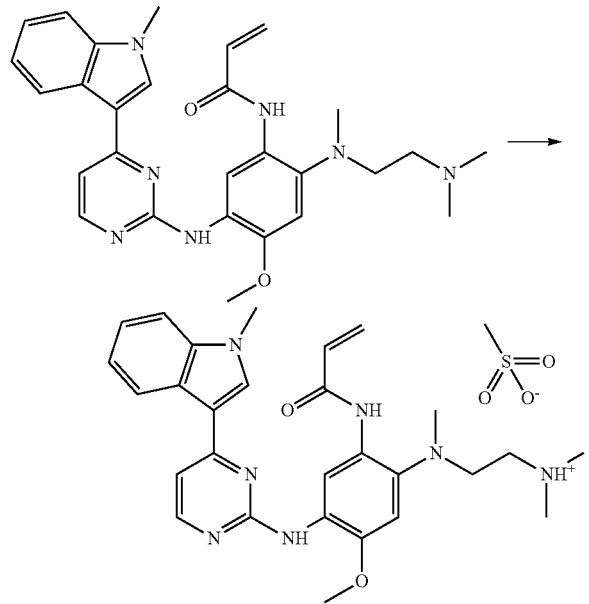

Procedure 1:
To a stirred solution of N-[2-[2-dimethylaminoethyl(methyl)amino]-4-methoxy-5-[[4-(1-methylindol-3-yl)pyrimidin-2-yl]amino]phenyl]prop-2-enamide (Example 28, 20 g, 36.63 mmol) in ethanol (120 mL) and EtOAc (80 mL) at 70° C. was added methane sulfonic acid (3.59 g, 36.63 mmol) as a solution in EtOAc (40 mL). The resulting mixture was stirred for 1.5 h. The resulting solid was collected by filtration and dried at 80° C. under vacuum overnight to give the title salt (20.5 g, 94%) in a solid form defined herein as polymorphic Form B for this salt.

Procedure 2:
To a stirred solution of N-[2-[2-dimethylaminoethyl(methyl)amino]-4-methoxy-5-[[4-(1-methylindol-3-yl)pyrimidin-2-yl]amino]phenyl]prop-2-enamide (Example 28, 5 g, 9.11 mmol) in acetone (45.5 mL) and water (4.55 mL) at 50° C. was added methane sulfonic acid (0.893 g, 9.11 mmol) as a solution in acetone (4.55 mL). The resulting mixture was stirred for 1.5 h. The resulting solid was collected by filtration and dried at 80° C. under vacuum overnight to give the title salt (4.9 g, 94%) in a solid form defined herein as polymorphic Form B for this salt; ¹H NMR (acetone-d⁶): 2.72 (3H, s), 2.96 (3H, s), 3.01 (6H, s), 3.58 (3H, t), 3.87-3.90 (7H, m), 5.76 (1H, dd), 6.38-6.53 (2H, m), 7.12 (1H, t), 7.20 (1H, t), 7.29 (1H, s), 7.40 (2H, t), 8.07-8.16 (3H, m), 8.56 (1H, s), 9.30 (1H, s), 9.60 (1H, s), 9.66 (1H, s); m/z: ES⁺ MH⁺ 500.26.

Procedure 3:
Polymorphic Form A of N-(2-{2-dimethylaminoethyl-methylamino}-4-methoxy-5-{[4-(1-methylindol-3-yl)pyrimidin-2-yl]amino}phenyl)prop-2-enamide mesylate salt was prepared in a similar manner as described above on a ~50 mg scale, except that acetonitrile was used as the solvent. Specifically, ~9.6 mg methanesulfonic acid was dissolved into a minimum volume of acetonitrile. ~50 mg N-(2-{2-dimethylamino-ethyl-methylamino}-4-methoxy-5-{[4-(1-methylindol-3-yl)pyrimidin-2-yl]amino}phenyl)-prop-2-enamide was also dissolved into a minimum volume of acetonitrile and then the resulting solution was added to the methanesulfonic acid solution. Formation of a solid resulted upon addition. This solid was collected by filtration and was air-dried and then analysed. The particular solid form produced in this experiment was designated as Polymorphic Form A for this salt.

Example 29: N-(5-{[5-Cyano-4-(1-methylindol-3-yl)pyrimidin-2-yl]amino}-2-{2-dimethylaminoethyl-methylamino}-4-methoxyphenyl)prop-2-enamide A solution of acryloyl chloride (0.035 mL, 0.44 mmol) in CH₂Cl₂ (1 mL) was added to a mixture of 2-{[5-amino-4-(2-dimethylaminoethyl-methylamino)-2-methoxyphenyl]amino}-4-(1-methylindol-3-yl)pyrimidine-5-carbonitrile (Intermediate 102, 171 mg, 0.36 mmol) and DIPEA (0.120 mL, 0.73 mmol) in CH₂Cl₂ (3 mL) at 0° C., then the mixture was stirred at 0° C. for 1 h. The mixture was then diluted with CH₂Cl₂, washed twice with sat. NaHCO₃, and then water, then dried (MgSO₄) and concentrated in vacuo. Purification by FCC, eluting with 0-5% methanolic ammonia in CH₂Cl₂ gave the title compound (68 mg, 36%) as a yellow solid; ¹H NMR: (100° C.) 2.22 (6H, s), 2.40 (2H, t), 2.76 (3H, s), 2.98 (2H, t), 3.77 (3H, s), 3.90 (3H, s), 5.69 (1H, dd), 6.17 (1H, dd), 6.40 (1H, dd), 7.02-7.06 (2H, m), 7.21-7.25 (1H, m), 7.49 (1H, d), 8.23 (1H, d), 8.45 (1H, s), 8.47 (1H, s), 8.63 (1H, s), 8.86 (1H, s), 9.59 (1H, s); m/z: ES⁺ MH⁺ 525.32.

Example 30: N-(2-{(3R)-3-Dimethylaminopyrrolidin-1-yl}-4-methoxy-5-{[4-(1-methylindol-3-yl)pyrimidin-2-yl]amino}phenyl)prop-2-enamide A solution of acryloyl chloride (53.4 mg, 0.59 mmol) in CH₂Cl₂ (1 mL) was added dropwise to a stirred mixture of 4-[(3R)-3-dimethylaminopyrrolidin-1-yl]-6-methoxy-N-[4-(1-methylindol-3-yl)pyrimidin-2-yl]benzene-1,3-diamine (Intermediate 103, 270 mg, 0.59 mmol) and DIPEA (0.112 mL, 0.65 mmol) in CH₂Cl₂ (10 mL), which was cooled in an ice/water bath. The mixture was stirred for 1.5 h and was then diluted with CH₂Cl₂ (25 mL) and washed with sat. NaHCO₃ (50 mL). The aqueous washes were extracted with CH₂Cl₂ (2×25 mL). The combined organic solutions were then dried (MgSO₄) and concentrated in vacuo. Purification by FCC, eluting with 0-4% 7N methanolic ammonia in CH₂Cl₂ provided the title compound mixed together with diacylated material. This material was dissolved in CH₂Cl₂ and triturated with diethyl ether. The resulting precipitate was collected by filtration, washed with diethyl ether (10 mL) and air dried to give impure product (120 mg) as a yellow solid. This solid was purified by crystallisation from CH₃CN to give the title compound (47 mg, 0.092 mmol, 16%) as a yellow solid. All the residues were combined, concentrated in vacuo and crystallised from CH₃CN to give a second crop of the title compound (26 mg, 0.051 mmol, 9%) as a yellow solid. Total yield of title compound=73 mg, 24%; ¹H NMR: (CDCl₃) 1.87-1.99 (1H, m), 2.11-2.24 (1H, m), 2.30 (6H, s), 2.83-2.95 (1H, m), 3-3.19 (4H, m), 3.88 (3H, s), 3.99 (3H, s), 5.75 (1H, dd), 6.34 (1H, dd), 6.44 (1H, dd), 6.79 (1H, s), 7.20 (1H, d), 7.23-7.32 (2H, m) partially obscured by CDCl$_3$ peak, 7.37-7.42 (1H, m), 7.67 (1H, s), 8.08 (1H, d), 8.38 (1H, d), 8.46 (1H, s), 9.00 (1H, s), 9.71 (1H, s); m/z: ES$^+$ MH$^+$ 512.26.

Example 31: N-{5-[(5-Chloro-4-pyrazolo[1,5-a]pyridin-3-ylpyrimidin-2-yl)amino]-4-methoxy-2-[methyl-(2-morpholin-4-ylethyl)amino]phenyl}prop-2-enamide Acryloyl chloride (0.413 mL, 1M in THF, 0.41 mmol) was added dropwise to a slurry of N$^4$-(5-chloro-4-pyrazolo[1,5-a]pyridin-3-ylpyrimidin-2-yl)-5-methoxy-N$^1$-methyl-N$^1$-(2-morpholin-4-ylethyl)benzene-1,2,4-triamine (Intermediate 105, 298 mg, 0.59 mmol) and DIPEA (0.153 mL, 0.88 mmol) in THF (5 mL) at −10° C. over a period of 2 minutes under N$_2$. The mixture was stirred at 0° C. for 10 minutes and then allowed to warm to r.t. over 20 minutes. The mixture was cooled again to −10° C. and further acryloyl chloride (0.103 mL, 1M in THF, 0.103 mmol) was added dropwise. The slurry was stirred at 0° C. for a further 10 minutes, then allowed to warm to r.t. over 20 minutes. The mixture was then concentrated in vacuo and the residue was dissolved in CH$_2$Cl$_2$ (5 mL). This solution was washed with sat. NaHCO$_3$ (2 mL), dried (MgSO$_4$) and concentrated in vacuo. Purification by FCC, eluting with 1.5-7% 7N methanolic ammonia in CH$_2$Cl$_2$ gave a gum. This gum was dissolved in EtOAc (1 mL), and diethyl ether (~1 mL) was added until just oiling out. The mixture was then stirred for 3 days, filtered and the collected solid was dried by suction to give the title compound (193 mg, 59%) as a cream crystalline solid; $^1$H NMR: 2.29-2.38 (4H, m), 2.41 (2H, t), 2.74 (3H, s), 3.03 (2H, t), 3.49-3.61 (4H, m), 3.78 (3H, s), 5.72 (1H, d), 6.18 (1H, m), 6.60 (1H, m), 7.00 (1H, s), 7.10 (1H, m), 7.27-7.38 (1H, m), 8.25 (1H, s), 8.40 (2H, m), 8.65 (1H, s), 8.82 (1H, d), 8.95 (1H, s), 9.28 (1H, s); m/z: ES$^+$ MH$^+$ 563.

Example 32: N-(5-{[5-Chloro-4-pyrazolo[1,5-a]pyridin-3-ylpyrimidin-2-yl]amino}-4-methoxy-2-{methyl-[2-(4-methylpiperazin-1-yl)ethyl]amino}phenyl)prop-2-enamide A solution of acryloyl chloride (0.028 mL, 0.35 mmol) in CH$_2$Cl$_2$ (1 mL) was added dropwise to a stirred mixture of N$^4$-(5-chloro-4-pyrazolo[1,5-a]pyridin-3-ylpyrimidin-2-yl)-5-methoxy-N$^1$-methyl-N$^1$-[2-(4-methylpiperazin-1-yl)ethyl]benzene-1,2,4-triamine (Intermediate 107, 0.174 g, 0.33 mmol) in CH$_2$Cl$_2$ (2.5 mL) under N$_2$. The mixture was then stirred at r.t. for 1 h and was then diluted with CH$_2$Cl$_2$ (25 mL). This solution was washed with sat. NaHCO$_3$ (25 mL) and the aqueous wash solution was extracted with CH$_2$Cl$_2$ (20 mL). The combined organic solutions were dried (MgSO$_4$) and concentrated in vacuo. Purification by FCC, eluting with 0-8% CH$_3$OH in CH$_2$Cl$_2$ gave the title compound (0.12 g, 63%) as a beige foam; $^1$H NMR: (CDCl$_3$) 2.31 (3H, s), 2.35-2.6 (10H, m), 2.67 (3H, s), 3.00 (2H, t), 3.88 (3H, s), 5.64-5.82 (1H, m), 6.31-6.50 (2H, m), 6.79 (1H, s), 6.91 (1H, t), 7.29 (1H, t), 7.48 (1H, s), 8.47 (1H, s), 8.54 (2H, t), 8.94 (1H, s), 9.15 (1H, s), 9.38 (1H, s); m/z: ES$^+$ MH$^+$ 576.59.

Example 33: N-(4-Methoxy-5-{[4-(1-methylindol-3-yl)pyrimidin-2-yl]amino}-2-{4-methylpiperazin-1-yl}phenyl)prop-2-enamide A solution of acryloyl chloride (58.4 mg, 0.64 mmol) in CH$_2$Cl$_2$ (1 mL) was added dropwise to a mixture of 4-methoxy-N'-[4-(1-methylindol-3-yl)pyrimidin-2-yl]-6-(4-methylpiperazin-1-yl)benzene-1,3-diamine (Intermediate 110, 286 mg, 0.64 mmol) and DIPEA (0.134 mL, 0.77 mmol) in CH$_2$Cl$_2$ (20 mL), which was cooled in an ice/water bath. The mixture was stirred for 1.5 h at 0° C. More DIPEA was added (30 µL) then more acryloyl chloride (20 mg) was added dropwise as a solution in CH$_2$Cl$_2$ (1 mL). This mixture was stirred for 2 h and then diluted with CH$_2$Cl$_2$ (50 mL). This solution was washed with sat. NaHCO$_3$ solution (2×25 mL) and then the combined aqueous washes were extracted with CH$_2$Cl$_2$ (2×25 mL). The combined organic solutions were washed with brine, dried (MgSO$_4$) and concentrated in vacuo. The resulting gum was triturated with diethyl ether to give a solid which was collected by filtration and dried in vacuo. Purification by FCC, eluting with 0-8% 7N methanolic ammonia in CH$_2$Cl$_2$ gave the title compound (55 mg, 17%) as a light grey solid after trituration with diethyl ether (with a few drops of CH$_3$OH); $^1$H NMR: 2.27 (3H, s), 2.53-2.59 (4H, m), 2.85-2.91 (4H, m), 3.87 (3H, s), 3.91 (3H, s), 5.75 (1H, d), 6.24 (1H, d), 6.67 (1H, dd), 6.89 (1H, s), 7.15-7.28 (3H, m), 7.53 (1H, d), 7.89 (1H, s), 8.28 (1H, d), 8.32 (1H, d), 8.58 (1H, s), 8.81 (1H, s), 9.07 (1H, s); m/z: ES$^+$ MH$^+$ 498.58.

Example 34: N-(5-{[5-Chloro-4-(1-methylindol-3-yl)pyrimidin-2-yl]amino}-2-{3-dimethylaminoazetidin-1-yl}-4-methoxyphenyl)prop-2-enamide A solution of acryloyl chloride (0.049 mL, 0.60 mmol) in CH$_2$Cl$_2$ (0.5 mL) was added dropwise to a mixture of N-[5-chloro-4-(1-methylindol-3-yl)pyrimidin-2-yl]-4-(3-dimethylaminoazetidin-1-yl)-6-methoxybenzene-1,3-diamine (Intermediate 112, 260 mg, 0.54 mmol) in CH$_2$Cl$_2$ (9 mL). This mixture was stirred for 1 h and then loaded onto a SCX column. The column was washed with CH$_3$OH and the desired product was then eluted from the column using 2M methanolic ammonia. Appropriate fractions were concentrated in vacuo to give a brown gum. Purification by FCC, eluting with 1-10% CH$_3$OH in CH$_2$Cl$_2$ (containing 1% concentrated aqueous ammonia) gave the title compound (214 mg, 74%) as a yellow solid after trituration with CH$_3$OH (0.5 mL) using an ultrasound bath for 2 mins; $^1$H NMR: 2.10 (6H, s), 3.03-3.14 (1H, m), 3.59 (2H, t), 3.77 (3H, s), 3.90 (3H, s), 3.97 (2H, t), 5.66 (1H, dd), 6.16 (1H, dd), 6.23 (1H, s), 6.46 (1H, dd), 7.12 (1H, t), 7.23 (1H, t), 7.44-7.54 (2H, m), 8.20-8.38 (3H, m), 8.51 (1H, s), 9.21 (1H, s); m/z: ES$^+$ MH$^+$ 532.

Example 35: N-(2-{3-Dimethylaminoazetidin-1-yl}-4-methoxy-5-{[5-methyl-4-(1-methylindol-3-yl)pyrimidin-2-yl]amino}phenyl)prop-2-enamide A solution of acryloyl chloride (0.024 mL, 0.30 mmol) in CH$_2$Cl$_2$ (1 mL) was added dropwise to a stirred solution of 4-(3-dimethylaminoazetidin-1-yl)-6-methoxy-N-[5-methyl-4-(1-methylindol-3-yl)pyrimidin-2-yl]benzene-1,3-diamine (Intermediate 114, 130 mg, 0.28 mmol) in CH$_2$Cl$_2$ (5 mL), which was cooled in an ice/brine bath to approx 0° C. The mixture was stirred for 1 h, then diluted with CH$_2$Cl$_2$ (50 mL) and CH$_3$OH (to fully dissolve suspension that had formed). This solution was then washed with sat. NaHCO$_3$ (100 mL) which had been diluted with water (10 mL). The aqueous wash solution was then extracted with CH$_2$Cl$_2$ (2×50 mL) and the combined organic solutions were dried (MgSO$_4$) and concentrated in vacuo. Purification by FCC, eluting with 0-5% 7N methanolic ammonia in CH$_2$Cl$_2$ gave a dark brown solid. This solid was heated in CH$_3$CN and isolated by vacuum filtration, to give the title compound (45 mg, 31%) as a pale brown solid. The mother liqours were concentrated in vacuo and also retained as a second batch of the title compound (30 mg, 21%) as a darker brown solid. Total yield of title compound=75 mg, 52%; $^1$H NMR: 2.08 (6H, s), 2.34 (3H, s), 3-3.1 (1H, m), 3.55 (2H, t), 3.83 (3H, s), 3.88 (3H, s), 3.93 (2H, t), 5.65 (1H, dd), 6.15 (1H, dd), 6.24 (1H, s), 6.44 (1H, dd), 7.13 (1H, t), 7.21 (1H, t), 7.47 (1H, d), 7.66 (1H, s), 7.81 (1H, s), 7.99 (1H, s), 8.17 (1H, s), 8.37 (1H, d), 9.19 (1H, s); m/z: ES$^+$ MH$^+$ 512.14.

Example 36: N-(2-{3-Dimethylaminoazetidin-1-yl}-4-methoxy-5-{[4-(1-methylindol-3-yl)pyrimidin-2-yl]amino}phenyl)prop-2-enamide A solution of acryloyl chloride (0.044 mL, 0.54 mmol) in CH$_2$Cl$_2$ (1 mL) was added dropwise to a mixture of 4-(3-dimethylaminoazetidin-1-yl)-6-methoxy-N-[4-(1-methylindol-3-yl)pyrimidin-2-yl]benzene-1,3-diamine (Intermediate 116, 240 mg, 0.54 mmol) and DIPEA (0.104 mL, 0.60 mmol) in CH$_2$Cl$_2$ (5 mL), which was cooled in an ice/water bath. The mixture was stirred for 1 h and was then washed with brine, dried (Na$_2$SO$_4$) and concentrated in vacuo. Purification by FCC, eluting with 0-2% 7N methanolic ammonia in CH$_2$Cl$_2$ gave the title compound (38 mg, 14%) as a yellow solid after trituration with diethyl ether and washing of the resulting solid with a small volume of CH$_3$OH; $^1$H NMR: 2.10 (6H, s), 3.08 (1H, t), 3.56 (2H, t), 3.86 (3H, s), 3.89 (3H, s), 3.96 (2H, t), 5.69 (1H, dd), 6.18-6.29 (2H, m), 6.52 (1H, dd), 7.14 (1H, d), 7.17-7.28 (2H, m), 7.51 (1H, d), 7.75 (1H, s), 7.98 (1H, s), 8.26 (1H, d), 8.34 (2H, d), 9.29 (1H, s); m/z: ES$^+$ MH$^+$ 498.44.

Example 37: N-(5-{[5-Chloro-4-(1H-indol-3-yl)pyrimidin-2-yl]amino}-2-{3-dimethylaminoazetidin-1-yl}-4-methoxyphenyl)prop-2-enamide A solution of acryloyl chloride (0.057 mL, 0.70 mmol) in CH$_2$Cl$_2$ (1 mL) was added dropwise to a stirred solution of N-[5-chloro-4-(1H-indol-3-yl)pyrimidin-2-yl]-4-(3-dimethylaminoazetidin-1-yl)-6-methoxybenzene-1,3-diamine (Intermediate 118, 310 mg, 0.67 mmol) and DIPEA (0.127 mL, 0.73 mmol) in CH$_2$Cl$_2$ (40 mL), which was cooled in an ice/water bath to 0° C. The mixture was stirred while in the ice/water bath for 1 h and was then allowed to warm to r.t. The mixture was then held at r.t. for 18 h, and was then diluted with CH$_2$Cl$_2$ (100 mL). This solution was then washed with sat. NaHCO$_3$ (200 mL) and the aqueous wash solution was extracted with CH$_2$Cl$_2$ (2×100 mL). The combined organic solutions were dried (MgSO$_4$) and concentrated in vacuo. Purification by FCC, eluting with 0-5% 7N methanolic ammonia in CH$_2$Cl$_2$ gave the title compound together with an impurity (172 mg, 50%) as a pale yellow solid. 120 mg of this material was purified by crystallisation from CH$_3$CN to give the title compound (85 mg, 0.164 mmol) as a yellow solid without evidence of the impurity by NMR analysis. The mother liqours from the crystallization and a further impure fraction from the FCC (containing a 75:25 mixture of product:starting material) were combined, concentrated in vacuo and was purified by crystallisation from CH$_3$CN to give more of the title compound (40 mg, 12%) as a tan solid; $^1$H NMR: 2.09 (6H, s), 3.03-3.12 (1H, m), 3.58 (2H, t), 3.78 (3H, s), 3.96 (2H, t), 5.66 (1H, dd), 6.16 (1H, dd), 6.25 (1H, s), 6.46 (1H, dd), 7.07 (1H, t), 7.16 (1H, t), 7.45 (1H, d), 7.48 (1H, s), 8.24 (1H, s), 8.27-8.31 (1H, br s), 8.31 (1H, s), 8.46 (1H, d), 9.22 (1H, s), 11.79 (1H, s); m/z: ES$^+$ MH$^+$ 518.23.

Example 38: N-{5-[(5-Cyano-4-pyrazolo[1,5-a]pyridin-3-ylpyrimidin-2-yl)amino]-2-[(3R)-3-dimethylaminopyrrolidin-1-yl]-4-methoxyphenyl}prop-2-enamide A solution of acryloyl chloride (0.027 mL, 0.33 mmol) in CH$_2$Cl$_2$ (1 mL) was added dropwise to a mixture of 2-({5-amino-4-[(3R)-3-(dimethylamine)pyrrolidin-1-yl]-2-methoxyphenyl}amino)-4-(pyrazolo[1,5-a]pyridin-3-yl)pyrimidine-5-carbonitrile (Intermediate 120, 155 mg, 0.33 mmol) and DIPEA (0.063 mL, 0.36 mmol) in CH$_2$Cl$_2$ (10 mL), which was cooled in an ice/water bath. The mixture was stirred for 2 h and then washed with brine, dried (Na$_2$SO$_4$) and concentrated in vacuo. Purification by FCC, eluting with 2% 7N methanolic ammonia in CH$_2$Cl$_2$ gave a foam. Concentration from a mixture of CH$_3$OH/CH$_2$Cl$_2$ gave a solid which was triturated in diethyl ether and collected by filtration to give the title compound (95 mg, 55%) as a yellow solid; $^1$H NMR: (100° C.) 1.82 (1H, dq), 2.08 (1H, ddd), 2.22 (6H, s), 2.8-2.89 (1H, m), 3.19-3.45 (4H, m), 3.78 (3H, s), 5.63 (1H, dd), 6.16 (1H, dd), 6.44 (1H, dd), 6.61 (1H, s), 7.12 (1H, td), 7.34-7.46 (1H, m), 7.54 (1H, s), 8.33 (1H, d), 8.64 (1H, s), 8.77 (1H, d), 8.90 (2H, s), 8.96 (1H, s); m/z: ES$^+$ MH$^+$ 524.57.

Example 39: N-{5-[(5-Cyano-4-pyrazolo[1,5-a]pyridin-3-ylpyrimidin-2-yl)amino]-2-[2-dimethylaminoethyl-methylamino]-4-methoxyphenyl}prop-2-enamide A solution of acryloyl chloride (0.087 mL, 1M, THF, 0.09 mmol) was added dropwise to a mixture of 2-{[5-amino-4-(2-dimethylaminoethyl-methylamino)-2-methoxyphenyl]-amino}-4-pyrazolo[1,5-a]pyridin-3-ylpyrimidine-5-carbonitrile (Intermediate 121, 0.036 g, 0.08 mmol) and DIPEA (0.017 mL, 0.09 mmol) in THF (5 mL) which was cooled to 0° C. The mixture was stirred at 0° C. for 3 h, then concentrated in vacuo. Purification by FCC, eluting with 0-20% CH$_3$OH in CH$_2$Cl$_2$ have crude product which appeared to contain the hydrochloride salt of DIPEA. The material was dissolved in CH$_2$Cl$_2$ (10 mL) and stirred with sat. NaHCO$_3$ solution (10 mL). The phases were separated and the organic solution was concentrated in vacuo to give the title compound (24 mg, 60%) as a yellow gum; $^1$H NMR: (CDCl$_3$) 2.22 (6H, s), 2.26 (2H, dd), 2.67 (3H, d), 2.77-2.86 (2H, m), 3.81 (3H, s), 5.61 (1H, dd), 6.16-6.35 (2H, m), 6.76 (1H, d), 6.88 (1H, d), 7.23 (1H, s), 7.65 (1H, s), 8.50 (2H, dd), 8.59 (1H, s), 9.02 (1H, s), 9.28 (1H, s), 10.08 (1H, s); m/z: ES$^+$ MH$^+$ 512.29.

Example 40: N-{5-[(5-Cyano-4-pyrazolo[1,5-a]pyridin-3-ylpyrimidin-2-yl)amino]-2-[3-dimethylaminoazetidin-1-yl]-4-methoxyphenyl}prop-2-enamide A solution of acryloyl chloride (0.025 mL, 0.31 mmol) in CH$_2$Cl$_2$ (1 mL) was added dropwise to a stirred solution of 2-{[5-amino-4-(3-dimethylaminoazetidin-1-yl)-2-methoxyphenyl]amino}-4-pyrazolo[1,5-a]pyridin-3-ylpyrimidine-5-carbonitrile (Intermediate 122, 136 mg, 0.30 mmol) in CH$_2$Cl$_2$ (15 mL), which was cooled in an ice bath to approximately 0° C. The mixture was stirred for 1 h, and was then diluted with CH$_2$Cl$_2$ (50 mL) and methanol (to fully dissolve suspension). This solution was then washed with sat. NaHCO$_3$ (100 mL) which had been diluted with water (10 mL). The aqueous wash solution was then extracted with CH$_2$Cl$_2$ (2×50 mL) and the combined organic solutions were dried (MgSO$_4$) and concentrated in vacuo. Purification by FCC, eluting with 0-5% 7N methanolic ammonia in $CH_2Cl_2$ gave the title compound (136 mg, 89%) as a yellow solid; $^1$H NMR: 2.10 (6H, s), 3.05-3.13 (1H, m), 3.62 (2H, t), 3.74 (3H, s), 4.00 (2H, s), 5.67 (1H, d), 6.17 (1H, d), 6.27 (1H, s), 6.45 (1H, dd), 7.16 (1H, br s), 7.25 (1H, s), 7.42 (1H, br s), 7.95 (1H, br s), 8.68 (1H, s), 8.87 (1H, br s), 8.91 (1H, s), 9.28 (1H, s), 9.32 (1H, br s); m/z: ES$^+$ MH$^+$ 510.18.

Example 41: N-(2-{(3aR,6aR)-5-Methyl-2,3,3a,4,6,6a-hexahydropyrrolo[3,4-b]pyrrol-1-yl}-4-methoxy-5-{[4-(1-methylindol-3-yl)pyrimidin-2-yl]amino}phenyl)prop-2-enamide Acryloyl chloride (41.3 mg, 0.46 mmol) in THF (1 mL) was added dropwise to a stirred solution of 4-[(3aR,6aR)-5-methyl-2,3,3a,4,6,6a-hexahydropyrrolo[3,4-b]pyrrol-1-yl]-6-methoxy-N-[4-(1-methylindol-3-yl)pyrimidin-2-yl]benzene-1,3-diamine (Intermediate 123, 195 mg, 0.42 mmol) in THF (3 mL), cooled in an ice/methanol bath to approximately −15° C. Upon slow addition of the acryloyl chloride a precipitate immediately formed. The mixture was stirred for 1 h while being gradually warmed to 0° C. The mixture was then diluted with $CH_2Cl_2$ (50 mL) and washed with sat. $NaHCO_3$ (50 mL). The resulting aqueous solution was extracted with $CH_2Cl_2$ (2×25 mL). The combined organic solutions were dried ($MgSO_4$) and concentrated onto silica. Purification by FCC, eluting with 0-5% 7N methanolic ammonia in $CH_2Cl_2$ gave crude solid product after concentration of appropriate fractions in vacuo. This solid was dissolved in the minimum amount of hot $CH_2Cl_2$ and triturated with diethyl ether to give the title compound (115 mg, 53%) as a white solid; $^1$H NMR (CDCl$_3$) 1.77-1.96 (2H, m), 2.15-2.26 (1H, m), 2.29 (3H, s), 2.26-2.37 (1H, m), 2.73 (1H, d), 2.80 (1H, d), 2.83-2.90 (1H, m), 2.95 (1H, td), 3.21 (1H, t), 3.57-3.68 (1H, m), 3.88 (3H, s), 4.00 (3H, s), 5.68-5.74 (1H, m), 6.45 (2H, d), 6.81 (1H, s), 7.20 (1H, d), 7.23-7.31 (2H, m) partially obscured under CDCl$_3$ signal, 7.37-7.43 (1H, m), 7.71 (1H, s), 8.02-8.10 (1H, m), 8.38 (1H, d), 9.09 (1H, s), 9.46 (1H, s), 9.85 (1H, s); m/z: ES$^+$ MH$^+$ 524.25.

Example 42: N-(2-{2-Dimethylaminoethyl-methyl-amino}-4-methoxy-5-{[4-(4,5,6,7-tetrahydropyrazolo[1,5-a]pyridin-3-yl)pyrimidin-2-yl]amino}phenyl)prop-2-enamide A solution of acryloyl chloride (0.354 mL, 4.35 mmol) in $CH_2Cl_2$ (5 mL) was added dropwise to a mixture of N$^1$-(2-dimethylaminoethyl)-5-methoxy-N$^1$-methyl-N$^4$-[4-(4,5,6,7-tetrahydropyrazolo[1,5-a]pyridin-3-yl)pyrimidin-2-yl]benzene-1,2,4-triamine (Intermediate 125, 1.9 g, 4.35 mmol) in $CH_2Cl_2$ (100 mL), which was cooled in an ice/water bath. The resulting mixture was stirred for 1 h and then washed with sat. $NaHCO_3$. The resulting organic solution was dried ($Na_2SO_4$) and concentrated in vacuo. Purification by FCC, eluting with 1.5% 7N methanolic ammonia in $CH_2Cl_2$ gave the title compound (1.069 g, 50%) as an oil which crystallised on standing to give a cream crystalline solid. Some later fractions from the FCC which had a brown colour were concentrated and re-chromatographed to give more of the title compound (334 mg, 16%) as a pale brown oil which crystallised on standing to give a tan-coloured crystalline solid. Total yield: 1.403 g, 66%; $^1$H NMR: 1.69-1.77 (2H, m), 1.88-1.97 (2H, m), 2.21 (6H, s), 2.29 (2H, t), 2.71 (3H, s), 2.88 (2H, t), 3.02 (2H, t), 3.84 (3H, s), 4.09 (2H, t), 5.74 (1H, dd), 6.24 (1H, dd), 6.40 (1H, dd), 6.97-7.02 (2H, m), 7.87 (1H, s), 8.13 (1H, s), 8.31 (1H, d), 8.85 (1H, s), 10.08 (1H, s); m/z: ES$^+$ MH$^+$ 491.34.

Example 43: N-(2-{(3aR,6aR)-5-Methyl-2,3,3a,4,6,6a-hexahydropyrrolo[3,4-b]pyrrol-1-yl}-4-methoxy-5-{[4-(4,5,6,7-tetrahydropyrazolo[1,5-a]pyridin-3-yl)pyrimidin-2-yl]amino}phenyl)prop-2-enamide A solution of acryloyl chloride (26 mg, 0.29 mmol) in THF (1 mL) was added dropwise to a stirred solution of 4-[(3aR,6aR)-5-methyl-2,3,3a,4,6,6a-hexahydropyrrolo[3,4-b]pyrrol-1-yl]-6-methoxy-N-[4-(4,5,6,7-tetrahydropyrazolo[1,5-a]pyridin-3-yl)pyrimidin-2-yl]benzene-1,3-diamine (Intermediate 132, 120 mg, 0.26 mmol) in THF (3 mL), which was cooled in an ice/methanol bath to approx −15° C. The mixture was stirred for 1 h, gradually warming to 0° C. The mixture was then diluted with $CH_2Cl_2$ (50 mL) and washed with sat. $NaHCO_3$ (50 mL). The resulting aqueous wash solution was further extracted with $CH_2Cl_2$ (2×25 mL) and the combined organic solutions were then dried ($MgSO_4$) and concentrated in vacuo onto silica. Part-purification was achieved by FCC, eluting with 0-5% 7N methanolic ammonia in $CH_2Cl_2$ and impure product containing fractions were combined and concentrated in vacuo. Purification by FCC, eluting with 0-2% 7N methanolic ammonia in $CH_2Cl_2$ and then eluting with 0-3% $CH_3OH$ in $CH_2Cl_2$ gave the title compound (19 mg, 14%) as a cream foam; $^1$H NMR (CDCl$_3$): 1.82-1.97 (4H, m), 2.00-2.06 (2H, m), 2.13-2.24 (1H, s), 2.25-2.39 (1H, m), 2.29 (3H, s), 2.67-2.98 (4H, m), 3.17-3.26 (3H, m), 3.66 (1H, br s), 3.86 (3H, s), 4.18 (2H, t), 5.64-5.71 (1H, m), 6.30-6.47 (2H, m), 6.78 (1H, s), 6.81 (1H, d), 7.44 (1H, s), 8.06 (1H, s), 8.34 (1H, d), 9.24 (1H, s), 9.40 (1H, s); m/z: ES$^+$ MH$^+$ 515.15.

Example 44: N-(2-{(3R)-3-Dimethylaminopyrrolidin-1-yl}-4-methoxy-5-{[4-(4,5,6,7-tetrahydropyrazolo[1,5-a]pyridin-3-yl)pyrimidin-2-yl]amino}phenyl)prop-2-enamide A solution of acryloyl chloride (32 mg, 0.36 mmol) in $CH_2Cl_2$ (1 mL) was added dropwise to a stirred solution of 4-[(3R)-3-dimethylaminopyrrolidin-1-yl]-6-methoxy-N-[4-(4,5,6,7-tetrahydropyrazolo[1,5-a]pyridin-3-yl)pyrimidin-2-yl]benzene-1,3-diamine (Intermediate 134, 152 mg, 0.34 mmol) in $CH_2Cl_2$ (15 mL), which was cooled in an ice/water bath. The solution was stirred for 10 minutes while cooled by the ice bath, and was then allowed to warm to r.t. then stirred for 1 h. The mixture was then diluted with $CH_2Cl_2$ and washed with sat. $NaHCO_3$ and then brine. The organic solution was then dried ($MgSO_4$) and concentrated in vacuo. Purification by FCC, eluting with 0-5% 7N methanolic ammonia in $CH_2Cl_2$ gave crude product (100 mg) as a beige solid after trituration with diethyl ether. $CH_3CN$ (~3 mL) was then added to the crude product and the resulting slurry was stirred at 50° C. for 4 h. After cooling to r.t. the suspended solid was collected by filtration, washed with $CH_3CN$ and dried at 45° C. overnight to give the title compound (72 mg, 42%) as a yellow solid; $^1$H NMR: 1.68-1.81 (3H, m), 1.89-1.98 (2H, m), 2.03-2.11 (1H, m), 2.17 (6H, s), 2.66-2.74 (1H, m), 3.00-3.05 (2H, m), 3.13-3.21 (3H, m), 3.31-3.38 (1H, m), 3.86 (3H, s), 4.09 (2H, t), 5.70 (1H, dd), 6.21 (1H, dd), 6.48-6.56 (2H, m), 6.96 (1H, d), 7.72 (1H, s), 8.03 (2H, d), 8.27 (1H, d), 9.30 (1H, s); m/z: ES$^+$ MH$^+$ 503.67.

Example 45: N-(4-Methoxy-2-{1-methyl-3,6-dihydro-2H-pyridin-4-yl}-5-{[4-(4,5,6,7-tetrahydropyrazolo[1,5-a]pyridin-3-yl)pyrimidin-2-yl]amino}phenyl)prop-2-enamide A solution of acryloyl chloride (30 μL, 0.37 mmol) in $CH_2Cl_2$ (2 mL) was added dropwise over 5 minutes to 4-methoxy-6-(1-methyl-3,6-dihydro-2H-pyridin-4-yl)-N'-[4-(4,5,6,7-tetrahydropyrazolo[1,5-a]pyridin-3-yl)pyrimidin-2-yl]benzene-1,3-diamine (Intermediate 136, 154 mg, 0.36 mmol) in $CH_2Cl_2$ (5 mL), which was cooled in an ice/$CH_3OH$ bath. The mixture was then stirred for 0.5 h. The mixture was then diluted with 10% $CH_3OH/CH_2Cl_2$ and the resulting solution was washed with sat. $NaHCO_3$, dried ($MgSO_4$) and then concentrated in vacuo. Purification by FCC, eluting with 0-10% methanolic ammonia in $CH_2Cl_2$ gave the title compound (104 mg, 60%) as an pale yellow solid after trituration with diethyl ether/heptane; $^1H$ NMR: 1.76-1.84 (2H, m), 1.91-1.98 (2H, m), 2.27 (3H, s), 2.32-2.39 (2H, m), 2.48-2.56 (2H, m), 2.96-2.99 (2H, m), 3.08 (2H, t), 3.90 (3H, s), 4.11 (2H, t), 5.65-5.76 (2H, m), 6.21 (1H, d), 6.49 (1H, dd), 6.84 (1H, s), 7.07 (1H, d), 7.84 (1H, s), 8.10 (1H, s), 8.32-8.37 (2H, m), 9.33 (1H, s); m/z: $ES^+$ $MH^+$ 486.73.

Example 46: N-(2-{3-Dimethylaminoazetidin-1-yl}-4-methoxy-5-{[4-(4,5,6,7-tetrahydropyrazolo[1,5-a]pyridin-3-yl)pyrimidin-2-yl]amino}phenyl)prop-2-enamide A solution of acryloyl chloride (22.5 mg, 0.25 mmol) in $CH_2Cl_2$ (1 mL) was added dropwise to a stirred solution of 4-(3-dimethylaminoazetidin-1-yl)-6-methoxy-N-[4-(4,5,6,7-tetrahydropyrazolo[1,5-a]pyridin-3-yl)pyrimidin-2-yl]benzene-1,3-diamine (Intermediate 139, 108 mg, 0.25 mmol) in $CH_2Cl_2$ (12 mL), which was cooled in an ice/water bath. The solution was stirred for 10 minutes while being cooled by the bath, was then allowed to warm to r.t. and was then stirred for 1 h. The mixture was then diluted with $CH_2Cl_2$ and washed with sat. $NaHCO_3$, brine and was then dried ($MgSO_4$). Purification by FCC, eluting with 0-5% 7N methanolic ammonia in $CH_2Cl_2$ gave the title compound (56 mg, 46%) as a brown solid after trituration with diethyl ether; $^1H$ NMR: 1.75-1.82 (2H, m), 1.90-1.97 (2H, m), 2.08 (6H, s), 2.98-3.09 (3H, m), 3.54 (2H, t), 3.85 (3H, s), 3.93 (2H, t), 4.09 (2H, t), 5.69 (1H, dd), 6.18-6.25 (2H, m), 6.49 (1H, dd), 6.95 (1H, d), 7.70 (1H, s), 7.89 (1H, s), 8.03 (1H, s), 8.26 (1H, d), 9.24 (1H, s); m/z: $ES^+$ $MH^+$ 489.63.

Example 47: N-(4-Methoxy-2-{8-methyl-2,8-diazaspiro[3.4]octan-2-yl}-5-{[4-(4,5,6,7-tetrahydropyrazolo[1,5-a]pyridin-3-yl)pyrimidin-2-yl]amino}phenyl)prop-2-enamide A solution of acryloyl chloride (42 μL, 0.52 mmol) in $CH_2Cl_2$ (1 mL) was added dropwise to 4-methoxy-6-(8-methyl-2,8-diazaspiro[3.4]octan-2-yl)-N'-[4-(4,5,6,7-tetrahydropyrazolo[1,5-a]pyridin-3-yl)pyrimidin-2-yl]benzene-1,3-diamine (Intermediate 141, 240 mg, 0.52 mmol) and DIPEA (0.099 mL, 0.57 mmol) in $CH_2Cl_2$ (10 mL), which was cooled in an ice/water bath. The mixture was stirred for 1 h and then washed with brine, dried ($Na_2SO_4$) and concentrated in vacuo. Purification by FCC, eluting with 2% 7N methanolic ammonia in $CH_2Cl_2$ gave the title compound (135 mg, 50%) as a yellow solid after trituration with $CH_3CN$; $^1H$ NMR: 1.61-1.74 (2H, m), 1.73-1.85 (2H, m), 1.87-1.99 (2H, m), 2.03 (2H, t), 2.35 (3H, s), 2.61 (2H, t), 3.01 (2H, t), 3.60 (2H, d), 3.84 (3H, s), 3.89 (2H, d), 4.09 (2H, t), 5.70 (1H, d), 6.14-6.30 (2H, m), 6.47 (1H, dd), 6.95 (1H, d), 7.73 (1H, s), 7.83 (1H, s), 8.05 (1H, s), 8.26 (1H, d), 9.26 (1H, s); m/z: $ES^+$ $MH^+$ 515.7.

Example 48: N-(4-Methoxy-2-{1-methyl-3,6-dihydro-2H-pyridin-4-yl}-5-{[4-(1-methylindol-3-yl)pyrimidin-2-yl]amino}phenyl)prop-2-enamide A solution of acryloyl chloride (37 μL, 0.45 mmol) in $CH_2Cl_2$ (2.32 mL) was added dropwise over 5 minutes to 4-methoxy-6-(1-methyl-3,6-dihydro-2H-pyridin-4-yl)-N'-[4-(1-methylindol-3-yl)pyrimidin-2-yl]benzene-1,3-diamine (Intermediate 143, 189 mg, 0.43 mmol) in $CH_2Cl_2$ (5.8 mL), which was cooled in an ice/$CH_3OH$ bath. The mixture was stirred for 0.5 h and was then diluted with 10% $CH_3OH/CH_2Cl_2$. The resulting solution was washed with sat. $NaHCO_3$, dried ($MgSO_4$) and concentrated in vacuo. Purification by FCC, eluting with 0-20% $CH_3OH$ in $CH_2Cl_2$ gave the title compound (67 mg, 32%) as an pale yellow solid after trituration with diethyl ether; $^1H$ NMR: 2.29 (3H, s), 2.36-2.41 (2H, m), 2.53-2.58 (2H, m), 2.98-3.02 (2H, m), 3.90 (3H, s), 3.91 (3H, s), 5.69-5.73 (2H, m), 6.22 (1H, dd), 6.52 (1H, dd), 6.86 (1H, s), 7.20-7.28 (3H, m), 7.52-7.55 (1H, m), 7.88 (1H, s), 8.33-8.37 (2H, m), 8.43 (1H, s), 8.45 (1H, s), 9.34 (1H, s); m/z: $ES^+$ $MH^+$ 495.70.

Example 49: N-(4-Methoxy-2-{8-methyl-2,8-diazaspiro[3.4]octan-2-yl}-5-{[4-(1-methylindol-3-yl)pyrimidin-2-yl]amino}phenyl)prop-2-enamide A solution of acryloyl chloride (24 μL, 0.30 mmol) in $CH_2Cl_2$ (1 mL) was added dropwise to 4-methoxy-6-(8-methyl-2,8-diazaspiro[3.4]octan-2-yl)-N'-[4-(1-methylindol-3-yl)pyrimidin-2-yl]benzene-1,3-diamine (Intermediate 146, 140 mg, 0.30 mmol) and DIPEA (57 μL, 0.33 mmol) in $CH_2Cl_2$ (10 mL), which was cooled in an ice/water bath. The mixture was stirred for 1 h and was then washed with brine, dried ($Na_2SO_4$) and concentrated in vacuo. Purification by FCC, eluting with 2% 7N methanolic ammonia in $CH_2Cl_2$ gave the title compound (43 mg, 28%) as a beige solid after trituration with $CH_3CN$; $^1H$ NMR: 1.63-1.76 (2H, m), 2.00-2.10 (2H, m), 2.38 (3H, s), 2.63 (2H, t), 3.64 (2H, d), 3.86 (3H, s), 3.89 (3H, s), 3.93 (2H, d), 5.70 (1H, dd), 6.21 (1H, dd), 6.26 (1H, s), 6.50 (1H, dd), 7.13 (1H, d), 7.16-7.29 (2H, m), 7.51 (1H, d), 7.73 (1H, s), 7.93 (1H, s), 8.26 (1H, d), 8.31-8.39 (2H, m), 9.24 (1H, s); m/z: $ES^+$ $MH^+$ 524.7.

Example 50: N-(2-{(3S)-3-Dimethylaminopyrrolidin-1-yl}-4-methoxy-5-{[4-(1-methylindol-3-yl)pyrimidin-2-yl]amino}phenyl)prop-2-enamide A solution of acryloyl chloride (1M in $CH_2Cl_2$, 0.36 mL, 0.36 mmol) was added dropwise to a solution of 4-[(3S)-3-dimethylaminopyrrolidin-1-yl]-6-methoxy-N-[4-(1-methylindol-3-yl)pyrimidin-2-yl]benzene-1,3-diamine (Intermediate 148, 183 mg, 0.40 mmol) in $CH_2Cl_2$ (5 mL) at −10° C. over a period of 2 minutes under an atmosphere of $N_2$. The resulting mixture was stirred at 0° C. for 10 minutes and was then allowed to warm to r.t. over 20 minutes. The mixture was then washed with sat. $NaHCO_3$ (2 mL), dried ($MgSO_4$) and concentrated in vacuo. Purification by FCC, eluting with 3-25% $CH_3OH$ in $CH_2Cl_2$ gave an oil which later crystallised. This solid was triturated and washed with EtOAc (3 mL) to give the title compound (67 mg, 33%) as a pale yellow solid; $^1H$ NMR: 1.77 (1H, m), 2.08 (1H, s), 2.18 (6H, s), 2.72 (1H, m), 3.17 (1H, s), 3.21 (2H, d), 3.32-3.45 (1H, m), 3.87 (3H, s), 3.89 (3H, s), 5.70 (1H, d), 6.22 (1H, d), 6.48-6.58 (1H, m), 6.59 (1H, s), 7.20 (3H, m), 7.51 (1H, d), 7.76 (1H, s), 8.17 (1H, s), 8.28 (1H, d), 8.32 (1H, d), 8.39 (1H, s), 9.33 (1H, s); m/z: $ES^+$ $MH^+$ 512.7.

Example 51: N-{4-Methoxy-2-[1-methyl-3,6-dihydro-2H-pyridin-4-yl]-5-[(4-pyrazolo[1,5-a]pyridin-3-ylpyrimidin-2-yl)amino]phenyl}prop-2-enamide A solution of acryloyl chloride (20 μL, 0.25 mmol) was added dropwise to 4-methoxy-6-(1-methyl-3,6-dihydro-2H- pyridin-4-yl)-N'-(4-pyrazolo[1,5-a]pyridin-3-ylpyrimidin-2-yl)benzene-1,3-diamine (Intermediate 150, 180 mg, 0.42 mmol) and triethylamine (73 µL, 0.53 mmol) in THF (3 mL) at −5° C. over a period of 1 minute under an atmosphere of $N_2$. The resulting mixture was stirred at 0° C. for 0.25 h. The reaction was judged to be incomplete so further acryloyl chloride (10 µL, 0.125 mmol) was added dropwise and the mixture was stirred at 0° C. for a further 15 minutes. The mixture was then concentrated in vacuo and the resulting residue was dissolved in $CH_2Cl_2$ (5 mL) plus a few drops of $CH_3OH$. This solution was washed with sat. $NaHCO_3$ (2 mL), dried ($MgSO_4$) and filtered through a 1 g silica pad, eluting with 4:1 $CH_2Cl_2$—$CH_3OH$. Eluent that contained desired product was concentrated in vacuo. Purification by FCC, eluting with 5-20% $CH_3OH$ in $CH_2Cl_2$ gave the title compound (31 mg, 14%) as a cream crystalline solid; $^1H$ NMR: 2.33 (3H, s), 2.40 (2H, s), 2.57 (2H, d), 3.03 (2H, s), 3.89 (3H, s), 5.70 (2H, m), 6.17 (1H, m), 6.46 (1H, m), 6.88 (1H, s), 7.09 (1H, t), 7.32 (1H, d), 7.47 (1H, t), 8.12 (1H, s), 8.21 (1H, s), 8.39 (1H, d), 8.51 (1H, d), 8.81 (2H, m), 9.36 (1H, s); m/z: $ES^+$ $MH^+$ 482.

Example 52: N-{2-[(3R)-3-Dimethylaminopyrrolidin-1-yl]-4-methoxy-5-[(4-pyrazolo[1,5-a]pyridin-3-ylpyrimidin-2-yl)amino]phenyl}prop-2-enamide A solution of acryloyl chloride (64 µL, 0.79 mmol) in $CH_2Cl_2$ (4 mL) was added dropwise over 10 minutes to 4-[(3R)-3-dimethylaminopyrrolidin-1-yl]-6-methoxy-N-(4-pyrazolo[1,5-a]pyridin-3-ylpyrimidin-2-yl)benzene-1,3-diamine (Intermediate 153, 336 mg, 0.76 mmol) in $CH_2Cl_2$ (11 mL), which was cooled in an ice/$CH_3OH$ bath. The mixture was stirred for 0.5 h, and was then diluted with 10% $CH_3OH/CH_2Cl_2$. The resulting solution was washed with sat.$NaHCO_3$, dried ($MgSO_4$) and concentrated in vacuo. Purification by FCC, eluting with 0-5% methanolic ammonia in $CH_2Cl_2$ gave the title compound (296 mg, 79%) as an orange solid after trituration with diethyl ether; $^1H$ NMR: 1.70-1.81 (1H, m), 2.05-2.13 (1H, m), 2.18 (6H, s), 2.68-2.76 (1H, m), 3.17-3.27 (3H, m), 3.35-3.42 (1H, m), 3.84 (3H, s), 5.67 (1H, dd), 6.17 (1H, dd), 6.51 (1H, dd), 6.56 (1H, s), 7.05 (1H, dd), 7.21 (1H, d), 7.40-7.45 (1H, m), 7.84 (1H, s), 8.02 (1H, s), 8.30 (1H, d), 8.46 (1H, d), 8.76 (1H, s), 8.78 (1H, d), 9.35 (1H, s); m/z: $ES^+$ $MH^+$ 499.69.

Example 53: N-{2-(3-Dimethylaminoazetidin-1-yl)-4-methoxy-5-[(4-pyrazolo[1,5-a]pyridin-3-ylpyrimidin-2-yl)amino]phenyl}prop-2-enamide A solution of acryloyl chloride (49 µL, 0.60 mmol) in $CH_2Cl_2$ (2.77 mL) was added dropwise over 5 minutes to 4-(3-dimethylaminoazetidin-1-yl)-6-methoxy-N-(4-pyrazolo[1,5-a]pyridin-3-ylpyrimidin-2-yl)benzene-1,3-diamine (Intermediate 156, 246 mg, 0.57 mmol) in $CH_2Cl_2$ (8.3 mL), which was cooled in an ice/$CH_3OH$ bath. The mixture was stirred for 0.5 h asn was then diluted with 10% $CH_3OH/CH_2Cl_2$. The resulting solution was washed with sat. $NaHCO_3$, dried ($MgSO_4$) and concentrated in vacuo. Purification by FCC, eluting with 0-5% methanolic ammonia in $CH_2Cl_2$ gave the title compound (182 mg, 66%) as a yellow solid after trituration with diethyl ether; $^1H$ NMR: 2.09 (6H, s), 3.04-3.12 (1H, m), 3.55-3.60 (2H, m), 3.83 (3H, s), 3.96 (2H, t), 5.67 (1H, dd), 6.18 (1H, dd), 6.26 (1H, s), 6.48 (1H, dd), 7.05 (1H, td), 7.20 (1H, d), 7.41-7.46 (1H, m), 7.71 (1H, s), 8.00 (1H, s), 8.29 (1H, d), 8.43 (1H, br d), 8.75 (1H, s), 8.77 (1H, d), 9.29 (1H, s); m/z: $ES^+$ $MH^+$ 485.69.

Example 54: N-{2-[2-Dimethylaminoethyl-methylamino]-4-methoxy-5-[(4-pyrazolo[1,5-a]pyridin-3-ylpyrimidin-2-yl)amino]phenyl}prop-2-enamide A solution of acryloyl chloride (63 µL, 0.78 mmol) in $CH_2Cl_2$ (3.60 mL) was added dropwise over 5 minutes to $N^1$-(2-dimethylaminoethyl)-5-methoxy-$N^1$-methyl-$N^4$-(4-pyrazolo[1,5-a]pyridin-3-ylpyrimidin-2-yl)benzene-1,2,4-triamine (Intermediate 158, 320 mg, 0.74 mmol) in $CH_2Cl_2$ (10.8 mL), which was cooled in an ice/$CH_3OH$ bath. The mixture was stirred for 0.5 h, and was then diluted with 10% $CH_3OH/CH_2Cl_2$. The resulting solution was washed with sat. $NaHCO_3$, dried ($MgSO_4$) and concentrated in vacuo. Purification by FCC, eluting with 0-5% methanolic ammonia in $CH_2Cl_2$ gave the title compound (228 mg, 63%) as a pale pink solid after trituration with diethyl ether; $^1H$ NMR: 2.22 (6H, s), 2.33 (2H, t), 2.74 (3H, s), 2.91 (2H, t), 3.82 (3H, s), 5.73 (1H, dd), 6.19 (1H, dd), 6.41 (1H, dd), 7.02-7.06 (2H, m), 7.25 (1H, d), 7.29-7.34 (1H, m), 8.17 (1H, s), 8.34 (1H, d), 8.44 (1H, d), 8.75-8.79 (2H, m), 8.82 (1H, s), 10.06 (1H, br s); m/z: $ES^+$ $MH^+$ 487.72.

Example 55: N-[2-[(3aR,6aR)-5-Methyl-2,3,3a,4,6,6a-hexahydropyrrolo[3,4-b]pyrrol-1-yl]-4-methoxy-5-[(4-pyrazolo[1,5-a]pyridin-3-ylpyrimidin-2-yl)amino]phenyl]prop-2-enamide A solution of acryloyl chloride (13 mg, 0.14 mmol) in THF (1 mL) was added dropwise to a stirred solution of 4-[(3aR,6aR)-5-methyl-2,3,3a,4,6,6a-hexahydropyrrolo[3,4-b]pyrrol-1-yl]-6-methoxy-N-(4-pyrazolo[1,5-a]pyridin-3-ylpyrimidin-2-yl)benzene-1,3-diamine (Intermediate 160, 100 mg, 0.13 mmol) in THF (3 mL), which was cooled in an ice/$CH_3OH$ bath to approximately −15° C. The mixture was stirred for 1 h and allowed to warm to −0° C. The mixture was then diluted with $CH_2Cl_2$ (50 mL) and the resulting solution was washed with sat. $NaHCO_3$ (50 mL). The aqueous solution was further extracted with $CH_2Cl_2$ (2×25 mL) and the combined organic solutions were dried ($MgSO_4$) and concentrated in vacuo onto silica. Patrial purification by FCC, eluting with 0-3.5% 7N methanolic ammonia in $CH_2Cl_2$ provided some of the title compound. Further purification by FCC, eluting with 0-1.5% 7N methanolic ammonia in $CH_2Cl_2$ gave the title compound (33 mg, 49%) as a yellow solid; $^1H$ NMR: 1.77 (1H, s), 1.94-2.15 (1H, m), 2.10 (3H, s), 2.29 (1H, d), 2.39-2.48 (1H, m), 2.87 (1H, s), 3.11-3.20 (1H, m), 3.33-3.42 (2H, m), 3.81 (3H, s), 4.26-4.34 (1H, m), 5.68 (1H, dd), 6.18 (1H, dd), 6.53 (1H, dd), 6.67 (1H, s), 7.04 (1H, td), 7.21 (1H, d), 7.36-7.43 (1H, m), 8.03 (1H, s), 8.08 (1H, s), 8.30 (1H, d), 8.42 (1H, d), 8.73-8.79 (2H, m), 9.41 (1H, s); m/z: $ES^+$ $MH^+$ 511.16.

Example 56: N-{4-Methoxy-2-[8-methyl-2,8-diazaspiro[3.4]octan-2-yl]-5-[(4-pyrazolo[1,5-a]pyridin-3-ylpyrimidin-2-yl)amino]phenyl}prop-2-enamide A solution of acryloyl chloride (0.766 mL, 0.77 mmol, 1.0 M in $CH_2Cl_2$) was added dropwise over 10 minutes to 4-methoxy-6-(8-methyl-2,8-diazaspiro[3.4]octan-2-yl)-N'-(4-pyrazolo[1,5-a]pyridin-3-ylpyrimidin-2-yl)benzene-1,3-diamine (Intermediate 162, 333 mg, 0.73 mmol) in $CH_2Cl_2$ (6 mL), which was cooled in an ice/$CH_3OH$ bath. The mixture was then stirred for 0.5 h, then diluted with 10% $CH_3OH$ in $CH_2Cl_2$. The resulting solution was washed with sat. $NaHCO_3$, dried ($MgSO_4$) and concentrated in vacuo. Purification by FCC, eluting with 1-10% methanolic ammonia in $CH_2Cl_2$ gave the title compound (193 mg, 52%) as an beige solid after trituration with diethyl ether; ¹H NMR: 1.69 (2H, dt), 2.03-2.08 (2H, m), 2.38 (3H, s), 2.63 (2H, t), 3.65 (2H, d), 3.83 (3H, s), 3.94 (2H, d), 5.68 (1H, dd), 6.19 (1H, dd), 6.25 (1H, s), 6.47 (1H, dd), 7.06 (1H, td), 7.19 (1H, d), 7.44 (1H, dd), 7.67 (1H, s), 7.98 (1H, s), 8.29 (1H, d), 8.47 (1H, d), 8.75 (1H, s), 8.78 (1H, d), 9.25 (1H, s); m/z: ES⁺ MH⁺ 511.34.

Example 57: N-(2-{(3R)-3-Dimethylaminopyrrolidin-1-yl}-5-{[4-(1H-indol-3-yl)pyrimidin-2-yl]amino}-4-methoxyphenyl)prop-2-enamide A solution of acryloyl chloride (0.604 mL, 1M in CH₂Cl₂, 0.60 mmol) was added dropwise to 4-[(3R)-3-dimethylaminopyrrolidin-1-yl]-N-[4-(1H-indol-3-yl)pyrimidin-2-yl]-6-methoxybenzene-1,3-diamine (Intermediate 164, 268 mg, 0.60 mmol) in CH₂Cl₂ (10 mL) and 10 mL DMA, which was cooled to −5° C. The resulting mixture was stirred at −5° C. for 1 h and was then diluted with CH₂Cl₂ (100 mL). The resulting solution was washed with sat. NaHCO₃ (25 mL), water (25 mL), and then sat. brine (4×25 mL), and was then concentrated in vacuo. Purification by FCC, eluting with 0-30% CH₃OH in CH₂Cl₂ gave the title compound (135 mg, 45%) as a beige solid; ¹H NMR (CDCl₃) 1.98 (1H, s), 2.18 (1H, d), 2.94 (1H, s), 3.11 (4H, d), 3.88 (3H, s), 5.73 (1H, d), 6.40 (2H, d), 6.76 (1H, s), 7.17 (1H, d), 7.22-7.24 (1H, m), 7.41-7.46 (1H, m), 7.62 (1H, s), 8.16 (1H, s), 8.39 (1H, d), 8.45 (1H, s), 8.75 (1H, s), 8.86 (1H, s), 9.56 (1H, s); m/z: ES⁺ MH⁺ 498.

Example 58: N-(2-[3-Dimethylaminoazetidin-1-yl]-5-{[4-(1H-indol-3-yl)pyrimidin-2-yl]amino}-4-methoxyphenyl)prop-2-enamide A solution of acryloyl chloride (0.522 mL, 1M in CH₂Cl₂, 0.52 mmol) was added dropwise to 4-(3-dimethylaminoazetidin-1-yl)-N-[4-(1H-indol-3-yl)pyrimidin-2-yl]-6-methoxybenzene-1,3-diamine (Intermediate 166, 224 mg, 0.52 mmol) in CH₂Cl₂ (10 mL) and the mixture was then stirred at −5° C. for 1 h. The mixture was then diluted with CH₂Cl₂ (100 mL), and the resulting solution was washed with sat. NaHCO₃ (25 mL), water (25 mL), and then sat. brine (25 mL) and then concentrated in vacuo. Purification by FCC, eluting with 0-30% CH₃OH in CH₂Cl₂ gave the title compound (46 mg, 18%) as a beige solid; ¹H NMR: 2.09 (6H, d), 3.09 (1H, s), 3.56 (2H, t), 3.85 (3H, s), 3.96 (2H, t), 5.68 (1H, dd), 6.20 (1H, dd), 6.26 (1H, s), 6.50 (1H, dd), 7.14 (2H, dt), 7.18 (1H, t), 7.40-7.46 (1H, m), 7.82 (1H, s), 7.90 (1H, s), 8.23 (1H, d), 8.31 (1H, d), 8.38 (1H, d), 9.34 (1H, s), 11.76 (1H, s); m/z: ES⁺ MH⁺ 484.

Example 59: N-(2-[2-Dimethylaminoethyl-methylamino]-5-{[4-(1H-indol-3-yl)pyrimidin-2-yl]amino}-4-methoxyphenyl)prop-2-enamide

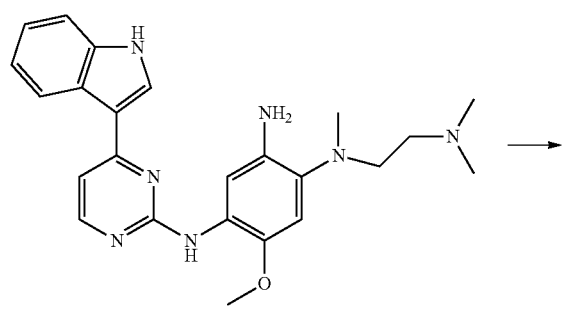

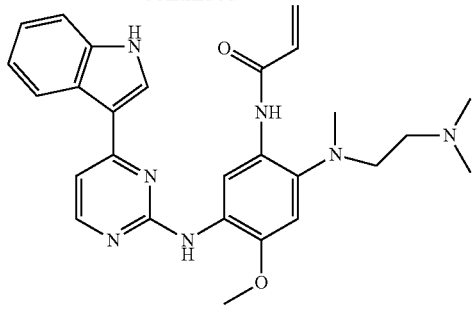

A solution of acryloyl chloride (0.584 mL, 1M in CH₂Cl₂, 0.58 mmol) was added dropwise to N¹-(2-dimethylaminoethyl)-N⁴-[4-(1H-indol-3-yl)pyrimidin-2-yl]-5-methoxy-N¹-methylbenzene-1,2,4-triamine (Intermediate 168, 252 mg, 0.58 mmol) in CH₂Cl₂ (10 mL) and the mixture was then stirred at −5° C. for 1 h. The mixture was then diluted with CH₂Cl₂ (100 mL), and the resulting solution was washed with sat. NaHCO₃ (25 mL), water (25 mL), and then sat. brine (25 mL), and was then concentrated in vacuo. Purification by FCC, eluting with 0-30% CH₃OH in CH₂Cl₂ gave the title compound (76 mg, 27%) as a white solid; ¹H NMR (CDCl₃) 2.25 (6H, s), 2.27-2.34 (3H, m), 2.69 (3H, s), 2.84-2.94 (2H, m), 3.87 (3H, s), 5.68 (1H, dd), 6.40 (1H, d), 6.48 (1H, dd), 6.78 (1H, s), 7.03 (1H, d), 7.08-7.20 (2H, m), 7.33 (1H, dd), 7.65 (1H, s), 8.12 (1H, d), 8.26 (1H, d), 8.59 (1H, s), 9.74 (1H, s), 9.97 (1H, s), 10.24 (1H, s); m/z: ES⁺ MH⁺ 486.

Example 60: N-(4-Methoxy-5-{[4-(1-methylindol-3-yl)pyrimidin-2-yl]amino}-2-[methyl-(2-methylaminoethyl)amino]phenyl)prop-2-enamide

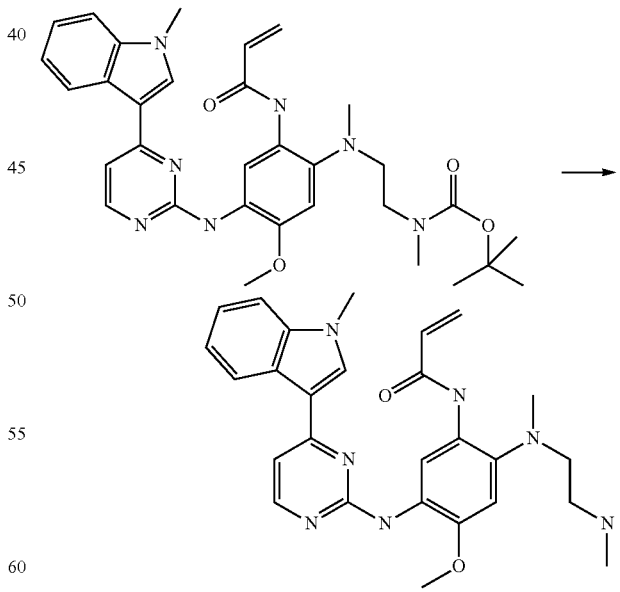

A solution of tert-butyl N-[2-[[5-methoxy-4-[[4-(1-methylindol-3-yl)pyrimidin-2-yl]amino]-2-(prop-2-enoylamino)phenyl]-methylamino]ethyl]-N-methylcarbamate (Intermediate 170, 321 mg, 0.55 mmol) in CH₂Cl₂ (10 mL) and TFA (2 mL) was stirred at r.t. for 0.5 h and then concentrated in vacuo. The residue was dissolved in 10% CH$_3$OH/CH$_2$Cl$_2$. The resulting solution was washed with sat. NaHCO$_3$, dried (MgSO$_4$) and concentrated in vacuo. Purification by FCC, eluting with 0-20% CH$_3$OH in CH$_2$Cl$_2$ gave the title compound (110 mg, 41%) as a pale yellow solid after trituration with diethyl ether; $^1$H NMR: 2.35 (3H, s), 2.58-2.62 (2H, m), 2.71 (3H, s), 2.85-2.89 (2H, m), 3.86 (3H, s), 3.92 (3H, s), 5.74 (1H, dd), 6.28 (1H, dd), 6.59 (1H, dd), 6.99 (1H, s), 7.15 (1H, t), 7.21-7.27 (2H, m), 7.53 (1H, d), 7.87 (1H, s), 8.24 (1H, d), 8.32 (1H, d), 8.66 (1H, s), 9.16 (1H, s), 10.33 (1H, s); m/z: ES$^+$ MH$^+$ 486.55.

Intermediate 1: 4-Methoxy-6-(1-methyl-3,6-dihydro-2H-pyridin-4-yl)-N'-(5-methyl-4-pyrazolo[1,5-a]pyridin-3-ylpyrimidin-2-yl)benzene-1,3-diamine A mixture of N-[2-methoxy-4-(1-methyl-3,6-dihydro-2H-pyridin-4-yl)-5-nitrophenyl]-5-methyl-4-pyrazolo[1,5-a]pyridin-3-ylpyrimidin-2-amine (Intermediate 2, 279 mg, 0.59 mmol), iron (198 mg, 3.55 mmol) and NH$_4$Cl (22.16 mg, 0.41 mmol) in ethanol (10.5 mL) and water (3.50 mL) was heated at reflux for 0.75 h. Further NH$_4$Cl (22.16 mg, 0.41 mmol) and iron (198 mg, 3.55 mmol) were then added and the mixture was heated at reflux for a further 1.5 h. The mixture was then cooled, filtered, and the filtrate was concentrated in vacuo. Purification by FCC, eluting with 2-10% 7N methanolic ammonia in CH$_2$Cl$_2$ gave the title compound (150 mg, 57%) as a beige crystalline solid after trituration with THF and washing the resulting solid with diethyl ether; $^1$H NMR: 2.30 (3H, s), 2.40 (5H, m), 2.59 (2H, t), 3.01 (2H, d), 3.73 (3H, s), 4.27 (2H, s), 5.71 (1H, s), 6.63 (1H, s), 7.10 (1H, m), 7.35-7.49 (2H, m), 7.83 (1H, s), 8.27 (1H, s), 8.50-8.63 (2H, m), 8.81 (1H, d); m/z: ES$^+$ MH$^+$ 442.

Intermediate 2: N-[2-Methoxy-4-(1-methyl-3,6-dihydro-2H-pyridin-4-yl)-5-nitro-phenyl]-5-methyl-4-pyrazolo[1,5-a]pyridin-3-ylpyrimidin-2-amine A solution of 3-(2-chloro-5-methylpyrimidin-4-yl)pyrazolo[1,5-a]pyridine (Intermediate 5, 271 mg, 1.00 mmol), p-toluene sulphonic acid monohydrate (271 mg, 1.43 mmol) and 2-methoxy-4-(1-methyl-3,6-dihydro-2H-pyridin-4-yl)-5-nitroaniline (Intermediate 3, 250 mg, 0.95 mmol) were heated in 2-pentanol (12 mL) at reflux under N$_2$ for 30 h. The mixture was then concentrated in vacuo and the residue was dissolved in CH$_3$OH. Purification by ion exchange chromatography (SCX column), eluting with 7M methanolic ammonia, gave the title compound (283 mg, 63%) as an orange powder after trituration with CH$_3$CN. $^1$H NMR: 2.28-2.36 (5H, m), 2.44 (3H, s), 2.60 (2H, t), 3.00 (2H, d), 4.00 (3H, d), 5.64 (1H, s), 6.97 (1H, s), 7.13 (1H, m), 7.40 (1H, m), 8.27 (1H, s), 8.39 (1H, s), 8.53 (1H, d), 8.61 (1H, s), 8.83 (1H, d), 8.87 (1H, s); m/z: ES$^-$ MH$^-$ 470.

Intermediate 3: 2-Methoxy-4-(1-methyl-3,6-dihydro-2H-pyridin-4-yl)-5-nitroaniline A mixture of 4-bromo-2-methoxy-5-nitroaniline (Intermediate 4, 1.112 g, 4.5 mmol), 1-methyl-4-(4,4,5,5-tetramethyl-1,3,2-dioxaborolan-2-yl)-3,6-dihydro-2H-pyridine (1.004 g, 4.50 mmol) and K$_2$CO$_3$ (2.488 g, 18.00 mmol) was stirred in 1,4-dioxane (20 mL) and water (5 mL). The mixture was purged with N$_2$ for 0.25 h. Tetrakis(triphenylphosphine)-palladium(0) (0.052 g, 0.05 mmol) was then added and the mixture was heated at reflux for 2 h. The mixture was then cooled, filtered and the filtrate was concentrated in vacuo to give an aqueous mixture. This mixture was dissolved in EtOAc and water and the phases were separated. The aqueous solution was extracted with EtOAc. The combined organic solutions were then extracted twice with 2M HCl (40 mL). The aqueous solutions were basified with 2M Na$_2$CO$_3$ (50 mL) and extracted with EtOAc (3×40 mL). The combined organic solutions were dried (MgSO$_4$) and concentrated in vacuo. The residue was dissolved in a mixture of CH$_2$Cl$_2$ and 2N methanolic ammonia (10:1, 10 mL) and the solution was filtered through a silica plug. The filtrate was concentrated in vacuo to give an oil which subsequently crystallised. Trituration with isohexane and diethyl ether (1:1, 5 mL) and collection of the resulting solid by filtration gave the title compound (1.093 g, 92%) as a yellow crystalline solid; $^1$H NMR: 2.23 (2H, dd), 2.27 (3H, s), 2.53 (2H, t), 2.93 (2H, d), 3.87 (3H, s), 5.27 (2H, s), 5.42-5.53 (1H, m), 6.65 (1H, s), 7.23 (1H, s); m/z: ES$^+$ MH$^+$ 264.

Intermediate 4: 4-Bromo-2-methoxy-5-nitroaniline

85% Sulfuric acid was made by adding 98% sulfuric acid (13 mL) cautiously to ice (2 g). Guanidine nitrate (1.221 g, 10.00 mmol) was added portionwise over a period of 10 minutes to a cooled (0-5° C.) mixture of 4-bromo-2-methoxyaniline (2.020 g, 10 mmol) in 85% sulfuric acid (15.68 mL, 250.00 mmol). The resulting dark blue mixture was stirred at 0-5° C. for 0.75 h and was then poured very slowly into a well-stirred mixture of 50% aq NaOH (40 mL) and ice (120 g). An orange precipitate was collected by filtration, washed with water (4×50 mL) and air dried. This material was dissolved into diethyl ether (100 mL) and filtered through a silica plug. The resulting solution was diluted with isohexane and purified by evaporative crystallisation from diethyl ether/isohexane to give the title compound (1.821 g, 74%) as an orange crystalline solid; $^1$H NMR: 3.90 (3H, s), 5.52 (2H, s), 7.14 (1H, s), 7.32 (1H, s).

Intermediate 5: 3-(2-Chloro-5-methylpyrimidin-4-yl)pyrazolo[1,5-a]pyridine

K$_2$CO$_3$ (10.60 g, 76.68 mmol) was added to a mixture of 4-[(E)-2-butoxyethenyl]-2-chloro-5-methylpyrimidine (Intermediate 6, 6.95 g, 30.67 mmol) and 1-aminopyridinium iodide (9.19 g, 41.40 mmol) in DMF (40 mL) at r.t. The resulting dark blue suspension was stirred at r.t. for 3 days (became deep red color) and was then heated at 110° C. for 3 h. The mixture was then cooled, diluted with EtOAc (100 mL) plus a little CH$_2$Cl$_2$. This solution was washed with water (100 mL) and the aqueous wash solution was extracted with EtOAc (100 mL). The combined organic solutions were washed with water (4×100 mL) and sat. brine (50 mL), dried (MgSO$_4$) and concentrated in vacuo. The residue was dissolved in THF (100 mL) and filtered through a 30 g silica pad. The eluted solution was concentrated in vacuo and the residue was washed with −70° C. CH$_3$OH to give the title compound (2.223 g, 30%) as a beige crystalline solid; $^1$H NMR: 2.53 (3H, s), 7.22 (1H, m), 7.64 (1H, m), 8.53-8.59 (2H, m), 8.70 (1H, s), 8.90 (1H, d); m/z: ES$^+$ MH$^+$ 245.

Intermediate 6: 4-[(E)-2-Butoxyethenyl]-2-chloro-5-methylpyrimidine

Diacetoxypalladium (0.482 g, 2.15 mmol) was added in one portion to a mixture of 1-(vinyloxy)butane (11.91 mL, 92.02 mmol), 2,4-dichloro-5-methylpyrimidine (5 g, 30.67 mmol) and triethylamine (4.51 mL, 32.21 mmol) in degassed polyethylene glycol 200 (25 mL) under $N_2$. The resulting mixture was stirred at 80° C. for 18 h. The mixture was then cooled and extracted with diethyl ether (3×75 mL). The combined organic solutions were dried ($MgSO_4$), diluted with heptane (115 mL) and filtered through a 75 g silica plug, eluting with 2:1 diethyl ether/heptanes, to give the title compound (8.62 g, 124%) as a yellow oil which was used without further purification; $^1$H NMR: 0.92 (3H, t), 1.35-1.43 (2H, m), 1.60-1.71 (2H, m), 2.17 (3H, d), 4.06 (2H, t), 5.93 (1H, d), 7.90 (1H, d), 8.33 (1H, d); m/z: $ES^+$ $MH^+$ 226.

Intermediate 7: N'-[5-Chloro-4-(1H-indol-3-yl)pyrimidin-2-yl]-4-methoxy-6-(1-methyl-3,6-dihydro-2H-pyridin-4-yl)benzene-1,3-diamine NaOH (2M, 1.488 mL, 2.98 mmol) was added in one portion to a mixture of N'-{4-[1-(benzenesulfonyl)indol-3-yl]-5-chloropyrimidin-2-yl}-4-methoxy-6-(1-methyl-3,6-dihydro-2H-pyridin-4-yl)benzene-1,3-diamine (Intermediate 8, 283 mg, 0.47 mmol) in $CH_3OH$ (6 mL) at r.t. under $N_2$. The resulting solution was stirred at reflux for 0.5 h. Dry ice was then added and the resulting mixture was concentrated in vacuo. The resulting residue was triturated with $CH_2Cl_2$/$CH_3OH$ (4:1, 20 mL), filtered and the filtrate was concentrated in vacuo to give a residue. Purification by FCC, eluting with 2-10% methanolic ammonia in $CH_2Cl_2$ gave the title compound (102 mg, 47%) as a pale yellow powder; $^1$H NMR: 2.30 (3H, s), 2.41 (2H, s), 2.60 (2H, t), 3.02 (2H, d), 3.70 (3H, s), 4.27 (2H, s), 5.73 (1H, s), 6.65 (1H, s), 7.08 (1H, t), 7.17-7.23 (1H, m), 7.26 (1H, s), 7.48 (1H, d), 8.18 (1H, s), 8.38 (1H, s), 8.41 (1H, d), 8.49 (1H, s), 11.85 (1H, s); m/z: $ES^+$ $MH^+$ 460.

Intermediate 8: N'-{4-[1-(Benzenesulfonyl)indol-3-yl]-5-chloropyrimidin-2-yl}-4-methoxy-6-(1-methyl-3,6-dihydro-2H-pyridin-4-yl)benzene-1,3-diamine A mixture of 4-[1-(benzenesulfonyl)indol-3-yl]-5-chloro-N-[2-methoxy-4-(1-methyl-3,6-dihydro-2H-pyridin-4-yl)-5-nitrophenyl]pyrimidin-2-amine (Intermediate 9, 349 mg, 0.47 mmol), iron (157 mg, 2.82 mmol) and $NH_4Cl$ (17.60 mg, 0.33 mmol) in ethanol (9 mL) and water (3 mL) was heated at reflux for 1.5 h. The mixture was cooled and concentrated in vacuo. $CH_2Cl_2$ (20 mL) and $CH_3OH$ (2 mL) were then added and the mixture was stirred for 5 minutes and then filtered. The organic solution was washed with brine, dried ($MgSO_4$) and concentrated in vacuo to give the title compound (396 mg, 140%) as a green foam which was used without further purification. m/z: $ES^+$ $MH^+$ 601.

Intermediate 9: 4-[1-(Benzenesulfonyl)indol-3-yl]-5-chloro-N-[2-methoxy-4-(1-methyl-3,6-dihydro-2H-pyridin-4-yl)-5-nitrophenyl]pyrimidin-2-amine A mixture of 1-(benzenesulfonyl)-3-(2,5-dichloropyrimidin-4-yl)indole (Intermediate 10, 384 mg, 0.95 mmol), p-toluene sulphonic acid monohydrate (271 mg, 1.43 mmol) and 2-methoxy-4-(1-methyl-3,6-dihydro-2H-pyridin-4-yl)-5-nitroaniline (Intermediate 3, 250 mg, 0.95 mmol) was heated in 2-pentanol (12 mL) at reflux under $N_2$ for 24 h. Further p-toluene sulphonic acid monohydrate (0.090 g, 0.48 mmol) was then added and the mixture was heated at reflux for a further 6 h. The mixture was then concentrated in vacuo and the resulting reside was dissolved into a mixture of $CH_2Cl_2$, $CH_3OH$ and EtOAc (10 mL, 3 mL and 3 mL). This solution was concentrated in vacuo onto silica. Purification by FCC, eluting with 4-10% $CH_3OH$ in $CH_2Cl_2$ gave the title compound (415 mg, 56%) as a yellow foam; $^1$H NMR: 2.29 (1.95H, s), 2.52 (0.7H, m), 2.73 (2.6H, s), 3.18 (1.4H, m), 3.57 (2H, s), 3.96 (3H, s), 5.68 (1H, s), 7.00 (1H, s), 7.11 (1.3H, d), 7.26 (1H, m), 7.44 (1H, m), 7.49 (1.3H, d), 7.64 (2H, t), 7.73 (1H, m), 8.01 (1H, d), 8.07-8.15 (2H, m), 8.19 (1H, d), 8.64 (2H, d), 8.70 (1H, s), 8.97 (1H, s); (the spectrum seems to appear to show a mixture of rotamers, arising due to restricted rotation of bonds within the molecule) m/z: $ES^+$ $MH^+$ 631.

Intermediate 10: 1-(Benzenesulfonyl)-3-(2,5-dichloropyrimidin-4-yl)indole

Sodium tert-butoxide (529 mg, 5.50 mmol) was added portionwise over a period of 2 minutes to a mixture of 3-(2,5-dichloro-pyrimidin-4-yl)-1H-indole (Intermediate 11, 1.321 g, 5.0 mmol) and benzenesulfonyl chloride (0.645 mL, 5.00 mmol) in DMF (30 mL) at r.t. under $N_2$. The resulting solution was stirred at r.t. for 1 h. Further benzenesulfonyl chloride (0.064 mL, 0.50 mmol) and sodium tert-butoxide (0.053 g, 0.055 mmol) were added and the mixture was stirred at r.t. for a further 0.25 h. The reaction was quenched by the addition of $CH_3OH$ (6 mL) and neutralised by the addition of solid $CO_2$ pellets until reaching pH=7. The solvent was then removed in vacuo and the resulting residue was dissolved in $CH_2Cl_2$ (100 mL). This solution was filtered through a 20 g silica pad, and the eluted solution was diluted with isohexane (50 mL). This solution was concentrated in vacuo to give a volume of 70 mL and was then cooled. A resulting crystalline precipitate was collected by filtration, washed with isohexane/$CH_2Cl_2$ (4:1, 50 mL) and dried by suction to give the title compound (923 mg, 46%) as an off-white crystalline solid, which was used without further purification; $^1$H NMR: 7.39-7.53 (2H, m), 7.64 (2H, t), 7.75 (1H, t), 8.04 (1H, d), 8.11-8.17 (2H, m), 8.28 (1H, d), 8.79 (1H, s), 9.00 (1H, s); m/z: $ES^+$ $MH^+$ 404.

Intermediate 11: 3-(2,5-Dichloropyrimidin-4-yl)-1H-indole $CH_3MgBr$ (3.2M in 2-methyltetrahydrofuran, 3.37 mL, 10.79 mmol) was added dropwise over 10 minutes to a solution of indole (1.28 g, 10.79 mmol) in THF (6 mL) at 0° C. The solution was then stirred at 0-2° C. for 0.5 h. 2,4,5-Trichloropyrimidine (1 g, 5.40 mmol) was then added dropwise, resulting in a yellow solution. The ice bath was removed, then the solution was stirrred at r.t. for 1 h, resulting in a red solution. The mixture was heated to 60° C. and then stirred at 60° C. for 1.5 h. The mixture was then cooled to r.t. and acetic acid (634 µL, 11.06 mmol) was added dropwise. Water (9.90 mL) and THF (2 mL) were added, then the mixture was stirred for 20 minutes at 60° C., resulting in a bi-phasic solution. The layers were separated and heptane (11 mL) was added to the organic solution, resulting in the crystallisation of a solid. The solid was collected by filtration, washed with heptane (2 mL), and dried in a vacuum oven to give the title compound (1.015 g, 66%) as a yellow solid; $^1$H NMR: 7.24-7.32 (2H, m), 7.55-7.58 (1H, m), 8.52-8.55 (1H, m), 8.71-8.73 (2H, m), 12.24 (1H, s); m/z: $ES^+$ $MH^+$ 264, 266.

Intermediate 12: N'-[4-(1H-Indol-3-yl)-5-methylpyrimidin-2-yl]-4-methoxy-6-(4-methylpiperazin-1-yl)benzene-1,3-diamine A mixture of 4-(1H-indol-3-yl)-N-[2-methoxy-4-(4-methylpiperazin-1-yl)-5-nitrophenyl]-5-methylpyrimidin-2- amine (Intermediate 13, 157 mg, 0.33 mmol), iron (111 mg, 1.99 mmol) and NH₄Cl (12.41 mg, 0.23 mmol) was heated in ethanol (6 mL) and water (2 mL) at reflux for 2 h. The mixture was then cooled and concentrated in vacuo to give a thick slurry. $CH_2Cl_2$ (100 mL) and $CH_3OH$ (10 mL) were then added and the mixture was stirred for 0.25 h, then filtered. The filter cake was washed with $CH_2Cl_2$ (50 mL) and $CH_3OH$ (5 mL) and the combined organic solutions were dried (MgSO₄) and concentrated in vacuo. Purification by FCC, eluting with 1-5% methanolic ammonia in $CH_2Cl_2$ gave the title compound (113 mg, 77%) as a pale yellow dry film; m/z: ES⁺ MH⁺ 444.53.

Intermediate 13: 4-(1H-Indol-3-yl)-N-[2-methoxy-4-(4-methylpiperazin-1-yl)-5-nitrophenyl]-5-methylpyrimidin-2-amine A mixture of 2-methoxy-4-(4-methylpiperazin-1-yl)-5-nitroaniline (Intermediate 14, 204 mg, 0.77 mmol), p-toluene sulphonic acid monohydrate (291 mg, 1.53 mmol) and 3-(2-chloro-5-methylpyrimidin-4-yl)-1H-indole (Intermediate 17, 192 mg, 0.77 mmol) were heated at 120° C. in 2-pentanol (15 mL) for 24 h, resulting in a dark brown suspension. The mixture was then concentrated in vacuo and the resulting residue was dissolved in a mixture of $CH_2Cl_2$ and $CH_3OH$ (50 mL and 5 mL) and this solution was concentrated onto silica in vacuo. Purification by FCC, eluting with 1-5% methanolic ammonia in $CH_2Cl_2$ gave the title compound (157 mg, 43%) as an orange gum; m/z: ES⁺ MH⁺ 474.24.

Intermediate 14: 2-Methoxy-4-(4-methylpiperazin-1-yl)-5-nitroaniline tert-Butyl N-[2-methoxy-4-(4-methylpiperazin-1-yl)-5-nitrophenyl]carbamate (Intermediate 15, 1.4 g, 3.82 mmol) was dissolved in $CH_2Cl_2$ (20 mL) and TFA (5 mL) was then added. The mixture was stirred for 2 h at r.t. and was then concentrated in vacuo.

The resulting residue was dissolved in $CH_3OH$, absorbed onto an SCX column, washed with $CH_3OH$ and eluted with methanolic ammonia. The fractions that contained product were combined and concentrated. Purification by FCC, eluting with 1.5% 7N methanolic ammonia in $CH_2Cl_2$ gave the title compound (0.6 g, 59%) as an orange oil which crystallised on standing; ¹H NMR: 2.22 (3H, s), 2.39-2.47 (4H, m), 2.87-2.97 (4H, m), 3.88 (3H, s), 4.99 (2H, s), 6.72 (1H, s), 7.20 (1H, s); m/z: ES⁺ MH⁺ 267.5.

Intermediate 15: tert-butyl N-[2-methoxy-4-(4-methylpiperazin-1-yl)-5-nitrophenyl]carbamate 2-Methoxy-4-(4-methylpiperazin-1-yl)-5-nitrobenzoic acid (Intermediate 16, 1.5 g, 5.08 mmol) was suspended in a mixture of t-butanol (20 mL) and DIPEA (1.318 mL, 7.62 mmol) and then diphenylphosphoryl azide (1.642 mL, 7.62 mmol) was added. The mixture was then heated at reflux for 2 h. The mixture was then cooled and concentrated in vacuo. The resulting residue was dissolved in EtOAc, washed with sat. NaHCO₃, dried (Na₂SO₄) and concentrated in vacuo. Purification by FCC, eluting with 2% 7N methanolic ammonia in $CH_2Cl_2$ gave the title compound (1.45 g, 78%) as an orange oil which crystallised on standing; ¹H NMR: 1.45 (9H, s), 2.23 (3H, s), 2.41-2.49 (4H, m), 2.99-3.07 (4H, m), 3.92 (3H, s), 6.74 (1H, s), 8.24-8.32 (2H, m); m/z: ES⁺ MH⁺ 367.3.

Intermediate 16: 2-Methoxy-4-(4-methylpiperazin-1-yl)-5-nitrobenzoic acid

1-Methylpiperazine (0.962 mL, 8.67 mmol) was added to a suspension of 2-methoxy-4,5-dinitrobenzoic acid (2.0 g, 8.26 mmol) in water (5 mL). The mixture was heated at 50° C. for 1.5 h then 75° C. for 3 h. A further 0.5 equivalents of 1-methylpiperazine was added and the mixture was heated overnight. The mixture was then allowed to cool and stand. A crystalline solid formed which was collected by filtration, washed with water and then dried on the filter to give the title compound (1.87 g, 77%) as a yellow crystalline solid; ¹H NMR: 2.25 (3H, s), 2.45-2.49 (4H, m), 3.13-3.21 (4H, m), 3.93 (3H, s), 6.63 (1H, s), 8.32 (1H, s); m/z: ES⁺ MH⁺ 296.5.

Intermediate 17: 3-(2-Chloro-5-methylpyrimidin-4-yl)-1H-indole $CH_3MgBr$ (3.2M in 2-methyltetrahydrofuran, 3.76 mL, 12.02 mmol) was added dropwise over 10 minutes to a solution of indole (1.42 g, 12.02 mmol) in THF (4.9 mL) at 0° C. The solution was then stirred at 0-2° C. for 0.5 h. A solution of 2,4-dichloro-5-methylpyrimidine (1 g, 6.01 mmol) in THF (3 mL) was then added dropwise to the solution. The ice bath was then removed, then the solution was stirred at r.t. for 1 h then 60° C. for 21 h. While still at 60° C., acetic acid (708 µL, 12.32 mmoles) was added dropwise, followed by water (10 mL). The resulting biphasic suspension was stirred at 60° C. for 0.5 h. The resulting solid was collected by filtration, washed with water (5 mL), and dried in a vacuum oven to give the title compound (805 mg, 50%) as a white solid; ¹H NMR: 2.49 (3H, s), 7.20-7.28 (2H, m), 7.52-7.55 (1H, m), 8.20 (1H, d), 8.48 (1H, d), 8.51-8.54 (1H, m), 12.10 (1H, s); m/z: ES⁺ MH⁺ 244.

Intermediate 18: N-(5-Chloro-4-pyrazolo[1,5-a]pyridin-3-ylpyrimidin-2-yl)-4-[(3R)-3-dimethylaminopyrrolidin-1-yl]-6-methoxybenzene-1,3-diamine A mixture of 5-chloro-N-{4-[(3R)-3-dimethylaminopyrrolidin-1-yl]-2-methoxy-5-nitrophenyl}-4-pyrazolo[1,5-a]pyridin-3-ylpyrimidin-2-amine (Intermediate 19, 145 mg, 0.28 mmol), iron (95 mg, 1.71 mmol) and NH₄Cl (11.4 mg, 0.21 mmol) was heated at reflux in ethanol (6 mL) and water (2 mL) for 1.5 h. The mixture was then cooled and concentrated in vacuo. The resulting residue was triturated using 10% $CH_3OH$ in $CH_2Cl_2$ (15 mL) for 15 minutes and the mixture was then filtered. The residues were triturated again using 10% $CH_3OH$ in $CH_2Cl_2$ (15 mL) and the mixture was filtered. The combined filtrates were washed with brine, dried (Na₂SO₄) and concentrated in vacuo. Purification by FCC, eluting with 2% 7N methanolic ammonia in $CH_2Cl_2$ gave the title compound (112 mg, 82%) as a yellow gum; ¹H NMR: (CDCl₃) 1.83-1.96 (1H, m), 2.08-2.23 (1H, m), 2.30 (6H, s), 2.82-2.92 (1H, m), 2.99-3.13 (2H, m), 3.17-3.28 (2H, m), 3.65 (2H, s), 3.84 (3H, s), 6.72 (1H, s), 6.96 (1H, td), 7.38 (1H, ddd), 7.52 (1H, s), 7.90 (1H, s), 8.36 (1H, s), 8.55-8.60 (1H, m), 8.65 (1H, dd), 8.94 (1H, s); m/z: ES⁺ MH⁺ 479.5.

Intermediate 19: 5-Chloro-N-[4-[(3R)-3-dimethylaminopyrrolidin-1-yl]-2-methoxy-5-nitrophenyl]-4-pyrazolo[1,5-a]pyridin-3-ylpyrimidin-2-amine (3R)—N,N-Dimethylpyrrolidin-3-amine dihydrochloride (90 mg, 0.48 mmol) was added to a suspension of 5-chloro-N-(4-fluoro-2-methoxy-5-nitrophenyl)-4-pyrazolo[1,5-a]

pyridin-3-ylpyrimidin-2-amine (Intermediate 20, 200 mg, 0.48 mmol) and DIPEA (0.250 mL, 1.45 mmol) in DMA (3 mL). This mixture was heated at 140° C. in a microwave for 0.5 h. The mixture was then diluted with CH$_3$OH and absorbed onto an SCX column, washed with CH$_3$OH and eluted with 1:1 methanolic ammonia in CH$_2$Cl$_2$. Fractions containing the product were combined and concentrated in vacuo. Purification by FCC, eluting with 1.5% 7N methanolic ammonia in CH$_2$Cl$_2$ gave the title compound (149 mg, 61%) as an orange foam; $^1$H NMR: 1.76-1.89 (1H, m), 2.14-2.25 (7H, m), 2.69-2.84 (1H, m), 3.12-3.27 (3H, m), 3.41-3.53 (1H, m), 3.89 (3H, s), 6.56 (1H, s), 7.13 (1H, td), 7.26-7.38 (1H, m), 8.06 (1H, s), 8.40-8.43 (2H, m), 8.73 (1H, s), 8.85 (1H, d), 8.95 (1H, s); m/z: ES$^+$ MH$^+$ 509.5.

Intermediate 20: 5-Chloro-N-(4-fluoro-2-methoxy-5-nitrophenyl)-4-pyrazolo[1,5-a]-pyridin-3-ylpyrimidin-2-amine A mixture of 3-(2,5-dichloropyrimidin-4-yl)pyrazolo[1,5-a]pyridine (Intermediate 21, 1.4 g, 5.28 mmol), 4-fluoro-2-methoxy-5-nitroaniline (Intermediate 23, 1.032 g, 5.55 mmol) and p-toluenesulfonic acid monohydrate (1.105 g, 5.81 mmol) was heated at 125° C. in 2-pentanol (40 mL) for 18 h. The mixture was then cooled and a solid was collected by filtration. The solid was washed with CH$_3$OH and diethyl ether, and was then dried on the filter to give the title compound (1.73 g, 79%) as a yellow powder; $^1$H NMR: 3.98 (3H, s), 7.16 (1H, td), 7.33-7.48 (2H, m), 8.49 (1H, d), 8.53 (1H, d), 8.66 (1H, d), 8.86 (1H, d), 8.90 (1H, s), 8.96 (1H, s).

Intermediate 21: 3-(2,5-Dichloropyrimidin-4-yl)pyrazolo[1,5-a]pyridine

K$_2$CO$_3$ (20.82 g, 150.65 mmol) and KOH (16.91 g, 301.31 mmol) were added in one portion to a mixture of (E)-4-(2-butoxyvinyl)-2,5-dichloropyrimidine (Intermediate 22, 74.46 g, 301.31 mmol) and 1-aminopyridinium iodide (66.9 g, 301.31 mmol) in DMSO (1.415 L) at r.t. The mixture was stirred at r.t. for 1.5 h and then at 90° C. for 4 h. After cooling, the mixture was diluted with water (5 L) and stirred for 0.5 h. The resulting solid was collected by filtration and washed with water (5 L). Purification by FCC, eluting with 0-20% EtOAc in CH$_2$Cl$_2$ gave the title compound (16.2 g, 20%) as a cream solid after trituration with diethyl ether; $^1$H NMR: 7.29 (1H, td), 7.74 (1H, ddd), 8.58 (1H, dt), 8.82 (1H, s), 8.98 (1H, dt), 9.10 (1H, s). m/z: ES$^+$, MH$^+$ 264.89.

Intermediate 22: 4-[(E)-2-Butoxyethenyl]-2,5-dichloropyrimidine

Degassed 1,4-dioxane (600 mL) was added to palladium (II) acetate (4.80 g, 21.37 mmol) under N$_2$. n-Butyl vinyl ether (275 mL, 2.137 mol), 2,4,5-trichloropyrimidine (200 g, 1.069 mol) and DIPEA (194 mL, 1.122 mol) were then added. The mixture was heated to 80° C. for 22.5 h and then cooled to 30° C. Palladium acetate (2.40 g, 10.68 mmol), n-butyl vinyl ether (138 mL, 1.068 mol) and DIPEA (97 mL, 561 mmol) were then added. The mixture was then heated to 80° C. for 4 h and then allowed to cool to r.t. overnight. The mixture was then added to water (2 L), and then sat. brine (2 L) was added. The phases were separated and the aqueous solution was extracted with methyl-tert-butylether (2×1 L). The combined organic solutions were washed with water resulting in an emulsion which would not separate. Everything was filtered and the two phases were then separated. The organic solution was dried (MgSO$_4$) and concentrated to give a brown oil (240 g). This material was split into two batches and each purified by FCC, eluting with 0-100% heptane in CH$_2$Cl$_2$ to give the title compound (130 g, 49%) as a yellow oil; $^1$H NMR: 0.89-0.97 (3H, t), 1.33-1.45 (2H, m), 1.62-1.72 (2H, m), 4.13 (2H, t), 6.08 (1H, d), 8.06 (1H, d), 8.64 (1H, s); m/z: ES$^+$ MH$^+$ 247.41.

Intermediate 23: 4-Fluoro-2-methoxy-5-nitroaniline

4-Fluoro-2-methoxyaniline (2.4 g, 17.00 mmol) was added portionwise to concentrated H$_2$SO$_4$ (15 mL) which was cooled in a ice/water bath, and where the temperature was kept below 15° C. during the addition. The mixture was stirred until all the solid that formed had dissolved. KNO$_3$ (0.815 mL, 17.00 mmol) was added portionwise such that the temperature was maintained below 10° C. The mixture was stirred overnight and then poured onto ice/water. The mixture was basified with concentrated NH$_4$OH. The resulting solid was filtered off and then dissolved in CH$_2$Cl$_2$, washed with water, dried (Na$_2$SO$_4$) and concentrated onto silica. Purification by FCC, eluting with 50-0% heptane in CH$_2$Cl$_2$ gave the title compound (2.450 g, 77%) as a yellow crystalline solid; $^1$H NMR: 3.91 (3H, s), 5.21 (2H, s), 7.03 (1H, d), 7.35 (1H, d); m/z: ES$^+$ MH$^+$ 187.4.

Intermediate 24: N-(5-Chloro-4-pyrazolo[1,5-a]pyridin-3-ylpyrimidin-2-yl)-4-(3-dimethylaminoazetidin-1-yl)-6-methoxybenzene-1,3-diamine A mixture of 5-chloro-N-[4-(3-dimethylaminoazetidin-1-yl)-2-methoxy-5-nitrophenyl]-4-pyrazolo[1,5-a]pyridin-3-ylpyrimidin-2-amine (Intermediate 25, 265 mg, 0.54 mmol), iron (179 mg, 3.21 mmol) and NH$_4$Cl (20.05 mg, 0.37 mmol) was heated at reflux in ethanol (6 mL) and water (2 mL) for 1 h. The crude product was purified by ion exchange chromatography, using an SCX column. The desired product was eluted from the column using 7M methanolic ammonia and appropriate fractions were concentrated in vacuo to give the title compound (235 mg, 94%) as a yellow solid which was used without further purification; $^1$H NMR: 2.13 (6H, s), 3.07 (1H, s), 3.50 (2H, t), 3.66 (3H, s), 4.00 (3H, t), 4.05 (2H, s), 6.28 (1H, s), 6.79 (1H, s), 7.10 (1H, t), 7.3-7.39 (1H, m), 8.33 (1H, s), 8.37 (1H, s), 8.80 (1H, d), 8.93 (1H, s); m/z: ES$^+$ MH$^+$ 465.25.

Intermediate 25: 5-Chloro-N-[4-(3-dimethylaminoazetidin-1-yl)-2-methoxy-5-nitrophenyl]-4-pyrazolo[1,5-a]pyridin-3-ylpyrimidin-2-amine DIPEA (0.341 mL, 1.96 mmol) was added to a mixture of 5-chloro-N-(4-fluoro-2-methoxy-5-nitrophenyl)-4-(pyrazolo[1,5-a]pyridin-3-yl)pyrimidin-2-amine (Intermediate 20, 254 mg, 0.61 mmol) and N,N-dimethylazetidin-3-amine dihydrochloride (Intermediate 26, 106 mg, 0.61 mmol) in DMA (4 mL) and the mixture was heated to 100° C. for 0.5 h. Further N,N-dimethylazetidin-3-amine (35 mg, 0.19 mmol) was then added and the mixture was heated at 100° C. for a further 2 h and was then left at r.t. overnight. The mixture was purified directly by ion exchange chromatography, using an SCX column. The desired product was eluted from the column using 7M methanolic ammonia and was concentrated in vacuo onto silica. Purification by FCC, eluting with 0-4% 7N methanolic ammonia in CH$_2$Cl$_2$ gave the title compound (310 mg, 102%) as an orange solid, which was used without further purification; $^1$H NMR: 2.14

(6H, s), 3.08-3.18 (1H, m), 3.76 (2H, dd), 3.89 (3H, s), 4.02-4.11 (2H, m), 6.28 (1H, s), 7.12 (1H, td), 7.30-7.39 (1H, m), 8.12 (1H, s), 8.37 (1H, br s), 8.42 (1H, s), 8.68 (1H, s), 8.83 (1H, d), 8.94 (1H, d); m/z: ES$^+$ MH$^+$ 495.56.

Intermediate 26: N,N-Dimethylazetidin-3-amine-hydrochloride salt

HCl in diethyl ether (200 mL) was slowly added to a solution of tert-butyl 3-dimethyl-aminoazetidine-1-carboxylate (Intermediate 27, 62 g, 0.31 mol) in diethyl ether (100 mL) and the mixture was stirred for 40 mins at r.t. The mixture was then concentrated in vacuo and the resulting solid was washed with diethyl ether to give the title salt (50 g, 119%) as a white solid, which was used without further purification; $^1$H NMR: 2.66 (6H, s), 4.00-4.05 (2H, m), 4.24-4.28 (m, 1H), 4.34-4.38 (m, 2H).

Intermediate 27: tert-butyl 3-dimethylaminoazetidine-1-carboxylate

To a solution of N,N-dimethylazetidin-3-amine (Intermediate 28, 100 g, 1.0 mol) and triethylamine (487 mL, 3.5 mol) in CH$_2$Cl$_2$ (500 mL) was added tert-butyl (2-methylpropan-2-yl)oxycarbonyl carbonate (326 g, 1.5 mol) at 0° C. The mixture was then stirred at r.t. for 5 h. The mixture was then washed with water (4×500 mL) and the organic solution were dried (Na$_2$SO$_4$) and concentrated in vacuo. Purification by FCC gave the title compound (62 g, 31%).

Intermediate 28: N,N-Dimethylazetidin-3-amine

1-Chloroethyl carbonochloridate (118 g, 0.83 mol) was added to a solution of 1-benzhydryl-N,N-dimethylazetidin-3-amine (Intermediate 29, 200 g, 0.75 mol) in dichloroethane (1 L) and the mixture was refluxed at 100° C. for 2 h. The mixture was then concentrated in vacuo and the resulting residue was dissolved in CH$_3$OH (1 L) and this mixture was refluxed at 90° C. for 2 h. The mixture was then concentrated to give the title compound which was used in next step without further purification.

Intermediate 29: 1-Benzhydryl-N,N-dimethylazetidin-3-amine

Aqueous dimethylamine (1 L, 33%) was added to a solution of (1-benzhydrylazetidin-3-yl) methanesulfonate (Intermediate 30, 260 g, 0.82 mol) in CH$_3$CN (1 L) and the mixture was refluxed at 100° C. overnight. The mixture was then cooled and the solvent was removed in vacuo. The mixture was partitioned between water (300 mL) and CH$_2$Cl$_2$ (300 mL) and the layers were separated. The aqueous phase was extracted with CH$_2$Cl$_2$ (3×500 mL). The combined organic solutions were dried (Na$_2$SO$_4$) and concentrated in vacuo. Purification by FCC gave the title compound (200 g, 92%) as a brown solid.

Intermediate 30: (1-Benzhydrylazetidin-3-yl) methanesulfonate

A solution of methanesulfonyl chloride (115 g, 1.01 mol) in CH$_2$Cl$_2$ (500 mL) was added dropwise to a solution of 1-benzhydrylazetidin-3-ol (Intermediate 31, 200 g, 0.84 mol) and triethylamine (119 g, 1.17 mmol) in CH$_2$Cl$_2$ (2 L) at 0° C., and the mixture was stirred at 0° C. for 1 h. The reaction was quenched by the addition of aqueous NaHCO$_3$. The phases were separated and the aqueous solution was extracted with CH$_2$Cl$_2$ (3×500 mL). The combined organic solutions were dried (Na$_2$SO$_4$) and concentrated in vacuo to give the title compound (260 g, 98%) as a white solid.

Intermediate 31: 1-Benzhydrylazetidin-3-ol

DIPEA (129 g, 1 mol) was added to a solution of 1-(benzhydrylamino)-3-chloropropan-2-ol (Intermediate 32, 276 g, 1 mol) in ethanol (2 L) at 0° C., then the mixture was refluxed at 90° C. overnight. The mixture was then concentrated in vacuo to give the title compound (179 g, 75%) which could be re-crystallized from acetone and petroleum ether.

Intermediate 32: 1-(Benzhydrylamino)-3-chloropropan-2-ol 2-(Chloromethyl)oxirane (92 g, 1 mol) was added dropwise to a solution of diphenyl-methanamine (183 g, 1 mol) in CH$_3$OH (1 L) at 0° C. then the mixture was stirred at r.t. overnight. The mixture was then concentrated in vacuo to give the title compound (201 g, 73%) which was used in next step without further purification.

Intermediate 33: N$^4$-(5-Chloro-4-pyrazolo[1,5-a]pyridin-3-ylpyrimidin-2-yl)-N$^1$-(2-dimethylaminoethyl)-5-methoxy-N$^1$-methylbenzene-1,2,4-triamine A solution of NH$_4$Cl (45 mg, 0.85 mmol) in water (10 mL) was added in one portion to a stirred mixture of N-(5-chloro-4-pyrazolo[1,5-a]pyridin-3-ylpyrimidin-2-yl)-N'-(2-dimethylaminoethyl)-2-methoxy-N'-methyl-5-nitrobenzene-1,4-diamine (Intermediate 34, 600 mg, 1.21 mmol) and iron (405 mg, 7.24 mmol) in ethanol (30 mL). The resulting mixture was stirred at 105° C. for 3 h. The mixture was then concentrated in vacuo and the resulting residue was mixed with DMF (10 mL) and purified by ion exchange chromatography, using an SCX column. The desired product was eluted from the column using 0.35M methanolic ammonia in CH$_2$Cl$_2$ and pure fractions were concentrated in vacuo to give the title compound (530 mg, 94%) as a brown gum; $^1$H NMR: 2.16 (6H, d), 2.38 (2H, t), 2.66 (3H, d), 2.92 (2H, t), 3.66 (3H, s), 4.60 (2H, s), 6.78 (1H, s), 6.92 (1H, s), 7.12 (1H, t), 7.27-7.4 (1H, m), 8.38 (1H, s), 8.43 (1H, d), 8.49 (1H, s), 8.83 (1H, d), 8.95 (1H, s); m/z: ES$^+$ MH$^+$ 467.

Intermediate 34: N-(5-Chloro-4-pyrazolo[1,5-a]pyridin-3-ylpyrimidin-2-yl)-N'-(2-dimethylaminoethyl)-2-methoxy-N'-methyl-5-nitrobenzene-1,4-diamine N,N,N'-Trimethylethylenediamine (0.188 mL, 1.45 mmol) was added to a mixture of 5-chloro-N-(4-fluoro-2-methoxy-5-nitrophenyl)-4-pyrazolo[1,5-a]pyrimidin-3-ylpyrimidin-2-amine (Intermediate 20, 500 mg, 1.21 mmol) and DIPEA (0.250 mL, 1.45 mmol) in DMA (5 mL) and the mixture was heated at 140° C. in a microwave for 0.5 h. The mixture was then diluted with CH$_3$OH and absorbed onto an SCX column. The column was washed with CH$_3$OH and eluted with 1:1 methanolic ammonia in CH$_2$Cl$_2$. Appropriate fractions were concentrated in vacuo to give the title compound (624 mg, 104%) as an orange solid, which was used without further purification; $^1$H NMR: 2.17 (6H, d), 2.89 (3H, d), 3.87-3.93 (3H, m), 6.84 (1H, s), 7.14 (1H, td), 7.31-7.38 (1H, m), 8.15 (1H, s), 8.39 (1H, d), 8.44 (1H, d), 8.69 (1H, s), 8.85 (1H, d), 8.95 (1H, s); m/z: ES+ MH+ 497.

Intermediate 35: 4-[(3aR,6aR)-5-Methyl-2,3,3a,4,6,6a-hexahydropyrrolo[3,2-c]pyrrol-1-yl]-N-(5-chloro-4-pyrazolo[1,5-a]pyridin-3-ylpyrimidin-2-yl)-6-methoxybenzene-1,3-diamine A mixture of N-[4-[(3aR,6aR)-5-methyl-2,3,3a,4,6,6a-hexahydropyrrolo[3,2-c]pyrrol-1-yl]-2-methoxy-5-nitrophenyl]-5-chloro-4-pyrazolo[1,5-a]pyridin-3-ylpyrimidin-2-amine (Intermediate 36, 155 mg, 0.30 mmol), iron (100 mg, 1.79 mmol) and $NH_4Cl$ (11.2 mg, 0.21 mmol) in ethanol (12 mL) and water (4 mL) was heated at reflux for 2 h. The mixture was then cooled and filtered though decalite (a type of diatomaceous earth) and the filtrate was concentrated in vacuo to provide a brown gum. Purification by FCC, eluting with 0-5% 7N methanolic ammonia in $CH_2Cl_2$ gave the title compound (105 mg, 72%) as a gum; $^1$H NMR: ($CDCl_3$) 1.76-1.80 (1H, m), 2.03-2.20 (2H, m), 2.28 (3H, s), 2.48 (1H, dd), 2.59-2.63 (2H, m), 2.76-2.98 (2H, m), 3.46 (1H, dt), 3.78 (2H, s), 3.84 (3H, s), 4.07-4.10 (1H, m), 6.73 (1H, s), 6.94 (1H, td), 7.36 (1H, ddd), 7.51 (1H, s), 7.86 (1H, s), 8.35 (1H, s), 8.54 (1H, d), 8.65 (1H, d), 8.93 (1H, s); m/z: ES+ MH+ 491.29.

Intermediate 36: N-{4-[(3aR,6aR)-5-Methyl-2,3,3a,4,6,6a-hexahydropyrrolo[3,2-c]-pyrrol-1-yl]-2-methoxy-5-nitrophenyl}-5-chloro-4-pyrazolo[1,5-a]pyridin-3-yl-pyrimidin-2-amine (3aR,6aR)-5-Methyl-2,3,3a,4,6,6a-hexahydro-1H-pyrrolo[3,2-c]pyrrole (Intermediate 37, 91 mg, 0.72 mmol) was added to a mixture of 5-chloro-N-(4-fluoro-2-methoxy-5-nitrophenyl)-4-pyrazolo[1,5-a]pyridin-3-ylpyrimidin-2-amine (Intermediate 20, 250 mg, 0.60 mmol) and DIPEA (0.334 mL, 1.93 mmol) in 2,2,2-trifluoroethanol (3 mL) and the mixture was heated at 140° C. in a microwave for 0.5 h. The mixture was then absorbed onto silica. Purification by FCC, eluting with 2% 7N methanolic ammonia in $CH_2Cl_2$ gave material that was concentrated in vacuo and dissolved in $CH_3OH$. The resulting solution was absorbed onto an SCX column and the column was washed with $CH_3OH$ then eluted with 7N methanolic ammonia. Appropriate fractions were concentrated in vacuo to give the title compound (155 mg, 49%) as a orange/red gummy solid; $^1$H NMR: ($CDCl_3$) 1.89 (1H, dd), 2.04-2.19 (1H, m), 2.24 (3H, s), 2.30-2.39 (1H, m), 2.40-2.57 (2H, m), 2.68 (1H, t), 2.98-3.11 (1H, m), 3.23 (1H, t), 3.51-3.63 (1H, m), 3.97 (3H, s), 4.36-4.48 (1H, m), 6.46 (1H, s), 6.90-7.02 (1H, m), 7.31-7.43 (2H, m), 8.38 (1H, s), 8.48 (1H, dd), 8.53-8.57 (1H, m), 8.82 (1H, s), 8.93 (1H, s); m/z: ES+ MH+ 521.45.

Intermediate 37: (3aR,6aR)-5-methyl-2,3,3a,4,6,6a-hexahydro-1H-pyrrolo[3,4-b]-pyrrole Palladium on carbon (10 g) was added to a solution of (3aR,6aR)-5-methyl-1-[(1R)-1-phenylethyl]-2,3,3a,4,6,6a-hexahydropyrrolo[3,2-c]pyrrole (Intermediate 38, 20 g, 0.087 mol) in ethanol (500 mL) under $N_2$. The resulting mixture was hydrogenated at 70° C./45 psi for 24 h. The mixture was then filtered and the filtrate was concentrated in vacuo to give the title compound as a (10.9 g, 99%) solid; $^1$H NMR: 1.59-1.66 (1H, m), 1.86-1.95 (1H, m), 2.18 (s, 3H), 2.28-2.34 (2H, m), 2.46-2.47 (1H, m), 2.73 (2H, d), 3.00 (2H, m), 3.90 (2H, m).

Intermediate 38: (3aR,6aR)-5-Methyl-1-[(1R)-1-phenylethyl]-2,3,3a,4,6,6a-hexahydropyrrolo[3,2-c]pyrrole 37% aqeous formaldehyde (1.6 L) was added to a solution of (3aR,6aR)-1-[(1R)-1-phenylethyl]-3,3a,4,5,6,6a-hexahydro-2H-pyrrolo[3,2-c]pyrrole (Intermediate 39, 108 g, 0.5 mol) in HCOOH (800 mL) at r.t., then the mixture was stirred at 70-80° C. for 2 h. The mixture was then cooled to 0° C. and basified with solid NaOH to pH~13. This mixture was then extracted with $CH_2Cl_2$ (2×2 L). The combined organic solutions were concentrated in vacuo. Purification by FCC, eluting with 2:1 to 1:10 hexanes/EtOAc, gave the title compound (80 g, 70%) as red oil; $^1$H NMR: ($CDCl_3$) 1.36 (3H, d), 1.65 (1H, m), 1.85 (1H, m), 2.22 (3H, m), 2.32 (3H, s), 2.54 (1H, m), 2.68 (2H, m), 2.83 (1H, m), 3.10 (1H, m), 3.40 (1H, m), 7.21-7.33 (5H, m).

Intermediate 39: (3aR,6aR)-1-[(1R)-1-phenylethyl]-3,3a,4,5,6,6a-hexahydro-2H-pyrrolo[3,2-c]pyrrole A solution of ethyl (3aR,6aR)-1-[(1R)-1-phenylethyl]-2,3,3a,4,6,6a-hexahydropyrrolo[3,2-c]-pyrrole-5-carboxylate (Intermediate 40, 300 g, 1.04 mol) in concentrated HCl (4 L, 37%) was refluxed overnight. The mixture was then cooled to 0° C. and extracted with by $CH_2Cl_2$ (1 L×2). The aqueous solution was adjusted to pH=12-13 using NaOH (solid). The combined organic solutions were washed with brine, dried ($Na_2SO_4$) and concentrated in vacuo to give the title compound (150 g, 67%) as dark oil which was used in the next step without further purification.

Intermediate 40: Ethyl (3aR,6aR)-1-[(1R)-1-phenylethyl]-2,3,3a,4,6,6a-hexahydro-pyrrolo[3,2-c]pyrrole-5-carboxylate A mixture of ethyl N-(2-oxoethyl)-N-prop-2-enylcarbamate (Intermediate 41, 466 g, 2.7 mol) and 2-{[(1R)-1-phenylethyl]amino}acetic acid (Intermediate 43A, 490 g, 2.7 mol) in toluene (4 L) was refluxed overnight. The resulting mixture was filtered and the filtrate was concentrated in vacuo. Purification by FCC, eluting with 10:1 petrol-EtOAc, gave the title compound (300 g, 38%) as red oil; $^1$H NMR: ($CDCl_3$) 1.10-1.40 (8H, m), 1.55 (1H, m), 1.90 (1H, m), 2.45 (1H, m), 2.77 (1H, m), 3.20-3.65 (5H, m), 4.10-4.20 (2H, m), 7.25-7.38 (5H, m).

Intermediate 41: Ethyl N-(2-oxoethyl)-N-prop-2-enylcarbamate

A solution of ethyl N-(2,2-dimethoxyethyl)-N-prop-2-enylcarbamate (Intermediate 42, 1218 g, 2.79 mol) in HCOOH (4.2 L) was refluxed for 0.5 h. Then crushed ice was added to quench the reaction, the mixture was extracted with $CH_2Cl_2$ (2 L×3). The combined organic solutions were washed with sat. $NaHCO_3$ (3 L), dried ($Na_2SO_4$) and concentrated in vacuo to give the title compound (480 g, 50%) as yellow oil; $^1$H NMR: ($CDCl_3$) 1.15-1.32 (3H, m), 3.89-4.00 (4H, m), 4.07-4.16 (2H, m), 5.10 (2H, m), 5.73 (1H, m), 9.53 (1H, s).

Intermediate 42: Ethyl N-(2,2-dimethoxyethyl)-N-prop-2-enylcarbamate

Crushed KOH (1417 g, 25.3 mol) was added in portions to a solution of ethyl N-(2,2-dimeth-oxyethyl)carbamate (Intermediate 43, 1123 g, 6.3 mol) in toluene (5 L). Benzyltriethyl-ammonium chloride (14.0 g, 0.06 mol) and allyl bromide (532 g, 4.4 mol) were then added at r.t. The mixture was then stirred at r.t. overnight. The mixture was then filtered and the reaction mixture was washed with brine (2 L), dried ($Na_2SO_4$) and concentrated in vacuo to give the title compound (1218 g, 89%) as a yellow oil; $^1$H NMR: ($CDCl_3$) 1.23 (3H, s), 3.28 (2H, s), 3.36 (6H, s), 3.92 (2H, d), 4.12 (2H, s), 4.47 (1H, d), 5.08 (2H, d), 5.73 (1H, s).

Intermediate 43: Ethyl N-(2,2-dimethoxyethyl)carbamate

A solution of NaOH (578.4 g, 14.46 mol) in $H_2O$ (2 L) was added to a solution of 2,2-dimethoxyethanamine (800 g, 7.6 mol) in toluene (2 L) and the resulting mixture was cooled to 0° C. using an ice bath. Ethyl chloroformate (825 g, 7.6 mol) was added dropwise while keeping the temperature near 10° C. The mixture was then stirred at r.t. overnight. The phases were then separated and the aqueous solution was saturated with solid NaCl. This solution was then extracted with toluene (1.25 L×3). The combined organic solutions were dried ($Na_2SO_4$) and concentrated in vacuo to give the title compound (1.123 kg, 83%) as colorless oil; $^1$H NMR: ($CDCl_3$) 1.17 (3H, t), 3.14 (2H, s), 3.32 (6H, s), 4.02-4.07 (2H, m), 4.30 (1H, t).

Intermediate 43A: 2-{[(1R)-1-Phenylethyl]amino}acetic acid

Methyl 2-{[(1R)-1-phenylethyl]amino}acetate (Intermediate 44, 587.0 g, 3.0 mol) was refluxed in aqueous KOH (3.36 g, 0.06 mol dissolved in 2.5 L water) overnight. The phases were then separated and the aqueous solution was washed with EtOAc (3×1 L). The combined organic solutions were concentrated in vacuo to give the title compound (490 g, 90%) as white solid; $^1$H NMR: 1.48 (3H, d), 2.89 (1H, d), 3.00 (1H, d), 4.20 (1H, m), 7.37-7.43 (5H, m).

Intermediate 44: Methyl 2-{[(1R)-1-phenylethyl]amino}acetate

Methyl 2-bromoacetate (621 g, 4.1 mol) was added dropwise to a mixture of (1R)-1-phenylethanamine (410 g, 3.4 mol) and triethylamine (377 g, 3.7 mol) in EtOAc (4.5 L) at r.t. The mixture was then stirred at 50-60° C. overnight then cooled to r.t. The mixture was then washed with water (800 mL) and brine (100 mL), dried ($Na_2SO_4$) and concentrated in vacuo to give the title compound (587 g, 90%) as yellow oil; $^1$H NMR: ($CDCl_3$) 1.29 (3H, d), 3.13-3.24 (2H, m), 3.60 (3H, s), 3.68-3.71 (1H, m), 7.13-7.26 (5H, m).

Intermediate 45: N'-(5-Chloro-4-pyrazolo[1,5-a]pyridin-3-ylpyrimidin-2-yl)-4-methoxy-6-(5-methyl-2,5-diazaspiro[3.4]octan-2-yl)benzene-1,3-diamine A mixture of 5-chloro-N-[2-methoxy-4-(5-methyl-2,5-diazaspiro[3.4]octan-2-yl)-5-nitrophenyl]-4-pyrazolo[1,5-a]pyridin-3-ylpyrimidin-2-amine (Intermediate 46, 95 mg, 0.18 mmol), iron (61 mg, 1.09 mmol) and $NH_4Cl$ (7.32 mg, 0.14 mmol) was heated at reflux in ethanol (10.5 mL) and water (3.5 mL) for 2 h. The mixture was cooled and filtered through diatomaceous earth (Celite™). The filtrate was concentrated in vacuo and the residue was dissolved in $CH_2Cl_2$. This solution was washed with brine, dried ($Na_2SO_4$) and concentrated in vacuo. Purification by FCC, eluting with 2-6% 7N methanolic ammonia in $CH_2Cl_2$ gave the title compound (30 mg, 34%) as a brown gum; m/z: $ES^+$ $MH^+$ 491.5.

Intermediate 46: 5-Chloro-N-[2-methoxy-4-(5-methyl-2,5-diazaspiro[3.4]octan-2-yl)-5-nitrophenyl]-4-pyrazolo[1,5-a]pyridin-3-ylpyrimidin-2-amine A mixture of 5-methyl-2,5-diazaspiro[3.4]octane dihydrochloride salt (Intermediate 47, 400 mg) in $CH_3OH$/water was absorbed onto an SCX column. The column was washed with $CH_3OH$ and eluted with methanolic ammonia. The fractions containing product were combined and concentrated (caution: product is volatile). A mixture of 5-chloro-N-(4-fluoro-2-methoxy-5-nitrophenyl)-4-pyrazolo[1,5-a]pyridin-3-ylpyrimidin-2-amine (Intermediate 20, 250 mg, 0.60 mmol), 5-methyl-2,5-diazaspiro[3.4]octane (91 mg, 0.72 mmol) and DIPEA (0.365 mL, 2.11 mmol) in DMA (3 mL) was heated at 140° C. for 0.5 h in a microwave. The mixture was then diluted with $CH_3OH$ and absorbed onto an SCX column. The column was washed with $CH_3OH$ and eluted with 1:1 methanolic ammonia in $CH_2Cl_2$. Fractions containing the product were combined and concentrated to provide a solid. This solid was suspended in $CH_3OH$, filtered, washed with diethyl ether and dried to give the title compound (267 mg, 85%) as a red solid; $^1$H NMR: 1.63-1.78 (2H, m), 2-2.12 (2H, m), 2.41 (3H, s), 2.69 (2H, t), 3.77 (2H, d), 3.90 (3H, s), 4.13 (2H, d), 6.30 (1H, s), 7.14 (1H, td), 7.34 (1H, t), 8.12 (1H, s), 8.41-8.46 (2H, m), 8.74 (1H, s), 8.86 (1H, d), 8.96 (1H, s); m/z: $ES^+$ $MH^+$ 521.46.

Intermediate 47: 5-Methyl-2,5-diazaspiro[3.4]octane dihydrochloride salt

A 4M solution of HCl in EtOAc (120 mL) was prepared by adding acetyl chloride (34 mL) to a solution of ethanol (28 mL) and EtOAc (58 mL). This solution was then added to a mixture of 2-benzyl-5-methyl-2,5-diazaspiro[3.4]octane (Intermediate 48, 48 g, 221.89 mmol) and $Pd(OH)_2$ (34 g, 20% on carbon) in 1.5 L of $CH_3OH$. The mixture was then stirred at 30° C. under 55 psi of $H_2$ for 24 h. The mixture was then filtered and the filtrate was concentrated in vacuo to give the title salt (42.7 g, 96%) as yellow oil; $^1$H NMR: ($d^4$-methanol) 1.98-2.11 (2H, m), 2.53 (2H, t), 3.02 (3H, s), 3.38 (2H, t), 4.17 (2H, d), 4.68 (2H, d).

Intermediate 48: 2-Benzyl-5-methyl-2,5-diazaspiro[3.4]octane

Paraformaldehyde (70.91 g, 787 mmol) and triethylamine (119.5 g, 1.18 mol) were added to a mixture of 2-benzyl-2,5-diazaspiro[3.4]octane dihydrochloride (Intermediate 49, 65 g, 236.2 mmol) in 1,2-dichloroethane (700 mL) and the mixture was stirred for 1 h at 10° C. Sodium triacetoxyborohydride (110.8 g, 1.18 mol) was then added and the mixture was stirred for 12 h at 15° C. The mixture was then filtered and the filter cake was washed with $CH_2Cl_2$ (3×500 mL). The combined organic solutions were washed with brine (500 mL), dried ($MgSO_4$) and concentrated in vacuo to give the title compound (51.1 g, 94%) as yellow oil; $^1$H NMR: (300 MHz, $CDCl_3$) 1.75 (2H, m), 2.16 (2H, m), 2.49 (3H, s), 2.64 (2H, d), 3.10 (2H, d), 3.28 (2H, d), 3.66 (2H, s), 7.22-7.62 (5H, m).

Intermediate 49: 2-Benzyl-2,5-diazaspiro[3.4]octane dihydrochloride

A 4M solution of HCl in EtOAc (2 L) was added to a solution of tert-butyl 2-benzyl-2,5-diazaspiro[3.4]octane-5- carboxylate (Intermediate 50, 195 g, 644.8 mmol) in EtOAc (0.5 L) and the mixture was stirred for 12 h. The resulting solid was collected by filtration and washed with tert-butylmethyl ether (2 L) to give the title salt (170 g, 96%) as white solid; $^1$H NMR: (d$^4$-methanol) 2.04-2.11 (2H, m), 2.41 (2H, t), 3.39 (2H, t), 4.33 (2H, s), 4.81-4.88 (2H, m), 7.49-7.58 (5H, m).

Intermediate 50: tert-Butyl 2-benzyl-2,5-diazaspiro[3.4]octane-5-carboxylate

A solution of CBr$_4$ (369.5 g, 1.115 mol) in 1 L of CH$_2$Cl$_2$ was added dropwise to a solution of tert-butyl 2-[(benzylamino)methyl]-2-(hydroxymethyl)pyrrolidine-1-carboxylate (Intermediate 51, 178.5 g, 555 mmol) and triphenylphosphine (292 g, 1.115 mol) in CH$_2$Cl$_2$ (1.8 L) at 0° C. The resulting mixture was stirred at r.t. for 2 h then concentrated in vacuo. The residue was suspended in a mixture of CH$_3$CN (2 L) and triethylamine (563.5 g, 5.57 mol) and refluxed at 80° C. for 24 h. The mixture was then concentrated in vacuo. Purification by FCC, eluting with 1:1 petrol-EtOAc gave the title compound (97.5 g, 58%) as yellow oil; $^1$H NMR: (300 MHz, CDCl$_3$) 1.47-1.72 (11H, m), 2.30 (2H, m), 3.19 (2H, d), 3.31-3.47 (2H, m), 3.82-4.12 (4H, m), 7.22-7.28 (5H, m).

Intermediate 51: 2-[(Benzylamino)methyl]-2-(hydroxymethyl)pyrrolidine-1-carboxylate Borane-dimethylsulfide (170 mL, 1.7 mol) was added to a solution of tert-butyl 2-benzyl-3-oxo-2,5-diazaspiro[3.4]octane-5-carboxylate (Intermediate 52, 179 g, 567 mmol) in 1.8 L of THF and the mixture was refluxed at 80° C. for 12 h. The reaction was then quenched by the addition of CH$_3$OH (1 L), and water (1.5 L). The phases were then separated and the aqueous solution was extracted with EtOAc (3×1 L), then the combined organic solutions were washed with brine (3×1 L), dried (MgSO$_4$) and concentrated in vacuo to the title compound (119 g, 66%) as yellow oil; $^1$H NMR: (CDCl$_3$) 1.47 (10H, m), 1.55-1.78 (3H, m), 2.06 (1H, m), 2.57 (2H, d), 3.17 (1H, m), 3.35 (2H, m), 3.37 (1H, m), 3.75-3.87 (3H, m), 7.23-7.40 (5H, m).

Intermediate 52: tert-Butyl 2-benzyl-3-oxo-2,5-diazaspiro[3.4]octane-5-carboxylate n-Butyllithum (268.7 mL, 0.672 mmol, 2.5 M in hexane) was added to a solution of diisopropylamine (70 g, 691.7 mmol) at −70° C. in dry THF (1.5 L) under N$_2$ then the mixture was stirred for 1 h at −70° C. A solution of 1-tert-butyl 2-methyl pyrrolidine-1,2-dicarboxylate (Intermediate 53, 140 g, 610 mmol) in anhydrous THF (360 mL) was then added dropwise at −70° C. After stirring at −70° C. for 1 h, a solution of 2-(benzylamino)-acetonitrile (Intermediate 54, 45.9 g, 305.7 mmol) in anhydrous THF (360 mL) was added dropwise at −70° C. over a period of 1 h. Then the resulting mixture was warmed to r.t. then stirred for 12 h. Sat. NH$_4$Cl (1.5 L) was then added and the resulting phases were separated. The aqueous solution was extracted with EtOAc (3×1 L). The combined organic solutions were washed with brine (3×1 L), dried (MgSO$_4$) and concentrated in vacuo. Purification by FCC, eluting with 2:1 petroleum ether/EtOAc gave the title compound (75.5 g, 76%) as yellow oil; $^1$H NMR: (CDCl$_3$) 1.44 (9H, m), 1.77 (1H, m), 1.93 (1H, m), 2.04 (1H, m), 2.37 (1H, m), 3.00 (1H, m), 3.40-3.67 (3H, m), 3.95 (1H, m), 4.25-4.89 (1H, m), 7.21-7.36 (5H, m).

Intermediate 53: 1-tert-Butyl 2-methyl pyrrolidine-1,2-dicarboxylate

K$_2$CO$_3$ (1.1 kg, 8.0 mol) and CH$_3$I (659 g, 4.65 mol) was added to a solution of 1-[(2-methylpropan-2-yl)oxycarbonyl]pyrrolidine-2-carboxylic acid (500 g, 2.32 mol) in DMF (2.5 L) at r.t. and the mixture was stirred for 12 h, then filtered. The filtrate was concentrated in vacuo. The residue was dissolved in EtOAc (2 L) and washed with water (2×1 L), brine (1 L), dried (MgSO$_4$) and concentrated in vacuo to give the title compound (417.8 g, 96%) as yellow oil; $^1$H NMR: (CDCl$_3$) 1.37 (9H, m), 1.72-1.84 (3H, m), 2.15 (1H, m), 3.26-3.51 (2H, m), 3.65 (3H, s), 4.17 (1H, m).

Intermediate 54: 2-(Benzylamino)acetonitrile

A solution of the ClCH$_2$CN (316 g, 4.19 mol) in EtOAc (200 mL) was added dropwise to benzylamine (900 g, 8.40 mol) while the mixture was vigorously stirred. The mixture was warmed gently to 45° C. for 0.5 h and a white precipitate was removed by filration. The filtrate was concentrated in vacuo to give the title compound (606 g, 99%) as yellow oil; $^1$H NMR: (CDCl$_3$) 3.56 (2H, s), 3.94 (2H, s), 7.28-7.40 (5H, m).

Intermediate 55: N'-(5-Chloro-4-pyrazolo[1,5-a]pyridin-3-ylpyrimidin-2-yl)-4-methoxy-6-(1-methyl-3,6-dihydro-2H-pyridin-4-yl)benzene-1,3-diamine A mixture of 5-chloro-N-[2-methoxy-4-(1-methyl-3,6-dihydro-2H-pyridin-4-yl)-5-nitrophenyl]-4-pyrazolo[1,5-a]pyridin-3-ylpyrimidin-2-amine (Intermediate 56, 470 mg, 0.96 mmol), iron (320 mg, 5.73 mmol) and NH$_4$Cl (35.8 mg, 0.67 mmol) in ethanol (19 mL) and water (6.33 mL) was heated at reflux for 4 h. Then the mixture was cooled and concentrated in vacuo to give a thick slurry which was triturated with 10% CH$_3$OH in CH$_2$Cl$_2$ (50 mL) for 15 minutes. The mixture was then filtered and a small amount of sat. NaHCO$_3$ was added to the filtrate. The resulting phases were separated and the aqueous solution was extracted with 10% CH$_3$OH in CH$_2$Cl$_2$ (50 mL). The combined organic solutions were washed with brine, dried (Na$_2$SO$_4$) and concentrated in vacuo. Purification by FCC, eluting with 2.5% 7N methanolic ammonia in CH$_2$Cl$_2$ gave the title compound (387 mg, 88%) as a yellow foam; $^1$H NMR: 2.31 (3H, s), 2.38-2.44 (2H, m), 2.61 (2H, t), 3.02 (2H, dd), 3.68 (3H, s), 4.33 (2H, d), 5.72-5.76 (1H, m), 6.66 (1H, s), 7.08 (1H, s), 7.14 (1H, td), 7.35-7.43 (1H, m), 8.41 (1H, s), 8.44 (1H, s), 8.49 (1H, d), 8.84 (1H, d), 8.96 (1H, s); m/z: ES$^+$ MH$^+$ 462.5.

Intermediate 56: 5-Chloro-N-[2-methoxy-4-(1-methyl-3,6-dihydro-2H-pyridin-4-yl)-5-nitrophenyl]-4-pyrazolo[1,5-a]pyridin-3-ylpyrimidin-2-amine A mixture of 3-(2,5-dichloropyrimidin-4-yl)pyrazolo[1,5-a]pyridine (Intermediate 21, 575 mg, 1.86 mmol) and 2-methoxy-4-(1-methyl-3,6-dihydro-2H-pyridin-4-yl)-5-nitroaniline (Intermediate 3, 490 mg, 1.86 mmol) was stirred in THF (30 mL) and cooled in an ice/water bath. Lithium bis(trimethylsilyl)amide (4.10 mL, 4.10 mmol, 1M in THF) was then added dropwise and the mixture was stirred for 1 h. CH$_3$OH was added and the mixture was concentrated in vacuo. The crude material was suspended in CH$_3$OH and the mixture was filtered. The collected solid was washed with CH$_3$OH and diethyl ether and dried on the filter to give the title compound (660 mg, 72%) as a yellow powder; $^1$H NMR: 2.29 (3H, s), 2.30-2.38 (2H, m), 2.58 (2H, t), 2.97 (2H, dd), 3.96 (3H, s), 5.60-5.68 (1H, m), 7.00 (1H, s), 7.16 (1H, td), 7.36-7.45 (1H, m), 8.49-8.56 (3H, m), 8.87 (1H, d), 8.90 (1H, s), 8.97 (1H, s); m/z: ES$^+$ MH$^+$ 492.4.

Intermediate 57: 2-(4-{2-Amino-4-[(5-chloro-4-pyrazolo[1,5-a]pyridin-3-ylpyrimidin-2-yl)amino]-5-methoxyphenyl}piperazin-1-yl)-N,N-dimethylacetamide A mixture of 2-(4-{4-[(5-chloro-4-pyrazolo[1,5-a]pyridin-3-ylpyrimidin-2-yl)amino]-5-methoxy-2-nitrophenyl}piperazin-1-yl)-N,N-dimethylacetamide (Intermediate 58, 0.234 g, 0.41 mmol), iron (0.139 g, 2.48 mmol) and NH$_4$Cl (0.015 g, 0.29 mmol) in ethanol (10 mL) and water (3.33 mL) was heated at reflux for 4 h. The mixture was then allowed to cool to r.t., was filtered and the filtrate concentrated in vacuo. Purification by ion exchange chromatography, using an SCX column and eluting with 1M methanolic ammonia, gave a brown gum after concentration of appropriate fractions. Further purification by FCC, eluting with 0-5% CH$_3$OH in CH$_2$Cl$_2$ gave the title compound (0.19 g, 86%) as a yellow foam; $^1$H NMR: (CDCl$_3$) 2.72 (4H, s), 2.93-3.01 (7H, m), 3.13 (3H, s), 3.27 (2H, s), 3.65-3.83 (2H, m), 3.84 (3H, s), 6.71 (1H, s), 6.96 (1H, td), 7.38 (1H, ddd), 7.55 (1H, s), 7.92 (1H, s), 8.36 (1H, s), 8.57 (1H, dt), 8.61-8.68 (1H, m), 8.94 (1H, s); m/z: ES$^+$ MH$^+$ 536.53.

Intermediate 58: 2-(4-{4-[(5-Chloro-4-pyrazolo[1,5-a]pyridin-3-ylpyrimidin-2-yl)amino]-5-methoxy-2-nitrophenyl}piperazin-1-yl)-N,N-dimethylacetamide DIPEA (0.105 mL, 0.60 mmol) was added to a mixture of 5-chloro-N-(4-fluoro-2-methoxy-5-nitrophenyl)-4-pyrazolo[1,5-a]pyridin-3-ylpyrimidin-2-amine (Intermediate 20, 207 mg, 0.5 mmol) and N,N-dimethyl-2-piperazin-1-ylacetamide (86 mg, 0.50 mmol) in 2,2,2-trifluoroethanol (2.5 mL). The mixture was heated in a microwave at 140° C. for 1 h then cooled to r.t. The mixture was purified directly by ion exchange chromatography, using an SCX column and eluting with 7M methanolic ammonia to provide crude product after concentration of appropriate fractions. Further purification by FCC, eluting with 0-5% CH$_3$OH in CH$_2$Cl$_2$ gave the title compound (234 mg, 83%) as an orange foam; $^1$H NMR: (CDCl$_3$) 2.71-2.78 (4H, m), 2.97 (3H, s), 3.09 (3H, s), 3.11-3.18 (4H, m), 3.26 (2H, s), 3.99 (3H, s), 6.66 (1H, s), 6.97 (1H, td), 7.35-7.42 (1H, m), 7.52 (1H, s), 8.41 (1H, s), 8.49 (1H, d), 8.56 (1H, d), 8.92 (1H, s), 9.02 (1H, s); m/z: ES$^+$ MH$^+$ 566.52.

Intermediate 59: (S)-tert-Butyl N-[1-(4-{2-amino-4-[(5-chloro-4-pyrazolo[1,5-a]-pyridin-3-ylpyrimidin-2-yl)amino]-5-methoxyphenyl}piperazin-1-yl)-1-oxopropan-2-yl]carbamate A mixture of (S)-tert-butyl N-[1-(4-{4-[(5-chloro-4-pyrazolo[1,5-a]pyridin-3-ylpyrimidin-2-yl)amino]-5-methoxy-2-nitrophenyl}piperazin-1-yl)-1-oxopropan-2-yl]carbamate (Intermediate 60, 100 mg, 0.15 mmol), iron (51.4 mg, 0.92 mmol) and NH$_4$Cl (5.74 mg, 0.11 mmol) was heated at reflux in ethanol (3 mL) and water (1 mL) for 1 h.
Purification by ion exchange chromatography, using an SCX column and eluting with 7M methanolic ammonia provided material that was further purified by FCC, eluting with 0-5% CH$_3$OH in CH$_2$Cl$_2$ to give the title compound (65 mg, 68%) as a yellow solid; m/z: ES$^+$ MH$^+$ 622.58.

Intermediate 60: (S)-tert-Butyl N-[1-(4-{4-[(5-chloro-4-pyrazolo[1,5-a]pyridin-3-ylyl-pyrimidin-2-yl)amino]-5-methoxy-2-nitrophenyl}piperazin-1-yl)-1-oxopropan-2-yl]-carbamate DIPEA (0.105 mL, 0.60 mmol) was added to a mixture of 5-chloro-N-(4-fluoro-2-methoxy-5-nitrophenyl)-4-pyrazolo[1,5-a]pyridin-3-ylpyrimidin-2-amine (Intermediate 20, 207 mg, 0.5 mmol) and (S)-tert-butyl 1-oxo-1-(piperazin-1-yl)propan-2-ylcarbamate (129 mg, 0.50 mmol) in 2,2,2-trifluoroethanol (2.5 mL). The mixture was heated in a microwave at 140° C. for 1 h then cooled to r.t. The mixture was purified directly by ion exchange chromatography, using an SCX column and eluting with 7M methanolic ammonia to give crude material. Further purification by FCC, eluting with 0-5% CH$_3$OH in CH$_2$Cl$_2$ gave the title compound (110 mg, 34%) as a solid/gum; m/z: ES$^+$ MH$^+$ 552.59.

Intermediate 61: N-(5-Chloro-4-pyrazolo[1,5-a]pyridin-3-ylpyrimidin-2-yl)-4-[1(3S)-3-dimethylaminopyrrolidin-1-yl]-6-methoxybenzene-1,3-diamine A mixture of 5-chloro-N-[4-[(3S)-3-dimethylaminopyrrolidin-1-yl]-2-methoxy-5-nitrophenyl]-4-pyrazolo[1,5-a]pyridin-3-ylpyrimidin-2-amine (Intermediate 62, 295 mg, 0.58 mmol), iron (194 mg, 3.48 mmol) and NH$_4$Cl (23 mg, 0.43 mmol) were heated at reflux in ethanol (12 mL) and water (4 mL) for 1.5 h. The mixture was then cooled and concentrated in vacuo. The residue was triturated in 10% CH$_3$OH in CH$_2$Cl$_2$ (25 mL) for 15 minutes and then filtered. The residues were triturated again with 10% CH$_3$OH in CH$_2$Cl$_2$ (25 mL) and filtered. The combined filtrates were washed with brine, dried (Na$_2$SO$_4$) and concentrated in vacuo. Purification by FCC, eluting with 2% 7N methanolic ammonia in CH$_2$Cl$_2$ gave the title compound (260 mg, 94%) as a yellow gum; $^1$H NMR: 1.73-1.86 (1H, m), 2.01-2.12 (1H, m), 2.20 (6H, s), 2.81-2.91 (1H, m), 2.92-3.05 (2H, m), 3.16 (1H, dd), 3.2-3.27 (1H, m), 3.67 (3H, s), 4.25 (2H, d), 6.71 (1H, s), 6.93 (1H, s), 7.12 (1H, td), 7.3-7.37 (1H, m), 8.36 (1H, s), 8.38-8.46 (2H, m), 8.82 (1H, dt), 8.94 (1H, s); m/z: ES$^+$ MH$^+$ 479.5.

Intermediate 62: 5-Chloro-N-{4-[(3S)-3-dimethylaminopyrrolidin-1-yl]-2-methoxy-5-nitrophenyl}-4-pyrazolo[1,5-a]pyridin-3-ylpyrimidin-2-amine (3S)—N,N-Dimethylpyrrolidin-3-amine (0.092 mL, 0.72 mmol) was added to a suspension of 5-chloro-N-(4-fluoro-2-methoxy-5-nitrophenyl)-4-pyrazolo[1,5-a]pyridin-3-ylpyrimidin-2-amine (Intermediate 20, 250 mg, 0.60 mmol) and DIPEA (0.125 mL, 0.72 mmol) in DMA (3 mL) and the mixture was heated at 140° C. in a microwave for 0.5 h. The mixture was then diluted with CH$_3$OH and absorbed onto an SCX column. The column was washed with CH$_3$OH and then eluted with 1:1 7M methanolic ammonia in CH$_2$Cl$_2$. Appropriate fractions were concentrated and further purification by FCC, eluting with 2% 7N methanolic ammonia in CH$_2$Cl$_2$ gave the title compound (300 mg, 98%) as an orange foam; $^1$H NMR: 1.75-1.95 (1H, m), 2.09-2.30 (7H, m), 2.72-2.87 (1H, m), 3.11-3.27 (3H, m), 3.42-3.56 (1H, m), 3.90 (3H, s), 6.57 (1H, s), 7.13 (1H, t), 7.26-7.41 (1H, m), 8.09 (1H, s), 8.28-8.50 (2H, m), 8.67 (1H, s), 8.84 (1H, d), 8.95 (1H, s); m/z: ES$^+$ MH$^+$ 509.5.

Intermediate 63: N'-(5-Chloro-4-pyrazolo[1,5-a]pyridin-3-ylpyrimidin-2-yl)-4-methoxy-6-(4-methylpiperazin-1-yl)benzene-1,3-diamine A mixture of 5-chloro-N-[2-methoxy-4-(4-methylpiperazin-1-yl)-5-nitrophenyl]-4-pyrazolo[1,5-a]pyridin-3-ylpyrimidin-2-amine (Intermediate 64, 775 mg, 1.57 mmol), iron (525 mg, 9.40 mmol) and NH$_4$Cl (62.8 mg, 1.17 mmol) was heated at reflux in ethanol (21 mL) and water (7 mL) for 2 h. The mixture was then cooled and filtered through diatomaceous earth (Celite™). The filtrate was concentrated in vacuo and then dissolved into CH$_2$Cl$_2$. This solution was washed with brine, dried (MgSO$_4$) and concentrated in vacuo. Purification by FCC, eluting with 2-6% 7N methanolic ammonia in CH$_2$Cl$_2$ gave the title compound (480 mg, 66%) as a brown gum; $^1$H NMR: 2.26 (3H, s), 2.52 (4H+ DMSO, m), 2.89 (4H, t), 3.68 (3H, s), 4.35 (2H, d), 6.73 (1H, s), 6.99 (1H, d), 7.13 (1H, td), 7.28-7.39 (1H, m), 8.38 (1H, d), 8.39-8.46 (2H, m), 8.82 (1H, d), 8.95 (1H, s); m/z: ES$^+$ MH$^+$ 465.5.

Intermediate 64: 5-Chloro-N-[2-methoxy-4-(4-methylpiperazin-1-yl)-5-nitrophenyl]-4-pyrazolo[1,5-a]pyridin-3-ylpyrimidin-2-amine 1-Methylpiperazine (0.267 mL, 2.41 mmol) was added to a suspension of 5-chloro-N-(4-fluoro-2-methoxy-5-nitrophenyl)-4-pyrazolo[1,5-a]pyridin-3-ylpyrimidin-2-amine (Intermediate 20, 500 mg, 1.21 mmol) in 2,2,2-trifluoroethanol (6 mL). The mixture was heated in a microwave at 140° C. for 1 h. The mixture was then loaded onto a SCX column, and the column was washed with CH$_3$OH. The column was then eluted with 2M methanolic ammonia and appropriate fractions were combined and concentrated in vacuo. Further purification by FCC, eluting with 0-10% CH$_3$OH in CH$_2$Cl$_2$ gave the title compound (596 mg, 100%), as an orange foam; $^1$H NMR: (CDCl$_3$) 2.37 (3H, s), 2.57-2.68 (4H, m), 3.08-3.14 (4H, m), 4.00 (3H, s), 6.64 (1H, s), 6.98 (1H, t), 7.34-7.43 (1H, m), 7.53 (1H, s), 8.41 (1H, s), 8.49 (1H, d), 8.53-8.6 (1H, m), 8.93 (1H, s), 9.04 (1H, s); m/z: ES$^+$ MH$^+$ 495.

Intermediate 65: 2-{[5-Amino-2-methoxy-4-(4-methylpiperazin-1-yl)phenyl]amino}-4-pyrazolo[1,5-a]pyridin-3-ylpyrimidine-5-carbonitrile A mixture of N'-(5-chloro-4-pyrazolo[1,5-a]pyridin-3-ylpyrimidin-2-yl)-4-methoxy-6-(4-methylpiperazin-1-yl)benzene-1,3-diamine (Intermediate 63, 157 mg, 0.34 mmol), zinc (2.209 mg, 0.03 mmol), tris(dibenzylideneacetone)dipalladium(0) (30.9 mg, 0.03 mmol), dicyclohexyl(2',4',6'-triisopropylbiphenyl-2-yl)phosphine ('XPhos', 32.2 mg, 0.07 mmol), and dicyanozinc (23.8 mg, 0.20 mmol) were placed in a reaction tube under N$_2$ and then degassed DMA (0.9 mL) was added. The resulting suspension was stirred to 95° C. for 1.5 h. The mixture was then diluted with EtOAc and washed five times with water, then brine. The solution was then dried (MgSO$_4$) and concentrated in vacuo. The residue was triturated with diethyl ether and the resulting solid was collected by filtration, and washed with diethyl ether. The solid was then dissolved in a mixture of CH$_2$Cl$_2$ and CH$_3$OH and the solution was allowed to pass through a stratospheres SPE cartridge PL-Thiol MP SPE (available from Polymer Laboratories) under gravity. The resulting solution was concentrated in vacuo to give the title compound (87 mg, 57%) as a yellow solid; $^1$H NMR: (100° C.) 2.28 (3H, s), 2.49-2.58 (4H, m), 2.90-2.98 (4H, m), 3.70 (3H, s), 4.28 (2H, br s), 6.77 (1H, s), 6.99 (1H, s), 7.14 (1H, t), 7.37 (1H, t), 8.37 (1H, d), 8.55 (1H, s), 8.78 (1H, d), 8.85 (1H, s), 8.92 (1H, s); m/z: ES$^+$ MH$^+$ 456.4.

Intermediate 66: N'-[4-(1H-Indol-3-yl)pyrimidin-2-yl]-4-methoxy-6-(4-methylpiperazin-1-yl)benzene-1,3-diamine A solution of NH$_4$Cl (0.021 g, 0.38 mmol) in water (3 mL) was added in one portion to a stirred suspension of 4-(1H-indol-3-yl)-N-[2-methoxy-4-(4-methylpiperazin-1-yl)-5-nitrophenyl]pyrimidin-2-amine (Intermediate 67, 0.235 g, 0.51 mmol) and iron (0.171 g, 3.07 mmol) in ethanol (9 mL) and the mixture was stirred at 105° C. for 18 h. The mixture was then concentrated in vacuo and the resulting residue was dissolved in DMF (20 mL). Purification by ion exchange chromatography, using an SCX column, eluting with 0.35M methanolic ammonia in CH$_2$Cl$_2$ and concentration of the appropriate fractions gave the title compound (0.206 g, 94%) as a yellow solid; m/z: ES$^+$ MH$^+$ 430.51.

Intermediate 67: 4-(1H-Indol-3-yl)-N-[2-methoxy-4-(4-methylpiperazin-1-yl)-5-nitrophenyl]pyrimidin-2-amine A mixture of 1-methylpiperazine (148 mg, 1.48 mmol), N-(4-fluoro-2-methoxy-5-nitrophenyl)-4-(1H-indol-3-yl)pyrimidin-2-amine (Intermediate 68, 224 mg, 0.59 mmol) and trifluoroethanol (5 mL) was sealed into a microwave tube and heated to 120° C. for 1 h in a microwave reactor and then cooled to r.t. The mixture was then concentrated in vacuo. Trituration of the resulting brown gum with ethanol and then diethyl ether gave a solid that was collected by filtration and dried under vacuum to give the title compound (89 mg, 33%) as a pale brown solid; $^1$H NMR: 3.02-3.13 (4H, m), 4.00 (3H, s), 6.86 (1H, s), 7.08 (1H, t), 7.18 (1H, t), 7.31 (1H, d), 7.45 (1H, d), 8.08 (1H, s), 8.33 (2H, dd), 8.82 (1H, d), 11.81 (1H, s); m/z: ES$^+$ MH$^+$ 460.5.

Intermediate 68: N-(4-Fluoro-2-methoxy-5-nitrophenyl)-4-(1H-indol-3-yl)pyrimidin-2-amine

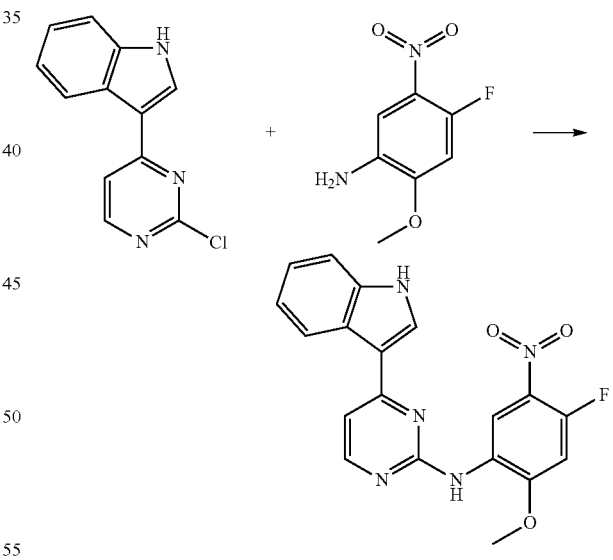

p-Toluenesulfonic acid hydrate (225 mg, 1.18 mmol) was added in one portion to a mixture of 4-fluoro-2-methoxy-5-nitroaniline (Intermediate 23, 200 mg, 1.07 mmol) and 3-(2-chloropyrimidin-4-yl)-1H-indole (247 mg, 1.07 mmol) in 2-pentanol (10 mL). The resulting mixture was then stirred at 120° C. for 18 h. The resulting precipitate was collected by filtration, washed with 2-pentanol (5 mL) and dried in vacuo to give a yellow solid. The solid was triturated with CH$_3$CN to give a solid which was collected by filtration and dried in vacuo to give the title compound (224 mg, 55%) as a yellow solid; m/z: ES$^+$ MH$^+$ 380.21.

Intermediate 69: 4-Methoxy-6-(4-methylpiperazin-1-yl)-N'-(4-pyrazolo[1,5-a]pyridin-3-ylpyrimidin-2-yl)benzene-1,3-diamine A solution of [(Z)-3-(dimethylamino)-3-pyrazolo[1,5-a]pyridin-3-yl-prop-2-enylidene]-dimethyl-ammonium hexafluorophosphate (Intermediate 70, 116 mg, 0.3 mmol) in 2-methoxyethanol (2 mL) was added dropwise to a stirred solution of 1-(5-amino-2-methoxy-4-(4-methylpiperazin-1-yl)phenyl)guanidine (Intermediate 72, 84 mg, 0.30 mmol) and 1,1,3,3-tetramethylguanidine (0.056 mL, 0.45 mmol) in 2-methoxyethanol (2 mL) at r.t. under $N_2$. The resulting solution was sealed into a microwave tube and heated to 120° C. for 0.25 h then cooled to r.t. Further 1,1,3,3-tetramethylguanidine (0.056 mL, 0.45 mmol) was then added and the mixture was stirred at 120° C. for 0.25 h, then at 140° C. for 0.25 h. The mixture was cooled, diluted with EtOAc (10 mL), and washed with water (2×5 mL). The aqueous solution was extracted with EtOAc (5 mL) and the organic solution was washed with water (2×3 mL). The combined organic solutions were dried ($MgSO_4$) and concentrated in vacuo. Purification by FCC, eluting with 1.5-5% 7N methanolic ammonia in $CH_2Cl_2$ gave the title compound (69 mg, 53%) as a yellow foam; $^1H$ NMR: 2.25 (3H, d), 2.51 (4H, m), 2.87 (4H, t), 3.73 (3H, s), 4.37 (2H, s), 6.72 (1H, s), 7.07 (1H, m), 7.22 (1H, d), 7.33 (1H, s), 7.40 (1H, m), 7.98 (1H, s), 8.31 (1H, d), 8.52 (1H, d), 8.76 (1H, s), 8.79 (1H, d); m/z: $ES^+$ $MH^+$ 431.

Intermediate 70: [(Z)-3-(Dimethylamino)-3-pyrazolo[1,5-a]pyridin-3-yl-prop-2-enylidene]-dimethyl-ammonium hexafluorophosphate Dimethylamine (24.0 mL, 48.0 mmol, 2M in THF) was added in one portion to a suspension of (Z)—N-(3-chloro-3-(pyrazolo[1,5-a]pyridin-3-yl)allylidene)-N-methylmethanaminium hexafluorophosphate (Intermediate 71, 6.07 g, 16 mmol) in $CH_3OH$ (40 mL) at r.t. under $N_2$. The resulting solution was stirred at r.t. for 0.25 h then stored in the freezer overnight. Crystals were produced and these were collected, washed with $CH_3OH$ at −50° C. and THF, then dried by suction under a stream of $N_2$. Two crops of crystals were collected to give the title compound (5.29 g, 85%) as a beige crystalline solid; m/z: $ES^+$ $M^+$244.

Intermediate 71: (Z)—N-(3-Chloro-3-(pyrazolo[1,5-a]pyridin-3-yl)allylidene)-N-methylmethanaminium hexafluorophosphate $POCl_3$ (0.951 mL, 10.20 mmol) was added to a solution of (E)-3-(dimethylamino)-1-(pyrazolo[1,5-a]pyridin-3-yl)prop-2-en-1-one (2.153 g, 10 mmol) in $CH_2Cl_2$ (15 mL) at 20° C. (using ice/water cooling) over a period of 3 minutes under $N_2$. The resulting solution was stirred at r.t. for 0.5 h and was then concentrated in vauco. The residue was dissolved into a minimum amount of $CH_3OH$ (100 mL). This solution was added over a period of 2 minutes to a solution of sodium hexafluorophosphate(V) (3.36 g, 20.00 mmol) in $CH_3OH$ (40 mL). After 5 minutes the precipitate was collected by filtration, washed well with $CH_3OH$ cooled to −50° C. and dried by suction under a stream of $N_2$ to give the title compound (3.40 g, 90%) as a yellow powder, which was used without further purification; $^1H$ NMR: 3.63 (6H, d), 7.36 (2H, m), 7.71-7.90 (1H, m), 8.45 (1H, d), 8.81 (1H, d), 9.05 (2H, d); m/z: $ES^+$ $M^+$234.

Intermediate 72: 1-[5-Amino-2-methoxy-4-(4-methylpiperazin-1-yl)phenyl]guanidine A mixture of 1-[2-methoxy-4-(4-methylpiperazin-1-yl)-5-nitrophenyl]guanidine (Intermediate 73, 1.47 g, 4.58 mmol) and 10% Pd on carbon (0.146 g, 0.14 mmol) in ethanol (30 mL) was stirred under an atmosphere of $H_2$ at r.t. for 18 h. The mixture was filtered through diatomaceous earth (Celite™) and the filtrate was concentrated in vacuo. The residue, together with 10% Pd on carbon (0.146 g, 0.14 mmol) in $CH_3OH$ (60 mL) was stirred under an atmosphere of $H_2$ at r.t. for 2 h. The mixture was then filtered through diatomaceous earth (Celite™) and the filtrate was concentrated in vacuo to give the title compound (1.253 g, 94%) as a brown foam; $^1H$ NMR: 2.24 (3H, s), 2.51 (4H, m), 2.86 (4H, m), 3.72 (3H, s), 4.47 (2H, s), 6.54 (1H, s), 6.69 (1H, s), 7.30 (3H, s); m/z: $ES^+$ $MH^+$ 279.

Intermediate 73: 1-[2-Methoxy-4-(4-methylpiperazin-1-yl)-5-nitrophenyl]guanidine Methanesulfonic acid (0.508 mL, 7.83 mmol) was added to a slurry of 2-methoxy-4-(4-methylpiperazin-1-yl)-5-nitroaniline (Intermediate 14, 1.39 g, 5.22 mmol) in butan-1-ol (10 mL) and water (0.5 mL) at r.t. The resulting slurry was heated to 90° C. and at that temperature a solution of cyanamide (0.439 g, 10.44 mmol) in water (0.22 mL) was added dropwise over a period of 1 minute. The mixture was heated at 90° C. for 0.5 h then methanesulfonic acid (0.339 mL, 5.22 mmol) was added dropwise. At 10-minute intervals more cyanamide (0.219 g, 5.22 mmol), more methanesulfonic acid (0.339 mL, 5.22 mmol) and more cyanamide (0.329 g, 7.83 mmol) and more methanesulfonic acid (0.339 mL, 5.22 mmol) were successively added. The mixture was allowed to cool and was diluted with 2-methyltetrahydrofuran (75 mL) and diethyl ether (75 mL). This solution was then basified using 5M NaOH to ~pH 13. The resulting phases were separated and the aqueous solution was extracted with 2-methyltetrahydrofuran (3×50 mL). The combined organic solutions were washed with sat. brine and dried ($MgSO_4$). The product precipitated onto the drying agent, so after filtration the $MgSO_4$ was washed with hot $CH_2Cl_2/CH_3OH$ 5:1 (5×100 mL) and the combined filtrate was concentrated in vacuo. The residue was dissolved in hot 2-propanol (80 mL), filtered while hot and then concentrated in vacuo. The residue was dissolved in $CH_2Cl_2$ (50 mL), filtered and the filtrate was concentrated in vacuo to give the title compound (1.49 g, 89%) as an orange foam. The product could only be deposited amorphously from the 2-propanol filtrate, but a 38 mg sample of the final product was crystallised from ethanol (~100 μL) and was collected by filtration, washed with −70° C. ethanol and diethyl ether and dried under vacuum to give the title compound (11 mg, 28%) as a yellow powder; $^1H$ NMR: 2.25 (3H, s), 2.44-2.49 (4H, m), 2.99-3.16 (4H, m), 3.91 (3H, s), 6.73 (1H, s), 7.38 (3H, s), 7.67 (1H, s); m/z: $ES^+$ $MH^+$ 309.

Intermediate 74: N'-[5-Chloro-4-(1H-indol-3-yl)pyrimidin-2-yl]-4-methoxy-6-(4-methylpiperazin-1-yl)benzene-1,3-diamine A mixture of 5-chloro-4-(1H-indol-3-yl)-N-[2-methoxy-4-(4-methylpiperazin-1-yl)-5-nitrophenyl]pyrimidin-2-amine (Intermediate 75, 350 mg, 0.71 mmol), iron (237 mg, 4.25 mmol) and $NH_4Cl$ (26.5 mg, 0.50 mmol) were heated at reflux in ethanol (24 mL) and water (8 mL) for 2 h. The mixture was then cooled and concentrated in vacuo to give a thick slurry. CH$_2$Cl$_2$ (100 mL) and CH$_3$OH (10 mL) were added and the mixture was stirred for 0.25 h and then filtered. The filter cake was washed with further CH$_2$Cl$_2$ and CH$_3$OH, and the combined organics were dried (MgSO$_4$) and concentrated in vacuo. Purification by FCC, eluting with 1-5% methanolic ammonia in CH$_2$Cl$_2$ gave the title compound (288 mg, 88%) as a yellow dry film; $^1$H NMR: 2.26 (3H, s), 2.47-2.56 (4H, m), 2.88 (4H, t), 3.70 (3H, s), 4.29 (2H, d), 6.72 (1H, s), 7.04 (1H, t), 7.14 (1H, s), 7.15-7.22 (1H, m), 7.46 (1H, d), 8.18 (1H, s), 8.35 (2H, d), 8.48 (1H, d), 11.81 (1H, s); m/z: ES$^+$ MH$^+$ 464.49.

Intermediate 75: 5-Chloro-4-(1H-indol-3-yl)-N-[2-methoxy-4-(4-methylpiperazin-1-yl)-5-nitrophenyl]pyrimidin-2-amine 1-Methylpiperazine (492 µL, 4.44 mmol) was added to a suspension of 5-chloro-N-(4-fluoro-2-methoxy-5-nitrophenyl)-4-(1H-indol-3-yl)pyrimidin-2-amine (Intermediate 76, 612 mg, 1.48 mmol). The mixture was heated at 120° C. for 1 h and was then concentrated in vacuo. The residue was dissolved in CH$_2$Cl$_2$ (25 mL) and washed with water (2×25 mL) and sat. brine (25 mL), then dried (MgSO$_4$) and concentrated in vacuo. Purification by FCC, eluting with 1-10% CH$_3$OH in CH$_2$Cl$_2$ gave the title compound as an orange gum. This gum was dissolved in ethanol (25 mL) and a solid precipitated. This solid was collected by filtration and washed with ethanol and diethyl ether to give the title compound (365 mg, 50%) as a yellow/orange solid; $^1$H NMR: 2.26 (3H, s), 2.47-2.55 (4H, m), 3.07-3.13 (4H, m), 3.93 (3H, s), 6.85 (1H, s), 6.99 (1H, t), 7.16-7.22 (1H, m), 7.48 (1H, d), 8.26 (1H, d), 8.36 (1H, s), 8.42 (1H, d), 8.51 (1H, s), 8.54 (1H, s), 11.88 (1H, s); m/z: ES$^+$ MH$^+$ 494.46.

Intermediate 76: 5-Chloro-N-(4-fluoro-2-methoxy-5-nitrophenyl)-4-(1H-indol-3-yl)-pyrimidin-2-amine A mixture of 3-(2,5-dichloropyrimidin-4-yl)-1H-indole (Intermediate 11, 391 mg, 1.48 mmol), 4-fluoro-2-methoxy-5-nitroaniline (Intermediate 23, 289 mg, 1.55 mmol) and p-toluenesulfonic acid monohydrate (310 mg, 1.63 mmol) in 2-pentanol (25 mL) was heated at 125° C. for 18 h. The mixture was cooled and used in the next step without further purification; m/z: ES$^+$ MH$^+$ 414.12.

Intermediate 77: 4-Methoxy-N'-[5-methyl-4-(1-methylindol-3-yl)pyrimidin-2-yl]-6-(4-methylpiperazin-1-yl)benzene-1,3-diamine A mixture of N-[2-methoxy-4-(4-methylpiperazin-1-yl)-5-nitrophenyl]-5-methyl-4-(1-methylindol-3-yl)pyrimidin-2-amine (Intermediate 78, 408 mg, 0.84 mmol), iron (280 mg, 5.02 mmol) and NH$_4$Cl (31.3 mg, 0.59 mmol) in ethanol (24 mL) and water (8.00 mL) was heated at reflux for 3 h. The mixture was cooled and concentrated in vacuo to give a thick slurry. CH$_2$Cl$_2$ (100 mL) and CH$_3$OH (10 mL) were added and the mixture was stirred for 0.25 h and then filtered. The filter cake was washed with further CH$_2$Cl$_2$ and CH$_3$OH and the combined organics were dried (MgSO$_4$) and concentrated in vacuo. Purification by FCC, eluting with 1-7% methanolic ammonia in CH$_2$Cl$_2$ gave the title compound (163 mg, 43%) as a yellow gum which crystallised on standing; $^1$H NMR: (CDCl$_3$) 2.36 (6H, s), 2.53 (3H, dd), 2.94 (4H, t), 3.69-3.79 (2H, m), 3.83 (3H, s), 3.86 (3H, s), 6.69 (1H, s), 7.24-7.27 (1H, m), 7.29 (1H, dd), 7.33 (1H, dd), 7.36-7.40 (1H, m), 7.49 (1H, s), 7.58 (1H, s), 8.23 (1H, d), 8.26 (1H, s), 8.56 (1H, d); m/z: ES+ MH$^+$458.37.

Intermediate 78: N-[2-Methoxy-4-(4-methylpiperazin-1-yl)-5-nitrophenyl]-5-methyl-4-(1-methylindol-3-yl)pyrimidin-2-amine 1-Methylpiperazine (0.453 mL, 4.08 mmol) was added to a suspension of N-(4-fluoro-2-methoxy-5-nitrophenyl)-5-methyl-4-(1-methylindol-3-yl)pyrimidin-2-amine (Intermediate 79, 554 mg, 1.36 mmol) in 2,2,2-trifluoroethanol (10 mL). The mixture was heated in a microwave at 120° C. for 1 h. The mixture was then concentrated in vacuo and the residue was dissolved in CH$_2$Cl$_2$ (50 mL). This solution was washed water (2×50 mL) and sat. brine (50 mL), then dried (MgSO$_4$) and concentrated in vacuo. Purification by FCC, eluting with 1-10% CH$_3$OH in CH$_2$Cl$_2$ gave an orange gum. This gum was dissolved in ethanol (25 mL) and a solid precipitated. This solid was collected by filtration and washed with ethanol to give the title compound (413 mg, 62%) as a yellow/orange solid; $^1$H NMR: 2.25 (3H, s), 2.39 (3H, s), 2.45-2.54 (4H, m), 3.03-3.10 (4H, m), 3.91 (3H, s), 3.98 (3H, s), 6.86 (1H, s), 7.06 (1H, dd), 7.22-7.28 (1H, m), 7.51 (1H, d), 8.02 (1H, s), 8.07 (1H, s), 8.26-8.30 (1H, m), 8.38 (1H, d), 8.69 (1H, s); m/z: ES$^+$ MH$^+$ 488.29.

Intermediate 79: N-(4-Fluoro-2-methoxy-5-nitrophenyl)-5-methyl-4-(1-methylindol-3-yl)pyrimidin-2-amine A mixture of 3-(2-chloro-5-methylpyrimidin-4-yl)-1-methyl-1H-indole (Intermediate 80, 350 mg, 1.36 mmol), 4-fluoro-2-methoxy-5-nitroaniline (Intermediate 23, 265 mg, 1.43 mmol) and p-toluenesulfonic acid (284 mg, 1.49 mmol) in 2-pentanol (25 mL) was heated at 125° C. for 24 h. The mixture was then cooled and concentrated in vacuo. The resulting gum was used without further purification; m/z: ES$^+$ MH$^+$ 240.13.

Intermediate 80: 3-(2-Chloro-5-methylpyrimidin-4-yl)-1H-indole

NaH (0.862 g, 21.54 mmol, 30% dispersion in mineral oil) was added to 3-(2-chloro-5-methylpyrimidin-4-yl)-1H-indole (Intermediate 17, 5.0 g, 20.5 mmol) in THF (200 mL) at 0° C. under N$_2$. The resulting solution was stirred at 0° C. for 0.25 h. CH$_3$I (1.347 mL, 21.54 mmol) was then added, the mixture was allowed to warm to r.t. and and was stirred for 2 h. The mixture was cooled again in an ice bath and further NaH (0.862 g, 21.54 mmol, 30% dispersion in mineral oil) was added. The resulting suspension was stirred at 0° C. for 10 minutes. CH$_3$I (1.347 mL, 21.54 mmol) was then added and the mixture was stirred for a further 1 h. The mixture was then diluted with water (100 mL) and extracted with EtOAc (100 mL). The organic solution was washed with water (75 mL) and some solid formed at the solvent interface. The solid was collected by filtration and was washed with water and EtOAc and then dried, giving the title compound as a white solid. The phases were separated and the organic solution was further washed with water and some more solid formed so this was also collected by filtration, washed with water and EtOAc and dried, to give more of the title compound as a white solid. (total so far: 3.82 g, 72%). The organic solution was then washed with sat. brine, dried (MgSO$_4$) and concentrated in vacuo. The residue was triturated with diethyl ether to give a solid which was collected by filtration and dried in vacuo to give the title compound (0.883 g, 17%) as a beige solid; (overall: 4.71 g, 89%); $^1$H NMR: 2.48 (3H, s), 3.94 (3H, s), 7.24-7.36 (2H, m), 7.58 (1H, d), 8.25 (1H, s), 8.48 (1H, s), 8.57 (1H, d); m/z: ES$^+$ MH$^+$ 258.12.

Intermediate 81: $N^1$-(2-Dimethylaminoethyl)-5-methoxy-N-methyl-$N^4$-[5-methyl-4-(1-methylindol-3-yl)pyrimidin-2-yl]benzene-1,2,4-triamine A mixture of N'-(2-dimethylaminoethyl)-2-methoxy-N'-methyl-N-[5-methyl-4-(1-methyl-indol-3-yl)pyrimidin-2-yl]-5-nitrobenzene-1,4-diamine (Intermediate 82, 202 mg, 0.41 mmol), iron (138 mg, 2.48 mmol) and NH$_4$Cl (15.45 mg, 0.29 mmol) in ethanol (16 mL) and water (5.33 mL) was heated at reflux for 3 h. The mixture was then cooled and concentrated in vacuo to give a thick slurry. CH$_2$Cl$_2$ (100 mL) and CH$_3$OH (10 mL) was then added and the mixture was stirred for 0.25 h and then filtered. The filter cake was washed further with CH$_2$Cl$_2$ and CH$_3$OH and the combined organics were dried (MgSO$_4$) and concentrated in vacuo. Purification by FCC, eluting with 1-8% methanolic ammonia in CH$_2$Cl$_2$ gave the title compound (147 mg, 78%) as a yellow dry film; m/z: ES$^+$ MH$^+$ 460.36.

Intermediate 82: N'-(2-Dimethylaminoethyl)-2-methoxy-N'-methyl-N-[5-methyl-4-(1-methylindol-3-yl)pyrimidin-2-yl]-5-nitrobenzene-1,4-diamine $N^1,N^1,N^2$-Trimethylethane-1,2-diamine (221 mg, 2.16 mmol) was added to a suspension of N-(4-Fluoro-2-methoxy-5-nitrophenyl)-5-methyl-4-(1-methylindol-3-yl)pyrimidin-2-amine (Intermediate 79, 400 mg, 0.98 mmol) in DMA (4 mL). The mixture was heated in a microwave at 140° C. for 0.5 h. The mixture was then concentrated in vacuo and the residue was dissolved in EtOAc (100 mL). This solution was washed with water (2×100 mL) and sat. brine (100 mL), dried (MgSO$_4$) and concentrated in vacuo. Purification by FCC, eluting with 1-8% methanolic ammonia in CH$_2$Cl$_2$ gave the title compound (202 mg, 42%) as an orange dry film; m/z: ES$^+$ MH$^+$ 444.55.

Intermediate 83: 4-[(3R)-3-Dimethylaminopyrrolidin-1-yl]-6-methoxy-N-[5-methyl-4-(1-methylindol-3-yl)pyrimidin-2-yl]benzene-1,3-diamine A mixture of N-{4-[(3R)-3-dimethylaminopyrrolidin-1-yl]-2-methoxy-5-nitrophenyl}-5-methyl-4-(1-methylindol-3-yl)pyrimidin-2-amine (Intermediate 84, 325 mg, 0.65 mmol), iron (217 mg, 3.89 mmol) and NH$_4$Cl (24.26 mg, 0.45 mmol) in ethanol (16 mL) and water (5.33 mL) was heated at reflux for 3 h. The mixture was then cooled and concentrated in vacuo to give a thick slurry. CH$_2$Cl$_2$ (100 mL) and CH$_3$OH (10 mL) were then added and the mixture was stirred for 0.25 h and then filtered. The filter cake was washed with further CH$_2$Cl$_2$ and CH$_3$OH and the combined organics were dried (MgSO$_4$) and concentrated in vacuo. Purification by FCC, eluting with 1-8% methanolic ammonia in CH$_2$Cl$_2$ gave the title compound (257 mg, 84%) as a yellow dry film; $^1$H NMR: 1.76 (1H, td), 2.03 (1H, dt), 2.18 (6H, s), 2.37 (3H, s), 2.79-2.87 (1H, m), 2.88-2.97 (2H, m), 3.08-3.14 (1H, m), 3.18 (1H, dd), 3.73 (3H, s), 3.90 (3H, s), 4.19 (2H, s), 6.70 (1H, s), 7.13 (1H, t), 7.25 (1H, t), 7.44 (1H, s), 7.51 (1H, d), 7.65 (1H, s), 8.04 (1H, s), 8.19 (1H, s), 8.46 (1H, d); m/z: ES$^+$ MH$^+$ 472.35.

Intermediate 84: N-{4-[(3R)-3-Dimethylaminopyrrolidin-1-yl]-2-methoxy-5-nitrophenyl}-5-methyl-4-(1-methylindol-3-yl)pyrimidin-2-amine (3R)—N,N-dimethylpyrrolidin-3-amine (255 mg, 2.24 mmol) was added to a suspension of N-(4-fluoro-2-methoxy-5-nitrophenyl)-5-methyl-4-(1-methylindol-3-yl)pyrimidin-2-amine (Intermediate 79, 414 mg, 1.02 mmol) in DMA (4 mL) and the mixture was heated in a microwave at 140° C. for 0.5 h. The mixture was then concentrated in vacuo and the residue was dissolved in EtOAc (50 mL). Purification by ion exchange chromatography, using an SCX column and eluting with 0.35M methanolic ammonia provided semi-purified material after concentration of appropriate fractions in vacuo. Purification by FCC, eluting with 1-8% CH$_3$OH in CH$_2$Cl$_2$ gave the title compound (330 mg, 65%) as an orange dry film; $^1$H NMR: 1.75-1.86 (1H, m), 2.13-2.19 (1H, m), 2.21 (6H, s), 2.37 (3H, s), 2.75 (1H, s), 3.10-3.20 (2H, m), 3.21-3.27 (1H, m), 3.46 (1H, td), 3.90 (3H, s), 3.94 (3H, s), 6.56 (1H, s), 7.03 (1H, t), 7.21-7.26 (1H, m), 7.49 (1H, d), 7.94 (1H, s), 8.05 (1H, s), 8.23 (1H, s), 8.37 (1H, d), 8.39 (1H, s); m/z: ES$^+$ MH$^+$ 502.33.

Intermediate 85: N-[5-Chloro-4-(1-methylindol-3-yl)pyrimidin-2-yl]-4-[(3R)-3-dimethylaminopyrrolidin-1-yl]-6-methoxybenzene-1,3-diamine A mixture of 5-chloro-N-{4-[(3R)-3-dimethylaminopyrrolidin-1-yl]-2-methoxy-5-nitrophenyl}-4-(1-methylindol-3-yl)pyrimidin-2-amine (Intermediate 86, 747 mg, 1.43 mmol), iron (479 mg, 8.59 mmol) and NH$_4$Cl (53.6 mg, 1.00 mmol) in ethanol (48 mL) and water (16 mL) was heated at reflux for 3 h. The mixture was then cooled and concentrated in vacuo to give a thick slurry. CH$_2$Cl$_2$ (100 mL) and CH$_3$OH (10 mL) were then added and the mixture was stirred for 0.25 h and then filtered. The filter cake was washed with further CH$_2$Cl$_2$ and MeOH and the combined organics were dried (MgSO$_4$) and concentrated in vacuo. Purification by FCC (split into two batches), eluting with 1-9% methanolic ammonia in CH$_2$Cl$_2$ gave the title compound (230 mg, 33%) as a yellow gum which crystallised on standing, and (2$^{nd}$ batch) more of the title compound (329 mg, 47%) as a yellow gum; $^1$H NMR: (CDCl$_3$) 1.87 (1H, ddt), 2.13 (1H, dtd), 2.29 (6H, s), 2.86 (1H, dq), 2.98-3.09 (2H, m), 3.20 (2H, dd), 3.66 (2H, s), 3.84 (3H, s), 3.88 (3H, s), 6.70 (1H, s), 7.25-7.35 (2H, m), 7.38 (1H, dd), 7.61 (1H, s), 8.10 (1H, s), 8.19 (1H, d), 8.32 (1H, s), 8.66 (1H, dd); m/z: ES$^+$ MH$^+$ 492.27.

Intermediate 86: 5-Chloro-N-{4-[(3R)-3-dimethylaminopyrrolidin-1-yl]-2-methoxy-5-nitrophenyl}-4-(1-methylindol-3-yl)pyrimidin-2-amine (3R)—N,N-Dimethylpyrrolidin-3-amine (126 mg, 1.11 mmol) was added to a suspension of 5-chloro-N-(4-fluoro-2-methoxy-5-nitrophenyl)-4-(1-methylindol-3-yl)pyrimidin-2-amine (Intermediate 87, 215 mg, 0.50 mmol) in DMA (5 mL) and the mixture was heated in a microwave at 140° C. for 0.5 h. The mixture was then concentrated in vacuo and combined with material from the reaction below for work up. (3R)—N,N-dimethylpyrrolidin-3-amine (276 mg, 2.42 mmol) was added to a suspension of 5-chloro-N-(4-fluoro-2-methoxy-5-nitrophenyl)-4-(1-methylindol-3-yl)pyrimidin-2-amine (Intermediate 87, 470 mg, 1.10 mmol) in DMA (10 mL) and the mixture was heated in a microwave at 140° C. for 0.5 h. The mixture was concentrated in vacuo and combined with the material from the first procedure described above, for work-up. The combined residues were dissolved in $CH_2Cl_2$ (100 mL), and the resulting solution was washed with water (2×100 mL) and sat. brine (100 mL), and then dried ($MgSO_4$) and concentrated in vacuo, Purification by FCC, eluting with 1-10% $CH_3OH$ in $CH_2Cl_2$ gave the title compound (747 mg, 89%) as an orange gum; m/z: $ES^+$ $M^+$522.30.

Intermediate 87: 5-Chloro-N-(4-fluoro-2-methoxy-5-nitrophenyl)-4-(1-methylindol-3-yl)pyrimidin-2-amine A mixture of 3-(2,5-dichloropyrimidin-4-yl)-1-methylindole (Intermediate 88, 1281 mg, 4.60 mmol), p-toluene sulphonic acid monohydrate (964 mg, 5.07 mmol) and 4-fluoro-2-methoxy-5-nitroaniline (Intermediate 23, 900 mg, 4.84 mmol) in 2-pentanol (50 mL) was heated at 125° C. for 18 h. A preciptate formed from the solution upon cooling. The precipitate was collected by filtration, washed with $CH_3OH$ (10 mL) and diethyl ether (20 mL) and dried on the filter to give the title compound (1.42 g, 72%) as a tan solid, which was used without further purification; $^1H$ NMR: 3.91 (3H, s), 3.96 (3H, s), 7.05 (1H, t), 7.23-7.3 (1H, m), 7.39 (1H, d), 7.53 (1H, d), 8.33 (1H, d), 8.47 (1H, s), 8.58 (1H, s), 8.65 (1H, d), 8.76 (1H, s); m/z: $ES^+$ $MH^+$ 428.10.

Intermediate 88: 3-(2,5-Dichloropyrimidin-4-yl)-1-methylindole

NaH (0.795 g, 19.88 mmol) was added to 3-(2,5-dichloropyrimidin-4-yl)-1H-indole (Intermediate 11, 5.0 g, 18.9 mmol) in THF (200 mL) at 0° C. under $N_2$ and the mixture was stirred at 0° C. for 0.25 h. $CH_3I$ (1.243 mL, 19.88 mmol) was then added and the mixture was allowed to warm to r.t. and was stirred for 1 h. The mixture was cooled again in an ice bath and further NaH (0.795 g, 19.88 mmol) was added. The suspension was stirred at 0° C. for 10 minutes then $CH_3I$ (1.243 mL, 19.88 mmol) was added and the mixture was stirred for 1 h. The mixture was then diluted with water (100 mL) which resulted in the formation of some solid. The solid was collected by filtration and was washed with water and EtOAc and then dried, to give the title compound (3.67 g, 70%) as a beige solid. The organic solution was further washed with water and sat. brine and then dried ($MgSO_4$) and concentrated in vacuo. Trituration of the residue with diethyl ether gave a solid which was collected by filtration and dried in vacuo to give the title compound (477 mg, 9%) as a brown solid: This material was only 71% pure so it was kept separate from the earlier batch; $^1H$ NMR: 3.97 (3H, s), 7.34 (2H, dtd), 7.59-7.65 (1H, m), 8.56 (1H, dd), 8.73 (1H, s), 8.79 (1H, s); m/z: $ES^+$ $MH^+$ 278.06.

Intermediate 89: 2-({5-Amino-4-[(3R)-3-dimethylaminopyrrolidin-1-yl]-2-methoxyphenyl}amino)-4-(1-methylindol-3-yl)pyrimidine-5-carbonitrile A mixture of N-[5-chloro-4-(1-methylindol-3-yl)pyrimidin-2-yl]-4-[(3R)-3-dimethylaminopyrrolidin-1-yl]-6-methoxybenzene-1,3-diamine (Intermediate 85, 324 mg, 0.66 mmol), zinc powder (4.3 mg, 0.07 mmol), tris(dibenzylideneacetone)-dipalladium(0) (60.3 mg, 0.07 mmol), dicyclohexyl(2',4',6'-triisopropylbiphenyl-2-yl)phosphine ('XPhos', 62.8 mg, 0.13 mmol), and dicyanozinc (46.4 mg, 0.40 mmol) was placed in a reaction tube under $N_2$ and then degassed DMA (1.75 mL) was added. The resulting suspension was heated to 95° C. and stirred for 2 h. The mixture was then diluted with EtOAc and washed 5 times with water, and then with brine. The solution was the dried ($MgSO_4$) and concentrated in vacuo. The residue was dissolved in $CH_3OH$ and was allowed to pass through a stratospheres SPE cartridge PL-Thiol MP SPE (available from Polymer Laboratories) under gravity. The resulting solution was concentrated in vacuo and the resulting residue was triturated with diethyl ether. The resulting solid was collected by filtration and washed with diethyl ether to give the title compound (184 mg, 58%) as a yellow solid; $^1H$ NMR: (100° C.) 1.8-1.88 (1H, m), 2.03-2.11 (1H, m), 2.24 (6H, s), 2.92-2.99 (1H, m), 3.01-3.05 (1H, m), 3.06-3.11 (1H, m), 3.20 (2H, ddd), 3.69 (3H, s), 3.90 (3H, s), 4.17 (2H, br s), 6.73 (1H, s), 7.04 (1H, s), 7.10 (1H, t), 7.26 (1H, t), 7.50 (1H, d), 8.31 (1H, d), 8.42 (1H, s), 8.60 (1H, s), 8.62 (1H, s); m/z: $ES^+$ $MH^+$ 483.31.

Intermediate 90: 2-{[5-Amino-2-methoxy-4-(4-methylpiperazin-1-yl)phenyl]amino}-4-(1-methylindol-3-yl)pyrimidine-5-carbonitrile A mixture of N'-[5-chloro-4-(1-methylindol-3-yl)pyrimidin-2-yl]-4-methoxy-6-(4-methylpiperazin-1-yl)benzene-1,3-diamine (Intermediate 91, 344 mg, 0.72 mmol), zinc powder (4.71 mg, 0.07 mmol), tris(dibenzylideneacetone) dipalladium(0) (65.9 mg, 0.07 mmol), dicyclohexyl(2',4',6'-triisopropylbiphenyl-2-yl)phosphine ('XPhos', 68.6 mg, 0.14 mmol), and dicyanozinc (50.7 mg, 0.43 mmol) were placed in a reaction tube under $N_2$ and then degassed DMA (1.91 mL) was added. The resulting suspension was shirred at 95° C. for 2 h. The mixture was then diluted with EtOAc and washed 5 times with water, and then with brine. The solution was then dried ($MgSO_4$) and concentrated in vacuo. The residue was dissolved in $CH_3OH$ and allowed to pass through a stratospheres SPE cartridge PL-Thiol MP SPE (available from Polymer Laboratories) under gravity. The resulting solution was concentrated in vacuo and the resulting residue was triturated with diethyl ether. The resulting solid was collected by filtration and washed with diethyl ether to give the title compound (208 mg, 62%) as a yellow solid; $^1H$ NMR: 2.28 (3H, s), 2.51-2.58 (4H, m), 2.89-2.95 (4H, m), 3.69 (3H, s), 3.91 (3H, s), 4.23 (2H, br s), 6.75 (1H, s), 7.08 (1H, s), 7.09-7.12 (1H, m), 7.26 (1H, ddd), 7.50 (1H, d), 8.31 (1H, d), 8.43 (1H, s), 8.61 (1H, s), 8.64 (1H, s); m/z: $ES^+$ $MH^+$ 469.33.

Intermediate 91: N'-[5-Chloro-4-(1-methylindol-3-yl)pyrimidin-2-yl]-4-methoxy-6-(4-methylpiperazin-1-yl)benzene-1,3-diamine A mixture of 5-chloro-N-[2-methoxy-4-(4-methylpiperazin-1-yl)-5-nitrophenyl]-4-(1-methylindol-3-yl)pyrimidin-2-amine (Intermediate 92, 750 mg, 1.48 mmol), iron (495 mg, 8.86 mmol) and $NH_4Cl$ (55.3 mg, 1.03 mmol) in ethanol (12 mL) and water (4 mL) was heated at reflux for 4 h. Purification by ion exchange chromatography, using an SCX column and eluting with 7M methanolic ammonia provided part-purified material that was concentrated in vacuo onto silica. Purification by FCC, eluting with 0-4% 7N methanolic ammonia in $CH_2Cl_2$ gave the title compound (367 mg, 52%) as a yellow solid. Impure fractions containing desired product were concentrated in vacuo and the resulting residue was triturated with $CH_2Cl_2$/diethyl ether to give more of the title compound (230 mg, 33%) as a yellow solid. Total: 597 mg, 85%; $^1H$ NMR: ($CDCl_3$) 2.37 (3H, s), 2.56 (4H, br s), 2.95 (4H, br t), 3.75 (2H, br s), 3.84 (3H, s), 3.90 (3H, s), 6.70 (1H, s), 7.27-7.36 (2H, m), 7.38-7.42 (1H, m), 7.63 (1H, s), 8.13 (1H, s), 8.21 (1H, s), 8.33 (1H, s), 8.63-8.69 (1H, m); m/z: ES$^+$ MH$^+$ 478.55.

Intermediate 92: 5-Chloro-N-[2-methoxy-4-(4-methylpiperazin-1-yl)-5-nitrophenyl]-4-(1-methylindol-3-yl)pyrimidin-2-amine 1-Methylpiperazine (0.50 mL, 4.51 mmol) was added to a suspension of 5-chloro-N-(4-fluoro-2-methoxy-5-nitrophenyl)-4-(1-methylindol-3-yl)pyrimidin-2-amine (Intermediate 87, 750 mg, 1.75 mmol) in 2,2,2-trifluoroethanol (15 mL) and the mixture was heated in a microwave at 120° C. for 1 h and then 140° C. for 0.5 h. The mixture was then concentrated in vacuo and the residue was dissolved in EtOAc (100 mL). This organic solution was washed with sat. NaHCO$_3$ (100 mL), water (2×100 mL) and then brine (100 mL). The solution was then dried (MgSO$_4$) and concentrated in vacuo onto silica. Purification by FCC, eluting with 0-4% CH$_3$OH in CH$_2$Cl$_2$ gave the title compound (772 mg, 87%) as a orange solid; $^1$H NMR: (CDCl$_3$) 2.37 (3H, s), 2.59-2.65 (4H, m), 3.07-3.14 (4H, m), 3.90 (3H, s), 3.99 (3H, s), 6.63 (1H, s), 7.25-7.3 (1H, m) partially obscured by chloroform peak, 7.31-7.36 (1H, m), 7.39 (1H, d), 7.56 (1H, s), 8.22 (1H, s), 8.39 (1H, s), 8.47 (1H, d), 9.18 (1H, s); m/z: ES$^+$ MH$^+$ 508.19.

Intermediate 93: N-[5-Chloro-4-(1H-indol-3-yl)pyrimidin-2-yl]-4-[(3R)-3-dimethylaminopyrrolidin-1-yl]-6-methoxybenzene-1,3-diamine A mixture of 5-chloro-N-{4-[(3R)-3-dimethylaminopyrrolidin-1-yl]-2-methoxy-5-nitro-phenyl}-4-(1H-indol-3-yl)pyrimidin-2-amine (Intermediate 94, 350 mg, 0.69 mmol), iron (231 mg, 4.13 mmol) and NH$_4$Cl (27.6 mg, 0.52 mmol) in ethanol (15 mL) and water (5 mL) was heated at reflux for 1.5 h. The mixture was then cooled and concentrated in vacuo. The residue was triturated with 10% CH$_3$OH in CH$_2$Cl$_2$ (15 mL) for 0.25 h and then filtered. The residues were triturated again with 10% CH$_3$OH in CH$_2$Cl$_2$ (15 mL) and then filtered. The combined filtrates were washed with brine, dried (Na$_2$SO$_4$) and concentrated in vacuo. Purification by FCC, eluting with 3% CH$_3$OH in CH$_2$Cl$_2$ and then 2-5% 7N methanolic ammonia in CH$_2$Cl$_2$ gave the title compound (261 mg, 79%) as a yellow foam; $^1$H NMR: 1.73-1.86 (1H, m), 1.99-2.12 (1H, m), 2.20 (6H, s), 2.81-2.91 (1H, m), 2.97 (2H, ddd), 3.12-3.26 (2H, m), 3.69 (3H, s), 4.20 (2H, d), 6.71 (1H, s), 7.03 (1H, t), 7.07 (1H, s), 7.14-7.22 (1H, m), 7.46 (1H, d), 8.18 (1H, s), 8.3-8.39 (2H, m), 8.48 (1H, s), 11.81 (1H, s); m/z: ES$^+$ MH$^+$ 478.5.

Intermediate 94: 5-Chloro-N-{4-[(3R)-3-dimethylaminopyrrolidin-1-yl]-2-methoxy-5-nitrophenyl}-4-(1H-indol-3-yl)pyrimidin-2-amine (R)-(+)-3-(Dimethylamino)pyrrolidine (0.111 mL, 0.87 mmol) was added to a suspension of 5-chloro-N-(4-fluoro-2-methoxy-5-nitrophenyl)-4-(1H-indol-3-yl)pyrimidin-2-amine (Intermediate 76, 300 mg, 0.73 mmol) and DIPEA (0.151 mL, 0.87 mmol) in DMA (3 mL) and the mixture was heated at 140° C. in a microwave for 0.5 h. The mixture was then diluted with CH$_3$OH and absorbed onto an SCX column. The column was washed with CH$_3$OH and eluted with 1:1 methanolic ammonia in CH$_2$Cl$_2$. Appropriate fractions were concentrated and further purification by FCC, eluting with 1.5% 7N methanolic ammonia in CH$_2$Cl$_2$ gave the title compound (353 mg, 96%) as an orange foam; $^1$H NMR: 1.78-1.91 (1H, m), 2.16-2.27 (7H, m), 2.70-2.85 (1H, m), 3.12-3.29 (3H, m), 3.41-3.55 (1H, m), 3.89 (3H, s), 6.57 (1H, s), 6.95 (1H, t), 7.17 (1H, t), 7.46 (1H, d), 8.09 (1H, s), 8.24 (1H, br s), 8.37 (1H, s), 8.50 (1H, d), 8.54 (1H, s), 11.88 (1H, s); m/z: ES$^+$ MH$^+$ 508.5.

Intermediate 95: N$^4$-[5-Chloro-4-(1H-indol-3-yl)pyrimidin-2-yl]-N$^1$-(2-dimethylamino-ethyl)-5-methoxy-N$^1$-methylbenzene-1,2,4-triamine A mixture of N-[5-chloro-4-(1H-indol-3-yl)pyrimidin-2-yl]-N'-(2-dimethylaminoethyl)-2-methoxy-N'-methyl-5-nitrobenzene-1,4-diamine (Intermediate 96, 350 mg, 0.71 mmol), iron (236 mg, 4.23 mmol) and NH$_4$Cl (28.3 mg, 0.53 mmol) in ethanol (15 mL) and water (5 mL) were heated at reflux for 1.5 h. The mixture was then cooled and concentrated in vacuo. The residue was triturated in 10% CH$_3$OH in CH$_2$Cl$_2$ (15 mL) for 0.25 h and then filtered. The residues were triturated again with 10% CH$_3$OH in CH$_2$Cl$_2$ (15 mL) and then filtered. The combined filtrates were washed with brine, dried (Na$_2$SO$_4$) and concentrated in vacuo. Purification by FCC, eluting with 5% CH$_3$OH in CH$_2$Cl$_2$ and then 2-5% 7N methanolic ammonia in CH$_2$Cl$_2$ gave the title compound (159 mg, 48%) as a yellow foam; $^1$H NMR: 2.18 (6H, s), 2.38 (2H, t), 2.66 (3H, s), 2.91 (2H, t), 3.68 (3H, s), 4.54 (2H, s), 6.77 (1H, s), 6.99-7.10 (2H, m), 7.12-7.22 (1H, m), 7.46 (1H, d), 8.25 (1H, s), 8.30-8.40 (2H, m), 8.49 (1H, d), 11.85 (1H, s); m/z: ES$^+$ MH$^+$ 466.6.

Intermediate 96: N-[5-Chloro-4-(1H-indol-3-yl)pyrimidin-2-yl]-N'-(2-dimethyl-aminoethyl)-2-methoxy-N'-methyl-5-nitrobenzene-1,4-diamine N,N,N'-Trimethylethylenediamine (0.113 mL, 0.87 mmol) was added to a suspension of 5-chloro-N-(4-fluoro-2-methoxy-5-nitrophenyl)-4-(1H-indol-3-yl)pyrimidin-2-amine (Intermediate 76, 300 mg, 0.73 mmol) and DIPEA (0.151 mL, 0.87 mmol) in DMA (3 mL) and the mixture was heated at 140° C. in a microwave for 0.5 h. The mixture was then diluted with CH$_3$OH and absorbed onto an SCX column. The column was washed with CH$_3$OH and eluted with 1:1 methanolic ammonia in CH$_2$Cl$_2$. Appropriate fractions were concentrated and purification by FCC, eluting with 2% 7N methanolic ammonia in CH$_2$Cl$_2$ gave the title compound (354 mg, 98%) as an orange foam; $^1$H NMR: 2.16 (6H, s), 2.52 (2H+DMSO, m), 2.87 (3H, s), 3.30 (2H, t), 3.89 (3H, s), 6.84 (1H, s), 6.97 (1H, t), 7.13-7.23 (1H, m), 7.46 (1H, d), 8.16 (1H, s), 8.23 (1H, br d), 8.40 (1H, s), 8.51 (1H, d), 8.55 (1H, s), 11.89 (1H, s); m/z: ES$^+$ MH$^+$ 469.5.

Intermediate 97: N$^4$-[5-Chloro-4-(1-methylindol-3-yl)pyrimidin-2-yl]-N$^1$-(2-dimethylaminoethyl)-5-methoxy-N$^1$-methylbenzene-1,2,4-triamine A mixture of N-[5-chloro-4-(1-methylindol-3-yl)pyrimidin-2-yl]-N'-(2-dimethylamino-ethyl)-2-methoxy-N'-methyl-5-nitrobenzene-1,4-diamine (Intermediate 98, 553 mg, 1.08 mmol), iron (363 mg, 6.51 mmol) and NH$_4$Cl (43.5 mg, 0.81 mmol) in ethanol (23 mL) and water (7.67 mL) were heated at reflux for 1.5 h. The mixture was then cooled and concentrated in vacuo. The resulting residue was dissolved in CH$_2$Cl$_2$ (100 mL) and CH$_3$OH (10 mL) and this mixture was stirred for 0.25 h and then filtered. The filter cake was washed with further CH$_2$Cl$_2$ and CH$_3$OH and the combined organics were dried (MgSO$_4$) and concentrated in vacuo. Purification by FCC, eluting with 0-5% methanolic ammonia in CH$_2$Cl$_2$ provided a solid. This solid was dissolved in diethyl ether and a small amount of brown precipitate was removed by filtration. The filtrate was concentrated in vacuo to give the title compound (409 mg, 79%) as a brown glass; $^1$H NMR: (CDCl$_3$) 2.26 (6H, s), 2.38-2.43 (2H, m), 2.68 (3H, s), 2.94-2.98 (2H, m), 3.84 (3H, s), 3.91 (3H, s), 6.71 (1H, s), 7.26-7.36 (2H, m), 7.40 (1H, d), 7.63 (1H, s), 8.09 (1H, s), 8.21 (1H, s), 8.33 (1H, s), 8.67 (1H, d); m/z: ES$^+$ MH$^+$ 480.32.

Intermediate 98: N-[5-Chloro-4-(1-methylindol-3-yl)pyrimidin-2-yl]-N'-(2-dimethylaminoethyl)-2-methoxy-N'-methyl-5-nitrobenzene-1,4-diamine N$^1$,N$^1$,N$^2$-trimethylethane-1,2-diamine (0.189 mL, 1.49 mmol) was added to a suspension 5-chloro-N-(4-fluoro-2-methoxy-5-nitrophenyl)-4-(1-methylindol-3-yl)pyrimidin-2-amine (Intermediate 87, 700 mg, 1.24 mmol) and DIPEA (0.431 mL, 2.48 mmol) in DMA (5 mL). The mixture was then heated in a microwave at 140° C. for 0.5 h. The mixture was diluted with CH$_3$OH and absorbed onto an SCX column. The column was washed with CH$_3$OH and eluted with ~1M methanolic ammonia. Appropriate fractions were concentrated and further purification by FCC, eluting with 0-5% methanolic ammonia in CH$_2$Cl$_2$ gave the title compound (561 mg, 89%) as an orange oil; $^1$H NMR: (CDCl$_3$) 2.26 (6H, s), 2.53-2.58 (2H, m), 2.88 (3H, s), 3.24-3.28 (2H, m), 3.91 (3H, s), 3.98 (3H, s), 6.68 (1H, s), 7.26-7.3 (1H, m), 7.31-7.4 (2H, m), 7.50 (1H, s), 8.23 (1H, s), 8.39 (1H, s), 8.47 (1H, d), 9.07 (1H, s); m/z: ES$^+$ MH$^+$ 510.27.

Intermediate 99: 2-{[5-Amino-2-methoxy-4-(4-methylpiperazin-1-yl)phenyl]amino}-4-(1H-indol-3-yl)pyrimidine-5-carbonitrile N'-[5-Chloro-4-(1H-indol-3-yl)pyrimidin-2-yl]-4-methoxy-6-(4-methylpiperazin-1-yl)benzene-1,3-diamine (Intermediate 74, 268 mg, 0.58 mmol), zinc powder (3.78 mg, 0.06 mmol), tris(dibenzylideneacetone)dipalladium(0) (52.9 mg, 0.06 mmol), dicyclohexyl(2',4',6'-triisopropylbiphenyl-2-yl)phosphine ('XPhos', 55.1 mg, 0.12 mmol), and dicyanozinc (40.7 mg, 0.35 mmol) were placed in a flask under N$_2$ and then degassed DMA (3 mL) was added. The resulting suspension was stirred for 3 h at 95° C. The mixture was then diluted with EtOAc and washed 5 times with water and then brine. The solution was then dried (MgSO$_4$) and concentrated in vacuo. The resulting residue was triturated with diethyl ether and the resulting solid was collected by filtration and washed with diethyl ether to give crude product. This crude material was dissolved into CH$_2$Cl$_2$/CH$_3$OH and concentrated in vacuo onto silica. Purification by FCC, eluting with 1.5-8% 7N methanolic ammonia in CH$_2$Cl$_2$ provided a solid which was washed with CH$_3$OH (0.2 mL) to give the title compound (48 mg, 18%) as a beige crystalline solid; $^1$H NMR: 2.26 (3H, s), 2.53 (4H, m), 2.91 (4H, s), 3.65 (3H, s), 4.38 (2H, d), 6.74 (1H, s), 6.85 (1H, s), 6.99 (1H, s), 7.19 (1H, s), 7.48 (1H, d), 8.01 (1H, s), 8.52 (1H, s), 8.65 (1H, s), 9.21 (1H, s), 11.97 (1H, s); m/z: ES$^+$ MH$^+$ 455.

Intermediate 100: N$^1$-(2-Dimethylaminoethyl)-5-methoxy-N$^1$-methyl-N$^4$-[4-(1-methylindol-3-yl)pyrimidin-2-yl]benzene-1,2,4-triamine

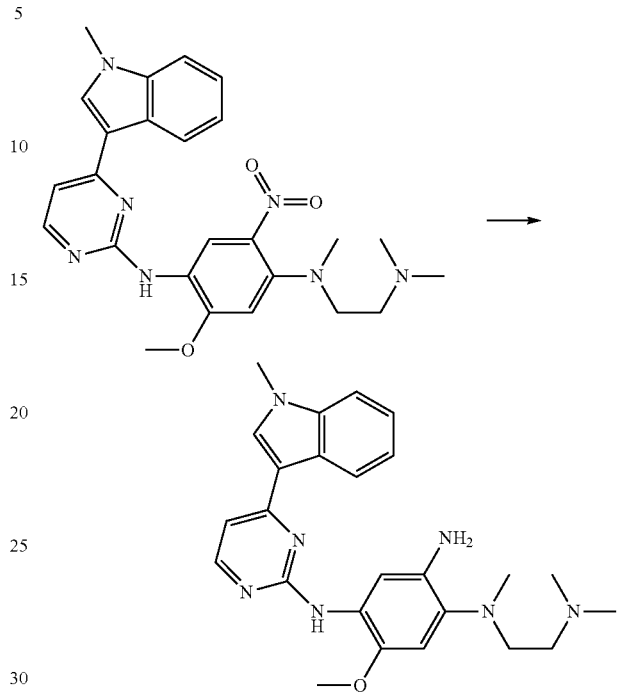

A mixture of N'-(2-dimethylaminoethyl)-2-methoxy-N'-methyl-N-[4-(1-methylindol-3-yl)pyrimidin-2-yl]-5-nitrobenzene-1,4-diamine (Intermediate 101, 220 mg, 0.46 mmol), iron (155 mg, 2.78 mmol) and NH$_4$Cl (17.32 mg, 0.32 mmol) in ethanol (12 mL) and water (4 mL) was heated at reflux for 2 h. The crude mixture was purified by ion exchange chromatography, using an SCX column. The desired product was eluted from the column using 7M methanolic ammonia and appropriate fractions were combined and concentrated in vacuo onto silica. Purification by FCC, eluting with 0-5% 7N methanolic ammonia in CH$_2$Cl$_2$ gave the title compound (175 mg, 85%) as a beige foam; $^1$H NMR: 2.17 (6H, s), 2.36 (2H, t), 2.63 (3H, s), 2.88 (2H, t), 3.74 (3H, s), 3.88 (3H, s), 4.58 (2H, br s), 6.76 (1H, s), 7.12-7.19 (2H, m), 7.21-7.27 (1H, m), 7.48 (1H, s), 7.51 (1H, d), 7.78 (1H, s), 8.27 (1H, d), 8.30 (1H, s), 8.42 (1H, d); m/z: ES$^+$ MH$^+$ 446.32.

Intermediate 101: N'-(2-Dimethylaminoethyl)-2-methoxy-N'-methyl-N-[4-(1-methylindol-3-yl)pyrimidin-2-yl]-5-nitrobenzene-1,4-diamine

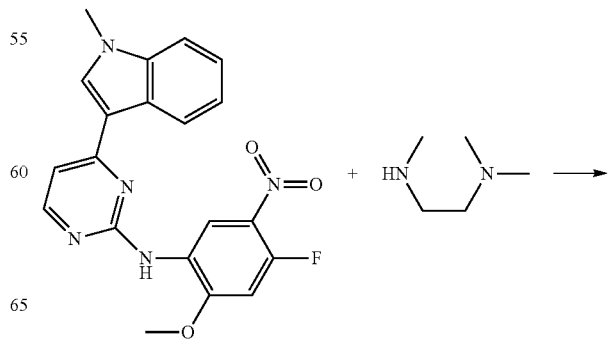

-continued

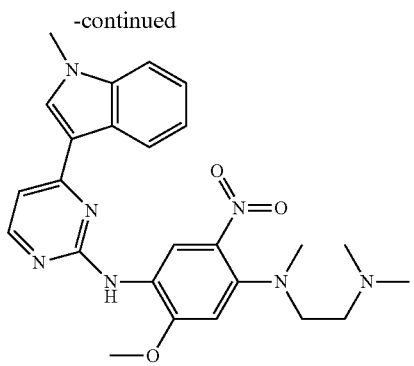

$N^1,N^1,N^2$-trimethylethane-1,2-diamine (80 mg, 0.79 mmol) was added to a suspension of N-(4-fluoro-2-methoxy-5-nitrophenyl)-4-(1-methylindol-3-yl)pyrimidin-2-amine (Intermediate 129, (which may be prepared by the method described for Intermediate 87); 350 mg, 0.79 mmol) and DIPEA (0.342 mL, 1.97 mmol) in 2,2,2-trifluoroethanol (5 mL). The mixture was heated in a microwave at 140° C. for 1 h. The cooled reaction mixture was purified by ion exchange chromatography, using an SCX column. The desired product was eluted from the column using 7M methanolic ammonia and appropriate fractions were combined and concentrated in vacuo onto silica. Purification by FCC, eluting with 0-4% 7N methanolic ammonia in $CH_2Cl_2$ gave the title compound (230 mg, 62%) as an orange solid; $^1$H NMR: 2.16 (6H, s), 2.45-2.49 (2H, t, obscured by DMSO peak), 2.86 (3H, s), 3.26 (2H, t), 3.87 (3H, s), 3.95 (3H, s), 6.85 (1H, s), 7.11 (1H, t), 7.21 (1H, d), 7.25 (1H, t), 7.52 (1H, d), 8.10 (1H, s), 8.31 (1H, d), 8.33 (1H, d), 8.36 (1H, d), 8.62 (1H, s); m/z: $ES^+$ $MH^+$ 476.40.

Intermediate 102: 2-{[5-Amino-4-(2-dimethylaminoethyl-methylamino)-2-methoxyphenyl]amino}-4-(1-methylindol-3-yl)pyrimidine-5-carbonitrile $N^4$-[5-Chloro-4-(1-methylindol-3-yl)pyrimidin-2-yl]-$N^1$-(2-dimethylaminoethyl)-5-methoxy-$N^1$-methylbenzene-1,2,4-triamine (Intermediate 97, 250 mg, 0.52 mmol), zinc (3.41 mg, 0.05 mmol), tris(dibenzylideneacetone)dipalladium(0) (47.7 mg, 0.05 mmol), dicyclohexyl(2',4',6'-triisopropylbiphenyl-2-yl)phosphine ('XPhos', 49.7 mg, 0.10 mmol), and dicyanozinc (36.7 mg, 0.31 mmol) were placed in a reaction tube under $N_2$ and then degassed DMA (1.38 mL) was added. The resulting suspension was shirred for 3.5 h at 95° C. The mixture was then diluted with EtOAc and washed 5 times with water, and then brine. The solution was then dried ($MgSO_4$) and concentrated in vacuo. The residue was dissolved in $CH_3OH/CH_2Cl_2$ and the solution was allowed to pass through a stratospheres SPE cartridge PL-Thiol MP SPE (available from Polymer Laboratories)under gravity. The resulting solution was concentrated in vacuo and the residue was triturated with diethyl ether. The resulting solid was collected by filtration and washed with diethyl ether to give the title compound (80 mg) as yellow solid. The aqueous work-up solutions were purified by ion exchange chromatography, using an SCX column. The desired product was eluted from the column using 7M methanolic ammonia and pure fractions were concentrated in vacuo to give a brown oil (126 mg). Purification by FCC, eluting with 0-5% methanolic ammonia in $CH_2Cl_2$ gave the title compound (94 mg) as a yellow solid. Both batches of product were combined to give (174 mg, 71%) as a yellow solid; m/z: $ES^+$ $MH^+$ 471.33.

Intermediate 103: 4-[(3R)-3-Dimethylaminopyrrolidin-1-yl]-6-methoxy-N-[4-(1-methylindol-3-yl)pyrimidin-2-yl]benzene-1,3-diamine A mixture of (N-{4-[(3R)-3-dimethylaminopyrrolidin-1-yl]-2-methoxy-5-nitrophenyl}-4-(1-methylindol-3-yl)pyrimidin-2-amine (Intermediate 104, 360 mg, 0.74 mmol), iron (247 mg, 4.43 mmol) and $NH_4Cl$ (27.6 mg, 0.52 mmol) in ethanol (12 mL) and water (4 mL) was heated at reflux for 2 h. The crude mixture was purified by ion exchange chromatography, using an SCX column. The desired product was eluted from the column using 7M methanolic ammonia and appropriate fractions were combined and concentrated in vacuo onto silica. Purification by FCC, eluting with 0-5% 7N methanolic ammonia in $CH_2Cl_2$ gave the title compound (280 mg, 83%) as a beige foam; $^1$H NMR: 1.69-1.83 (1H, m), 1.97-2.10 (1H, m), 2.18 (6H, s), 2.78-2.87 (1H, m), 2.88-2.98 (2H, m), 3.11 (1H, dd), 3.15-3.22 (1H, m), 3.74 (3H, s), 3.87 (3H, s), 4.29 (2H, br s), 6.70 (1H, s), 7.1-7.19 (2H, m), 7.21-7.28 (1H, m), 7.46 (1H, s), 7.51 (1H, d), 7.78 (1H, s), 8.25 (1H, d), 8.29 (1H, s), 8.43 (1H, d); m/z: $ES^+$ $MH^+$ 458.35.

Intermediate 104: N-[4-[(3R)-3-Dimethylaminopyrrolidin-1-yl]-2-methoxy-5-nitrophenyl]-4-(1-methylindol-3-yl)pyrimidin-2-amine (3R)—N,N-Dimethylpyrrolidin-3-amine (107 mg, 0.94 mmol) was added to a suspension of N-(4-fluoro-2-methoxy-5-nitrophenyl)-4-(1-methylindol-3-yl)pyrimidin-2-amine (Intermediate 129; (which may be prepared by the method described for Intermediate 87), 0.372 mL, 2.13 mmol) in 2,2,2-trifluoroethanol (5 mL) and the mixture was heated in a microwave at 140° C. for 1 h. The cooled mixture was purified by ion exchange chromatography, using an SCX column. The desired product was eluted from the column using 7M methanolic ammonia and appropriate fractions were combined and concentrated in vacuo onto silica. Purification by FCC, eluting with 0-4% 7N methanolic ammonia in $CH_2Cl_2$ gave the title compound (364 mg, 87%) as an orange solid; $^1$H NMR: 1.74-1.87 (1H, m), 2.11-2.22 (1H, m), 2.21 (6H, s), 2.70-2.81 (1H, m), 3.10-3.21 (2H, m), 3.21-3.28 (1H, m), 3.47 (1H, td), 3.87 (3H, s), 3.95 (3H, s), 6.56 (1H, s), 7.10 (1H, t), 7.18 (1H, d), 7.21-7.27 (1H, m), 7.51 (1H, d), 8.07 (1H, s), 8.29 (1H, d), 8.32 (1H, s), 8.36 (1H, d), 8.54 (1H, s); m/z: $ES^+$ $MH^+$ 488.31.

Intermediate 105: $N^4$-(5-Chloro-4-pyrazolo[1,5-a]pyridin-3-ylpyrimidin-2-yl)-5-methoxy-$N^1$-methyl-$N^1$-(2-morpholin-4-ylethyl)benzene-1,2,4-triamine A solution of $NH_4Cl$ (28.1 mg, 0.53 mmol) in water (13.00 mL) was added in one portion to a stirred mixture of N-(5-chloro-4-pyrazolo[1,5-a]pyridin-3-ylpyrimidin-2-yl)-2-methoxy-N'-methyl-N'-(2-morpholin-4-ylethyl)-5-nitrobenzene-1,4-diamine (Intermediate 106, 426 mg, 0.75 mmol) and iron (251 mg, 4.50 mmol) in ethanol (39 mL). The resulting mixture was stirred at reflux for 2 h. Further iron (251 mg, 4.50 mmol) and $NH_4Cl$ (28.1 mg, 0.53 mmol) was added and the mixture was stirred at reflux for a further 0.5 h. The mixture was concentrated in vacuo and the residue was mixed with with DMF (5 mL) and then purified by ion exchange chromatography, using an SCX column. The desired product was eluted from the column using 7M methanolic ammonia in $CH_2Cl_2$ and appropriate fractions were combined and concentrated in vacuo. Purification by FCC, eluting with 1.5-7% 2M methanolic ammonia in CH$_2$Cl$_2$ gave the title compound (304 mg, 80%) as a yellow foam; $^1$H NMR: 2.43 (4H, m), 2.45 (2H, t), 2.68 (3H, s), 2.93 (2H, t), 3.51-3.61 (4H, m), 3.66 (3H, s), 4.73 (2H, s), 6.77 (1H, s), 6.90 (1H, s), 7.12 (1H, m), 7.34 (1H, m), 8.37 (1H, s), 8.43 (1H, d), 8.49 (1H, s), 8.84 (1H, d), 8.95 (1H, s); m/z: ES$^+$ MH$^+$ 509.

Intermediate 106: N-(5-Chloro-4-pyrazolo[1,5-a]pyridin-3-ylpyrimidin-2-yl)-2-methoxy-N'-methyl-N'-(2-morpholin-4-ylethyl)-5-nitrobenzene-1,4-diamine 5-Chloro-N-(4-fluoro-2-methoxy-5-nitrophenyl)-4-pyrazolo[1,5-a]pyrimidin-3-ylpyrimidin-2-amine (Intermediate 20, 311 mg, 0.75 mmol), N-methyl-2-morpholinoethanamine (130 mg, 0.90 mmol) and DIPEA (0.157 mL, 0.90 mmol) were dissolved in DMA (3 mL) and sealed into a microwave tube. The mixture was heated to 140° C. for 0.75 h in the microwave then cooled to r.t. The mixture was then diluted with CH$_3$OH and purified by ion exchange chromatography, using an SCX column and eluting with 1:1 7N methanolic ammonia in CH$_2$Cl$_2$. Appropriate fractions were combined and concentrated in vacuo to give the title compound (429 mg, 106%) as an orange solid which was used without further purification; $^1$H NMR: 2.36 (4H, s), 2.54 (2H, m), 2.89 (3H, s), 3.34 (2H, m), 3.49 (4H, m), 3.91 (3H, s), 6.81 (1H, s), 7.15 (1H, m), 7.35 (1H, t), 8.16 (1H, s), 8.45 (2H, m), 8.76 (1H, s), 8.86 (1H, d), 8.96 (1H, s); m/z: ES$^+$ MH$^+$ 539.

Intermediate 107: N$^4$-(5-Chloro-4-pyrazolo[1,5-a]pyridin-3-ylpyrimidin-2-yl)-5-methoxy-N$^1$-methyl-N$^1$-[2-(4-methylpiperazin-1-yl)ethyl]benzene-1,2,4-triamine A mixture of N-(5-chloro-4-pyrazolo[1,5-a]pyrimidin-3-ylpyrimidin-2-yl)-2-methoxy-N'-methyl-N'-[2-(4-methylpiperazin-1-yl)ethyl]-5-nitrobenzene-1,4-diamine (0.182 g, 0.33 mmol), iron (0.110 g, 1.98 mmol) and NH$_4$Cl (0.012 g, 0.23 mmol) in EtOH (10 mL) and water (3.33 mL) was heated at reflux for 1.5 h. The mixture was then cooled to r.t., filtered and concentrated in vacuo. Purification by ion exchange chromatography, using an SCX column and eluting with 1M methanolic ammonia provided a brown gum (162 mg) after concentration of appropriate fractions. Further purification by FCC, eluting with 2-7% 1M methanolic ammonia in CH$_2$Cl$_2$ gave the title compound (0.148 g, 86%) as a yellow gum; $^1$H NMR: (CDCl$_3$) 2.28 (3H, s), 2.32-2.63 (10H, m), 2.70 (3H, s), 2.98 (2H, t), 3.84 (3H, s), 4.05 (2H, d), 6.71 (1H, s), 6.95 (1H, td), 7.38 (1H, ddd), 7.52 (1H, d), 7.88 (1H, s), 8.36 (1H, s), 8.57 (1H, d), 8.65 (1H, d), 8.93 (1H, s); m/z: ES$^+$ MH$^+$ 522.57.

Intermediate 108: N-(5-Chloro-4-pyrazolo[1,5-a]pyridin-3-ylpyrimidin-2-yl)-2-methoxy-N'-methyl-N'-[2-(4-methylpiperazin-1-yl)ethyl]-5-nitrobenzene-1,4-diamine DIPEA (0.105 mL, 0.60 mmol) was added to a mixture of 5-chloro-N-(4-fluoro-2-methoxy-5-nitrophenyl)-4-pyrazolo[1,5-a]pyridin-3-ylpyrimidin-2-amine (Intermediate 20, 0.207 g, 0.5 mmol) and N-methyl-2-(4-methylpiperazin-1-yl)ethanamine (Intermediate 109, 0.079 g, 0.50 mmol) in DMA (5 mL). The mixture was heated in a microwave at 140° C. for 3 h. An additional portion of N-methyl-2-(4-methylpiperazin-1-yl)ethanamine (8 mg, 0.05 mmol) was added and the mixture was heated in a microwave at 140° C. for a further 1 h before being cooled to r.t. The mixture was then concentrated in vacuo and the residue was dissolved in CH$_3$OH. Purification by ion exchange chromatography, using an SCX column and eluting with 1M methanolic ammonia provided crude material after concentration of appropriate fractions in vacuo. Further purification by FCC, eluting with 2-8% CH$_3$OH in CH$_2$Cl$_2$ gave the title compound (0.186 g, 67%) as an orange foam; $^1$H NMR: (CDCl$_3$) 2.26 (3H, s), 2.32-2.45 (4H, m), 2.45-2.57 (4H, m), 2.61 (2H, t), 2.89 (3H, s), 3.29 (2H, t), 3.98 (3H, s), 6.65 (1H, s), 6.93-7.00 (1H, m), 7.38 (1H, ddd), 7.44 (1H, s), 8.40 (1H, s), 8.49 (1H, d), 8.55 (1H, d), 8.91 (2H, d); m/z: ES$^+$ MH$^+$ 552.59.

Intermediate 109: N-Methyl-2-(4-methylpiperazin-1-yl)ethanamine

Ethyl carbonochloridate (8.14 mL, 85.14 mmol) was added dropwise to N-methyl-2-piperazin-1-ylethanamine (5.0 g, 38.7 mmol) and triethylamine (12.95 mL, 92.88 mmol) in THF (40 mL) at 0° C. over a period of 10 minutes under N$_2$. The resulting mixture was allowed to warm to r.t. and stirred for 2 h. The resulting white suspension was filtered, and washed through with THF (2×20 mL). The filtrate was concentrated in vacuo and the resulting residue was dissolved in EtOAc (75 mL). This solution was washed with sat. Na$_2$CO$_3$ (50 mL). The aqueous wash solution was then extracted with EtOAc (50 mL). The combined organic solutions were dried (MgSO$_4$) and concentrated in vacuo to give crude intermediate (10.55 g). This was dissolved in THF (60 mL) and cooled to 0° C. LiAlH$_4$ (101 mL, 100.6 mmol, 1M in THF) was added dropwise under N$_2$. The resulting mixture was stirred at reflux overnight, then cooled to 0° C. and treated successively (dropwise) with water (3.8 mL), 15% aq. NaOH (3.8 mL) and water (11.4 mL) with rapid stirring. Diatomaceous earth (Celite™) and MgSO$_4$ were added and the mixture was filtered, washed with EtOAc and the filtrate was concentrated in vacuo to give a colourless oil (3.35 g). The filtercake was washed with EtOAc (100 mL), heated to 70° C. and then filtered. The filtrate was concentrated in vacuo to give a further batch (1.023 g) of the title compound. Total: 4.37 g, 72%; $^1$H NMR: (CDCl$_3$) 2.28 (3H, s), 2.33-2.6 (13H, m), 2.67 (2H, t).

Intermediate 110: 4-Methoxy-N'-[4-(1-methylindol-3-yl)pyrimidin-2-yl]-6-(4-methylpiperazin-1-yl)benzene-1,3-diamine A mixture of N-[2-methoxy-4-(4-methylpiperazin-1-yl)-5-nitrophenyl]-4-(1-methylindol-3-yl)pyrimidin-2-amine (Intermediate 111, 329 mg, 0.69 mmol), iron (233 mg, 4.17 mmol) and NH$_4$Cl (26.0 mg, 0.49 mmol) in ethanol (12 mL) and water (4 mL) were heated at reflux for 3 h. The mixture was allowed to cool to r.t. and then filtered. The filtrate was concentrated in vacuo. Purification by ion exchange chromatography, using an SCX column and eluting with 0.7M methanolic ammonia gave a brown gum after concentration of appropriate fractions in vacuo. Further purification by FCC, eluting with 0-5% 7N methanolic ammonia in CH$_2$Cl$_2$ gave the title compound (287 mg, 93%) as a light brown gum; $^1$H NMR: (CDCl$_3$) 2.37 (3H, br s), 2.59 (4H, s), 2.92-2.99 (4H, m), 3.79-3.86 (5H, m), 3.87 (3H, s), 6.71 (1H, s), 7.01 (1H, d), 7.27-7.34 (2H, m), 7.35-7.40 (1H, m), 7.57 (1H, s), 7.78 (1H, s), 8.17 (1H, s), 8.32 (1H, d), 8.47-8.53 (1H, m); m/z: ES+ MH+ 444.54.

Intermediate 111: N-[2-Methoxy-4-(4-methylpiperazin-1-yl)-5-nitrophenyl]-4-(1-methylindol-3-yl)pyrimidin-2-amine 1-Methylpiperazine (89 mg, 0.89 mmol), N-(4-fluoro-2-methoxy-5-nitrophenyl)-4-(1-methylindol-3-yl)pyrimidin-2-amine (Intermediate 129 (which may be prepared by the method described for Intermediate 87), 350 mg, 0.89 mmol) and DIPEA (0.186 mL, 1.07 mmol) were suspended in DMA (6 mL) and sealed into a microwave tube. The reaction was heated to 140° C. for 1 h in a microwave and then cooled to r.t. CH$_3$OH was added and an orange solid precipitated from solution. The solid was collected by filtration and was washed with CH$_3$OH and then diethyl ether. The solid was then dried to give the title compound (339 mg, 80%) as an orange solid; $^1$H NMR: 2.26 (3H, s), 3.06-3.11 (4H, m), 3.88 (3H, s), 3.99 (3H, s), 6.86 (1H, s), 7.13 (1H, t), 7.23-7.29 (2H, m), 7.53 (1H, d), 8.10 (1H, s), 8.32-8.38 (3H, m), 8.81 (1H, s); (signals for 4 protons were not observed and are likely to be obscured under the DMSO peak); m/z: ES+ MH+ 474.56.

Intermediate 112: N-[5-Chloro-4-(1-methylindol-3-yl)pyrimidin-2-yl]-4-(3-dimethylaminoazetidin-1-yl)-6-methoxybenzene-1,3-diamine A mixture of 5-chloro-N-[4-(3-dimethylaminoazetidin-1-yl)-2-methoxy-5-nitrophenyl]-4-(1-methylindol-3-yl)pyrimidin-2-amine (Intermediate 113, 285 mg, 0.56 mmol), iron (188 mg, 3.37 mmol) and NH$_4$Cl (22.51 mg, 0.42 mmol) in ethanol (9 mL) and water (3 mL) was heated at reflux for 2 h. The mixture was then cooled and filtered through diatomaceous earth (Celite™). The filtrate was concentrated in vacuo and the resulting residue was dissolved in CH$_2$Cl$_2$. This solution was washed with brine, dried (MgSO$_4$) and concentrated in vacuo. Purification by FCC, eluting with 1-20% 7N methanolic ammonia in CH$_2$Cl$_2$ gave the title compound (263 mg, 98%) as a brown dry film; $^1$H NMR: (CDCl$_3$) 2.21 (6H, s), 3.08-3.18 (1H, m), 3.30 (2H, br s), 3.58 (2H, t), 3.86 (3H, s), 3.88 (3H, s), 3.93 (2H, t), 6.38 (1H, s), 7.2-7.42 (3H, m, partially obscured by chloroform signal), 7.50 (1H, s), 7.99 (1H, s), 8.20 (1H, s), 8.31 (1H, s), 8.63 (1H, d); m/z: ES+ MH+ 478.

Intermediate 113: 5-Chloro-N-[4-(3-dimethylaminoazetidin-1-yl)-2-methoxy-5-nitrophenyl]-4-(1-methylindol-3-yl)pyrimidin-2-amine DIPEA (0.408 mL, 2.33 mmol) was added to a mixture of 5-chloro-N-(4-fluoro-2-methoxy-5-nitrophenyl)-4-(1-methylindol-3-yl)pyrimidin-2-amine. 0.8 toluene-4-sulfonic acid salt (Intermediate 87, 330 mg, 0.58 mmol) in DMA (3 mL). N,N-Dimethylazetidin-3-amine dihydrochloride (Intermediate 26, 121 mg, 0.70 mmol) was then added in one portion. The mixture was heated in a microwave at 100° C. for 0.5 h then the mixture was cooled and diluted with CH$_3$OH and absorbed onto an SCX column. The column was washed with CH$_3$OH and eluted with 1:1 methanolic ammonia in CH$_2$Cl$_2$. Appropriate fractions were concentrated in vacuo. Further purification by FCC, eluting with 1-10% CH$_3$OH in CH$_2$Cl$_2$ gave the title compound (295 mg, 100%) as a brown gum; $^1$H NMR: (CDCl$_3$) 2.18 (6H, s), 3.13-3.24 (1H, m), 3.67-3.75 (2H, m), 3.89 (3H, s), 3.96 (3H, s), 4.13 (2H, t), 6.04 (1H, s), 7.21-7.29 (1H, m, partially obscured by chloroform signal), 7.29-7.41 (3H, m), 8.22 (1H, s), 8.37 (1H, s), 8.46 (1H, d), 9.05 (1H, s); m/z: ES+ MH+ 508.

Intermediate 114: 4-(3-Dimethylaminoazetidin-1-yl)-6-methoxy-N-[5-methyl-4-(1-methylindol-3-yl)pyrimidin-2-yl]benzene-1,3-diamine A mixture of N-[4-(3-dimethylaminoazetidin-1-yl)-2-methoxy-5-nitrophenyl]-5-methyl-4-(1-methylindol-3-yl)pyrimidin-2-amine (Intermediate 115, 210 mg, 0.43 mmol), iron (144 mg, 2.58 mmol) and NH$_4$Cl (16.13 mg, 0.30 mmol) in ethanol (6 mL) and water (2 mL) were heated at reflux for 2 h. The crude mixture was purified by ion exchange chromatography, using an SCX column and eluting with 7M methanolic ammonia. Appropriate fractions were combined and concentrated in vacuo onto silica. Further purification by FCC, eluting with 0-5% 7N methanolic ammonia in CH$_2$Cl$_2$ gave a brown foam after concentration of appropriate fractions in vacuo. Further purification by ion exchange chromatography, using an SCX column and eluting with 7M methanolic ammonia provided material that was concentrated in vacuo onto silica. Further purification by FCC, eluting with 0-4% CH$_3$OH in CH$_2$Cl$_2$ gave the title compound (135 mg, 69%) as a brown foam; $^1$H NMR: 2.11 (6H, s), 2.35 (3H, s), 3.04 (1H, p), 3.44 (2H, t), 3.89 (3H, s), 3.92 (2H, s), 3.9-3.97 (2H, m), 6.28 (1H, s), 7.12 (1H, dd), 7.2-7.26 (1H, m), 7.28 (1H, s), 7.48 (1H, d), 7.55 (1H, s), 8.00 (1H, s), 8.15 (1H, s), 8.43 (1H, d); m/z: ES+ MH+ 458.31.

Intermediate 115: N-[4-(3-Dimethylaminoazetidin-1-yl)-2-methoxy-5-nitrophenyl]-5-methyl-4-(1-methylindol-3-yl)pyrimidin-2-amine N,N-dimethylazetidin-3-amine (Intermediate 26, 113 mg, 0.65 mmol) was added to a suspension of N-(4-fluoro-2-methoxy-5-nitrophenyl)-5-methyl-4-(1-methylindol-3-yl)-pyrimidin-2-amine (Intermediate 79, 250 mg, 0.61 mmol) and DIPEA (0.374 mL, 2.15 mmol) in 2,2,2-trifluoroethanol (5 mL). The mixture was heated in a microwave at 140° C. for 1 h. The cooled mixture was purified by ion exchange chromatography, using an SCX column and eluting with 7M methanolic ammonia. Appropriate fractions were combined and concentrated in vacuo onto silica. Further purification by FCC, eluting with 0-4% 7N methanolic ammonia in CH$_2$Cl$_2$ gave the title compound (213 mg, 71%) as an orange foam; $^1$H NMR: 2.13 (6H, s), 2.37 (3H, s), 3.09-3.16 (1H, m), 3.72 (2H, dd), 3.89 (3H, s), 3.93 (3H, s), 4-4.08 (2H, m), 6.27 (1H, s), 7.04 (1H, t), 7.20-7.26 (1H, m), 7.49 (1H, d), 7.90 (1H, s), 8.03 (1H, s), 8.23 (1H, s), 8.35 (1H, d), 8.46 (1H, s); m/z: ES+ MH+ 488.63.

Intermediate 116: 4-(3-Dimethylaminoazetidin-1-yl)-6-methoxy-N-[4-(1-methylindol-3-yl)pyrimidin-2-yl]benzene-1,3-diamine A mixture of N-[4-(3-dimethylaminoazetidin-1-yl)-2-methoxy-5-nitrophenyl]-4-(1-methylindol-3-yl)pyrimidin-2-amine (Intermediate 117, 160 mg, 0.34 mmol), iron (113 mg, 2.03 mmol) and NH$_4$Cl (13.56 mg, 0.25 mmol) in ethanol (5 mL) and water (1.67 mL) was heated at reflux for 2 h. The cooled mixture was purified by ion exchange chromatography, using an SCX column and eluting with 1:1 7M methanolic ammonia in CH$_2$Cl$_2$. Appropriate fractions were combined and concentrated in vacuo. Further purification by FCC, eluting with 0-5% 7N methanolic ammonia in CH$_2$Cl$_2$ gave the title compound (120 mg, 80%) as a brown gum; m/z: ES$^+$ MH$^+$ 444.61.

Intermediate 117: N-[4-(3-Dimethylaminoazetidin-1-yl)-2-methoxy-5-nitrophenyl]-4-(1-methylindol-3-yl)pyrimidin-2-amine N,N-dimethylazetidin-3-amine dihydrochloride (Intermediate 26, 79 mg, 0.46 mmol) was added to a suspension of N-(4-fluoro-2-methoxy-5-nitrophenyl)-4-(1-methylindol-3-yl)pyrimidin-2-amine (Intermediate 129 (which may be prepared by the method described for Intermediate 87), 150 mg, 0.38 mmol) and DIPEA (0.264 mL, 1.53 mmol) in 2,2,2-trifluoroethanol (3 mL). The mixture was heated at 140° C. in a microwave for 1 h. The mixture was then purified directly by ion exchange chromatography, using an SCX column (50 g) and eluting with 1:1 7M methanolic ammonia in CH$_2$Cl$_2$. Concentration of appropriate fractions in vacuo gave a brick red solid. This solid was suspended in CH$_3$OH and the solid was collected by filtration, washed with CH$_3$OH (10 mL) and dried in vacuo to give the title compound (160 mg, 89%) as a red solid; m/z: ES$^+$ MH$^+$ 474.61.

Intermediate 118: N-[5-Chloro-4-(1H-indol-3-yl)pyrimidin-2-yl]-4-(3-dimethylaminoazetidin-1-yl)-6-methoxybenzene-1,3-diamine A mixture of 5-chloro-N-[4-(3-dimethylaminoazetidin-1-yl)-2-methoxy-5-nitrophenyl]-4-(1H-indol-3-yl)pyrimidin-2-amine (Intermediate 119, 347 mg, 0.70 mmol), iron (235 mg, 4.22 mmol) and NH$_4$Cl (26.3 mg, 0.49 mmol) in ethanol (9 mL) and water (3 mL) was heated at reflux for 1 h. The mixture was then purified by ion exchange chromatography, using an SCX column and eluting with 7M methanolic ammonia. Appropriate fractions were combined and concentrated in vacuo onto silica. Further purification by FCC, eluting with 0-5% 7M methanolic ammonia in CH$_2$Cl$_2$ gave the title compound (323 mg, 99%) as a tan solid; $^1$H NMR: 2.12 (6H, s), 3.06 (1H, p), 3.48 (2H, t), 3.68 (3H, s), 3.92-4.02 (4H, m), 6.28 (1H, s), 6.91 (1H, s), 7.04 (1H, dd), 7.12-7.19 (1H, m), 7.44 (1H, d), 8.14 (1H, s), 8.28 (1H, s), 8.30 (1H, d), 8.46 (1H, s), 11.77 (1H, s); m/z: ES$^+$ MH$^+$ 464.21.

Intermediate 119: 5-Chloro-N-[4-(3-dimethylaminoazetidin-1-yl)-2-methoxy-5-nitrophenyl]-4-(1H-indol-3-yl)pyrimidin-2-amine N,N-dimethylazetidin-3-amine (Intermediate 26, 144 mg, 0.83 mmol) was added to a suspension of 5-chloro-N-(4-fluoro-2-methoxy-5-nitrophenyl)-4-(1H-indol-3-yl)pyrimidin-2-amine (Intermediate 76, 312 mg, 0.75 mmol) and DIPEA (0.460 mL, 2.64 mmol) in 2,2,2-trifluoroethanol (5 mL). The mixture was heated in a microwave at 140° C. for 1 h. The cooled mixture was purified by ion exchange chromatography, using an SCX column and eluting with 7M methanolic ammonia. Appropriate fractions were combined and concentrated in vacuo onto silica. Further purification by FCC, eluting with 0-4% 7N methanolic ammonia in CH$_2$Cl$_2$ gave the title compound (347 mg, 93%) as an orange solid after trituration with diethyl ether; $^1$H NMR: 2.14 (6H, s), 3.09-3.18 (1H, m), 3.76 (2H, dd), 3.89 (3H, s), 4.01-4.11 (2H, m), 6.28 (1H, s), 6.98 (1H, t), 7.13-7.20 (1H, m), 7.46 (1H, d), 8.15 (1H, s), 8.23 (1H, d), 8.37 (1H, s), 8.47 (1H, s), 8.49 (1H, s), 11.84 (1H, s); m/z: ES$^+$ MH$^+$ 494.16.

Intermediate 120: 2-({5-Amino-4-[(3R)-3-dimethylaminopyrrolidin-1-yl]-2-methoxyphenyl}amino)-4-pyrazolo[1,5-a]pyridin-3-ylpyrimidine-5-carbonitrile A mixture of N-(5-chloro-4-pyrazolo[1,5-a]pyridin-3-ylpyrimidin-2-yl)-4-[(3R)-3-dimethylaminopyrrolidin-1-yl]-6-methoxybenzene-1,3-diamine (Intermediate 18, 250 mg, 0.52 mmol), zinc cyanide (36.8 mg, 0.31 mmol), zinc powder (3.41 mg, 0.05 mmol) and 2-(dicyclohexylphosphino)-2',4',6'-tri-i-propyl-1,1'-biphenyl ('XPhos' 49.8 mg, 0.10 mmol) was stirred in DMA (2 mL) and purged with N$_2$ for 0.25 h. Tris(dibenzylidene-acetone)dipalladium(0) (47.8 mg, 0.05 mmol) was then added and the mixture was heated at 95° C. for 2 h. The cooled mixture was then absorbed onto an SCX column, washed with CH$_3$OH and eluted with 7M methanolic ammonia solution. Appropriate fractions were combined and concentrated in vacuo. The resulting residue was suspended in CH$_3$OH then the mixture was filtered. The collected solid was dried on the filter to give the title compound (160 mg, 65%) as a tan powder; $^1$H NMR: (100° C.) 1.78-1.92 (1H, m), 2.00-2.15 (1H, m), 2.26 (6H, s), 2.95-3.02 (1H, m), 3.02-3.07 (1H, m), 3.07-3.13 (1H, m), 3.16-3.27 (2H, m), 3.68 (3H, s), 6.74 (1H, s), 6.95 (1H, s), 7.13 (1H, td), 7.33-7.43 (1H, m), 8.37 (1H, d), 8.64 (1H, s), 8.77 (1H, dt), 8.84 (1H, s), 8.91 (1H, s); m/z: ES$^+$ MH$^+$ 470.60.

Intermediate 121: 2-{[5-Amino-4-(2-dimethylaminoethyl-methylamino)-2-methoxyphenyl]amino}-4-pyrazolo[1,5-a]pyridin-3-ylpyrimidine-5-carbonitrile N$^4$-(5-Chloro-4-pyrazolo[1,5-a]pyridin-3-ylpyrimidin-2-yl)-N$^1$-(2-dimethylaminoethyl)-5-methoxy-N$^1$-methylbenzene-1,2,4-triamine (Intermediate 33, 120 mg, 0.26 mmol), dicyanozinc (18.11 mg, 0.15 mmol), dicyclohexyl(2',4',6'-triisopropylbiphenyl-2-yl)phosphine (24.50 mg, 0.05 mmol), tris(dibenzylideneacetone)dipalladium(0) (23.5 mg, 0.03 mmol) and zinc powder (1.681 mg, 0.03 mmol) were suspended in degassed DMA (1.1 mL) and sealed into a microwave tube. The mixture was then heated to 95° C. for 1 h in a microwave. The cooled mixture was then diluted with EtOAc (50 mL) and washed with sat. NaHCO$_3$ (20 mL), water (20 mL), and sat. brine (10 mL). The organic solution was then concentrated in vacuo. Purification by FCC, eluting with 0-20% CH$_3$OH in CH$_2$Cl$_2$ gave the title compound (36 mg, 31%) as a yellow gum; $^1$H NMR: (CDCl$_3$) 2.41 (6H, s), 2.60 (2H, s), 2.72 (3H, s), 3.07 (2H, t), 3.86 (3H, s), 6.72 (1H, s), 7.02 (1H, t), 7.41-7.53 (1H, m), 7.80 (2H, d), 8.60 (2H, d), 8.70 (1H, d), 9.09 (1H, s); m/z: ES$^+$ MH$^+$ 458.30.

Intermediate 122: 2-{[5-Amino-4-(3-dimethylaminoazetidin-1-yl)-2-methoxyphenyl]amino}-4-pyrazolo[1,5-a]pyridin-3-ylpyrimidine-5-carbonitrile N-(5-Chloro-4-pyrazolo[1,5-a]pyridin-3-ylpyrimidin-2-yl)-4-(3-dimethylaminoazetidin-1-yl)-6-methoxybenzene-1,3-diamine (Intermediate 24, 297 mg, 0.64 mmol), tris(dibenzylidene-acetone)dipalladium(0) (14.62 mg, 0.02 mmol), 2-(dicyclohexylphosphino)-2',4',6'-tri-i-propyl-1,1'-biphenyl ('XPhos', 30.5 mg, 0.06 mmol), and dicyanozinc (45.0 mg, 0.38 mmol) were placed in a microwave tube under N$_2$. Poly(methylhydrosiloxane) (12 mg, 0.06 mmol) was then added in degassed DMA (1.92 mL). The resulting mixture was then heated at 120° C. for 2 h in a microwave. The crude mixture was loaded on to a SCX column. The column was flushed with water followed by CH$_3$OH/CH$_2$Cl$_2$. The desired product was eluted from the column using 7M methanolic ammonia in CH$_2$Cl$_2$ and pure fractions were combined and concentrated in vacuo. The residue was dissolved in CH$_3$OH/CH$_2$Cl$_2$ and allowed to pass through a stratospheres SPE cartridge PL-Thiol MP SPE (available from Polymer Laboratories) under gravity. The resulting solution was concentrated in vacuo. Purification by FCC, eluting with 0-5% CH$_3$OH in CH$_2$Cl$_2$ gave the title compound (139 mg, 48%) as a brown solid after trituration with diethyl ether; $^1$H NMR: (100° C.) 2.18 (6H, s), 3.17 (1H, t), 3.60 (2H, t), 3.69 (3H, s), 3.87 (2H, br s), 4.00 (2H, t), 6.32 (1H, s), 6.86 (1H, s), 7.11 (1H, t), 7.34-7.46 (1H, m), 8.34 (1H, d), 8.61 (1H, s), 8.72 (1H, br s), 8.76 (1H, d), 8.90 (1H, s); m/z: ES$^+$ MH$^+$ 456.23.

Intermediate 123: 4-[(3aR,6aR)-5-Methyl-2,3,3a,4,6,6a-hexahydropyrrolo[3,4-b]pyrrol-1-yl]-6-methoxy-N-[4-(1-methylindol-3-yl)pyrimidin-2-yl]benzene-1,3-diamine A mixture of N-[4-[(3aR,6aR)-5-methyl-2,3,3a,4,6,6a-hexahydropyrrolo[3,4-b]pyrrol-1-yl]-2-methoxy-5-nitrophenyl]-4-(1-methylindol-3-yl)pyrimidin-2-amine (Intermediate 124, 256 mg, 0.51 mmol), iron powder (172 mg, 3.07 mmol) and NH$_4$Cl (19.19 mg, 0.36 mmol) were heated in ethanol (3 mL) and water (1 mL) at reflux for 18 h. The crude mixture was then purified by ion exchange chromatography, using an SCX column. The desired product was eluted from the column using 7M methanolic ammonia and concentrated in vacuo. Further purification by FCC, eluting with 0-5% 7N methanolic ammonia in CH$_2$Cl$_2$ gave the title compound (198 mg, 82%) as a yellow foam; $^1$H NMR (CDCl$_3$) 1.78 (1H, td), 2.07-2.13 (1H, m), 2.15 (1H, dd), 2.29 (3H, s), 2.47 (1H, dd), 2.57-2.65 (2H, m), 2.82-2.95 (2H, m), 3.45 (1H, dt), 3.85 (3H, s), 3.88 (3H, s), 4.07 (1H, ddd), 6.74 (1H, s), 7.01 (1H, d), 7.27-7.35 (2H, m), 7.38 (1H, dd), 7.55 (1H, s), 7.79 (1H, s), 8.14 (1H, s), 8.33 (1H, d), 8.45-8.52 (1H, m); m/z: ES$^+$ MH$^+$ 470.29.

Intermediate 124: N-[4-[(3aR,6aR)-5-Methyl-2,3,3a,4,6,6a-hexahydropyrrolo[3,4-b]pyrrol-1-yl]-2-methoxy-5-nitrophenyl]-4-(1-methylindol-3-yl)pyrimidin-2-amine DIPEA (0.411 mL, 2.36 mmol) was added to a suspension of N-(4-fluoro-2-methoxy-5-nitrophenyl)-4-(1-methylindol-3-yl)pyrimidin-2-amine (Intermediate 129, 425 mg, 0.94 mmol) and (3aR,6aR)-5-methyl-2,3,3a,4,6,6a-hexahydro-1H-pyrrolo[3,4-b]pyrrole (Intermediate 37, 250 mg, 1.98 mmol) in 2,2,2-trifluoroethanol (4 mL). The mixture was heated in a microwave at 140° C. for 1 h. The cooled mixture was then purified by ion exchange chromatography, using an SCX column. The desired product was eluted from the column using 7M methanolic ammonia and concentrated in vacuo. Further purification by FCC, eluting with 0-5% 7N methanolic ammonia in CH$_2$Cl$_2$ gave impure title compound (396 mg, 84%) as an orange/red solid. This solid was dissolved in the minimum amount of CH$_2$Cl$_2$ and the resulting solution was triturated with methanol. The resulting solid was collected by filtration to give the title compound (272 mg, 58%) as a red solid which was used without further purification; $^1$H NMR: 1.86 (1H, dd), 1.94-2.06 (1H, m), 2.12 (3H, s), 2.23 (1H, dd), 2.36-2.45 (2H, m), 2.52-2.58 (1H, m) partially obscured by DMSO peak, 2.91-3.04 (1H, m), 3.18 (1H, t), 3.49 (1H, td), 3.87 (3H, s), 3.95 (3H, s), 4.40 (1H, t), 6.61 (1H, s), 7.11 (1H, t), 7.18 (1H, d), 7.24 (1H, t), 7.51 (1H, d), 8.02 (1H, s), 8.27-8.31 (2H, m), 8.34 (1H, d), 8.51 (1H, s); m/z: ES$^+$ MH$^+$ 500.17.

Intermediate 125: N-(2-Dimethylaminoethyl)-5-methoxy-N$^1$-methyl-N$^4$-[4-(4,5,6,7-tetrahydropyrazolo[1,5-a]pyridin-3-yl)pyrimidin-2-yl]benzene-1,2,4-triamine A mixture of N'-(2-dimethylaminoethyl)-2-methoxy-N'-methyl-5-nitro-N-[4-(4,5,6,7-tetrahydropyrazolo[1,5-a]pyridin-3-yl)pyrimidin-2-yl]benzene-1,4-diamine (Intermediate 126, 3.7 g, 7.93 mmol), iron (2.66 g, 47.58 mmol) and NH$_4$Cl (0.318 g, 5.95 mmol) was heated in ethanol (120 mL) and water (40 mL) at reflux for 2.5 h. The mixture was then cooled, filtered and concentrated. The solids were triturated in 5% CH$_3$OH/CH$_2$Cl$_2$ (100 mL) for 15 minutes and then filtered. The filtrate was combined with the concentrated, filtered reaction mixture, washed with brine, dried (Na$_2$SO$_4$) and concentrated in vacuo. Purification by FCC, eluting with 0-2.5% 7N methanolic ammonia in CH$_2$Cl$_2$ gave the title compound (2.50 g, 72%) as a brown gum; $^1$H NMR (CDCl$_3$): 1.90-1.99 (2H, m), 2.04-2.13 (2H, m), 2.25 (6H, s), 2.37-2.42 (2H, m), 2.67 (3H, s), 2.92-2.98 (2H, m), 3.25 (2H, t), 3.83 (3H, s), 4.00 (2H, s), 4.21 (2H, t), 6.70 (1H, s), 6.79 (1H, d), 7.48 (1H, s), 7.97 (2H, d), 8.30 (1H, d); m/z: ES$^+$ MH$^+$ 437.39.

Intermediate 126: N'-(2-Dimethylaminoethyl)-2-methoxy-N'-methyl-5-nitro-N-[4-(4,5,6,7-tetrahydropyrazolo[1,5-a]pyridin-3-yl)pyrimidin-2-yl]benzene-1,4-diamine A mixture of N-(4-fluoro-2-methoxy-5-nitrophenyl)-4-(4,5,6,7-tetrahydropyrazolo[1,5-a]pyridin-3-yl)pyrimidin-2-amine (Intermediate 127, 3.0 g, 7.81 mmol), N,N',N'-trimethylethane-1,2-diamine (1.190 mL, 9.37 mmol) and DIPEA (1.620 mL, 9.37 mmol) in DMA (45 mL) was heated at 100° C. for 1.5 h. The mixture was then cooled and absorbed onto an SCX column, washed with MeOH and eluted with methanolic ammonia. Fractions that contained desired product were concentrated in vacuo and the resulting residue was dissolved in EtOAc. This solution was washed twice with brine, dried (Na$_2$SO$_4$) and concentrated in vacuo to give the title compound (3.70 g, 102%) as an orange oil; $^1$H NMR (CDCl$_3$): 1.90-1.98 (2H, m), 2.04-2.12 (2H, m), 2.26 (6H, s), 2.51-2.60 (2H, m), 2.87 (3H, m), 3.21-3.30 (4H, m), 3.96 (3H, s), 4.20 (2H, t), 6.67 (1H, s), 6.88 (1H, d), 7.43 (1H, s), 7.95 (1H, s), 8.31 (1H, d), 9.00 (1H, s); m/z: ES$^+$ MH$^+$ 467.63.

Intermediate 127: N-(4-Fluoro-2-methoxy-5-nitrophenyl)-4-(4,5,6,7-tetrahydropyrazolo[1,5-a]pyridin-3-yl)pyrimidin-2-amine A mixture of 3-(2-chloropyrimidin-4-yl)-4,5,6,7-tetrahydropyrazolo[1,5-a]pyridine (Intermediate 128, 3.6857 g, 15.70 mmol), 4-fluoro-2-methoxy-5-nitroaniline (Intermediate 23, 2.92 g, 15.70 mmol) and p-toluenesulfonic acid hydrate (3.29 g, 17.28 mmol) in 2-pentanol (100 mL) was stirred at 85° C. under an atmosphere of N$_2$ for 1.5 h. The mixture was then concentrated in vacuo and the resulting reside was dissolved in CH$_2$Cl$_2$ (250 mL). This solution was washed with sat. NaHCO$_3$ (2×100 mL), water (100 mL), and sat. brine (100 mL). The organic solution was concentrated in vacuo to give crude product. Purification by FCC, eluting with 0-10% CH$_3$OH in CH$_2$Cl$_2$ provided an orange solid. This material was triturated with CH$_3$OH to give a solid which was collected by filtration and dried in vacuo to give the title compound (2.26 g, 37%) as a yellow solid; $^1$H NMR: 1.75-1.86 (2H, m), 1.92-2.04 (2H, m), 3.09 (2H, t), 4.02 (3H, s), 4.12 (2H, t), 7.13 (1H, d), 7.35 (1H, d), 8.14 (1H, s), 8.25 (1H, s), 8.42 (1H, d), 9.02 (1H, d); m/z: ES$^+$ MH$^+$ 385.

Intermediate 128: 3-(2-Chloropyrimidin-4-yl)-4,5,6, 7-tetrahydropyrazolo[1,5-a]-pyridine Bis(di-tert-butyl(4-dimethylaminophenyl)phosphine)dichloropalladium(II) (1.284 g, 1.81 mmol) was added in one portion to 3-(4,4,5,5-tetramethyl-1,3,2-dioxaborolan-2-yl)-4,5,6,7-tetrahydropyrazolo[1,5-a]pyridine (9 g, 36.27 mmol), 2,4-dichloropyrimidine (5.40 g, 36.27 mmol) and 2M Na$_2$CO$_3$ solution (39.9 mL, 79.80 mmol) in dimethoxyethane (250 mL) under an atmosphere of N$_2$. The resulting mixture was stirred at 85° C. for 4 h. and then allowed to cool to r.t. The mixture was then concentrated in vacuo and the residue was dissolved in CH$_2$Cl$_2$ (500 mL). This solution was washed with water (200 mL) and then sat. brine (200 mL). The organic solution was concentrated in vacuo. Purification by FCC, eluting with 0-10% CH$_3$OH in CH$_2$Cl$_2$ gave the title compound (7.91 g, 93%) as a orange oil which solidified on standing; $^1$H NMR: 1.86 (2H, dt), 1.93-2.00 (2H, m), 3.11 (2H, t), 4.13 (2H, t), 7.68 (1H, d), 8.18 (1H, s), 8.57 (1H, d); m/z: ES$^+$ MH$^+$ 235.

Intermediate 129: N-(4-Fluoro-2-methoxy-5-nitrophenyl)-4-(1-methylindol-3-yl)pyrimidin-2-amine

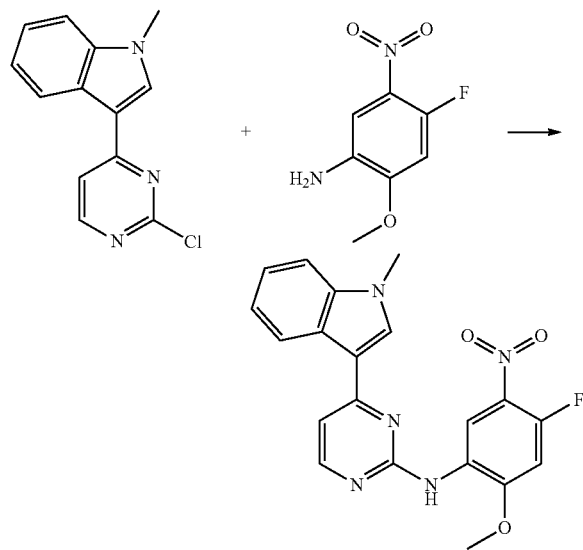

p-Toluenesulfonic acid hydrate (22.73 g, 119.5 mmol) was added in one portion to a mixture of 3-(2-chloropyrimidin-4-yl)-1-methylindole (Intermediate 130, 24.27 g, 99.58 mmol) and 4-fluoro-2-methoxy-5-nitroaniline (Intermediate 23, 18.54 g, 99.58 mmol) in 2-pentanol (500 mL). The resulting mixture was stirred at 105° C. for 2.5 h. and then cooled to r.t. The resulting precipitate was collected by filtration, washed with 2-pentanol (50 mL) and dried under vacuum to give some of the desired product as a yellow solid. The filtrate was cooled and the resulting precipitate was collected by filtration and washed with 2-pentanol (10 mL). The two crops of product were combined and triturated with CH$_3$CN to give a solid which was collected by filtration and dried under vacuum to give the title compound (37.4 g, 95%) as a yellow solid; $^1$H NMR: 3.92 (3H, s), 4.01 (3H, s), 7.13 (1H, dd), 7.27-7.36 (1H, m), 7.40-7.51 (2H, m), 7.59 (1H, d), 8.26 (1H, t), 8.35 (1H, d), 8.61 (1H, s), 8.85 (1H, d), 9.46 (1H, s); m/z: ES-M-392.

Intermediate 130:
3-(2-Chloropyrimidin-4-yl)-1-methylindole

NaH (1.707 g, 42.68 mmol, 40% dispersion in mineral oil) was added in small portions to a cooled (0° C.) mixture of 3-(2-chloropyrimidin-4-yl)-1H-indole (Intermediate 131, 8.168 g, 35.57 mmol) in THF (250 mL). The resulting mixture was stirred at 0° C. for 0.5 h and then CH$_3$I (2.67 mL, 42.68 mmol) was added and the mixture stirred at 0° C. for a further 3 h. The reaction was quenched by the addition of sat. NaHCO$_3$ (25 mL). The mixture was then diluted with EtOAc (100 mL), and the resulting solution was washed with sat. NaHCO$_3$ (50 mL), water (50 mL) and sat. brine (50 mL). The organic solution was then concentrated in vacuo. Purification by FCC, eluting with 0-20% CH$_3$OH in CH$_2$Cl$_2$ gave the title compound (8.35 g, 96%) as a pale yellow solid; $^1$H NMR: 3.90 (3H, s), 7.30 (2H, pd), 7.54-7.60 (1H, m), 7.82 (1H, d), 8.38-8.44 (1H, m), 8.49 (1H, s), 8.53 (1H, d); m/z: ES$^+$ MH$^+$ 244.

Intermediate 130:
3-(2-Chloropyrimidin-4-yl)-1-methylindole
(Alternative Synthesis)

AlCl$_3$ (197 g, 1.477 mol) was added portionwise to a solution of 2,4-dichloro-pyrimidine (200 g, 1342 mmol) in dimethoxyethane (2 L) while maintaining the temperature below 30° C., and the mixture was stirred for 10 minutes. 1-Methylindole (0.172 L, 1.342 mol) was then added and the mixture was heated to 80° C. for 2 h and then left to cool overnight. The mixture was then poured into stirring water (20 L) and then was stirred for a further 1 h. The mixture was then filtered and the resulting solid was washed with water (3 L). The solid was then air-dried for 16 h, to give a pink solid (315 g). This solid was then stirred in refluxing CH$_3$CN (6.3 L) for 1.5 h at which point water (630 mL) was added. The mixture was then allowed to cool to r.t. and was stirred for 18 h. The mixture was then stirred at 5° C. for 0.5 h then the resulting solid was collected by filtration. The solid was then washed with cold 10% CH$_3$CN/water (2×1 L) and then dried to give the title compound (220 g, 67%) as a cream solid.

Intermediate 131:
3-(2-Chloropyrimidin-4-yl)-1H-indole

CH$_3$MgBr (3M in diethyl ether, 22.68 mL, 68.03 mmol) was added dropwise over a period of 10 minutes to a stirred solution of 1H-indole (7.97 g, 68.03 mmol) in 1,2-dichloroethane (250 mL) at 0° C. under an atmosphere of N$_2$. The resulting solution was stirred for 15 minutes and then 2,4-dichloropyrimidine (15.00 g, 100.69 mmol) was added in one portion. The resulting solution was allowed to warm to r.t. and was stirred for a further 16 h. The reaction was quenched by the addition of CH$_3$OH (25 mL) then the mixture was concentrated in vacuo and absorbed onto silica. Purification by FCC, eluting with 0-20% CH$_3$OH in CH$_2$Cl$_2$ gave the title compound (7.17 g, 46%) as a yellow solid; $^1$H NMR: 7.20-7.28 (2H, m), 7.49-7.53 (1H, m), 7.91 (1H, d), 8.42 (1H, dd), 8.50 (1H, d), 8.53 (1H, d), 12.06 (1H, s); m/z: ES+ MH+ 230.

Intermediate 132: 4-[(3aR,6aR)-5-Methyl-2,3,3a,4, 6,6a-hexahydropyrrolo[3,4-b]-pyrrol-1-yl]-6-methoxy-N-[4-(4,5,6,7-tetrahydropvrazolo[1,5-a]pyridin-3-yl)-pyrimidin-2-yl]benzene-1,3-diamine A mixture of N-{4-[(3aR,6aR)-5-methyl-2,3,3a,4,6,6a-hexahydropyrrolo[3,4-b]pyrrol-1-yl]-2-methoxy-5-nitrophenyl}-4-(4,5,6,7-tetrahydropyrazolo[1,5-a]pyridin-3-yl)pyrimidin-2-amine (Intermediate 133, 400 mg, 0.82 mmol), iron (273 mg, 4.89 mmol) and NH$_4$Cl (30.5 mg, 0.57 mmol) in ethanol (12 mL) and water (4 mL) was heated at reflux for 4 h and then stirred at r.t.overnight. Part-purification by ion exchange chromatography, using an SCX column, eluting with 7M methanolic ammonia provided crude material that was concentrated in vacuo onto silica. Purification by FCC, eluting with 0-5% 7N methanolic ammonia in CH$_2$Cl$_2$ provided impure product as a brown gum. Further purification by FCC, eluting with 0-2% 7N methanolic ammonia in CH$_2$Cl$_2$ provided the title compound (123 mg, 33%) as a brown gum; m/z: ES+ MH+ 461.26.

Intermediate 133: N-{4-[(3aR,6aR)-5-Methyl-2,3, 3a,4,6,6a-hexahydropyrrolo[3,4-b]-pyrrol-1-yl]-2-methoxy-5-nitrophenyl}-4-(4,5,6,7-tetrahydropyrazolo[1,5-a]pyridin-3-yl)pyrimidin-2-amine DIPEA (0.583 mL, 3.35 mmol) was added to a suspension of N-(4-fluoro-2-methoxy-5-nitrophenyl)-4-(4,5,6,7-tetrahydropyrazolo[1,5-a]pyridin-3-yl)pyrimidin-2-amine (Intermediate 127, 515 mg, 1.34 mmol) and (3aR,6aR)-5-methyl-2,3,3a,4,6,6a-hexahydro-1H-pyrrolo[3,4-b]pyrrole (Intermediate 37, 186 mg, 1.47 mmol) in 2,2,2-trifluoroethanol (5 mL) and the mixture was heated in a microwave at 140° C. for 1 h. After cooling, the mixture was part-purified by ion exchange chromatography, using an SCX column, eluting with 7M methanolic ammonia, and then concentrated in vacuo onto silica. Purification by FCC, eluting with 0-5% 7N methanolic ammonia in CH$_2$Cl$_2$ gave the title compound (400 mg, 61%) as an orange/red foam; $^1$H NMR (CDCl$_3$): 1.87 (1H, dd), 1.90-1.98 (2H, m), 2.03-2.14 (3H, m), 2.20 (3H, s), 2.28 (1H, dd), 2.45 (2H, ddd), 2.60-2.67 (1H, m), 2.97-3.07 (1H, m), 3.18-3.34 (3H, m), 3.48-3.58 (1H, m), 3.96 (3H, s), 4.20 (2H, t), 4.40 (1H, ddd), 6.43 (1H, s), 6.86 (1H, d), 7.35 (1H, s), 7.95 (1H, s), 8.30 (1H, d), 8.92 (1H, s); m/z: ES+ MH+ 491.15.

Intermediate 134: 4-[(3R)-3-Dimethylaminopyrrolidin-1-yl]-6-methoxy-N-[4-(4,5,6,7-tetrahydropyrazolo[1,5-a]pyridin-3-yl)pyrimidin-2-yl]benzene-1,3-diamine A mixture of N-{4-[(3R)-3-dimethylaminopyrrolidin-1-yl]-2-methoxy-5-nitrophenyl}-4-(4,5,6,7-tetrahydropyrazolo[1,5-a]pyridin-3-yl)pyrimidin-2-amine (Intermediate 135, 198.7 mg, 0.42 mmol), iron (139 mg, 2.49 mmol) and NH$_4$Cl (15.6 mg, 0.29 mmol) in ethanol (15 mL) and water (5 mL) was heated at reflux for 2.5 h. The mixture was then allowed to cool to r.t., filtered and concentrated in vacuo. Part-purification by ion exchange chromatography, using an SCX column, eluting with 0.7M methanolic ammonia provided crude material as a yellow gum. Further purification by FCC, eluting with 0-5% 7N methanolic ammonia in CH$_2$Cl$_2$ gave the title compound (159 mg, 85%) as a brown foam; $^1$H NMR (CDCl$_3$): 1.83-1.97 (3H, m), 2.05-2.17 (3H, m), 2.29 (6H, s), 2.83-2.91 (1H, m), 2.98-3.08 (2H, m), 3.15-3.20 (2H, m), 3.24 (2H, t), 3.69 (2H, s), 3.83 (3H, s), 4.20 (2H, t), 6.69 (1H, s), 6.78 (1H, d), 7.45 (1H, s), 7.97 (2H, d), 8.29 (1H, d); m/z: ES+ MH+ 449.65.

Intermediate 135: N-{4-[(3R)-3-Dimethylaminopyrrolidin-1-yl]-2-methoxy-5-nitrophenyl}-4-(4,5,6,7-tetrahydropyrazolo[1,5-a]pyridin-3-yl)pyrimidin-2-amine (3R)—N,N-Dimethylpyrrolidin-3-amine (64 mg, 0.56 mmol), N-(4-fluoro-2-methoxy-5-nitrophenyl)-4-(4,5,6,7-tetrahydropyrazolo[1,5-a]pyridin-3-yl)pyrimidin-2-amine (Intermediate 127, 267 mg, 0.53 mmol) and DIPEA (0.186 mL, 1.07 mmol) were suspended in DMA (2 mL), sealed into a microwave tube and then heated to 140° C. for 1 h in a microwave reactor. After cooling to r.t. the mixture was part-purified by ion exchange chromatography, using an SCX column. The column was first washed with CH$_3$OH and then eluted with 0.7M methanolic ammonia. Clean fractions were concentrated in vacuo to give crude material as an orange gum. Purification by FCC, eluting with 0-5% 7N methanolic ammonia in CH$_2$Cl$_2$ gave the title compound (201 mg, 79%) as a orange gum; $^1$H NMR (CDCl$_3$): 1.89-1.98 (3H, m), 2.05-2.12 (2H, m), 2.16-2.23 (1H, m), 2.30 (6H, s), 2.78-2.87 (1H, m), 3.14-3.37 (5H, m), 3.54 (1H, td), 3.96 (3H, s), 4.20 (2H, t), 6.34 (1H, s), 6.85 (1H, d), 7.33 (1H, s), 7.95 (1H, s), 8.30 (1H, d), 8.95 (1H, s); m/z: ES+ MH+ 479.60.

Intermediate 136: 4-Methoxy-6-(1-methyl-3,6-dihydro-2H-pyridin-4-yl)-N'-[4-(4,5,6,7-tetrahydropyrazolo[1,5-a]pyridin-3-yl)pyrimidin-2-yl]benzene-1,3-diamine 1,1 Bis(di-tert-butylphosphino)ferrocene palladium dichloride (16.7 mg, 0.03 mmol) was added to a solution of 1-methyl-4-(4,4,5,5-tetramethyl-1,3,2-dioxaborolan-2-yl)-1,2,3,6-tetrahydropyridine (139 mg, 0.62 mmol), 4-bromo-6-methoxy-N-[4-(4,5,6,7-tetrahydropyrazolo[1,5-a]pyridin-3-yl)pyrimidin-2-yl]benzene-1,3-diamine (Intermediate 137, 215 mg, 0.52 mmol), and K$_3$PO$_4$ (220 mg, 1.04 mmol) in 1,4-dioxane (6 mL) and water (1.5 mL, degassed for 20 minutes prior to use). The mixture was then heated at 100° C. for 1 h and then concentrated in vacuo. The resulting residue was dissolved in EtOAc and this solution was washed three times with water, then with brine. The solution was then dried (MgSO$_4$) and concentrated in vacuo. Purification by FCC, eluting with 0-10% methanolic ammonia in CH$_2$Cl$_2$ gave the title compound (160 mg, 72%) as a tan solid after trituration with diethyl ether; $^1$H NMR: 1.79-1.87 (2H, m), 1.96-2.03 (2H, m), 2.29 (3H, s), 2.34-2.40 (2H, m), 2.58 (2H, t), 2.98-3.02 (2H, m), 3.15 (2H, t), 3.75 (3H, s), 4.12 (2H, t), 4.32 (2H, br s), 5.67-5.71 (1H, m), 6.60 (1H, s), 7.01 (1H, d), 7.58 (1H, s), 7.69 (1H, s), 8.09 (1H, s), 8.32 (1H, d); m/z: ES+ MH+ 432.72.

Intermediate 137: 4-Bromo-6-methoxy-N-[4-(4,5,6, 7-tetrahydropyrazolo[1,5-a]-pyridin-3-yl)pyrimidin-2-yl]benzene-1,3-diamine N-(4-Bromo-2-methoxy-5-nitrophenyl)-4-(4,5,6,7-tetrahydropyrazolo[1,5-a]pyridin-3-yl)pyrimidin-2-amine (Intermediate 138, 944 mg, 2.12 mmol), iron (710 mg, 12.7 mmol) and NH$_4$Cl (85 mg, 1.59 mmol) were heated in ethanol (40 mL) and water (13 mL) at reflux for 1.5 h. The mixture was then cooled and filtered. The residue was triturated in 10% CH$_3$OH in CH$_2$Cl$_2$ (30 mL) for 15 minutes and then filtered. The residues were triturated again with 10% CH$_3$OH in CH$_2$Cl$_2$ (30 mL) and filtered. The combined filtrates were washed with brine, dried (MgSO$_4$) and concentrated in vacuo. Purification by FCC, eluting with 0-5% CH$_3$OH in CH$_2$Cl$_2$ gave the title compound (814 mg, 92%) as a brown solid after trituration with diethyl ether; $^1$H NMR: 1.80-1.87 (2H, m), 1.96-2.03 (2H, m), 3.13 (2H, t), 3.77 (3H, s), 4.12 (2H, t), 4.82 (2H, s), 7.02 (1H, s), 7.05 (1H, d), 7.75 (1H, s), 7.77 (1H, s), 8.10 (1H, s), 8.34 (1H, d); m/z: ES$^+$ MH$^+$ 415/417.

Intermediate 138: N-(4-Bromo-2-methoxy-5-nitrophenyl)-4-(4,5,6,7-tetrahydropyrazolo[1,5-a]pyridin-3-yl)pyrimidin-2-amine A solution of 3-(2-chloropyrimidin-4-yl)-4,5,6,7-tetrahydropyrazolo[1,5-a]pyridine (Intermediate 128, 0.893 g, 3.80 mmol), p-toluene sulphonic acid monohydrate (1.034 g, 5.43 mmol) and 4-bromo-2-methoxy-5-nitroaniline (Intermediate 4, 0.895 g, 3.62 mmol) in 2-pentanol (35 mL) was heated at reflux for 16 h under an atmosphere of N$_2$. The mixture was then allowed to cool, and was concentrated in vacuo. The resulting residue was triturated in CH$_3$CN until a yellow precipitate formed. The solid was collected by filtration and was washed with diethyl ether. The solid then was dissolved in 10% CH$_3$OH in CH$_2$Cl$_2$ and the resulting solution was washed twice with sat. NaHCO$_3$, then with water. The solution was then dried (MgSO$_4$) and concentrated in vacuo. The resulting residue was triturated with CH$_3$CN, the resulting solid collected by filtration, washed with diethyl ether, and then air dried to give the title compound (0.946 g, 59%) as a yellow solid; $^1$H NMR: 1.80-1.87 (2H, m), 1.96-2.03 (2H, m), 3.11 (2H, t), 4.04 (3H, s), 4.13 (2H, t), 7.17 (1H, d), 7.50 (1H, s), 8.13 (1H, s), 8.21 (1H, s), 8.45 (1H, d), 9.10 (1H, s); m/z: ES$^+$ MH$^+$ 445/447.

Intermediate 139: 4-(3-Dimethylaminoazetidin-1-yl)-6-methoxy-N-[4-(4,5,6,7-tetrahydropyrazolo[1,5-a]pyridin-3-yl)pyrimidin-2-yl]benzene-1,3-diamine A mixture of N-[4-(3-dimethylaminoazetidin-1-yl)-2-methoxy-5-nitrophenyl]-4-(4,5,6,7-tetrahydropyrazolo[1,5-a]pyridin-3-yl)pyrimidin-2-amine (Intermediate 140, 130 mg, 0.28 mmol), iron (94 mg, 1.68 mmol) and NH$_4$Cl (10.48 mg, 0.20 mmol) in ethanol (12 mL) and water (4 mL) was heated at reflux for 2.5 h. The mixture was allowed to cool to r.t., filtered and concentrated in vacuo. Part-purification by ion exchange chromatography, using an SCX column, eluting with 0.7M methanolic ammonia provided crude material as a brown gum. Further purification by FCC, eluting with 0-5% 7N methanolic ammonia in CH$_2$Cl$_2$ gave the title compound (111 mg, 91%) as a brown gum; $^1$H NMR (CDCl$_3$): 1.90-1.98 (2H, m), 2.04-2.12 (2H, m), 2.20 (6H, s), 3.08-3.16 (1H, m), 3.23 (2H, t), 3.35 (1H, s), 3.56 (2H, t), 3.84 (3H, s), 3.93 (2H, dd), 4.20 (2H, t), 6.37 (1H, s), 6.76 (1H, d), 7.35 (1H, s), 7.87 (1H, s), 7.95 (1H, s), 8.28 (1H, d); m/z: ES$^+$ MH$^+$ 435.58.

Intermediate 140: N-[4-(3-Dimethylaminoazetidin-1-yl)-2-methoxy-5-nitrophenyl]-4-(4,5,6,7-tetrahydropyrazolo[1,5-a]pyridin-3-yl)pyrimidin-2-amine N,N-Dimethylazetidin-3-amine dihydrochloride (Intermediate 26, 109 mg, 0.63 mmol), N-(4-fluoro-2-methoxy-5-nitrophenyl)-4-(4,5,6,7-tetrahydropyrazo[1,5-a]pyridin-3-yl)pyrimidin-2-amine (Intermediate 127, 300 mg, 0.60 mmol), DIPEA (0.386 mL, 2.22 mmol) and DMA (4 mL) was sealed into a microwave tube and heated to 140° C. for 1 h in the microwave reactor. After cooling, to r.t., the mixture was part-purified by ion exchange chromatography, using an SCX column. The column was first washed with CH$_3$OH and then the desired product was eluted from the column using 0.7M methanolic ammonia. Clean fractions were concentrated in vacuo to give an orange gum. Further purification by FCC, eluting with 0-5% 7N methanolic ammonia in CH$_2$Cl$_2$ gave the title compound (140 mg, 50%) as an orange solid; $^1$H NMR (CDCl$_3$): 1.90-1.98 (2H, m), 2.05-2.12 (2H, m), 2.20 (6H, s), 3.15-3.23 (1H, m), 3.28 (2H, t), 3.69 (2H, dd), 3.96 (3H, s), 4.18 (4H, dt), 6.03 (1H, s), 6.87 (1H, d), 7.35 (1H, s), 7.97 (1H, s), 8.31 (1H, d), 9.02 (1H, s); m/z: ES$^+$ MH$^+$ 465.61.

Intermediate 141: 4-Methoxy-6-(8-methyl-2,8-diazaspiro[3.4]octan-2-yl)-N'-[4-(4,5,6,7-tetrahydropyrazolo[1,5-a]pyridin-3-yl)pyrimidin-2-yl]benzene-1,3-diamine N-[2-Methoxy-4-(8-methyl-2,8-diazaspiro[3.4]octan-2-yl)-5-nitrophenyl]-4-(4,5,6,7-tetrahydropyrazolo[1,5-a]pyridin-3-yl)pyrimidin-2-amine (Intermediate 142, 320 mg, 0.65 mmol), iron (219 mg, 3.91 mmol) and NH$_4$Cl (26.2 mg, 0.49 mmol) were heated at reflux in ethanol (18 mL) and water (6 mL) for 4 h. The mixture was then cooled, filtered and concentrated in vacuo. The resulting residue was triturated in 10% CH$_3$OH in CH$_2$Cl$_2$ (15 mL) for 15 minutes and the mixture was then filtered. The residues were re-triturated with 10% CH$_3$OH in CH$_2$Cl$_2$ (15 mL) and the mixture was then filtered. The combined filtrates were washed with brine, dried (Na$_2$SO$_4$) and concentrated in vacuo. Purification by FCC, eluting with 2% 7N methanolic ammonia in CH$_2$Cl$_2$ gave the title compound (251 mg, 84%) as a brown gum which crystallised on standing; $^1$H NMR: 1.64-1.76 (2H, m), 1.75-1.87 (2H, m), 1.91-2.03 (2H, m), 2.08 (2H, dd), 2.39 (3H, s), 2.63 (2H, t), 3.06 (2H, t), 3.56 (2H, d), 3.72 (3H, s), 3.82 (2H, d), 4.01 (2H, s), 4.10 (2H, t), 6.25 (1H, s), 6.91 (1H, d), 7.21 (1H, s), 7.67 (1H, s), 8.04 (1H, s), 8.23 (1H, d); m/z: ES$^+$ MH$^+$ 461.37.

Intermediate 142: N-[2-Methoxy-4-(8-methyl-2,8-diazaspiro[3.4]octan-2-yl)-5-nitrophenyl]-4-(4,5,6,7-tetrahydropyrazolo[1,5-a]pyridin-3-yl)pyrimidin-2-amine N-(4-Fluoro-2-methoxy-5-nitrophenyl)-4-(4,5,6,7-tetrahydropyrazolo[1,5-a]pyridin-3-yl)pyrimidin-2-amine (Intermediate 127, 300 mg, 0.78 mmol), 8-methyl-2,8-diazaspiro[3.4]octane (Intermediate 47, 118 mg, 0.94 mmol) and DIPEA (0.162 mL, 0.94 mmol) were heated at 100° C. in DMA (4 mL) for 1.75 h. The mixture was then absorbed onto an SCX column, then the column was washed with CH$_3$OH and then eluted with 1:1 7M methanolic ammonia in CH$_2$Cl$_2$. Fractions that contained the desired product were combined and concentrated in vacuo. Purification by FCC, eluting with 2.5% 7N methanolic ammonia in CH$_2$Cl$_2$ gave the title compound (321 mg, 84%) as an orange foam; $^1$H NMR: 1.62-1.74 (2H, m), 1.74-1.85 (2H, m), 1.91-2.00 (2H, m), 2.00-2.06 (2H, m), 2.38 (3H, s), 2.65 (2H, t), 3.03 (2H, t), 3.71 (2H, d), 3.95 (3H, s), 4.04-4.15 (4H, m), 6.27 (1H, s), 7.01 (1H, d), 8.01 (1H, s), 8.09 (1H, s), 8.33 (1H, d), 8.54 (1H, s); m/z: ES$^+$ MH$^+$ 491.6.

Intermediate 143: 4-Methoxy-6-(1-methyl-3,6-dihydro-2H-pyridin-4-yl)-N'-[4-(1-methylindol-3-yl)pyrimidin-2-yl]benzene-1,3-diamine 1,1 Bis(di-tert-butylphosphino)ferrocene palladium dichloride (16.74 mg, 0.03 mmol) was added to a solution containing 1-methyl-4-(4,4,5,5-tetramethyl-1,3,2-dioxaborolan-2-yl)-1,2,3,6-tetrahydropyridine (139 mg, 0.62 mmol), 4-bromo-6-methoxy-N-[4-(1-methylindol-3-yl)pyrimidin-2-yl]benzene-1,3-diamine (Intermediate 144, 220 mg, 0.52 mmol), and K₃PO₄ (220 mg, 1.04 mmol) in 1,4-dioxane (6 mL) and water (1.5 mL, degassed for 20 minutes prior to use). The mixture was heated at 100° C. for 1 h and then concentrated in vacuo. The resulting residue was dissolved in EtOAc. This solution was washed with water (×3), brine, and was then dried (MgSO₄) and concentrated in vacuo. Purification by FCC, eluting with 0-10% methanolic ammonia in CH₂Cl₂ gave the title compound (191 mg, 84%) as a tan solid after trituration with diethyl ether; ¹H NMR: 2.31 (3H, s), 2.37-2.43 (2H, m), 2.61 (2H, t), 3.01-3.04 (2H, m), 3.76 (3H, s), 3.89 (3H, s), 4.37 (2H, br s), 5.70-5.73 (1H, m), 6.63 (1H, s), 7.18-7.22 (2H, m), 7.25-7.29 (1H, m), 7.54 (1H, d), 7.63 (1H, s), 7.81 (1H, s), 8.31 (1H, d), 8.34 (1H, s), 8.46 (1H, d); m/z: ES⁺ MH⁺ 441.57.

Intermediate 144: 4-Bromo-6-methoxy-N-[4-(1-methylindol-3-yl)pyrimidin-2-yl]-benzene-1,3-diamine N-(4-Bromo-2-methoxy-5-nitrophenyl)-4-(1-methylindol-3-yl)pyrimidin-2-amine (Intermediate 145, 1.074 g, 2.36 mmol), iron (0.792 g, 14.19 mmol) and NH₄Cl (95 mg, 1.77 mmol) were heated at reflux in ethanol (39 mL) and water (13 mL) for 1.5 h. The mixture was then cooled and concentrated in vacuo. The resulting residue was triturated in 10% CH₃OH in CH₂Cl₂ (30 mL) for 15 minutes and the mixture was then filtered. The residues were triturated again with 10% CH₃OH in CH₂Cl₂ (30 mL) and the mixture then filtered. The combined filtrates were washed with brine, dried (MgSO₄) and concentrated in vacuo. Purification by FCC, eluting with CH₂Cl₂ gave the title compound (0.937 g, 93%) as a cream foam; ¹H NMR: 3.79 (3H, s), 3.89 (3H, s), 4.86 (2H, s), 7.06 (1H, s), 7.18-7.30 (3H, m), 7.54 (1H, d), 7.83 (1H, s), 7.87 (1H, s), 8.33 (1H, d), 8.35 (1H, s), 8.43 (1H, d); m/z: ES⁺ MH⁺ 424/426.

Intermediate 145: N-(4-Bromo-2-methoxy-5-nitrophenyl)-4-(1-methylindol-3-yl)pyrimidin-2-amine

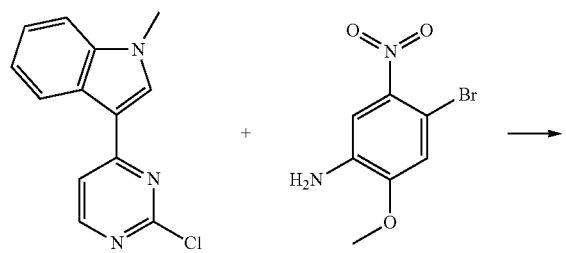

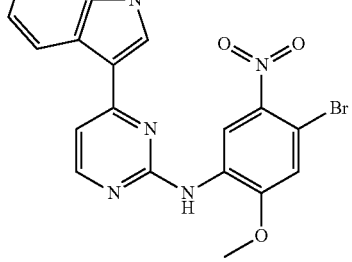

A solution of 3-(2-chloropyrimidin-4-yl)-1-methylindole (Intermediate 130, 0.829 g, 3.40 mmol), p-toluene sulphonic acid monohydrate (0.924 g, 4.86 mmol) and 4-bromo-2-methoxy-5-nitroaniline (Intermediate 4, 0.8 g, 3.24 mmol) was heated at reflux in 2-pentanol (32 mL) under an atmosphere of N₂ for 18 h. The mixture was then allowed to cool, and was then concentrated in vacuo. The resulting residue was triturated with CH₃CN until a yellow precipitate formed. This solid was collected by filtration and was washed with diethyl ether. The solid was suspended in 10% CH₃OH in CH₂Cl₂ and washed with saturated aqueous NaHCO₃ (2×) followed by water. The organic solution was then concentrated in vacuo, and the resulting residue was triturated in CH₃CN/water. The mixture was then filtered, and the collected solid was washed with CH₃CN followed by diethyl ether and was then air dried to give the title compound (1.082 g, 74%) as a yellow solid; ¹H NMR: 3.90 (3H, s), 4.05 (3H, s), 7.15-7.21 (1H, m), 7.26-7.31 (1H, m), 7.36 (1H, d), 7.52 (1H, s), 7.56 (1H, d), 8.34 (1H, s), 8.39 (1H, s), 8.40-8.45 (2H, m), 9.20 (1H, s); m/z: ES⁺ MH⁺ 454/456.

Intermediate 146: 4-Methoxy-6-(8-methyl-2,8-diazaspiro[3.4]octan-2-yl)-N'-[4-(1-methylindol-3-yl)pyrimidin-2-yl]benzene-1,3-diamine A mixture of N-[2-Methoxy-4-(8-methyl-2,8-diazaspiro[3.4]octan-2-yl)-5-nitrophenyl]-4-(1-methylindol-3-yl)pyrimidin-2-amine (Intermediate 147, 200 mg, 0.40 mmol), iron (134 mg, 2.40 mmol) and NH₄Cl (16 mg, 0.30 mmol), ethanol (18 mL) and water (6 mL) was heated at reflux for 1 h then the mixture was allowed to cool. The mixture was then filtered and concentrated in vacuo. The resulting residue was triturated in 10% CH₃OH in CH₂Cl₂ (15 mL) for 15 minutes and the mixture was then filtered. The residues were triturated again with 10% CH₃OH in CH₂Cl₂ (15 mL) and the mixture then filtered. The combined filtrates were washed with brine, dried (Na₂SO₄) and concentrated in vacuo. Purification by FCC, eluting with 2% 7N methanolic ammonia in CH₂Cl₂ gave the title compound (144 mg, 77%) as a dark green foam; ¹H NMR: 1.66-1.80 (2H, m), 2.06-2.16 (2H, m), 2.42 (3H, s), 2.66 (2H, t), 3.59 (2H, d), 3.75 (3H, s), 3.83-3.91 (5H, m), 4.01 (2H, s), 6.30 (1H, s), 7.09 (1H, d), 7.16 (1H, t), 7.21-7.28 (1H, m), 7.31 (1H, s), 7.51 (1H, d), 7.70 (1H, s), 8.23 (1H, d), 8.26 (1H, s), 8.43 (1H, d); m/z: ES⁺ MH⁺ 470.7.

Intermediate 147: N-[2-Methoxy-4-(8-methyl-2,8-diazaspiro[3.4]octan-2-yl)-5-nitrophenyl]-4-(1-methylindol-3-yl)pyrimidin-2-amine A mixture of N-(4-fluoro-2-methoxy-5-nitrophenyl)-4-(1-methylindol-3-yl)pyrimidin-2-amine (Intermediate 129, 300 mg, 0.76 mmol), 8-methyl-2,8-diazaspiro[3.4]octane (Intermediate 47, 115 mg, 0.92 mmol), DIPEA (0.158 mL, 0.92 mmol) and DMA (4 mL) was heated at 100° C. for 1 h. The mixture was then absorbed onto an SCX column, and the column was washed with $CH_3OH$. The column was then eluted with 1:1 methanoic ammonia in $CH_2Cl_2$ and fractions containing the desired product were combined and concentrated in vacuo. Purification by FCC, eluting with 1.5% $CH_3OH$ in $CH_2Cl_2$ gave the title compound (209 mg, 55%) as an orange solid; $^1H$ NMR: 1.71 (2H, dt), 2.00-2.10 (2H, m), 2.40 (3H, s), 2.67 (2H, t), 3.74 (2H, d), 3.88 (3H, s), 3.96 (3H, s), 4.11 (2H, d), 6.31 (1H, s), 7.12 (1H, t), 7.20 (1H, d), 7.25 (1H, dd), 7.52 (1H, d), 8.02 (1H, s), 8.28-8.34 (2H, m), 8.36 (1H, d), 8.63 (1H, s); m/z: $ES^+$ $MH^+$ 500.6.

Intermediate 148: 4-[(3S)-3-Dimethylaminopyrrolidin-1-yl]-6-methoxy-N-[4-(1-methylindol-3-yl)pyrimidin-2-yl]benzene-1,3-diamine A mixture of N-[4-[(3S)-3-dimethylaminopyrrolidin-1-yl]-2-methoxy-5-nitrophenyl]-4-(1-methylindol-3-yl)pyrimidin-2-amine (Intermediate 149, 230 mg, 0.47 mmol), iron (158 mg, 2.83 mmol), $NH_4Cl$ (17.7 mg, 0.33 mmol), ethanol (9 mL) and water (3 mL) was heated at reflux for 50 minutes. The reaction was judged to be incomplete so further iron (158 mg, 2.83 mmol) and $NH_4Cl$ (17.7 mg, 0.33 mmol) was added and the mixture was heated at reflux for a further 0.5 h. After cooling, the mixture was filtered and concentrated in vacuo. Purification by FCC, eluting with 1.5-7% 7M methanolic ammonia in $CH_2Cl_2$ gave the title compound (187 mg, 87%) as a grey foam; $^1H$ NMR: 1.78 (1H, m), 2.06 (1H, m), 2.20 (6H, s), 2.86 (1H, d), 2.90-3.01 (2H, m), 3.12 (1H, m), 3.15-3.23 (1H, m), 3.76 (3H, s), 3.88 (3H, s), 4.27 (2H, s), 6.72 (1H, s), 7.14 (1H, d), 7.15-7.21 (1H, m), 7.22-7.34 (1H, m), 7.50 (1H, s), 7.52 (1H, d), 7.74 (1H, s), 8.26 (1H, s), 8.28 (1H, s), 8.43 (1H, d); m/z: $ES^+$ $MH^+$ 458.75.

Intermediate 149: N-{4-[(3S)-3-Dimethylaminopyrrolidin-1-yl]-2-methoxy-5-nitrophenyl}-4-(1-methylindol-3-yl)pyrimidin-2-amine N-(4-Fluoro-2-methoxy-5-nitrophenyl)-4-(1-methylindol-3-yl)pyrimidin-2-amine (Intermediate 129, 295 mg, 0.75 mmol), ((3S)—N,N-dimethylpyrrolidin-3-amine (103 mg, 0.90 mmol) and DIPEA (0.196 mL, 1.13 mmol) were dissolved in DMA (3 mL) and sealed into a microwave tube. The mixture was heated to 100° C. for 45 minutes in a microwave reactor, then cooled to r.t., diluted with $CH_3OH$ and absorbed onto an SCX column. The column was washed with $CH_3OH$ and then eluted with 1:1 methanolic ammonia in $CH_2Cl_2$. Fractions containing the desired product were combined and concentrated in vacuo. Purification by FCC, eluting with 2-7% methanolic ammonia in $CH_2Cl_2$ gave the title compound (235 mg, 64%) as a red solid; $^1H$ NMR: 1.83 (1H, m), 2.17 (1H, m), 2.22 (6H, s), 2.72-2.86 (1H, m), 3.17 (2H, m), 3.26 (1H, m), 3.47 (1H, m), 3.88 (3H, s), 3.97 (3H, s), 6.58 (1H, s), 7.12 (1H, t), 7.19 (1H, d), 7.21-7.31 (1H, m), 7.52 (1H, d), 8.01 (1H, s), 8.23-8.33 (2H, m), 8.36 (1H, d), 8.58 (1H, s); m/z: $ES^-$ $MH^+$ 488.35.

Intermediate 150: 4-Methoxy-6-(1-methyl-3,6-dihydro-2H-pyridin-4-yl)-N'-(4-pyrazolo[1,5-a]pyridin-3-ylpyrimidin-2-yl)benzene-1,3-diamine A mixture of N-[2-methoxy-4-(1-methyl-3,6-dihydro-2H-pyridin-4-yl)-5-nitrophenyl]-4-pyrazolo[1,5-a]pyridin-3-ylpyrimidin-2-amine (Intermediate 151, 285 mg, 0.56 mmol), iron (188 mg, 3.36 mmol), $NH_4Cl$ (21 mg, 0.39 mmol) ethanol (10.5 mL) and water (3.5 mL) was heated at reflux for 1.5 h. The reaction was judged to be incomplete so further $NH_4Cl$ (21 mg, 0.39 mmol) and iron (188 mg, 3.36 mmol) were added and the mixture was heated at reflux for a further 1.5 h. After cooling, the mixture was filtered and concentrated in vacuo. Purification by FCC, eluting with 2-10% 7N methanolic ammonia in $CH_2Cl_2$ gave the title compound (183 mg, 69%) as an orange gum which was used without further purification; $^1H$ NMR: 2.30 (3H, s), 2.36-2.45 (2H, m), 2.60 (2H, t), 2.98-3.06 (2H, m), 3.74 (3H, s), 4.34 (2H, s), 5.73 (1H, s), 6.64 (1H, s), 7.09 (1H, m), 7.26 (1H, d), 7.38-7.49 (2H, m), 8.00 (1H, s), 8.35 (1H, d), 8.58 (1H, d), 8.80 (2H, m); m/z: $ES^+$ $MH^+$ 427.

Intermediate 151: N-[2-Methoxy-4-(1-methyl-3,6-dihydro-2H-pyridin-4-yl)-5-nitrophenyl]-4-pyrazolo[1,5-a]pyridin-3-ylpyrimidin-2-amine A solution of 3-(2-chloropyrimidin-4-yl)pyrazolo[1,5-a]pyridine (Intermediate 152, 256 mg, 1.00 mmol), p-toluene sulphonic acid monohydrate (271 mg, 1.43 mmol) and 2-methoxy-4-(1-methyl-3,6-dihydro-2H-pyridin-4-yl)-5-nitroaniline (Intermediate 3, 250 mg, 0.95 mmol) and 2-pentanol (12 mL) was heated at reflux for 4 h under an atmosphere of $N_2$. The mixture was then concentrated in vacuo and the residue was dissolved in $CH_3OH$. This solution was purified by ion exchange chromatography, using an SCX column, eluting with 7M methanolic ammonia. Fractions containing the desired product were concentrated in vacuo to give a residue that was dissolved into hot DMF (10 mL). This solution was filtered and concentrated in vacuo to provide a gum that was triturated with $CH_3CN$ (10 mL) to give the title compound (285 mg, 66%) as a yellow powder; $^1H$ NMR: 2.36 (5H, s), 2.67 (2H, s), 3.07 (2H, s), 4.02 (3H, s), 5.66 (1H, s), 7.00 (1H, s), 7.12 (1H, t), 7.41 (1H, m), 7.45 (1H, m), 8.45 (2H, t), 8.59 (1H, d), 8.83 (2H, t), 8.90 (1H, s); m/z: $ES^-$ $M-H^-$ 456.

Intermediate 152: 3-(2-Chloropyrimidin-4-yl)pyrazolo[1,5-a]pyridine $K_2CO_3$ (5.18 g, 37.50 mmol) was added to 1-aminopyridinium iodide (4.50 g, 20.25 mmol) and (E)-2-chloro-4-(2-ethoxyvinyl)pyrimidine (Intermediate 153, 2.77 g, 15 mmol) in DMF (20 mL) at 25° C. The resulting dark blue suspension was stirred at 25° C. for 15 h (became deep blood colour), and then was heated to 110° C. for 2 h. After cooling, the mixture was added to water (100 mL) and the resulting brown solid was collected by filtration, washed with water and dried by suction. The aqueous filtrate was extracted with EtOAc (2×100 mL) and the combined organic solutions were washed with water (100 mL×4) and saturated brine (50 mL). The solution was then dried ($MgSO_4$) and concentrated in vacuo. The resulting residue was combined with the previously collected brown solid, and dissolved in THF (100 mL). This solution was filtered through a 30 g silica pad. The eluent was concentrated and the resulting residue was washed with −70° C. $CH_3OH$ to give the title compound (1.274 g, 37%) as a beige crystalline solid; $^1H$ NMR: 7.19 (1H, m), 7.65 (1H, m), 7.95 (1H, d), 8.49 (1H, m), 8.61 (1H, d), 8.85-8.91 (1H, m), 8.92 (1H, s); m/z: $ES^+$ $MH^+$ 231.

Intermediate 153: 4-[(3R)-3-Dimethylaminopyrrolidin-1-yl]-6-methoxy-N-(4-pyrazolo[1,5-a]pyridin-3-ylpyrimidin-2-yl)benzene-1,3-diamine A mixture of N-[4-[(3R)-3-dimethylaminopyrrolidin-1-yl]-2-methoxy-5-nitrophenyl]-4-pyrazolo[1,5-a]pyridin-3- ylpyrimidin-2-amine (Intermediate 154, 440 mg, 0.93 mmol), iron (311 mg, 5.56 mmol), NH₄Cl (37.2 mg, 0.70 mmol), ethanol (15 mL) and water (5 mL) was heated at reflux for 1.5 h. After cooling the mixture was concentrated in vacuo. The resulting residue was triturated in 10% CH₃OH in CH₂Cl₂ (20 mL) for 15 minutes and then filtered. The residues were triturated again with 10% CH₃OH in CH₂Cl₂ (10 mL) and then filtered. The combined filtrates were washed with brine, dried (MgSO₄) and concentrated in vacuo. Purification by FCC, eluting with 0-10% methanolic ammonia in CH₂Cl₂ gave the title compound (339 mg, 82%) as a yellow solid after trituration with diethyl ether; $^1$H NMR: 1.73-1.83 (1H, m), 2.00-2.10 (1H, m), 2.20 (6H, s), 2.81-2.90 (1H, m), 2.92-3.00 (2H, m), 3.11-3.16 (1H, m), 3.17-3.24 (1H, m), 3.73 (3H, s), 4.28 (2H, br s), 6.71 (1H, s), 7.07 (1H, td), 7.20 (1H, d), 7.27 (1H, s), 7.37-7.42 (1H, m), 7.97 (1H, s), 8.30 (1H, d), 8.53 (1H, d), 8.76 (1H, s), 8.79 (1H, d); m/z: ES⁺ MH⁺ 445.33.

Intermediate 154: N-[4-[(3R)-3-Dimethylaminopyrrolidin-1-yl]-2-methoxy-5-nitrophenyl]-4-pyrazolo[1,5-a]pyridin-3-ylpyrimidin-2-amine (3R)—N,N-Dimethylpyrrolidin-3-amine (0.166 mL, 1.31 mmol) was added to a suspension of N-(4-fluoro-2-methoxy-5-nitrophenyl)-4-pyrazolo[1,5-a]pyridin-3-ylpyrimidin-2-amine (Intermediate 155, 415 mg, 1.09 mmol) and DIPEA (0.227 mL, 1.31 mmol) in DMA (3.2 mL) and the mixture was heated at 85° C. for 1 h. Part purification was achieved by ion exchange chromatography, using an SCX column, eluting with 7M methanolic ammonia. Clean fractions were combined and concentrated. Further purification by FCC, eluting with 0-7% CH₃OH in CH₂Cl₂ gave the title compound (443 mg, 86%) as an orange solid; $^1$H NMR: 1.77-1.88 (1H, m), 2.13-2.20 (1H, m), 2.23 (6H, s), 2.75-2.84 (1H, m), 3.14-3.26 (3H, m), 3.43-3.51 (1H, m), 3.96 (3H, s), 6.58 (1H, s), 7.08 (1H, td), 7.27 (1H, d), 7.34-7.39 (1H, m), 8.24 (1H, s), 8.35 (1H, d), 8.40 (1H, s), 8.49 (1H, d), 8.78 (1H, s), 8.80 (1H, d); m/z: ES⁺ MH⁺ 475.31.

Intermediate 155: N-(4-Fluoro-2-methoxy-5-nitrophenyl)-4-pyrazolo[1,5-a]pyridin-3-ylpyrimidin-2-amine A mixture of 3-(2-chloropyrimidin-4-yl)pyrazolo[1,5-a]pyridine (Intermediate 152, 1.476 g, 6.40 mmol), 4-fluoro-2-methoxy-5-nitroaniline (Intermediate 23, 1.310 g, 7.04 mmol), p-toluenesulfonic acid monohydrate (1.339 g, 7.04 mmol) and 2-pentanol (45 mL) was heated at 125° C. for 22 h. After cooling, the mixture was filtered. The solid was washed with CH₃OH, diethyl ether and then dried on the filter to give a brown solid. The solid was dissolved in CH₂Cl₂ and this solution was washed with sat. NaHCO₃ (×3), water and brine, then dried (MgSO₄) and concentrated in vacuo. The resulting residue was triturated in boiling CH₃CN and then allowed to cool. The resulting solid was collected by filtration and air dried to give the title compound (1.29 g, 53%) as a brown solid; $^1$H NMR: 4.03 (3H, s), 7.11 (1H, td), 7.37 (1H, d), 7.41 (1H, d), 7.43-7.48 (1H, m), 8.45 (1H, d), 8.51 (1H, s), 8.58 (1H, d), 8.82-8.84 (2H, m), 9.00 (1H, d); m/z: ES⁺ MH⁺ 381.54.

Intermediate 156: 4-(3-Dimethylaminoazetidin-1-yl)-6-methoxy-N-(4-pyrazolo[1,5-a]-pyridin-3-ylpyrimidin-2-yl)benzene-1,3-diamine A mixture of N-[4-(3-dimethylaminoazetidin-1-yl)-2-methoxy-5-nitrophenyl]-4-pyrazolo[1,5-a]pyridin-3-ylpyrimidin-2-amine (Intermediate 157, 355 mg, 0.77 mmol), iron (258 mg, 4.63 mmol), NH₄Cl (30.9 mg, 0.58 mmol), ethanol (12.6 mL) and water (4.2 mL) was heated at reflux for 1.5 h. After cooling the mixture was concentrated in vacuo. The resulting residue was triturated in 10% CH₃OH in CH₂Cl₂ (20 mL) for 15 minutes and the mixture was then filtered. The residues were triturated again with 10% CH₃OH in CH₂Cl₂ (20 mL) and then filtered. The combined filtrates were washed with brine, dried (MgSO₄) and concentrated in vacuo. Purification by FCC, eluting with 0-10% methanolic ammonia in CH₂Cl₂ gave the title compound (249 mg, 75%) as a brown solid after trituration with diethyl ether; $^1$H NMR: 2.12 (6H, s), 3.02-3.09 (1H, m), 3.47 (2H, t), 3.71 (3H, s), 3.98 (2H, t), 4.04 (2H, br s), 6.28 (1H, s), 7.05 (1H, td), 7.09 (1H, s), 7.16 (1H, d), 7.36-7.41 (1H, m), 7.93 (1H, s), 8.27 (1H, d), 8.48 (1H, d), 8.74 (1H, s), 8.77 (1H, d); m/z: ES⁺ MH⁺ 431.35.

Intermediate 157: N-[4-(3-Dimethylaminoazetidin-1-yl)-2-methoxy-5-nitrophenyl]-4-pyrazolo[1,5-a]pyridin-3-ylpyrimidin-2-amine N,N-Dimethylazetidin-3-amine dihydrochloride (Intermediate 26, 227 mg, 1.31 mmol) was added to a suspension of N-(4-fluoro-2-methoxy-5-nitrophenyl)-4-pyrazolo[1,5-a]-pyridin-3-ylpyrimidin-2-amine (Intermediate 155, 415 mg, 1.09 mmol) and DIPEA (0.755 mL, 4.36 mmol) in DMA (3.2 mL) and the mixture was heated at 85° C. for 1 h. The mixture was part-purified by ion exchange chromatography, using an SCX column and eluting with 7M methanolic ammonia. Clean fractions were combined and concentrated in vacuo. Further purification by FCC, eluting with 0-7% CH₃OH in CH₂Cl₂ gave the title compound (360 mg, 72%) as an orange solid; $^1$H NMR: 2.15 (6H, s), 3.12-3.19 (1H, m), 3.74-3.78 (2H, m), 3.95 (3H, s), 4.04-4.09 (2H, m), 6.29 (1H, s), 7.08 (1H, td), 7.28 (1H, d), 7.36-7.41 (1H, m), 8.26 (1H, s), 8.35 (1H, d), 8.45-8.49 (2H, m), 8.78 (1H, s), 8.80 (1H, d); m/z: ES⁺ MH⁺ 461.33.

Intermediate 158: N$^1$-(2-Dimethylaminoethyl)-5-methoxy-N-methyl-N$^4$-(4-pyrazolo[1,5-a]pyridin-3-ylpyrimidin-2-yl)benzene-1,2,4-triamine A mixture of N'-(2-dimethylaminoethyl)-2-methoxy-N'-methyl-5-nitro-N-(4-pyrazolo[1,5-a]pyridin-3-ylpyrimidin-2-yl)benzene-1,4-diamine (Intermediate 159, 440 mg, 0.95 mmol), iron (319 mg, 5.71 mmol), NH₄Cl (38.2 mg, 0.71 mmol), ethanol (15 mL) and water (5 mL) was heated at reflux for 1.5 h. After cooling, the mixture was concentrated in vacuo. The resulting residue was triturated in 10% CH₃OH in CH₂Cl₂ (20 mL) for 15 minutes and the mixture was then filtered. The residues were triturated again with 10% CH₃OH in CH₂Cl₂ (20 mL) and then filtered. The combined filtrates were washed with brine, dried (MgSO₄) and concentrated in vacuo. Purification by FCC, eluting with 0-10% methanolic ammonia in CH₂Cl₂ gave the title compound (321 mg, 78%) as a brown gum after trituration with diethyl ether; $^1$H NMR: 2.18 (6H, s), 2.37 (2H, t), 2.65 (3H, s), 2.91 (2H, t), 3.72 (3H, s), 4.57 (2H, br s), 6.77 (1H, s), 7.07 (1H, td), 7.22 (1H, d), 7.29 (1H, s), 7.37-7.42 (1H, m), 7.97 (1H, s), 8.31 (1H, d), 8.52 (1H, d), 8.76 (1H, s), 8.77-8.80 (1H, m); m/z: ES⁺ MH⁺ 433.36.

Intermediate 159: N'-(2-Dimethylaminoethyl)-2-methoxy-N'-methyl-5-nitro-N-(4-pyrazolo[1,5-a]pyridin-3-ylpyrimidin-2-yl)benzene-1,4-diamine N$^1$,N$^1$,N$^2$-trimethylethane-1,2-diamine (138 mg, 1.35 mmol) was added to a suspension of N-(4-fluoro-2- methoxy-5-nitrophenyl)-4-pyrazolo[1,5-a]pyridin-3-ylpyrimidin-2-amine (Intermediate 155, 428 mg, 1.13 mmol) and DIPEA (0.234 mL, 1.35 mmol) in DMA (3.3 mL), and the mixture was heated at 85° C. for 1.5 h. Part-purification was achieved by ion exchange chromatography, using an SCX column and eluting with 7M methanolic ammonia. Clean fractions were combined and concentrated in vacuo. Further purification by FCC, eluting with 0-10% $CH_3OH$ in $CH_2Cl_2$ gave the title compound (444 mg, 85%) as an orange oil; $^1H$ NMR: 2.18 (6H, s), 2.50-2.53 (2H, m), 2.87 (3H, s), 3.26-3.30 (2H, m), 3.95 (3H, s), 6.86 (1H, s), 7.09 (1H, td), 7.30 (1H, d), 7.35-7.40 (1H, m), 8.27 (1H, s), 8.37 (1H, d), 8.47-8.51 (2H, m), 8.79 (1H, s), 8.79-8.82 (1H, m); m/z: $ES^+$ $MH^+$ 463.33.

Intermediate 160: 4-[(3aR,6aR)-5-Methyl-2,3,3a,4,6,6a-hexahydropyrrolo[3,4-b]-pyrrol-1-yl]-6-methoxy-N-(4-pyrazolo[1,5-a]pyrimidin-2-yl)benzene-1,3-diamine A mixture of N-[4-[(3aR,6aR)-5-methyl-2,3,3a,4,6,6a-hexahydropyrrolo[3,4-b]pyrrol-1-yl]-2-methoxy-5-nitrophenyl]-4-pyrazolo[1,5-a]pyridin-3-ylpyrimidin-2-amine (Intermediate 161, 190 mg, 0.39 mmol), iron (131 mg, 2.34 mmol), $NH_4Cl$ (14.62 mg, 0.27 mmol), ethanol (6 mL) and water (2 mL) was heated at reflux for 4 h and then stirred at r.t. overnight. Part-purification was achieved by ion exchange chromatography, using an SCX column and eluting with 7N methanolic ammonia. Appropriate fractions were then concentrated in vacuo onto silica. Purification by FCC, eluting with 0-5% 7N methanolic ammonia in $CH_2Cl_2$ provided impure material. The fractions containing desired product were combined and further purified by FCC, eluting with 0-2.5% 7N methanolic ammonia in $CH_2Cl_2$ to give the title compound (100 mg, 56%); m/z: $ES^+$ $MH^+$ 457.21.

Intermediate 161: N-[4-[(3aR,6aR)-5-Methyl-2,3,3a,4,6,6a-hexahydropyrrolo[3,4-b]-pyrrol-1-yl]-2-methoxy-5-nitrophenyl]-4-pyrazolo[1,5-a]pyridin-3-ylpyrimidin-2-amine DIPEA (0.343 mL, 1.97 mmol) was added to a suspension of N-(4-fluoro-2-methoxy-5-nitrophenyl)-4-pyrazolo[1,5-a]pyridin-3-ylpyrimidin-2-amine (Intermediate 155, 300 mg, 0.79 mmol) and (3aR,6aR)-5-methyl-2,3,3a,4,6,6a-hexahydro-1H-pyrrolo[3,4-b]pyrrole (Intermediate 37, 109 mg, 0.87 mmol) in 2,2,2-trifluoroethanol (5 mL) and the mixture was heated in a microwave at 140° C. for 1 h. After cooling, the mixture was part-purified by ion exchange chromatography, using an SCX column and eluting with 7M methanolic ammonia. Appropriate fractions were then concentrated in vacuo onto silica. Further purification by FCC, eluting with 0-4% 7N methanolic ammonia in $CH_2Cl_2$ gave the title compound (198 mg, 52%) as a slightly impure orange/red solid which was used without further purification; $^1H$ NMR ($CDCl_3$): 1.89 (1H, dd), 2.06-2.18 (1H, m), 2.21 (3H, s), 2.31 (1H, dd), 2.47 (2H, ddd), 2.65 (1H, t), 2.99-3.10 (1H, m), 3.26 (1H, t), 3.51-3.60 (1H, m), 3.98 (3H, s), 4.39-4.46 (1H, m), 6.46 (1H, s), 6.93 (1H, td), 7.04 (1H, d), 7.38 (1H, s), 7.43 (1H, ddd), 8.36 (1H, d), 8.46 (1H, s), 8.52 (1H, m), 8.58 (1H, m), 8.98 (1H, s); m/z: $ES^+$ $MH^+$ 487.15.

Intermediate 162: 4-Methoxy-6-(8-methyl-2,8-diazaspiro13.41 octan-2-yl)-N'-(4-pyrazolo[1,5-a]pyridin-3-ylpyrimidin-2-yl)benzene-1,3-diamine A mixture of N-[2-methoxy-4-(8-methyl-2,8-diazaspiro[3.4]octan-2-yl)-5-nitrophenyl]-4-pyrazolo[1,5-a]pyridin-3-ylpyrimidin-2-amine (Intermediate 163, 404 mg, 0.83 mmol), iron (278 mg, 4.98 mmol), $NH_4Cl$ (33.3 mg, 0.62 mmol), ethanol (15 mL) and water (5 mL) was heated at reflux for 1.5 h. After cooling, the mixture was filtered and the residues were washed with 1:10 $CH_3OH$—$CH_2Cl_2$ (20 mL). The combined filtrates were concentrated in vacuo onto silica. Purification by FCC, eluting with 1-10% methanolic ammonia in $CH_2Cl_2$ gave the title compound (338 mg, 89%) as a yellow solid; $^1H$ NMR: 1.72 (2H, dt), 2.11 (2H, dd), 2.42 (3H, s), 2.66 (2H, t), 3.63 (2H, d), 3.72 (3H, s), 3.87 (2H, d), 4.03 (2H, s), 6.29 (1H, s), 7.06 (1H, td), 7.10 (1H, s), 7.16 (1H, d), 7.35-7.42 (1H, m), 7.93 (1H, s), 8.27 (1H, d), 8.52 (1H, d), 8.74 (1H, s), 8.77 (1H, t); m/z: $ES^+$ $MH^+$ 457.36.

Intermediate 163: N-[2-Methoxy-4-(8-methyl-2,8-diazaspiro[3.4]octan-2-yl)-5-nitrophenyl]-4-pyrazolo[1,5-a]pyridin-3-ylpyrimidin-2-amine 8-Methyl-2,8-diazaspiro[3.4]octane (Intermediate 47, 133 mg, 0.88 mmol) was added to a suspension of N-(4-fluoro-2-methoxy-5-nitrophenyl)-4-(pyrazolo[1,5-a]pyridin-3-yl)-pyrimidin-2-amine (Intermediate 155, 280 mg, 0.74 mmol) and DIPEA (0.153 mL, 0.88 mmol) in DMA (3 mL) and the mixture was heated at 100° C. for 1 h. The mixture was then part-purified by ion exchange chromatography, using an SCX column, eluting with 7M methanolic ammonia. Clean fractions were combined and concentrated in vacuo. Further purification by FCC, eluting with 1-8% $CH_3OH$ in $CH_2Cl_2$ gave the title compound (300 mg) as an orange dry film; $^1H$ NMR: 1.71 (2H, dt), 2.05 (2H, dd), 2.40 (3H, s), 2.67 (2H, t), 3.75 (2H, d), 3.95 (3H, s), 4.11 (2H, d), 6.31 (1H, s), 7.09 (1H, td), 7.28 (1H, d), 7.35-7.41 (1H, m), 8.25 (1H, s), 8.36 (1H, d), 8.47 (1H, s), 8.50 (1H, d), 8.79 (1H, s), 8.79-8.82 (1H, m); m/z: $ES^+$ $MH^+$ 487.30.

Intermediate 164: 4-[(3R)-3-Dimethylaminopyrrolidin-1-yl]-N-[4-(1H-indol-3-yl)pyrimidin-2-yl]-6-methoxybenzene-1,3-diamine Water (4 mL) was added to a stirred mixture of N-{4-[(3R)-3-dimethylaminopyrrolidin-1-yl]-2-methoxy-5-nitrophenyl}-4-(1H-indol-3-yl)pyrimidin-2-amine (Intermediate 165, 286 mg, 0.60 mmol), iron (202 mg, 3.62 mmol), $NH_4Cl$ (22.6 mg, 0.42 mmol) and ethanol (24 mL). The resulting mixture was stirred at 105° C. for 3 h and was then filtered through diatomaceous earth (Celite™) and concentrated in vacuo. Part-purification by ion exchange chromatography, using an SCX column and eluting with 0.35M methanolic ammonia gave the title compound (312 mg, 116%) as a brown gum, which was used without further purification; $^1H$ NMR: 2.13 (2H, d), 2.32 (2H, d), 2.80 (6H, d), 2.87-2.98 (2H, m), 3.19 (2H, d), 3.77 (3H, s), 6.74 (1H, s), 7.17 (4H, ddd), 7.46 (1H, d), 7.56 (1H, s), 7.77 (1H, s), 8.28 (2H, dd), 8.43 (1H, d), 11.76 (1H, s); m/z: $ES^+$ $MH^+$ 444.

Intermediate 165: N-{4-[(3R)-3-dimethylaminopyrrolidin-1-yl]-2-methoxy-5-nitrophenyl}-4-(1H-indol-3-yl)pyrimidin-2-amine (3R)—N,N-Dimethylpyrrolidin-3-amine (92 mg, 0.81 mmol) was added to a mixture of N-(4-fluoro-2-methoxy- 5-nitrophenyl)-4-(1H-indol-3-yl)pyrimidin-2-amine (Intermediate 68, 404 mg, 0.73 mmol) and DIPEA (0.256 mL, 1.46 mmol) in DMA 3 mL. The mixture was then heated in a microwave at 140° C. for 0.5 h. Part-purification was achieved by ion-exchange chromatography, using an SCX column (20 g) and eluting with 0.35M methanolic ammonia. Appropriate fractions were combined and concentrated in vacuo to provide an orange/brown gum. This gum was triturated with ethanol (15 mL) to give a solid which was collected by filtration and dried under vacuum to give the title compound (291 mg, 84%) as an orange solid; $^1$H NMR: 1.82 (1H, dt), 2.12-2.20 (1H, m), 2.22 (6H, s), 2.73-2.83 (1H, m), 3.12-3.22 (2H, m), 3.22-3.27 (1H, m), 3.41-3.51 (1H, m), 3.97 (3H, s), 6.58 (1H, s), 7.07 (1H, t), 7.18 (1H, t), 7.26 (1H, d), 7.45 (1H, d), 8.00 (1H, s), 8.28-8.31 (2H, m), 8.35 (1H, d), 8.57 (1H, s), 11.78 (1H, s); m/z: ES$^+$ MH$^+$ 474.30.

Intermediate 166: 4-(3-Dimethylaminoazetidin-1-yl)-N-[4-(1H-indol-3-yl)pyrimidin-2-yl]-6-methoxy-benzene-1,3-diamine Water (4 mL) was added to a mixture of N-[4-(3-dimethylaminoazetidin-1-yl)-2-methoxy-5-nitrophenyl]-4-(1H-indol-3-yl)pyrimidin-2-amine (Intermediate 167, 240 mg, 0.52 mmol), iron (175 mg, 3.13 mmol), NH$_4$Cl (19.56 mg, 0.37 mmol) and ethanol (24 mL).

The resulting mixture was stirred at 105° C. for 3 h, and was then filtered through diatomaceous earth (Celite™). The filtrate was concentrated in vacuo and part-purified by ion exchange chromatography, using an SCX column and eluting with 0.35M methanolic ammonia. Appropriate fractions were combined and concentrated in vacuo to give the title compound (241 mg, 107%) as a brown gum which was used without further purification; m/z: ES$^+$ MH$^+$ 430.

Intermediate 167: N-[4-(3-Dimethylaminoazetidin-1-yl)-2-methoxy-5-nitrophenyl]-4-(1H-indol-3-yl)pyrimidin-2-amine N,N-Dimethylazetidin-3-amine dihydrochloride (Intermediate 26, 140 mg, 0.81 mmol) was added to a suspension of N-(4-fluoro-2-methoxy-5-nitrophenyl)-4-(1H-indol-3-yl)pyrimidin-2-amine (Intermediate 68, 406 mg, 0.74 mmol) and DIPEA (0.514 mL, 2.94 mmol) in DMA (3 mL). The mixture was heated in a microwave at 140° C. for 0.5 h. The mixture was then part-purified by ion exchange chromatography, using an SCX column (20 g) and eluting with 0.35M methanolic ammonia. Appropriate fractions were combined and concentrated in vacuo to provide an orange/brown gum. This gum was triturated with ethanol (15 mL) to give a solid which was collected by filtration and dried under vacuum to give the title compound (245 mg, 72%) as an orange solid; $^1$H NMR: 2.15 (6H, s), 3.17 (1H, dd), 3.76 (2H, dd), 3.97 (3H, s), 4.03-4.10 (2H, m), 6.29 (1H, s), 7.08 (1H, t), 7.14-7.21 (1H, m), 7.27 (1H, d), 7.45 (1H, d), 8.01 (1H, s), 8.28-8.37 (3H, m), 8.64 (1H, s), 11.79 (1H, s); m/z: ES$^+$ MH$^+$ 460.32.

Intermediate 168: N$^1$-(2-Dimethylaminoethyl)-N$^4$-[4-(1H-indol-3-yl)pyrimidin-2-yl]-5-methoxy-N$^1$-methylbenzene-1,2,4-triamine

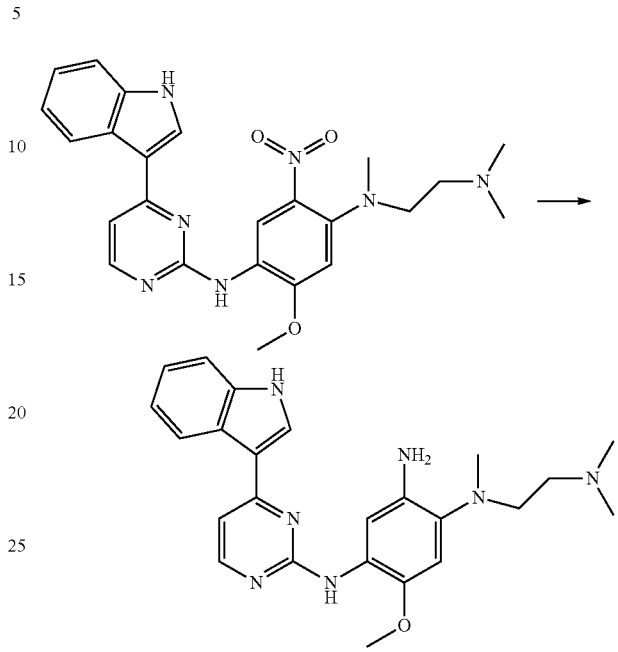

Water (4 mL) was added in one portion to a mixture of N'-(2-dimethylaminoethyl)-N-[4-(1H-indol-3-yl)pyrimidin-2-yl]-2-methoxy-N'-methyl-5-nitrobenzene-1,4-diamine (Intermediate 169, 270 mg, 0.59 mmol), iron (196 mg, 3.51 mmol), NH$_4$Cl (21.9 mg, 0.41 mmol) and ethanol (24 mL). The resulting mixture was heated at 105° C. for 3 h then filtered through diatomaceous earth (Celite™). The filtrate was concentrated in vacuo and then part-purified by ion exchange chromatography, using an SCX column and eluting with 0.35M methanolic ammonia. Appropriate fractions were combined and concentrated in vacuo to give the title compound (244 mg, 97%) as a brown solid which was used without further purification; $^1$H NMR: 2.18 (6H, s), 2.37 (2H, s), 2.64 (3H, s), 2.90 (2H, s), 3.76 (3H, s), 6.77 (1H, s), 7.03-7.26 (3H, m), 7.46 (1H, d), 7.52 (1H, s), 7.74 (1H, s), 8.18-8.35 (2H, m), 8.42 (1H, d), 11.72 (1H, s); m/z: ES$^+$ MH$^+$ 432.

Intermediate 169: N'-(2-Dimethylaminoethyl)-N-[4-(1H-indol-3-yl)pyrimidin-2-yl]-2-methoxy-N'-methyl-5-nitrobenzene-1,4-diamine

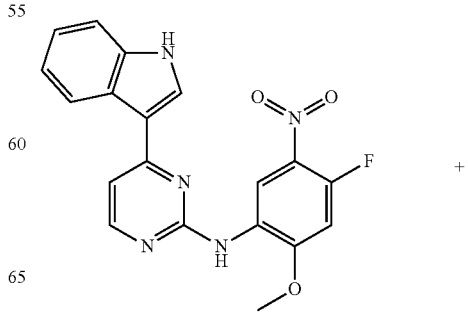

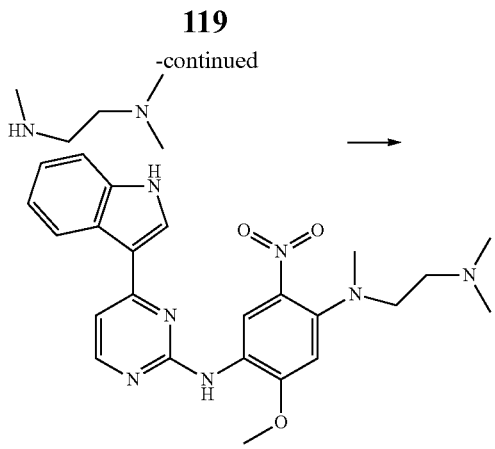

$N^1,N^1,N^2$-Trimethylethane-1,2-diamine (83 mg, 0.82 mmol) was added to a mixture of N-(4-fluoro-2-methoxy-5-nitrophenyl)-4-(1H-indol-3-yl)pyrimidin-2-amine (Intermediate 68, 409 mg, 0.74 mmol), DIPEA (0.259 mL, 1.48 mmol) and DMA (3 mL). The resulting mixture was heated in a microwave at 140° C. for 0.5 h. Part-purification was achieved by ion exchange chromatography, using an SCX column (20 g) and eluting with 0.35 M methanolic ammonia. Appropriate fractions were concentrated in vacuo to provide an orange/brown gum. This gum was triturated with ethanol (15 mL) to give a solid which was collected by filtration and dried under vacuum to give the title compound (275 mg, 80%) as an orange solid; $^1$H NMR: 2.18 (6H, s), 2.45-2.55 (2H, m), 2.87 (3H, s), 3.25-3.30 (2H, m), 3.97 (3H, s), 6.87 (1H, s), 7.08 (1H, t), 7.18 (1H, t), 7.29 (1H, d), 7.46 (1H, d), 8.03 (1H, s), 8.33 (3H, dd), 8.66 (1H, s), 11.80 (1H, s); m/z: ES$^+$ MH$^+$ 462.34.

Intermediate 170: tert-Butyl N-[2-[[5-methoxy-4-[[4-(1-methylindol-3-yl)pyrimidin-2-yl]amino]-2-(prop-2-enoylamino)phenyl]-methylamino]ethyl]-N-methylcarbamate Acryloyl chloride (0.069 mL, 0.85 mmol) in CH$_2$Cl$_2$ (2.5 mL) was added dropwise over 5 minutes to a solution of tert-butyl N-[2-[[2-amino-5-methoxy-4-[[4-(1-methylindol-3-yl)pyrimidin-2-yl]amino]phenyl]-methylamino]ethyl]-N-methylcarbamate (Intermediate 171, 377 mg, 0.71 mmol) and DIPEA (0.234 mL, 1.42 mmol) in CH$_2$Cl$_2$ (8 mL) cooled in an ice/methanol bath. The mixture was stirred for 0.5 h. The mixture was then diluted with 10% CH$_3$OH in CH$_2$Cl$_2$. The resulting solution was washed with sat. NaHCO$_3$, dried (MgSO$_4$) and then concentrated in vacuo. Purification by FCC, eluting with 0-3% CH$_3$OH in CH$_2$Cl$_2$ gave the title compound (325 mg, 78%) as a yellow foam; $^1$H NMR: 1.38 (9H, s), 2.71 (3H, s), 2.77 (3H, s), 3.00 (2H, t), 3.34 (2H, t), 3.88 (3H, s), 3.91 (3H, s), 5.73-5.78 (1H, m), 6.27 (1H, dd), 6.67 (1H, dd), 6.99 (1H, s), 7.17 (1H, t), 7.21-7.27 (2H, m), 7.53 (1H, d), 7.87 (1H, s), 8.26 (1H, d), 8.33 (1H, d), 8.62 (1H, s), 8.99 (1H, s), 9.10 (1H, s); m/z: ES$^+$ MH$^+$ 584.73.

Intermediate 171: tert-butyl N-[2-[[2-amino-5-methoxy-4-[[4-(1-methylindol-3-yl)pyrimidin-2-yl]amino]phenyl]-methylamino]ethyl]-N-methylcarbamate tert-Butyl N-[2-[[5-methoxy-4-[[4-(1-methylindol-3-yl)pyrimidin-2-yl]amino]-2-nitrophenyl]-methylamino]ethyl]-N-methylcarbamate (Intermediate 172, 428 mg, 0.76 mmol), iron (255 mg, 4.57 mmol) and NH$_4$Cl (30.6 mg, 0.57 mmol) were heated in ethanol (16 mL) and water (5.33 mL) at reflux for 1.5 h (heating block at 100° C.) and then the mixture was cooled and concentrated in vacuo. The resulting residue was triturated in 10% CH$_3$OH/CH$_2$Cl$_2$ (30 mL) and filtered. The residues were triturated again with 10% CH$_3$OH/CH$_2$Cl$_2$ (30 mL) and filtered. The combined filtrates were washed with brine, dried (MgSO$_4$) and concentrated in vacuo. Purification by FCC, eluting with 0-5% CH$_3$OH in CH$_2$Cl$_2$ gave the title compound (380 mg, 94%) as a light brown foam; $^1$H NMR: 1.41 (9H, s), 2.64 (3H, s), 2.80 (3H, s), 2.95 (2H, t), 3.34 (2H, t), 3.77 (3H, s), 3.89 (3H, s), 4.40 (2H, s), 6.78 (1H, s), 7.14-7.20 (2H, m), 7.23-7.27 (1H, m), 7.52 (1H, d), 7.55 (1H, s), 7.75 (1H, s), 8.28 (1H, d), 8.29 (1H, s), 8.42 (1H, d); m/z: ES$^+$ MH$^+$ 532.37.

Intermediate 172: tert-butyl N-[2-[[5-methoxy-4-[[4-(1-methylindol-3-yl)pyrimidin-2-yl]amino]-2-nitrophenyl]-methylamino]ethyl]-N-methylcarbamate tert-Butyl N-methyl-N-(2-methylaminoethyl)carbamate (Intermediate 173, 300 mg, 1.59 mmol) was added to a suspension of N-(4-fluoro-2-methoxy-5-nitrophenyl)-4-(1-methyl-indol-3-yl)pyrimidin-2-amine (Intermediate 129, 522 mg, 1.33 mmol) and DIPEA (0.462 mL, 2.65 mmol) in DMA (5 mL). The mixture was heated in a microwave at 100° C. for 4 h. The mixture was then diluted with EtOAc and washed with water (5×), brine, dried (MgSO$_4$) and concentrated in vacuo. Purification by FCC, eluting with 0-2% CH$_3$OH in CH$_2$Cl$_2$ gave the title compound (431 mg, 58%) as an orange solid after trituration with diethyl ether; $^1$H NMR: 1.37 (9H, s), 2.79 (3H, s), 2.88 (3H, s), 3.29-3.36 (2H, m), 3.39-3.44 (2H, m), 3.89 (3H, s), 3.99 (3H, s), 6.85 (1H, d), 7.14 (1H, t), 7.21-7.28 (2H, m), 7.53 (1H, br d), 8.04 (1H, s), 8.31-8.38 (3H, m), 8.72 (1H, br s); m/z: ES$^+$ MH$^+$ 562.35.

Intermediate 173: tert-Butyl N-methyl-N-(2-methylaminoethyl)carbamate

A solution of di-tert-butyl dicarbonate (4.95 g, 22.69 mmol) in CH$_2$Cl$_2$ (240 mL) was added dropwise to a stirred solution of N,N'-dimethylethane-1,2-diamine (4 g, 45.38 mmol) in CH$_2$Cl$_2$ (80 mL) over a period of 20 h. The resulting mixture was stirred at r.t. for 3 h. The mixture was then washed sequentially with sat. Na$_2$CO$_3$ (2×100 mL), water (50 mL), and sat. brine (50 mL). The organic solution was dried (MgSO$_4$) and concentrated in vacuo. Purification by FCC, eluting with 0-10% CH$_3$OH in CH$_2$Cl$_2$ gave the title compound (2.177 g, 51%) as a pale yellow oil; $^1$H NMR: 1.40 (9H, s), 2.28 (3H, s), 2.57 (2H, t), 2.79 (3H, s), 3.20 (2H, t).

Intermediate 174: 3-Chloro-N-[2-[2-dimethylaminoethyl(methyl)amino]-4-methoxy-5-[[4-(1-methylindol-3-yl)pyrimidin-2-yl]amino]phenyl]propanamide

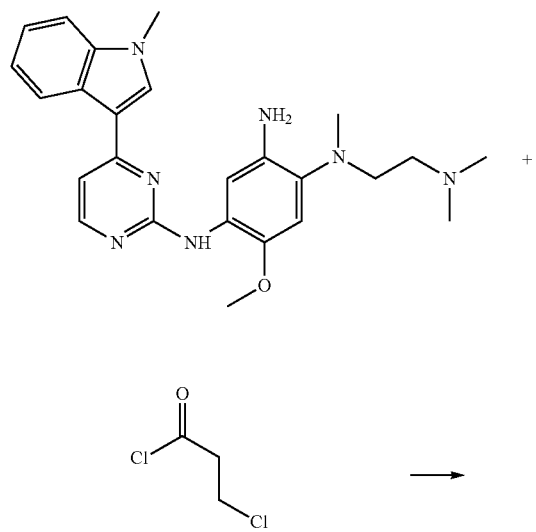

To a stirred suspension of N$^1$-(2-dimethylaminoethyl)-5-methoxy-N$^1$-methyl-N$^4$-[4-(1-methylindol-3-yl)pyrimidin-2-yl]benzene-1,2,4-triamine (Intermediate 175, 33 g, 62.29 mmol) and K$_2$CO$_3$ (6.09 g, 43.6 mmol) in acetone (300 mL) was added 3-chloropropanoyl chloride (9.78 g, 74.74 mmol) at −50° C. The resulting mixture was heated to −20° C. and stirred for 0.5 h. CH$_3$OH (27.75 mL) and NaOH solution (2.24 g, 56.06 mmol in 300 mL water) were added. The resulting mixture was stirred for 3-4 h at r.t. Solid was collected by filtration and dried at 50° C. to give the title compound (32.5 g, 95%). $^1$H NMR: (CDCl$_3$) 2.95 (2H, t), 3.04 (6H, d), 3.50 (3H, s), 3.63 (2H, s), 3.81 (2H, t), 4.01 (6H, s), 4.33-4.37 (2H, m), 7.33-7.42 (3H, m), 7.47 (1H, t), 7.51-7.55 (1H, m), 8.11-8.21 (3H, m), 8.48 (1H, s), 8.87 (1H, s), 9.17 (1H, s); m/z: ES$^+$ MH$^+$ 536.24.

Intermediate 175: N$^4$-(2-Dimethylaminoethyl)-2-methoxy-N$^4$-methyl-N$^1$-[4-(1-methylindol-3-yl)pyrimidin-2-yl]-5-nitro-benzene-1,4-diamine

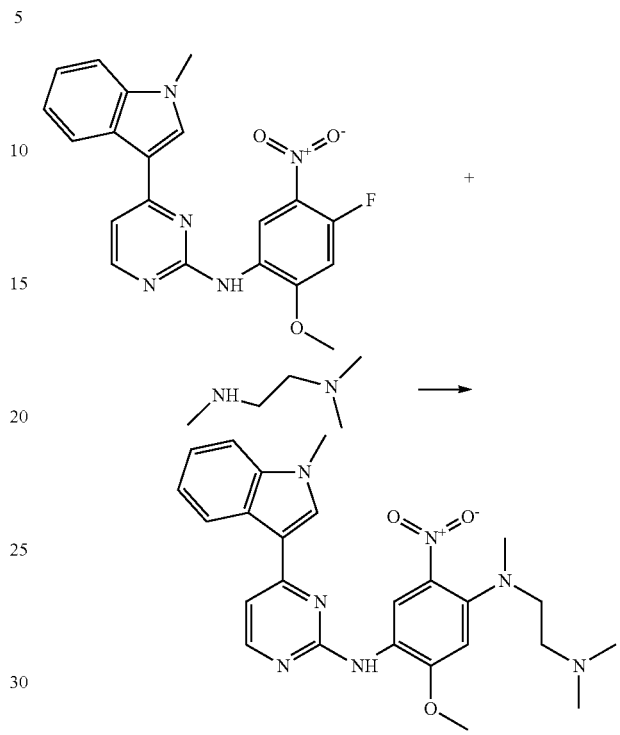

To a stirred solution of N-(4-fluoro-2-methoxy-5-nitrophenyl)-4-(1-methylindol-3-yl)pyrimidin-2-amine (Intermediate 176, 65 g, 160.28 mmol) and N,N',N'-trimethylethane-1,2-diamine (19.65 g, 192.3 mmol) in DMA (630 mL) was added N-ethyl-N-isopropyl-propan-2-amine (26.93 g, 208.4 mmol) at r.t. The resulting mixture was stirred at 85° C. for 5-6 h then cooled to r.t. Water (630 mL) was then added and the mixture was stirred for 3-4 h. Solid material was collected by filtration, washed with water (315 mL) and dried at 50° C. for 12 h to give the title compound (79.4 g, 96%) as orange solid; $^1$H NMR (CDCl$_3$): 2.29 (6H, s) 2.60 (2H, t), 2.93 (3H, s), 3.31 (2H, t), 3.96 (3H, s), 4.00 (3H, s), 6.69 (1H, s), 7.21 (1H, d), 7.30-7.38 (2H, m), 7.43 (1H, d), 7.56 (1H, s), 8.18 (1H, d), 8.30 (1H, s), 8.41 (1H, d), 9.59 (1H, s); m/z: ES$^+$ MH$^+$ 476.23.

Intermediate 176: N-(4-Fluoro-2-methoxy-5-nitrophenyl)-4-(1-methylindol-3-yl)-pyrimidin-2-amine

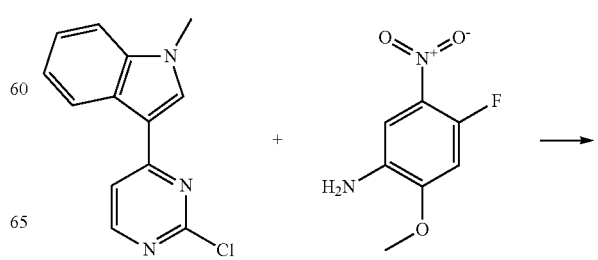

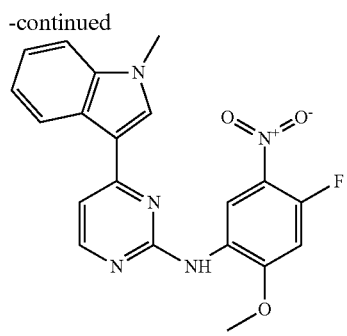

1,4-Dioxane (585 mL) was added to a mixture of 3-(2-chloropyrimidin-4-yl)-1-methylindole (Intermediate 177, 50 g, 160.04 mmol), 4-fluoro-2-methoxy-5-nitro-aniline (38.03 g, 192.04 mmol) and p-toluenesulfonic acid monohydrate (37.09 g, 192.04 mmol) at r.t. The resulting mixture was stirred at 85° C. for 3 h. After cooling to r.t., the mixture was quenched with 23% aqueous ammonia (39.59 mL, 480.1 mmol) and water (195 mL, 510.1 mmol) and a solid precipitated. The resulting slurry was stirred at r.t. for 3-4 h. The solid was collected by filtration and dried at 50° C. in vacuo for 12 h to give the title compound (74.6 g, 85%) as yellow solid; $^1$H NMR (CDCl$_3$): 4.01 (6H, s), 6.90 (1H, d), 7.37-7.48 (4H, m), 8.05-8.12 (2H, m), 8.43 (1H, s), 8.90 (1H, s), 9.34 (1H, s); m/z: ES$^+$ MH$^+$ 394.12.

Intermediate 177:
3-(2-Chloropyrimidin-4-yl)-1-methyl-indole

To a stirred solution 2, 4-dichloropyrimidine (70.5 g, 463.76 mmol) in dimethoxyethane (900 mL) was added FeCl$_3$ (77.16 g, 459.12 mmol) and 1-methyl indole (68.28 g) at 60° C. The resulting mixture was stirred overnight at 60° C. After cooling, a solid was precipitated by adding methanol (345 mL) and water (900 mL). The resulting slurry was stirred for 3 h. The solid was collected by filtration, washed with CH$_3$OH (1.38 L) and dried at 50° C. overnight to give the title compound (138.7 g, 81.5%) as a purple solid; $^1$H NMR (CDCl$_3$) 3.89 (3H, s), 7.36-7.41 (3H, m), 7.49 (1H, s), 7.96 (1H, s), 8.34 (1H, s), 8.45 (1H, s); m/z: ES$^+$ MH$^+$ 244.05.

Useful Crystalline Polymorphic Forms of N-(2-{2-dimethylaminoethyl-methylamino}-4-methoxy-5-{[4-(1-methylindol-3-yl)pyrimidin-2-yl]amino}phenyl)prop-2-enamide (Referred to Herein as "Compound X") and its Mesylate Salt (Referred to Herein as "Mesylate Salt Y")

Polymorphic Form A of Compound X

Figure 2:
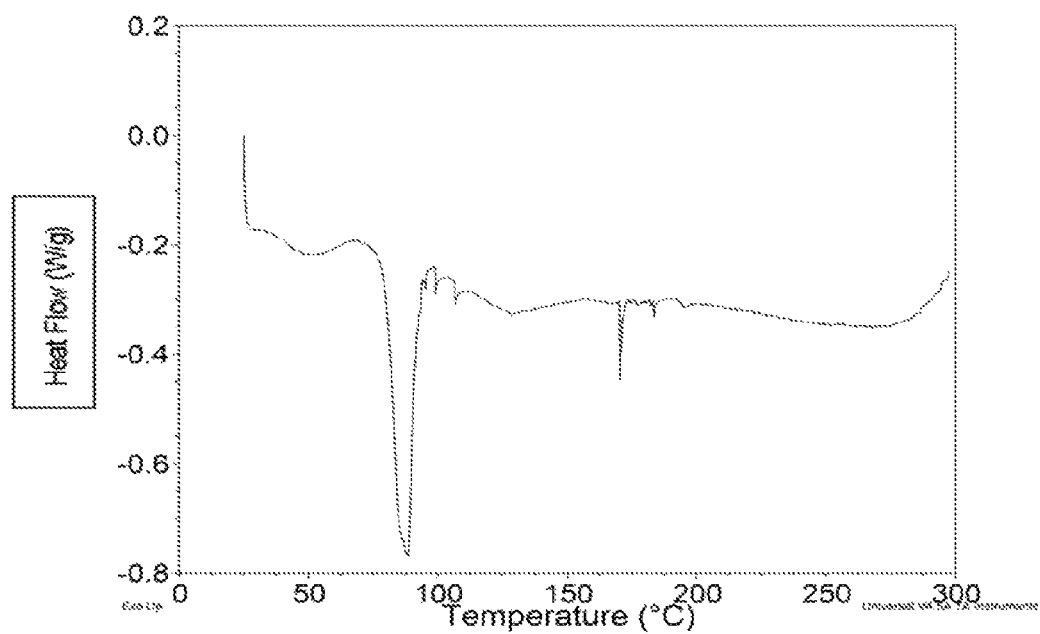

The initially produced Compound X was found to be an amorphous solid. Crystalline polymorphic Form A of Compound X was then prepared by taking some of this amorphous Compound X (~20 mg) and slurring it in cyclohexane (~2 mL) at 50° C. while stirring with a magnetic stirrer bar for ~4 days. Then the sample was allowed to cool, the cap removed from the vial, and the sample was left to dry under ambient conditions to provide Form A of Compound X. The X-ray powder diffraction pattern for Form A of Compound X is shown in FIG. 1. The DSC thermogram of Form A of Compound X is shown in FIG. 2 which shows an initial event with an onset of 35.1° C. and a peak at 50.1° C. followed by a subsequent melting endotherm with an with an onset of 80.2° C. and a peak at 88.3° C.

Polymorphic Form B of Compound X

Figure 4:
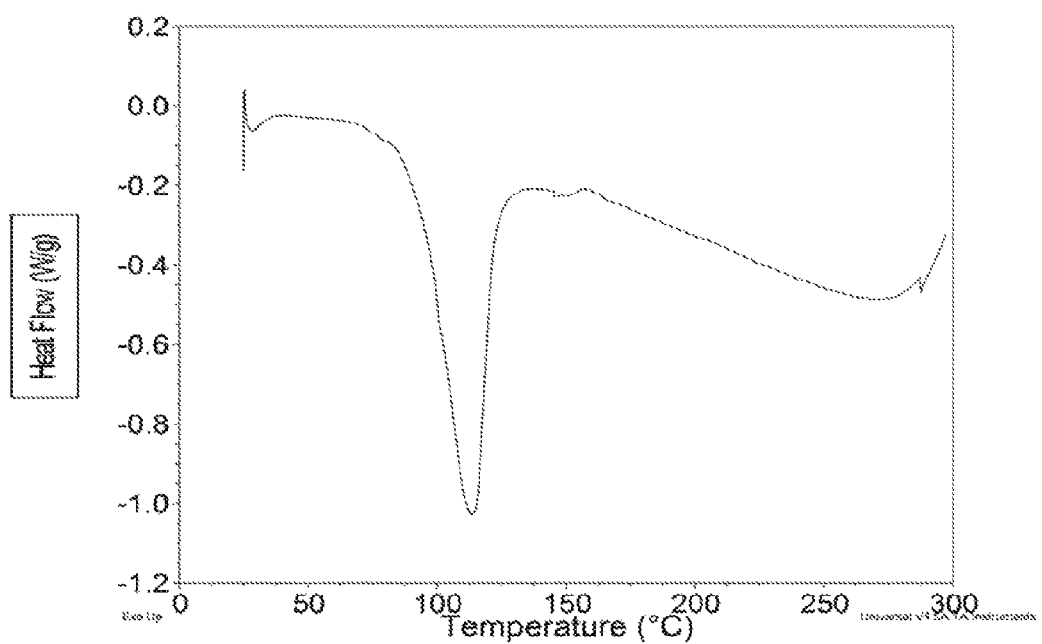

The initially produced Compound X was found to be an amorphous solid. Crystalline polymorphic Form B of Compound X was then prepared by taking some of this amorphous Compound X (~20 mg) and dissolving it in the minimum required amount of EtOAc to achieve full dissolution. This solution was then allowed to evaporate to dryness under ambient conditions to provide Form B of Compound X. The X-ray powder diffraction pattern for Form B of Compound X is shown in FIG. 3. The DSC thermogram of Form B of Compound X is shown in FIG. 4 which shows a melting endotherm with an onset of 94.1° C. and a peak at 113.6° C.

Polymorphic Form C of Compound X

Figure 6:
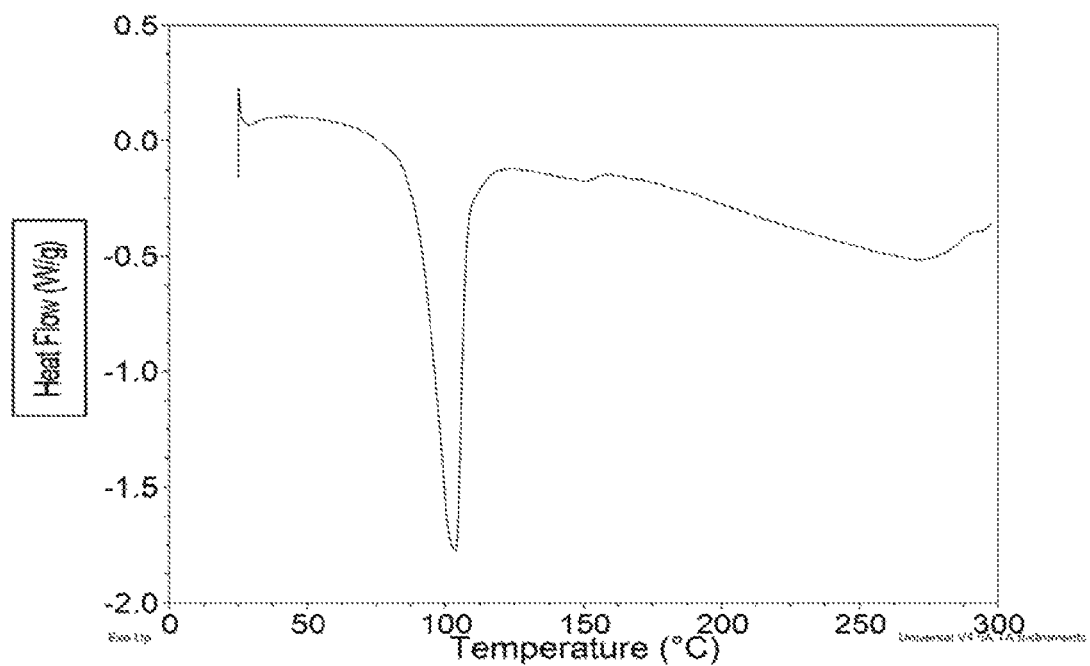

The initially produced Compound X was found to be an amorphous solid. Crystalline polymorphic form C of Compound X was then prepared by taking some of this amorphous Compound X (~20 mg) and dissolving it in the minimum amount of diethyl ether required to achieve full dissolution. This solution was then allowed to evaporate to dryness under ambient conditions to provide Form C of Compound X. The X-ray powder diffraction pattern for Form C of Compound X is shown in FIG. 5. The DSC thermogram of Form C of Compound X is shown in FIG. 6 which shows a melting endotherm with an onset of 91.1° C. and a peak at 103.8° C.

Polymorphic Form D of Compound X

Figure 8:
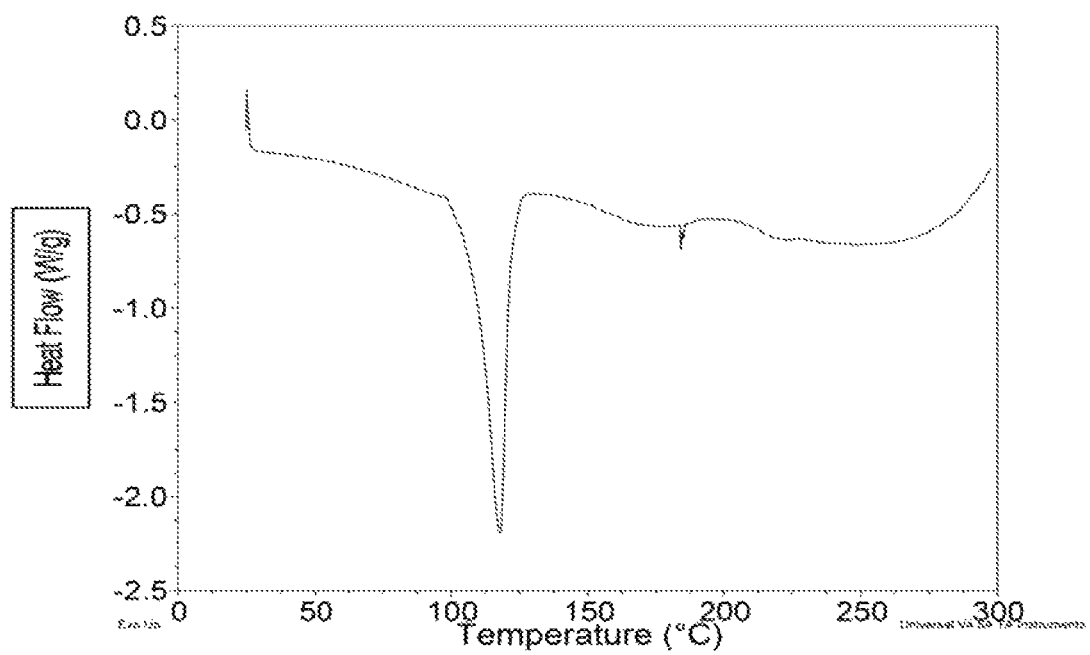
Figure 9:
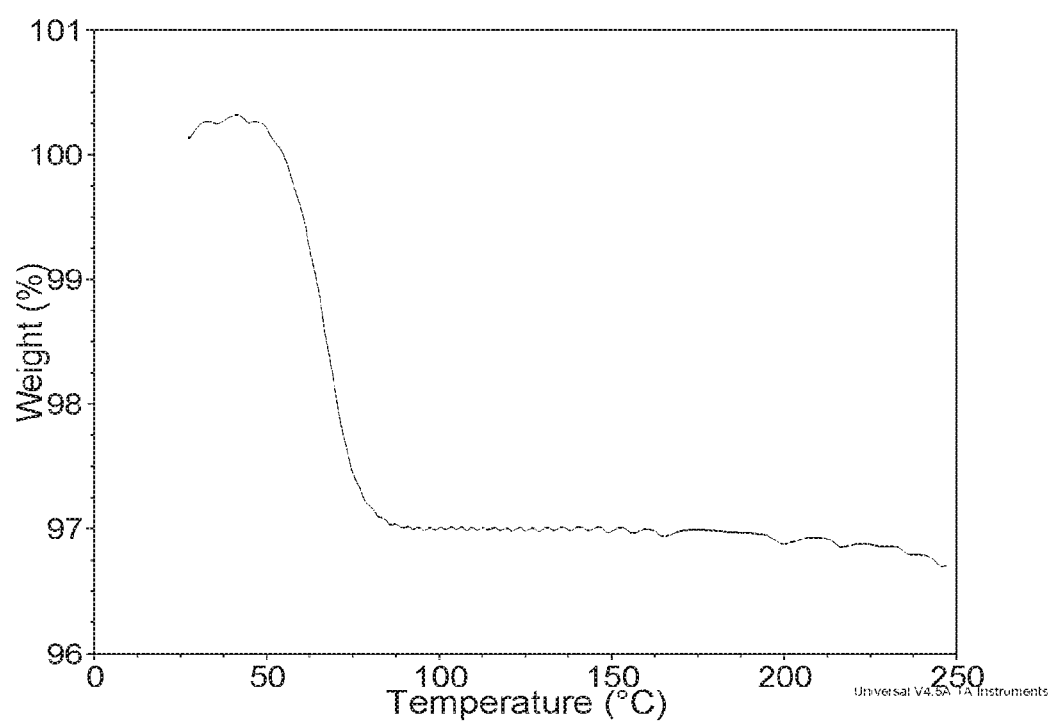

Polymorphic Form D of Compound X, which is believed to be a crystalline monohydrate form of Compound X, was produced via the method described above for Example 28—Alternative syntheses 1 & 2. The X-ray powder diffraction pattern for Form D of Compound X is shown in FIG. 7. The DSC thermogram of Form C of Compound X is shown in FIG. 8 which shows a melting endotherm with an onset of 108.8° C. and a peak at 117.7° C. Thermogravimetric analysis indicated a weight loss of approximately 3.3%. which suggests a monohydrated form (theoretical monohydrate=3.5%). The TGA thermogram is shown in FIG. 9.

Polymorphic Form E of Compound X

Figure 11:
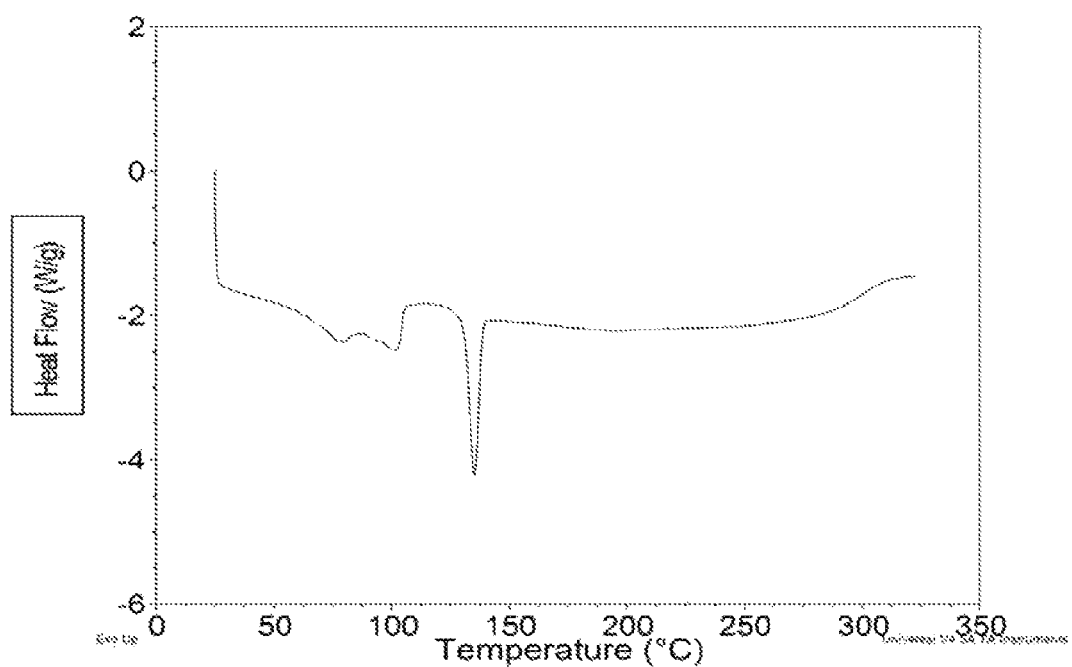
Figure 12:
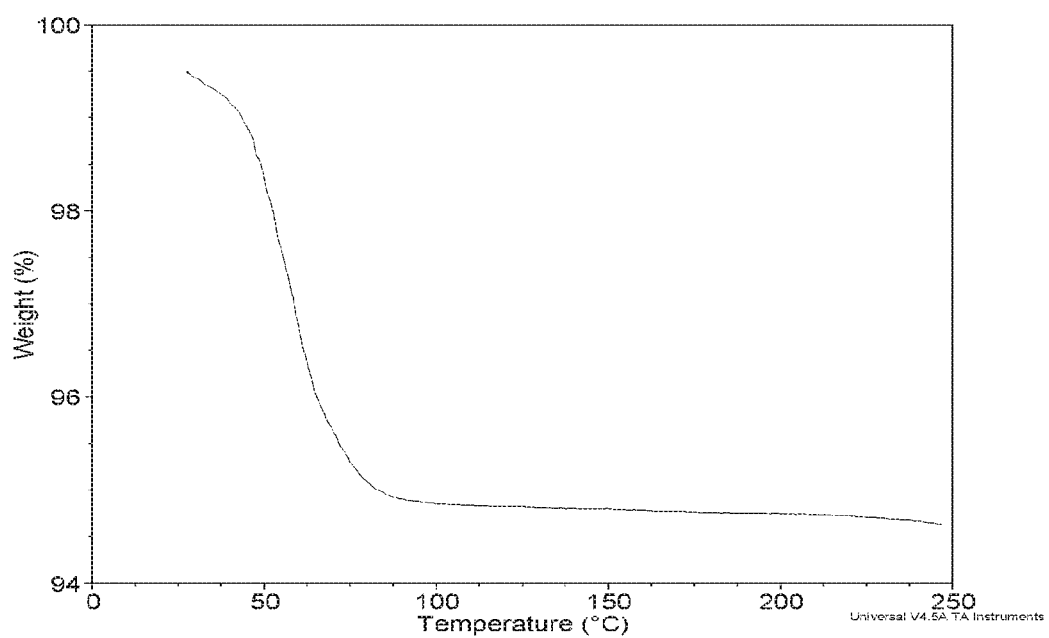

Polymorphic Form E of Compound X, which is believed to be a 1.25 stoichiometry hydrated form of Compound X, was produced by slurrying Compound X [154 g, prepared as described for Example 28 (using acryloyl chloride)] in a mixture of methanol (150 mL) and water (600 mL). 10 g of Compound X (Form D) was added and the slurry was stirred at r.t. for 4 days. The resulting solid was then collected by filtration and washed with water and allowed to dry. The X-ray powder diffraction pattern for Form E of Compound X is shown in FIG. 10. The DSC thermogram of Form E of Compound X is shown in FIG. 11 which shows an initial event with an onset at 66.1° C. and a peak at 77.2° C. followed by a further event with an onset at 93.6° C. and a peak at 101.5° C. followed by a subsequent melting endotherm with an with an onset of 130.9° C. and a peak at 135.3° C. Thermogravimetric analysis indicated a weight loss of approximately 4.7% which suggests a hydrated form equivalent to a 1.25 stoichiometric hydrate. (theoretical 1.25 hydrate=4.3%). The TGA thermogram is shown in FIG. 12.

Polymorphic Form F of Compound X

Figure 14:
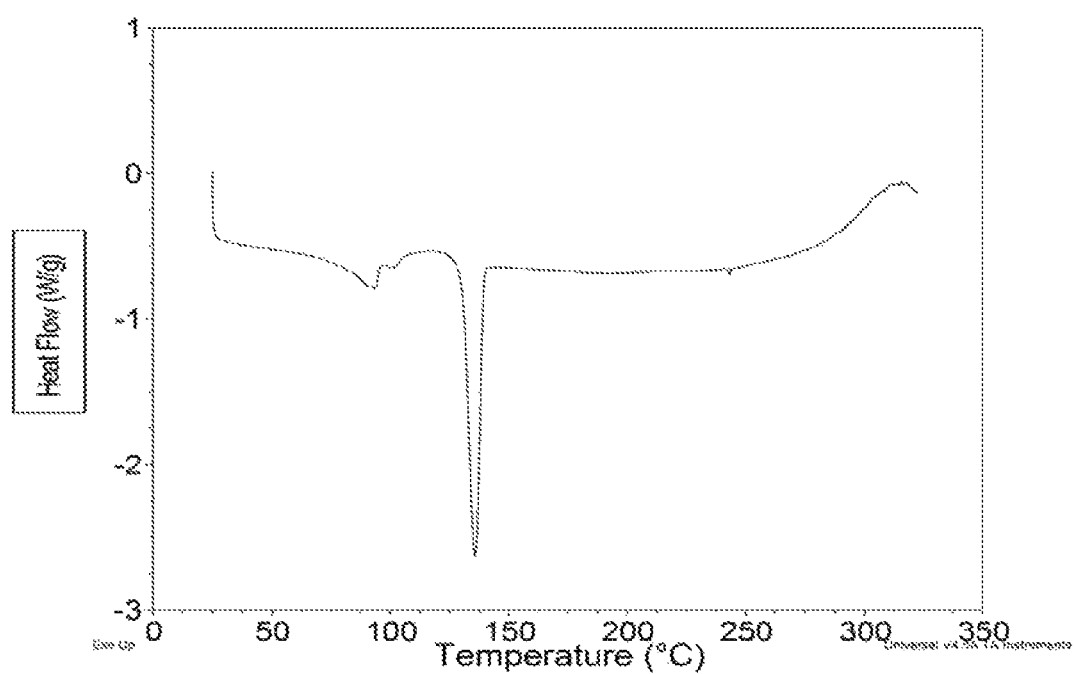
Figure 15:
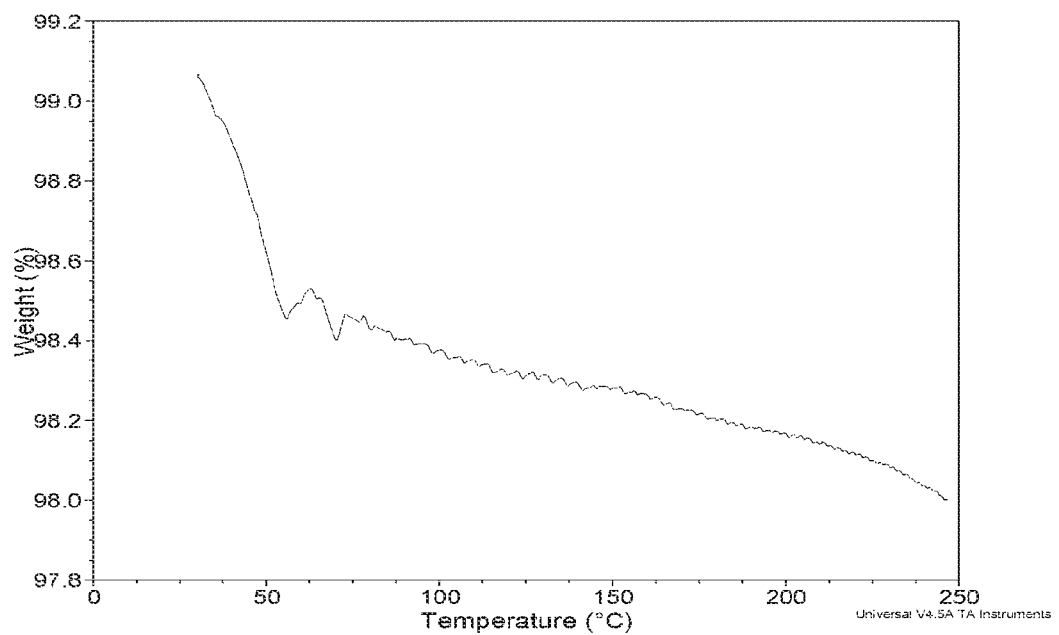

Polymorphic Form F of Compound X, which is believed to be a 0.25 stoichiometry hydrated form of Compound X, was produced by taking some of the Form E of Compound X and drying it in a vacuum oven, at r.t., to constant weight. The X-ray powder diffraction pattern for Form F of Compound X is shown in FIG. 13. The DSC thermogram of Form F of Compound X is shown in FIG. 14 which shows an initial event with an onset at 80.9° C. and a peak at 92.8° C. followed by a subsequent melting endotherm with an with an onset of 130.7° C. and a peak at 135.7° C. Thermogravimetric analysis indicated a weight loss of approximately 0.7% which suggests a partially hydrated form equivalent to a 0.25 stoichiometric hydrate. (theoretical 0.25 hydrate=0.89%). The TGA thermogram is shown in FIG. 15.

Polymorphic Form K of Compound X

This polymorphic form of Compound X was produced according to the following method: A solution of acryloyl chloride (0.026 L, 318.48 mmol) in $CH_2Cl_2$ (290 mL) was added dropwise over 25 minutes to a stirred suspension of $N^1$-(2-(dimethylamino)ethyl)-5-methoxy-$N^1$-methyl-$N^4$-(4-(1-methyl-1H-indol-3-yl)pyrimidin-2-yl)benzene-1,2,4-triamine (129 g, 289.52 mmol) in $CH_2Cl_2$ (2.9 L) that was cooled to −5° C. The addition is exothermic but the mixture was not permitted to warm to more than 1° C. during the addition. The resulting mixture was stirred at −5° C. for 2 h. Cold sat. $NaHCO_3$ solution (1 L) was then added dropwise, while keeping the temperature below −2° C. The mixture was then allowed to warm to r.t. The phases were separated, and the resulting organic solution was washed with water (100 mL) and saturated brine (100 mL). The solution was then dried ($MgSO_4$) and concentrated in vacuo. The residue was dissolved into 5% $CH_3OH$ in $CH_2Cl_2$ (60 mL) and then filtered. The filtered solution was purified by FCC, eluting with 5% $CH_3OH$ in $CH_2Cl_2$ and clean fractions were combined and concentrated to give impure Compound X as a brown gum (96 g). Further purification by chiral preparative HPLC provided a sample of Compound X which was slurried in $CH_3OH$ (50 mL). Not all of the Compound X material would dissolve. Water was then added (250 mL) and the resulting mixture was slurried overnight with magnetic stirring. The resulting solid was then collected by filtration and dried in a vacuum oven over a weekend to provide 16.2 g of Compound X in the polymorphic form defined herein as Form K. $^1$H NMR: 2.20 (6H, s), 2.28 (2H, m), 2.71 (3H, s), 2.88 (2H, m), 3.85 (3H, s), 3.90 (3H, s), 5.76 (1H, d), 6.27 (1H, d), 6.43 (1H, m), 7.03 (1H, s), 7.15 (1H, m), 7.22 (2H, m), 7.51 (1H, d), 7.87 (1H, s), 8.23 (1H, m), 8.33 (1H, m), 8.68 (1H, s), 9.18 (1H, s), 10.16 (1H, s).

Figure 17:
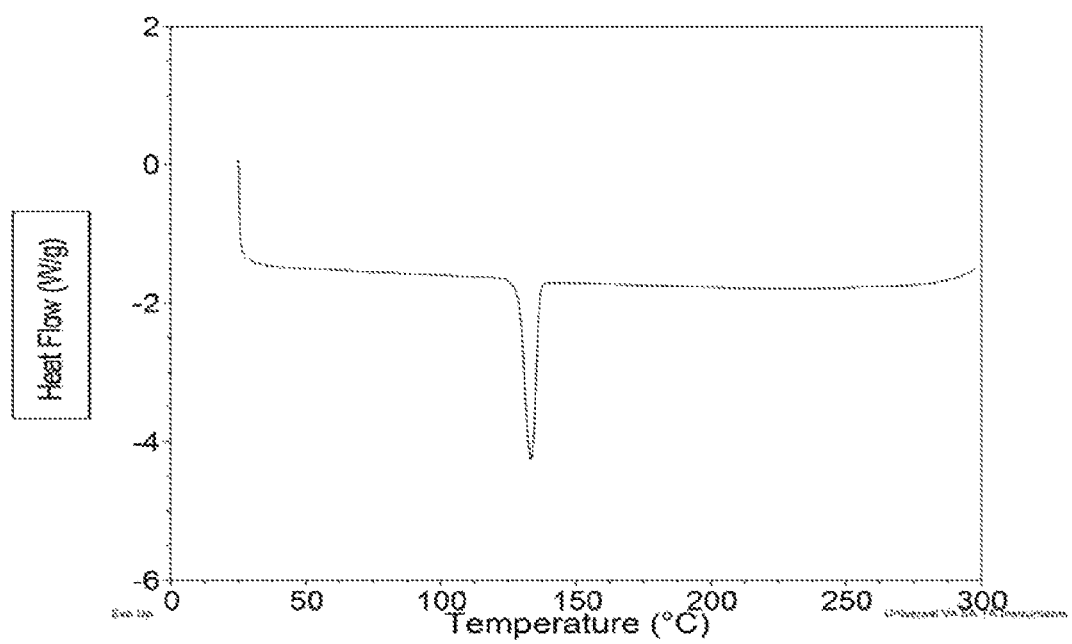

The X-ray powder diffraction pattern for Form K of Compound X is shown in FIG. 16. The DSC thermogram of Form K of Compound X is shown in FIG. 17 which shows a melting endotherm with an onset of 129.3° C. and a peak at 133.4° C.

Polymorphic Form A of Mesylate Salt Y

Figure 19:
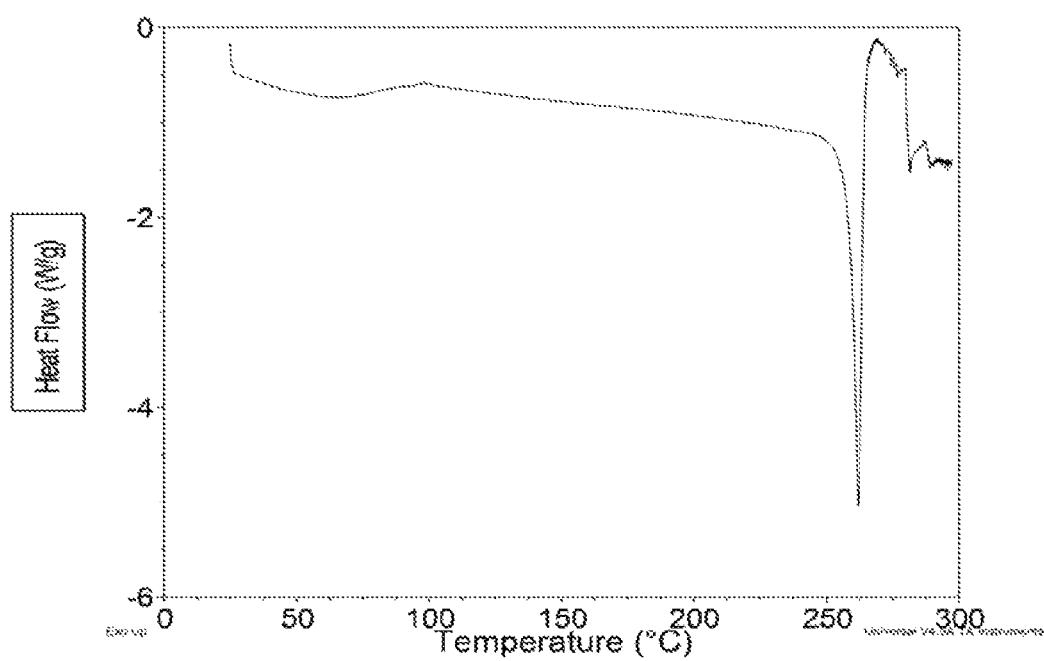

Polymorphic Form A of Mesylate Salt Y was prepared by the method described previously (Example 28A, Procedure 3). The X-ray powder diffraction pattern for Form A of Mesylate Salt Y is shown in FIG. 18. The DSC thermogram of Form A of Mesylate salt Y is shown in FIG. 19 which shows an initial event with an onset at 28.1° C. and a peak at 62.2° C. followed by a subsequent melting endotherm with an with an onset of 258.8° C. and a peak at 262.0° C.

Polymorphic Form B of Mesylate Salt Y

Figure 21:
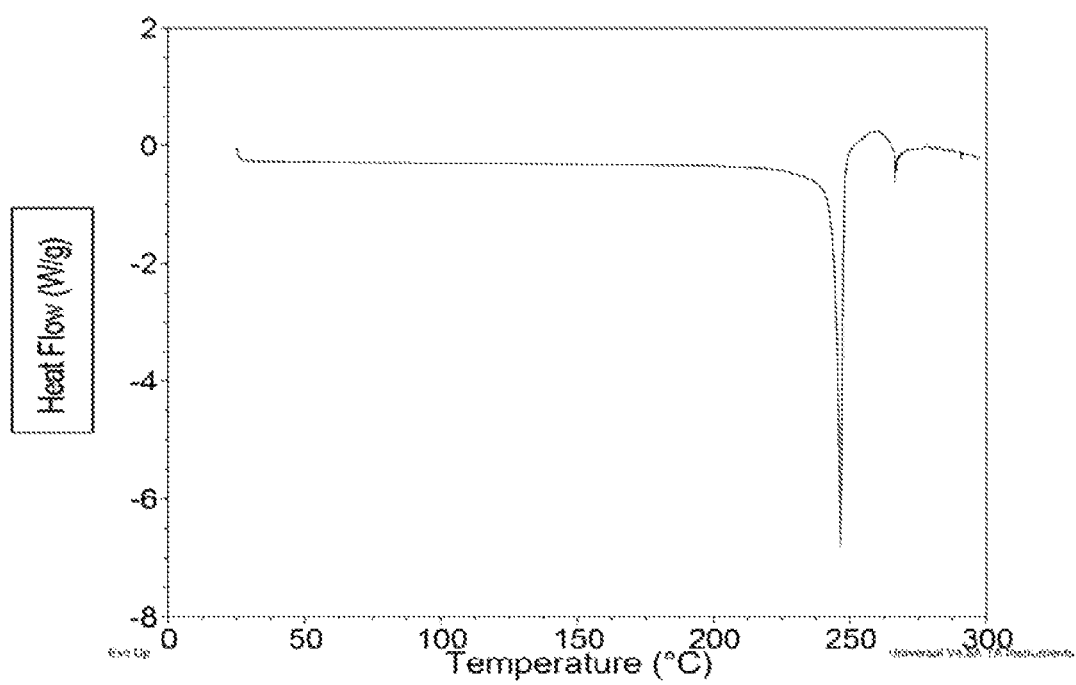

Polymorphic Form A of Mesylate Salt Y was prepared by the method described to previously (Example 28A, Procedures 1 and 2). The X-ray powder diffraction pattern for Form A of Mesylate Salt Y is shown in FIG. 20. The DSC thermogram of Form A of Mesylate salt Y is shown in FIG. 21 which shows a melting endotherm with an onset of 245.0° C. and a peak at 246.5° C.

The invention claimed is:

1. A compound of Formula (II):

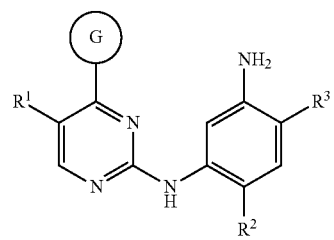

(II)

wherein:

G is 1H-indol-3-yl or 1-methyl-1H-indol-3-yl;

$R^1$ is hydrogen;

$R^2$ is methoxy; and $R^3$ is [2-(dimethylamino)ethyl](methyl)amino or [2-(methylamino)ethyl](methyl)amino;

or a salt thereof.

2. A compound of Formula (II) or a salt thereof, as claimed in claim 1, wherein $R^3$ is [2-(dimethylamino)ethyl](methyl)amino.

3. A compound of Formula (II) as claimed in claim 1 which is $N^1$-(2-dimethylaminoethyl)-5-methoxy-$N^1$-methyl-$N^4$-[4-(1-methylindol-3-yl)pyrimidin-2-yl]benzene-1,2,4-triamine, or a salt thereof.

4. A compound of Formula (II) as claimed in claim 1 which is $N^1$-(2-dimethylaminoethyl)-$N^4$-[4-(1H-indol-3-yl)pyrimidin-2-yl]-5-methoxy-$N^1$-methylbenzene-1,2,4-triamine, or a salt thereof.

5. A compound of Formula (III):

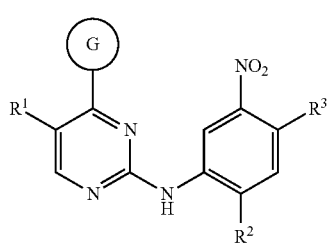

(III)

wherein:

G is 1H-indol-3-yl or 1-methyl-1H-indol-3-yl;

$R^1$ is hydrogen;

$R^2$ is methoxy; and $R^3$ is [2-(dimethylamino)ethyl](methyl)amino or [2-(methylamino)ethyl](methyl)amino;

or a salt thereof.

6. A compound of Formula (III) or a salt thereof, as claimed in claim 5 wherein $R^3$ is [2-(dimethylamino)ethyl](methyl)amino.

7. A compound of Formula (III) as claimed in claim 5, which is N'-(2-dimethylaminoethyl)-2-methoxy-N'-methyl-N-[4-(1-methylindol-3-yl)pyrimidin-2-yl]-5-nitrobenzene-1,4-diamine, or a salt thereof.

8. A compound of Formula (III) as claimed in claim 5, which is N'-(2-dimethylaminoethyl)-N-[4-(1H-indol-3-yl)pyrimidin-2-yl]-2-methoxy-N'-methyl-5-nitrobenzene-1,4-diamine, or a salt thereof.

9. A compound of Formula (IV):

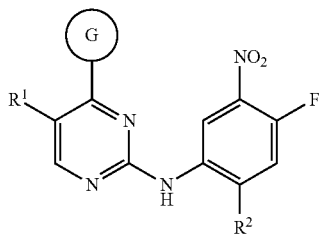

wherein:
G is 1H-indol-3-yl or 1-methyl-1H-indol-3-yl;
R$^1$ is hydrogen; and
R$^2$ is methoxy;
or a salt thereof.

10. A compound of Formula (IV) as claimed in claim 9 which is N-(4-fluoro-2-methoxy-5-nitrophenyl)-4-(1-methylindol-3-yl)pyrimidin-2-amine, or a salt thereof.

11. A compound of Formula (IV) as claimed in claim 9 which is N-(4-fluoro-2-methoxy-5-nitrophenyl)-4-(1H-indol-3-yl)pyrimidin-2-amine, or a salt thereof.

12. A compound of Formula (VI):

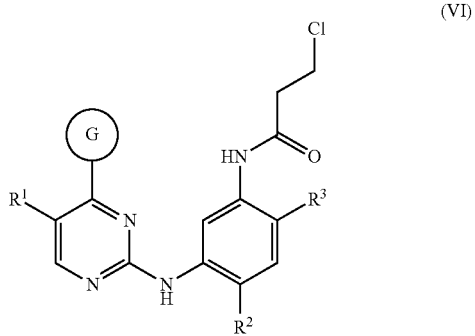

wherein:
G is 1H-indol-3-yl or 1-methyl-1H-indol-3-yl;
R$^1$ is hydrogen;
R$^2$ is methoxy; and
R$^3$ is [2-(dimethylamino)ethyl](methyl)amino or [2-(methylamino)ethyl](methyl)amino;
or a salt thereof.

13. A compound of Formula (VI) or salt thereof, as claimed in claim 12, wherein R$^3$ is [2-(dimethylamino)ethyl](methyl)amino.

14. A compound of Formula (VI) as claimed in claim 12 which is 3-chloro-N-[2-[2-dimethylaminoethyl-(methyl)amino]-4-methoxy-5-[[4-(1-methylindol-3-yl)pyrimidin-2-yl]amino]phenyl]-propanamide, or a salt thereof.

* * * * *